US012751722B2

(12) United States Patent
Rasmussen

(10) Patent No.: US 12,751,722 B2
(45) Date of Patent: Oct. 6, 2026

(54) SYSTEMS AND METHODS FOR PROVIDING A TIBIAL BASEPLATE SYSTEM

(71) Applicant: G. Lynn Rasmussen, Salt Lake City, UT (US)

(72) Inventor: G. Lynn Rasmussen, Salt Lake City, UT (US)

(73) Assignee: G. L Rasmussen, Salt Lake City, UT (US)

( * ) Notice: Subject to any disclaimer, the term of this patent is extended or adjusted under 35 U.S.C. 154(b) by 0 days.

(21) Appl. No.: 17/736,889

(22) Filed: May 4, 2022

(65) Prior Publication Data

US 2022/0361895 A1 Nov. 17, 2022

Related U.S. Application Data

(60) Provisional application No. 63/184,104, filed on May 4, 2021.

(51) Int. Cl.
*A61B 17/15* (2006.01)
*A61B 17/17* (2006.01)

(52) U.S. Cl.
CPC .......... *A61B 17/157* (2013.01); *A61B 17/155* (2013.01); *A61B 17/1764* (2013.01)

(58) Field of Classification Search
CPC .. A61B 17/157; A61B 17/155; A61B 17/1764
See application file for complete search history.

(56) References Cited

U.S. PATENT DOCUMENTS

| | | | | |
|---|---|---|---|---|
| 5,342,367 | A | 8/1994 | Ferrante et al. | |
| 2006/0036257 | A1 | 2/2006 | Steffensmeier | |
| 2011/0066247 | A1 | 3/2011 | Ries et al. | |
| 2019/0046217 | A1* | 2/2019 | Rasmussen | A61B 17/157 |
| 2022/0287724 | A1* | 9/2022 | Yeager | A61B 17/1725 |

* cited by examiner

*Primary Examiner* — Sameh R Boles
(74) *Attorney, Agent, or Firm* — David B. Tingey; Kirton McConkie

(57) ABSTRACT

A tibial baseplate system is described. While the system can include any suitable component, in some instances, it includes tibial baseplate having a first and second surface, the second surface being substantially opposite to the first surface, which is configured to be seated on a resected surface at a proximal end of a tibia. In some cases, the baseplate also includes a first spacer coupling that is configured to couple a first spacer to at least one of a lateral side and a medial side of the baseplate such that the spacer is disposed between, and is configured to maintain a set minimal distance between, the proximal end of the tibia and a distal end of a femur when the tibial baseplate is seated on the resected surface at the proximal end of the tibia and the spacer is coupled to the tibial baseplate. Other implementations are discussed.

20 Claims, 125 Drawing Sheets

SYSTEMS AND METHODS FOR PROVIDING A TIBIAL BASEPLATE SYSTEM

CROSS-REFERENCE TO RELATED APPLICATION

This application claims priority to U.S. Provisional Patent Application Ser. No. 63/184,104, filed May 4, 2021, and entitled "SYSTEMS AND METHODS FOR PROVIDING A TIBIAL BASEPLATE SYSTEM"; the entire disclosure of which is hereby incorporated by reference.

BACKGROUND OF THE INVENTION

Field of the Invention

The present invention relates to systems and methods that are configured to provide ligament tensioning, ligament balancing, bone cutting, bone gap balancing, and/or to otherwise prepare a joint to receive a prosthetic implant during joint arthroplasty. In particular, some implementations of the described systems and methods provide for ligament tensioning, ligament balancing, gap balancing, and/or bone cutting in a knee joint in preparation for the implantation of one or more femoral and/or tibial prostheses in the knee joint.

Description of Related Art

During a knee arthroplasty, a surgeon typically must gain access to the knee joint in order to perform resections of existing bone and cartilage so as to shape the tibia and femur to fit one or more mating surfaces of the implant. Some arthroplasty procedures seek to minimize the invasiveness of the approach to the knee joint by minimizing the size of the incision in the surrounding soft tissue structure of the knee and/or the patella. Preserving the soft tissue structure also preserves some of the natural support provided by these tissues. However, preserving the soft tissues surrounding the knee can be difficult at times due to the need to firmly support the resection guides relative to the bone of the tibia and the femur.

The manner in which the natural knee joint performs is largely affected by the tension in the collateral ligaments of the knee, as well as by the alignment of the articular surfaces of the knee joint relative to the collateral ligaments. In the natural knee joint, the plane of the articular surfaces of the femur and the tibia often bisects the collateral ligaments at an optimal, physiological position. This optimal, physiological position can enable the knee joint to flex and extend in a balanced and properly aligned manner. In some arthroplasty procedures, resectioning of the femur and/or the tibia is configured to preserve the optimal, physiological position of the knee joint when fitted with a prosthesis.

Preservation of the ligamentous and other soft tissue structures around the knee can provide a reference point for accurately positioning the tibial and femoral components of the knee implant, in particular, when said structure is in a tensed or otherwise loaded condition. For example, ligament tensions can be used to guide placement of resection guides. Conversely, preservation of the soft tissue structures requires balancing of the forces exerted by the soft tissues to promote normal kinematics in the knee and normal patellar tracking. Therefore, ligament forces can play a significant role in restoring normal function to a knee. Generally, therefore, reductions in the invasiveness of the knee arthroplasty procedure combined with improvements in the positioning and installation of knee components can result in a better overall surgical outcome for the patient.

It would therefore be advantageous to have systems and methods for guiding resection of the femur, tibia, and/or other structures in the knee during a knee arthroplasty that works well with minimally invasive approaches to the tibia and femur. It would be further advantageous if the instrumentation were to assist the balancing of forces between the knee implant components and the preserved ligamentous and soft tissue structures for improved function of the knee implant. Also, it would be advantageous to have instrumentation for guiding resection that uses the ligamentous structure of the knee to guide placement of the instrumentation and the resulting optimal alignment and physiological positioning of the knee prosthesis.

BRIEF SUMMARY OF THE INVENTION

At least some implementations of the described systems and methods meet the above needs, and achieve other advantages, by providing an assembly for guiding resection of a femur and/or a tibia of a knee joint in preparation for installing femoral and/or tibial knee components. The components of the present invention may be configured for use in both total knee replacement and uni-compartmental, or partial knee arthroplasty.

Some implementations of the present assembly include tibial and femoral intramedullary (IM) rods that are connected through a torque bolt (and/or any other suitable threaded member) that allows controlled adjustment of the distraction of the tibia and femur during cut positioning in one or more of a range of flexion and/or extension angles. Also, some implementations of such an assembly are usable with relatively small, noninvasive approaches to the knee joint by way of relatively narrow, low profile components that attach to tibial and/or femoral IM rods (and/or any other suitable tibial and/or femoral mounts). Further, some implementations of such an assembly include several quick-release components to allow fast assembly and disassembly in a surgical setting. Each of these aspects, along with the ability of the assembly to accurately guide initial reference cuts to the tibia and/or femur, can promote an improved outcome for the patient.

An assembly of one implementation of the present invention includes femoral and/or tibial IM rods, a flexion cutting guide, an extension cutting guide, and/or a selection of selectively lockable components. In some such implementations, one or both of the IM rods includes a shaft portion that is configured to extend within the IM canal of the femur and/or tibia. Some implementations of the femoral IM rod also include a femoral mount on an end of the shaft that is configured to extend away from the femur when the shaft is in the femoral IM canal. Similarly, some implementations of the tibial IM rod include a tibial mount on an end of the shaft that is configured to extend away from the tibia when the shaft is in the tibial IM canal. In some implementations, each of the mounts is configured to attach to one or more of the selectively lockable components. Flexion and/or extension cutting guides of some such implementations define one or more slots wherein the slots are configured to guide the use of cutting instrument and/or any other suitable instruments to make preparatory cuts to the femur and/or the tibia with the knee in flexion and/or extension. One or more of the cutting guides is configured, in accordance with some implementations, to attach to one or more of the selectively lockable components so as to be supported by the femoral and/or tibial IM rods. The selectively lockable components are configured, in at least some implementations, to attach to the femoral and/or tibial IM rods, to have at least one portion with a relatively small cross section extending anteriorly and/or anterior-medially out of the knee joint compartment and to attach to the flexion and/or extension cutting guides and support and limit the motion thereof.

In one aspect, the femoral mount has a portion having a cylindrical shape that is configured to extend in an anterior-posterior direction between the femoral condyles and that includes a central opening and/or a plurality of gauge marks extending along its outside surface. In some cases, the central opening also includes an anterior anti-rotation portion (e.g., a hexagonal and/or any other suitably shaped portion) and a larger diameter cylindrical portion. In some implementations, the tibial mount includes or supports a flexion bolt with a threaded shaft at one end that is configured to extend into an opening in the tibial IM shaft, a bushing at the other end, and/or an exterior hexagonal flange in between the ends. The bushing is configured, in some cases, to extend into the cylindrical portion and also contains an interior hexagonal bore. The hexagonal flange is, in some cases, configured to allow gripping by an external torque wrench and/or an internal torque driver to urge the femoral mount away from the tibial mount (e.g., by turning of the threaded shaft) and to distract the tibia and femur to a desired amount of torque. This allows the surgeon, in some cases, to apply the appropriate amount of tension to the ligamentous structure as defined by said surgeon and recorded for comparison later in the technique.

Included in at least one implementation of the selectively lockable components is a first locking mechanism that has an arm, a plunger assembly, and/or an anti-rotation extension, defined in some instances as a hex. In some such implementations, the arm has an elongate portion extending away from a head portion. Also extending from the head portion is the hex-shaped anti-rotation extension. Defined through the head portion and the hex extension is, in some cases, an opening that is configured to receive a shaft of the plunger assembly. In some implementations, the plunger assembly includes a thumb press at one end of the shaft and an anti-rotation feature similar to anti-rotation extension, defined in some instances as a hexagonal tip, at the other end of the shaft that extends out of the hex extension. Also, in some cases, the shaft includes a peg that extends into a helically shaped slot defined in the head portion. In some cases, a spring extends between the head portion and the thumb press. In some such cases, depression of the thumb press advances the shaft, while the peg and helical slot cause the shaft to rotate, and the flats of the hexagonal tip to align with the hex extension. This allows the hexagonal tip and hex extension to become concentric and to be inserted into the anterior hex portion of the central opening of the femoral mount. In addition, the hexagonal tip is, in some cases, configured to extend out of the hex portion of the opening and into the cylindrical portion, and to rotate (e.g., due to the helical slot and peg) into an eccentric position upon release of the thumb press, thereby locking the locking mechanism into the femoral mount. In some cases, when attached, the head portion of the arm extends proximally out of the knee joint compartment and the elongate portion extends anteriorly (with respect to the tibia) through the surgical incision.

At least some implementations of a flexion guide support member of the assembly of the present invention include a slider member and a ratchet bar. In some such implementations, the slider member is configured to attach to, and slide along, the elongate portion of the arm of the first locking mechanism, such as by having an opening defined therein matching the cross-section of the elongate portion. In some cases, the ratchet bar is configured to extend toward a plane defined by the tibial plateau. Moreover, in some cases, when assembled, the femoral mount, the first locking mechanism, and/or the flexion guide support member roughly form a U-shape that is relatively narrow in the medial-lateral direction to allow its use with narrow incisions.

Also included in some implementations of the selectively lockable components is a quick release mechanism that is configured to slide along and lock to the ratchet bar of the flexion guide support member. For example, some implementations of the quick release mechanism define an opening configured to extend and slide along the ratchet bar, and/or a locking pin that is spring loaded to extend into a portion of the ratchet to stop the sliding motion. In some such implementations, the locking pin is spring biased, but can be overcome with a manual draw pull (for example) to allow further sliding or repositioning of the quick release mechanism. In some cases, the quick release mechanism also includes a spring-biased locking lever that, along with an engagement member of the quick release mechanism, is configured to extend into an opening and to lock to the flexion cutting guide. In some such cases, depressing the locking lever again easily releases the flexion cutting guide after k-wire and/or any other suitable fasteners have been used to secure the flexion cutting guide in place to the tibia or femur. This allows the resection guide to translate toward the proximal tibia and away from the tensioning assembly with the knee in flexion.

Once the flexion resection guide is fixed to the proximal tibia, the resection guide (in some implementations) has a plurality of slots for which to resect multiple components of the femur and/or tibia, most notably a measured proximal tibial resection and/or a posterior condylar resection. Making these resections with the knee in tension at 90 degrees will, in some cases, allow the user to theoretically make a tensed flexion gap resection.

The selectively lockable components can also include any other suitable components that are configured to attach to the femoral and/or tibial IM rods (and/or mounts) when the knee is in extension. For example, the components may include a cannulated extension bolt, a tibial angulation guide, an extension guide support member, and/or a second locking mechanism. In some cases, the tibial angulation guide is configured to attach to the tibial IM rod (and/or tibial mount) through the cannulated extension bolt, which is, in turn, coupled to the tibial IM rod (and/or mount) and extends around the femoral mount, such as by having a block defining an arc-shaped channel that is configured to receive the cylindrical outer surface of the femoral mount. Included on the tibial angulation guide are a plurality of gauge marks that, when correlated to gauge marks on the outer surface of the femoral mount, register an amount of valgus angulation of the tibia with respect to the femur. In some cases, the tibial angulation guide is configured to extend into the bushing of the bolt described above, and/or to have its own threaded shaft and hexagonal flange—thus allowing it to be used to distract the tibia and/or femur in extension to a torque value corresponding to the torque value previously measured with the knee in flexion.

At least some implementations of the extension guide support member are configured to have a relatively narrow profile and extend anteriorly out of the joint compartment through the incision providing access thereto. For example, some implementations of the extension guide support member include a mounting portion that is cylindrical and defines a cylindrical opening and/or a support arm that is configured to extend proximally from the mounting portion. The second locking mechanism is, in some cases, generally configured similar to the first, except it lacks the fixed elongate portion of the arm. Rather, in some cases, it includes a cylindrical head portion that is configured to extend through the cylindrical opening of the mounting portion of the extension guide support member so as to connect the extension guide support member to the femoral mount while allowing said support member to rotate in a desired position, independent of the previously selected valgus angle.

Some implementations of the extension guide support member also include one or more support arms that are configured to extend proximally from the mounting portion when the mounting portion is attached to the femoral mount using the second locking member. In some such implementations, the extension cutting guide is configured to slidably attach over the support arm, such as via a channel defined in its body. Also, in some implementations, the extension cutting guide includes a swivel arm that can be swung into an abutting relationship with the tibial plateau and/or the plateau flange of the tibial mount to provide an additional reference point for making a femoral resection with the knee in extension. In accordance with some implementations, the extension cutting guide, similar to some implementations of the flexion cutting guide, defines a plurality of fixation openings allowing fasteners to extend there-through and attach the extension cutting guide to the tibia or femur. This allows removal of the selectively lockable components to provide room for the cuts to the tibia and/or the femur.

The swivel arm, once referenced off the proximal tibial resection, will (in accordance with some implementations) allow the extension cutting guide to make a pre-determined resection of the distal femur. Resecting with the knee tensed in the extended position will, in some cases, allow the user to make a balanced extension gap resection when compared with the tensed resections made with the knee previously positioned in flexion.

The aforementioned assembly of the present invention can have many advantages. Indeed, in some implementations, it provides a relatively narrow and low profile collection of locking components that securely attach cutting guides to tibial and/or femoral IM rods (and/or mounts). This provides a robust guide to reference cuts being made to the tibia and the femur with an approach to the joint that minimizes invasiveness. Further, many of the components, such as the first locking mechanism, the second locking mechanism, and/or the quick release mechanism, facilitate quick assembly, easy adjustment and quick disassembly for improved efficiency. Additionally, the use of the flexion bolt in flexion and/or the extension bolt in extension, combined with the other components of the tensioning assembly, allow (in some cases) the tibia and the femur to be distracted under a matching amount of tension in flexion and extension to ensure a better fit for the tibial and/or femoral knee replacement components throughout a range of flexion.

In accordance with some implementations, spacers, as well as limited radial movement of the tensioning assembly components, further allow the knee to adjust to accommodate the natural physiology of the patient's knee throughout the tensioning and resection processes. Thus, some implementations of the described procedures and assemblies allow the surgeon to adjust the amount of varus-valgus angulation of the tibia as desired to match the anatomy of the patient.

In addition to the foregoing, some implementations of the described systems and methods relate to systems and methods for preparing a knee for resection, as well as for guiding preparation of a knee for installation of one or more implants during an arthroplasty. In particular, some implementations of the present invention relate to a system for guiding a milling tool along a specific axis to provide an aperture of a desired depth, prior to resection.

An implementation of such a system includes a bone milling system having a milling tool member and/or a guide rod. In some implementations, the guide rod is partially deposited within the IM canal of the bone, and a portion of the guide rod extends outwardly from the IM canal along a desired axis. In some cases, the exposed portion of the guide rod is adapted to be coupled to the milling tool member in any suitable manner, including, without limitation, being rotatably inserted within a cavity of the milling tool member. As such, the milling tool member is guided along the desired axis by the exposed portion of the guide rod.

In some cases, the milling tool member includes a cutting head portion and a shaft. In accordance with some implementations, the cutting head portion includes a blade having a cutting edge and a window. Thus, in some implementations, the cutting edge cuts the aperture into the bone, and the window provides an escape route for the removed bits of bone debris. In some cases, a cavity is also provided running through the shaft and cutting head portion. In some such cases, the cavity is generally tube shaped having an open end and a closed end. The open end is (in some cases) in fluid communication with an opening in the blade. The closed end includes (in some cases) a shank for coupling the milling tool member to a drill and/or any other suitable device for rotating the member.

Following creation of the aperture, a resection block is combined with the bone milling system to resect the bone. In some implementations, the aperture is first made in the tibia and then used as a reference point and/or mounting surface for tensioning the knee and/or making resections to the exposed femur. In other implementations, the aperture is first made in the tibia and then used as a reference point and/or mounting surface for positioning a resection block to resect the tibia. Other implementations of include a bone milling device that incorporates a guide rod, a cutting surface, and/or a shank into a singular unit.

In addition to the foregoing, some implementations of the described systems and methods further include one or more wedges, blocks, and/or other spacers that are configured to be inserted in between a femur and a tibia in a knee joint to apply tension to one or more of the knee joint's ligaments/tendons (e.g., the collateral ligaments and/or any other suitable ligaments), to balance ligament tension in the knee joint, to properly align the tibia and/or femur for resection, to support and/or to otherwise place a cutting guide block in a desired position, and/or to otherwise prepare the knee joint for resection and/or implantation of one or more prostheses.

With respect to the spacers, the spacers can have any suitable characteristic that allows them to function as described herein. Indeed, the spacers can be any suitable shape, including, without limitation, being wedged shaped, being cup shaped, being dish shaped, having a rounded posterior end, having a rounded anterior end, having a squared anterior end, having a concave superior surface, having a flat superior surface, having a flat inferior surface, having a roughened inferior surface, and/or being any other suitable shape.

Additionally, the spacers' external surface can have any suitable texture that allows the spacers to function as intended. In some implementations, the spacer includes one or more smooth surfaces that allow a portion of the femur and/or the tibia to articulate against (and/or to otherwise contact) the spacer as the knee joint is moved through its range of motion (and/or as otherwise desired). Indeed, in some implementations, a proximal (or superior) side of the spacer comprises a smooth articular surface that is configured to allow a distal end of the femur to articulate against it as the knee joint moves through a range of motion.

Also, while some implementations of the spacers comprise a flat and/or angled surface that is configured to contact at least one of the femur and the tibia when the spacer is inserted in the knee joint, in some other implementations, the spacer comprises a recessed superior and/or inferior portion (e.g., a dish-like and/or concave surface) that is configured to cradle a portion of at least one of the tibia and the femur. In some implementations, however, one or more of the spacers comprise a substantially rectangular cuboidal (or prism) shape. In some embodiments, one or more ends of such spacers (e.g., a posterior end that is configured to be disposed posteriorly within a knee joint) are optionally notched, rounded, angled, wedge-shaped, chamfered, curved, and/or otherwise shaped to allow such spacers to easily be slid in between (and/or to separate) the femur from the tibia (e.g., without damaging soft tissue in the patient).

In some other implementations, the spacer comprises one or more non-smooth surfaces. Some non-limiting examples of such non-smooth surfaces include one or more surfaces comprising one or more roughened textures, spongiosa metals (and/or other materials), knurled textures, barbs, ridges, processes, protrusions, catches, frictional fittings, zig-zagged surfaces, cog-like surfaces, teeth, porous claddings, external frames, pins, guides, rails, recesses, slots, and/or any other suitable surface and/or component that is configured to help prevent the spacer from sliding out from between the femur and tibia.

Although, in some implementations, each spacer comprises a single monolithic object, in some other implementations, each spacer comprises multiple components. Indeed, in some implementations, the spacer comprises a proximal (or superior) portion that is configured to contact a distal portion of the femur and a distal (or inferior) portion that is configured to contact a proximal portion of the tibia and/or of a tibial baseplate when the spacer is inserted into the knee joint.

In some such implementations, the spacer comprises one or more springs (and/or other resilient materials) that are configured to force (or bias) the distal and proximal portions of the spacer apart. While such a configuration can perform any suitable function, in some cases, it allows the spacer to apply a substantially consistent and/or constant pressure to the femur and/or the tibia when the spacer is inserted into the knee joint.

In some implementations, the spacer further comprises one or more mechanisms for measuring and/or identifying a pressure that is placed on the spacer (e.g., pressure sensors, piezochromic polymers, pressure indicating pigments, pressure indicating coatings, scales, and/or any other suitable mechanism that is capable of identifying one or more pressures in the knee joint) as and/or when the spacer is placed in the knee joint. Accordingly, in some implementations, when a first spacer is placed in a lateral side of the knee joint and a second spacer is placed in a medial side of the knee joint, a practitioner and/or computer device can determine whether or not tension and/or pressure in the knee joint is properly balanced.

In some implementations, the spacer is configured to be used with any suitable conventional and/or novel method of joint arthroplasty. In some other implementations, however, the spacer is configured to be used with one or more of the apparatuses, systems, and/or methods described herein. Indeed, in some implementations, one or more spacers are configured to couple (e.g., adjustably, non-adjustably, removably, and/or fixedly) to one or more of the components described herein, including, without limitation, to a tibial baseplate, a tibial baseplate system, the tibial mount, the tibial component, the femoral mount, the tibial tensioning adapter, and/or any other suitable component that allows the spacer to be selectively held in place while the spacer is disposed in the knee joint.

Although, in some implementations, the spacer comprises no handle, in some other implementations, the spacer comprises (and/or is otherwise configured to work with) one or more handles that are configured to help a user readily manipulate the spacer, even when the spacer is disposed in the knee joint. While, in some cases, a handle is permanently coupled with a spacer, in some other cases, the spacer and a corresponding handle are configured to selectively couple to and/or decouple from each other in any suitable manner, including, without limitation, by having a projection at an end of the handle fit into a recess at an anterior portion (and/or any other suitable portion) of the spacer, via one or more catches, recesses, magnets and/or magnetic materials disposed in the handle and the spacer, hooks, hook and loop fasteners, and/or in any other suitable manner. Indeed, in some implementations, an anterior portion of the spacer (or a portion that is configured to be disposed towards an anterior portion of the knee joint when the spacer is disposed between the tibia and the femur) defines a recess that is configured to receive a projection at an end of the handle. In some such implementations, the handle's projection comprises a raised member that is configured to extend into a corresponding opening in the recess of the spacer (e.g., when the handle is disposed at a certain angle) such that the handle can be used to pull the spacer from between the tibia and the femur. In still other implementations, the handle comprises a relatively straight shaft that is configured to fit within a recess in an anterior end of the spacer.

In addition to the aforementioned features, some implementations of the described systems and methods comprise one or more articulated connections that extend between the described tibial and femoral components to allow a knee joint with such components to move through a range of motion without requiring a user to change between a 0 degree extension adapter and a 90 degree flexion adapter. In such implementations, the articulated connection can comprise any suitable component, including, without limitation, a femoral component, a femoral mount, a tibial component, a tibial mount, a tibial angulation guide, an extension bolt, a flexion bolt, a ratcheting device, and/or any other suitable component that comprises a joint and that is configured to couple (directly or indirectly) with a tibial component and/or a femoral component to maintain a desired tension in the knee joint while allowing the knee joint to flex and/or extend.

In some implementations, the described apparatuses and/or systems further comprise one or more soft tissue retractors and/or lamina spreaders. Indeed, in some implementations, one or more soft tissue retractors are attached to any suitable portion of the described apparatuses and/or systems. Accordingly, in some such implementations, one or more soft tissue retractors are (permanently, selectively, adjustably, and/or otherwise) coupled to, formed on, and/or otherwise associated with one or more of a tibial baseplate, a tibial baseplate system, the femoral mount, a femoral component, the tibial mount, a tibial component, a tensioning assembly, a cutting block, the spacers and/or any other suitable portion of the described apparatuses and/or systems to provide better exposure to the bones in the knee joint while the described systems and methods are in use.

Additionally (and as mentioned), some implementations of the described systems and apparatuses further include one or more tibial baseplates (and/or tibial baseplate systems). In such implementations, the tibial baseplate can perform any suitable purpose, including, without limitation, providing a guide for driving a keel punch (and/or any other suitable device) into a proximal end of a tibia; coupling with, guiding, and/or holding one or more spacers in place; coupling with one or more tensioning assemblies to allow the tensioning assembly to press against the tibial baseplate to allow for adjusting the distance between the tibia and the femur via actuation of the tensioning assembly; coupling with one or more alignment tools; coupling with one or more alignment rods; coupling with one or more cutting tool blocks and/or guides; coupling with one or more gap resection blocks; coupling with one or more saw blade capture blocks; coupling with, guiding, and/or maintain a position of one or more trial tibial components; coupling with one or more pressure gauges and/or sensors; and/or for any other suitable purpose.

Indeed, in some embodiments, the tibial baseplate has a first surface and a second surface that is substantially opposite to the first surface, the first surface being configured to be seated on a resected surface at a proximal end of a tibia. In some such implementations, the tibial baseplate further defines a keel punch guide and/or in any other suitable punch guide. In some cases, however, the baseplate comprises a keel punch guide, which includes a first wing that is configured to extend over to a lateral portion of the proximal end of the tibia and a second wing that is configured to extend over to a medial portion of the proximal end of the tibia when the tibial baseplate is properly seated on the resected surface at the proximal end of the tibia.

In some implementations, the tibial baseplate has a first surface and a second surface that is substantially opposite to the first surface, the first surface being configured to be seated on a resected surface at a proximal end of a tibia, wherein the tibial baseplate includes a first spacer coupling that is configured to couple a first spacer to at least one of: a lateral side and a medial side of the tibial baseplate such that the first spacer is disposed between, and is configured to maintain a set minimal distance between the proximal end of the tibia and a distal end of a femur when the tibial baseplate is seated on the resected surface at the proximal end of the tibia and the first spacer is coupled to the tibial baseplate.

In still other implementations, the tibial baseplate has a first surface and a second surface that is substantially opposite to the first surface, with the first surface being configured to be seated on a resected surface at a proximal end of a tibia, and with the tibial baseplate including: a first spacer coupling that is configured to couple a first spacer to a lateral side of the tibial baseplate such that the first spacer is disposed between, and is configured to maintain a set minimal distance between the lateral side of the tibial baseplate and a lateral side of a distal end of a femur when the tibial baseplate is seated on the resected surface at the proximal end of the tibia and the first spacer is coupled to the first spacer coupling; and a second spacer coupling that is configured to couple a second spacer to a medial side of the tibial baseplate such that the second spacer is disposed between, and is configured to maintain a set minimal distance between the medial side of the tibial baseplate and a medial side of the distal end of the femur when the tibial baseplate is seated on the resected surface at the proximal end of the tibia and the second spacer is coupled to the second spacer coupling.

In yet other implementations, the tibial baseplate system includes a tibial baseplate having a first surface that is configured to be seated on a resected surface at a proximal end of a tibia, a second surface that is substantially opposite to the first surface, an anterior end portion, a posterior end portion, a lateral side portion, and a medial side portion; and a cutting block guide that runs from the anterior end portion towards the posterior end portion at the second surface of the tibial baseplate, wherein the cutting block guide is configured to couple to at least one of a femoral cutting block, an alignment block, a gap resection block, a femoral cutting block, and/or any other suitable component, such that the component is configured to slide parallel with the second surface when the component is coupled to the cutting block guide.

In still other implementations, the tibial baseplate system includes a tibial baseplate having a first surface that is configured to be seated on a resected surface at a proximal end of a tibia, a second surface that is substantially opposite to the first surface, an anterior end portion, a posterior end portion, a lateral side portion, and a medial side portion; a cutting block guide that runs from the anterior end portion towards the posterior end portion at the second surface of the tibial baseplate, wherein the cutting block guide is configured to couple to at least one of a femoral cutting block, an alignment block, a gap resection block, a femoral cutting block, and/or any other suitable component, such that the component is configured to slide parallel with the second surface when the component is coupled to the cutting block guide.

In some implementations, the baseplate further includes a first spacer guide that is disposed at the medial side portion of the tibial baseplate, that extends from the anterior end portion towards the posterior end portion of the tibial baseplate, and that is configured to slidingly couple a first spacer block to the second surface. Moreover, some implementations include a second spacer guide that is disposed at the lateral side portion of the tibial baseplate, that extends from the anterior end portion towards the posterior end portion of the tibial baseplate, and that is configured to slidingly couple a second spacer block to the second surface.

In even further implementations, the tibial baseplate system includes a tibial baseplate having a first surface that is configured to be seated on a resected surface at a proximal end of a tibia, a second surface that is substantially opposite to the first surface, an anterior end portion, a posterior end portion, a lateral side portion, and a medial side portion. In some such implementations, the baseplate includes a cutting block guide that defines a first elongated groove that runs from the anterior end portion towards the posterior end portion at the second surface of the tibial baseplate, wherein the cutting block guide is configured to couple at least one of a femoral cutting block, an alignment block, a gap resection block, a femoral cutting block, and/or any other suitable component such that the component is configured to slide parallel with the second surface when the component is coupled to the cutting block guide.

Moreover, in some such implementations, the baseplate defines a first spacer guide that includes a second elongated groove that is defined at the medial side portion of the tibial baseplate, that extends from the anterior end portion towards the posterior end portion of the tibial baseplate, and that is configured to slidingly couple a first spacer block to the second surface. Furthermore, some implementations of the baseplate define a second spacer guide that includes a third elongated groove that is defined at the lateral side portion of the tibial baseplate, that extends from the anterior end portion towards the posterior end portion of the tibial baseplate, and that is configured to slidingly couple a second spacer block to the second surface.

While the tibial baseplate system can include any suitable feature, in some cases, the cutting block guide has an elongated groove that is defined in the baseplate's second surface and/or that opens from the anterior end portion of the tibial baseplate. In some cases, such an elongated groove comprises a keyed elongated groove (e.g., a groove that comprises a narrowed portion defined by the second surface (and/or any other suitable portion of the baseplate) that is configured to prevent one or more couplers of the femoral cutting guide, the spacer block, the gap resection block, the alignment rod block, the saw blade capture block, and/or any other suitable component from being lifted from a portion of the cutting block guide when the coupler of the femoral cutting guide and/or any other suitable component is disposed in the keyed elongated groove.

Moreover, in some cases, the tibial baseplate further includes one or more spacer guides (e.g., a first, a second, and/or any other suitable number of spacer guides) that extend from the anterior end portion (and/or any other suitable portion) of the tibial baseplate toward the posterior end portion, with the spacer guide or guides being configured to slidingly couple with one or more spacers that each have a coupler that is configured to slidingly couple with the spacer guide. In some such cases, the spacer guide comprises one or more catches that are configured to selectively catch and retain a spacer block at a set position with respect to the tibial baseplate. In some such cases, the catch comprises a recess and an inferior portion of the spacer block includes a projection that slidingly mates with the spacer guide, and the projection comprises a first protrusion that is configured to engage with the catch to selectively retain the spacer block in the first position along a length of the spacer guide.

Additionally, in some cases, the tibial baseplate system includes one or more alignment rod blocks that are configured to couple to one or more alignment rods (e.g., to allow the alignment rod block to slidingly couple with the cutting block guide, with an alignment rod being coupled to the alignment rod block (e.g., by passing through a hole or otherwise) such that the alignment rod is disposed anterior to a length of the patient's tibia). Thus, in some implementations, the tibial baseplate is coupled to an alignment rod to readily identify a varus and/or valgus variation to a patient's leg.

In some cases, the tibial baseplate system includes a gap resection block that comprises a first coupler that is configured to slidingly couple the gap resection block with the cutting block guide of the tibial baseplate. In some such cases, the gap resection block optionally includes a second coupler that is configured to couple the gap resection block to the femoral cutting block and/or any other suitable component.

Furthermore, in some cases, the anterior end portion of the tibial baseplate is configured to extend anteriorly more than 5 mm past an anterior end of the resected surface at the proximal end of the tibia when the tibial baseplate is properly seated on and coupled to resected surface. Indeed, in some cases, the anterior end portion of the tibial baseplate includes an elongated tongue that extends any suitable length more than about 5 mm (e.g., more than about 1 cm) from an anterior-most end of the spacer guide. Said differently, in some cases, the anterior-most end of the tibial baseplate is more than 4.4 cm (e.g., between 4.5 cm and 10 cm (or within any subrange thereof)) from the posterior-most end of the tibial baseplate. Indeed, in some cases, the anterior-most end of the tibial baseplate (and/or a tongue or other extension that extends from the tibial baseplate) is anteriorly disposed between about 4.7 cm and about 6.5 cm from the posterior-most end of the baseplate.

When spacers are used with the tibial baseplate, the spacers can be any suitable height (including, without limitation, between about 1 mm and about 2.5 cm, or within any subrange thereof). Indeed, in some cases, the spacers are configured to keep the femur between about 4 mm and about 15 mm away from the superior surface of the baseplate. Additionally, while the spacers can be the same height, in some cases, one spacer is larger than the other (e.g., the lateral spacer is larger than the medial spacer, or vice versa).

In addition to the foregoing, some implementations of the described systems and methods involve the use of one or more robots. In this regard, the robots can perform any suitable function, including, without limitation, using the milling tool member to resect a portion of the tibia (e.g., with and/or without the guide rod), to resect a proximal end of the tibia, to resect one or more portions of a distal end of the femur (e.g., to make a distal cut, an anterior femoral cut, an anterior rough cut, a posterior femoral cut, an anterior chamfer cut, a posterior chamfer cut, and/or any other suitable cut). Indeed, in some implementations, the described systems and methods are further configured to allow one or more robots to resect portions of the knee joint while one or more of the described apparatuses and/or systems are disposed in and providing a desired ligamentous tension in the knee joint.

While the methods and processes of the present invention can be particularly useful in the area orthopedics, those skilled in the art can appreciate that the methods and processes can be used in a variety of different applications and in a variety of different areas of manufacture to yield functionally equivalent results.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE SEVERAL VIEWS OF THE DRAWINGS

In order that the manner in which the above recited and other features and advantages of the present invention are obtained, a more particular description of the invention will be rendered by reference to specific embodiments thereof, which are illustrated in the appended drawings. The drawings depict only typical embodiments of the present invention and are not, therefore, to be considered as limiting the scope of the invention. Additionally, any measurements provided in the drawings are simply provided as possible examples, noting that all such measurements can adjusted in any suitable manner and that such measurements in no way limit the scope of the invention. Accordingly, the present invention will be described and explained with additional specificity and detail through the use of the accompanying drawings in which:

FIGS. 65J-65AS illustrate various views of some embodiments of a tibial baseplate system and portions thereof;

DETAILED DESCRIPTION OF THE INVENTION

Figure 1:
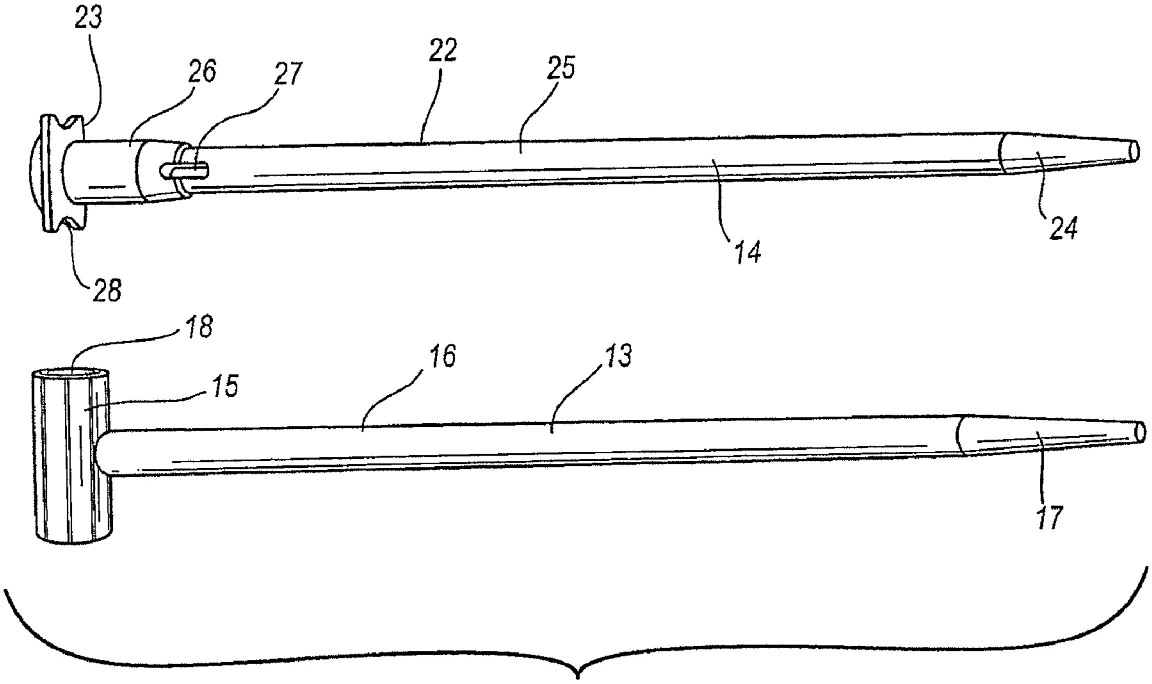
FIG. 1 is a perspective view of a tibial intramedullary (IM) rod and a femoral IM rod of an assembly of one embodiment of the present invention.

Reference throughout this specification to "one embodiment," "an embodiment," "an implementation," and similar language means that a particular feature, structure, or characteristic described in connection with the embodiment or implementation is included in at least one embodiment of the present invention. Thus, appearances of the phrases "in one embodiment," "in an embodiment," "in another embodiment," "in some implementations," "in some other embodiments," "in some other implementations," and similar language throughout this specification may all refer to the same or another embodiment or implementation.

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

The following disclosure of the described systems and methods is grouped into three subheadings, namely "Representative Systems and Methods", "Bone Milling", and "Spacers and Tibial Baseplate System". Utilization of the subheadings is for convenience of the reader only and is not to be construed as limiting in any sense.

Representative Systems and Methods

An assembly 10 of the present invention for facilitating preparation of a knee joint, including guiding positioning of cuts to a femur 11 and tibia 12 of the knee joint, for later mating with femoral and tibial knee replacement components, is shown in the accompanying FIGS. Generally, the assembly 10 includes various components selected and arranged to attach to a reference point inside the knee joint compartment (such as one or more intramedullary (IM) rods), extend through a relatively narrow, small or noninvasive approach defined in the soft-tissues of the knee and attach outside the knee to a selection of resection guides.

Anatomical directions as used herein are in reference to the knee during the preparatory surgery and correspond to the illustrated embodiment of the assembly 10. However, depending upon the handedness of the knee, or variations in individual morphology and ligamentous structure, these directions could vary and should not typically be considered limiting.

The assembly 10 can be configured to be applied at different knee flexion angles to facilitate positioning of the components throughout the range of flexion or extension. Illustrated herein are components of the assembly 10 for guiding cuts and preparation of the knee at two different flexion angles, namely 90° and full extension. However, the components can be adjusted or configured, or other components employed within the spirit and scope of the present invention, to extend through relatively non-invasive approaches to the knee joint at any range of flexion be it hyper-extension, 30°, 45°, 60°, etc., through to hyper-flexion.

Figure 2:
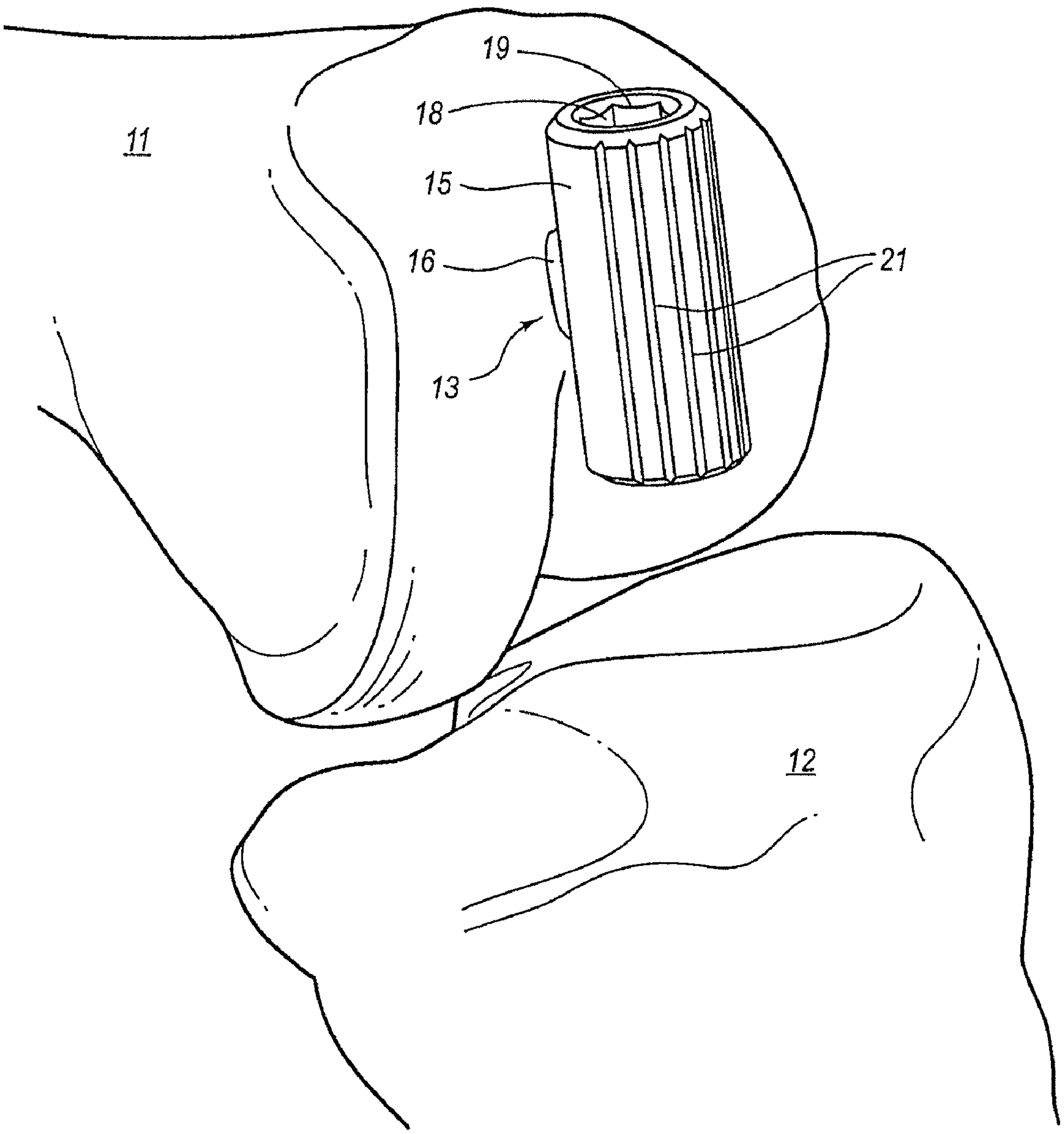
FIG. 2 is a perspective view of the femoral IM rod of FIG. 1 inserted into a femur.

In the illustrated embodiment, the assembly 10 includes two IM rods, a femoral IM rod 13 and a tibial IM rod 14 that provide a reference point for supporting the remainder of the assembly 10 with the knee in flexion, in this case 90° of flexion. The femoral IM rod 13 includes a femoral mount 15 and a main shaft 16, as shown in FIG. 1. The main shaft 16 of the femoral IM rod 13 is preferably an elongate, relatively rigid shaft that, when installed, extends within the IM canal of the femur 11 in a proximal-distal direction, as shown in FIG. 2. The main shaft 16 can include structure that facilitates its insertion into the femur 11, such as a tapered end 17. Preferably, the main shaft 16 is constructed of a relatively rigid material, such as a hard plastic, stainless steel, titanium or other metal or material that is capable of insertion into bone without damage and of stably supporting the femoral mount 15.

Figure 3:
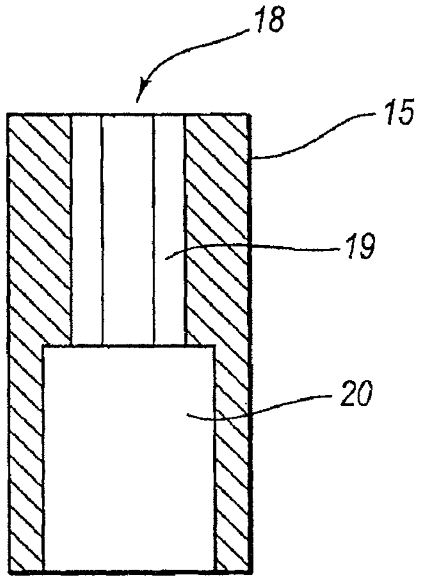
FIG. 3 is a cross-section of a femoral mount of the femoral IM rod shown in FIG. 2.

Attached to the distal end of the main shaft 16, opposite the tapered end 17, is the femoral mount 15. Generally, the femoral mount has a cylindrical shape with an axis extending perpendicular to a long axis of the main shaft 16. Defined along the axis of the femoral mount 15 is a central opening 18, as shown by the cross-sectional view of the femoral mount in FIG. 3. The central opening includes two portions, an anti-rotation portion, in this instance a hex portion, 19 and a cylindrical portion 20 which allow locking of other components of the assembly 10 to the femoral mount 15, as will be described in greater detail below. Regardless, once the femoral IM rod 13 is installed, the femoral mount 15 and its central opening 18 preferably extend in an anterior-posterior direction along the femoral notch between the femoral condyles. Defined on the outer cylindrical surface of the femoral mount 15 is a plurality of longitudinally extending gauge marks 21 that aid in positioning of the tibial and femoral components, as will be described in more detail below.

Figure 4:
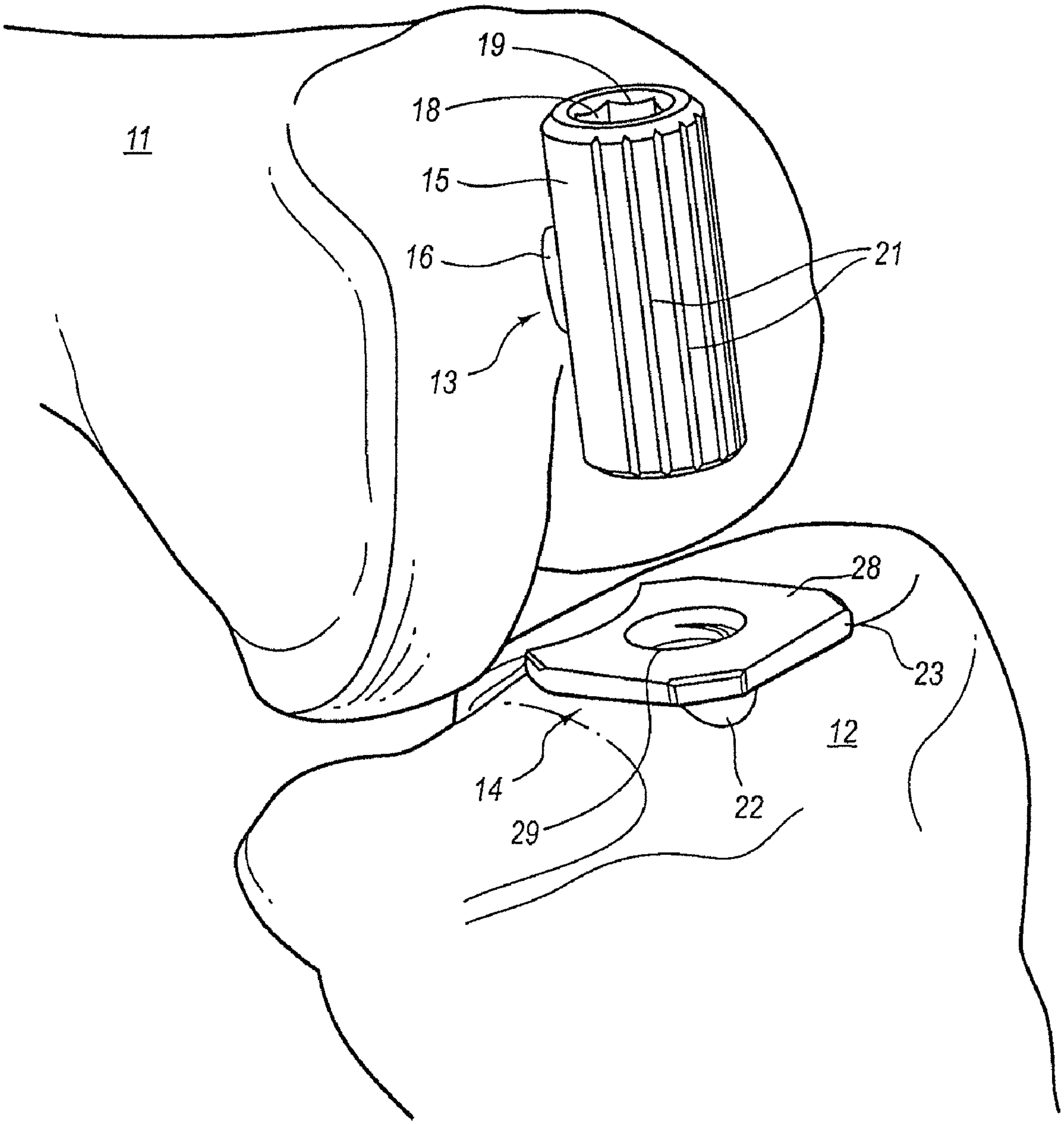
FIG. 4 is a perspective view of the femoral and tibial IM rods of FIG. 1 inserted in the femur and tibia of a knee, respectively.

As shown in FIGS. 1 and 4, the tibial IM rod 14 includes a main shaft 22 supporting a tibial mount 23. Similar to the main shaft 16 of the femoral IM rod 13, the main shaft 22 has an elongate structure with a tapered distal end 24 to facilitate its insertion into the IM canal of the tibia. However, the main shaft 22 preferably includes one or more flutes 25 extending along its length in order to further facilitate insertion and to resist rotation within the IM canal of the tibia. These flutes may also, optionally, be included on the main shaft 16. Defined in the main shaft 22 at its proximal end is an opening 27 that extends into the flutes 25. These openings further facilitate insertion into the IM canal of the tibia. As with the main shaft 16 of the femoral IM rod 13, the main shaft 22 may be constructed of a range of relatively rigid materials to provide firm support for the tibial mount 23. In some embodiments of the current invention, the main shaft 22 of the tibial IM rod is truncated to form a short extension for engaging an opening in the upper surface of the tibia. As such, the tibial IM canal is not accessed but rather the tibial mount 23 and the truncated tibial IM rod primarily engage and interface with the external surface of the tibia. In other embodiments, the tibial mount 23 is provided without a tibial IM rod, such that a flat surface of the tibial mount 23 seats directly on the resectioned surface of the tibia. As such, the interface between the tibial mount 23 the tibia is completely extramedullary. In these embodiments, the position of the tibial mount 23 with respect to the tibia is maintained by the perpendicular compression force between the tibial mount 23 and the tibia. In other embodiments, the flat surface of the tibial mount 23 is modified to include a plurality of spikes which further interface with the resectioned tibial surface to prevent undesirable movement of the tibial mount component 23 during tensioning.

Included in the tibial mount 23 are a thickened cylindrical portion 26 and a plateau flange 28, as shown in FIG. 4. The cylindrical portion 26 is preferably sized to fit the IM canal of the tibia 12. The cylindrical portion is connected at its distal end to the main shaft 22 and at its proximal end supports the plateau flange 28. The plateau flange extends outward at right angles from the cylindrical portion 26 and has three flat sides and one crescent-shaped side. The crescent shaped side is a cutout to provide room for the anterior cruciate ligament prior to resection of the proximal tibia. The flat sides can further aid in guide positioning and cutting, such as during a tibial compartmental resection in a uni-condylar arthroplasty procedure wherein only a single condyle and a portion of the tibial plateau are reconstructed.

Figure 5:
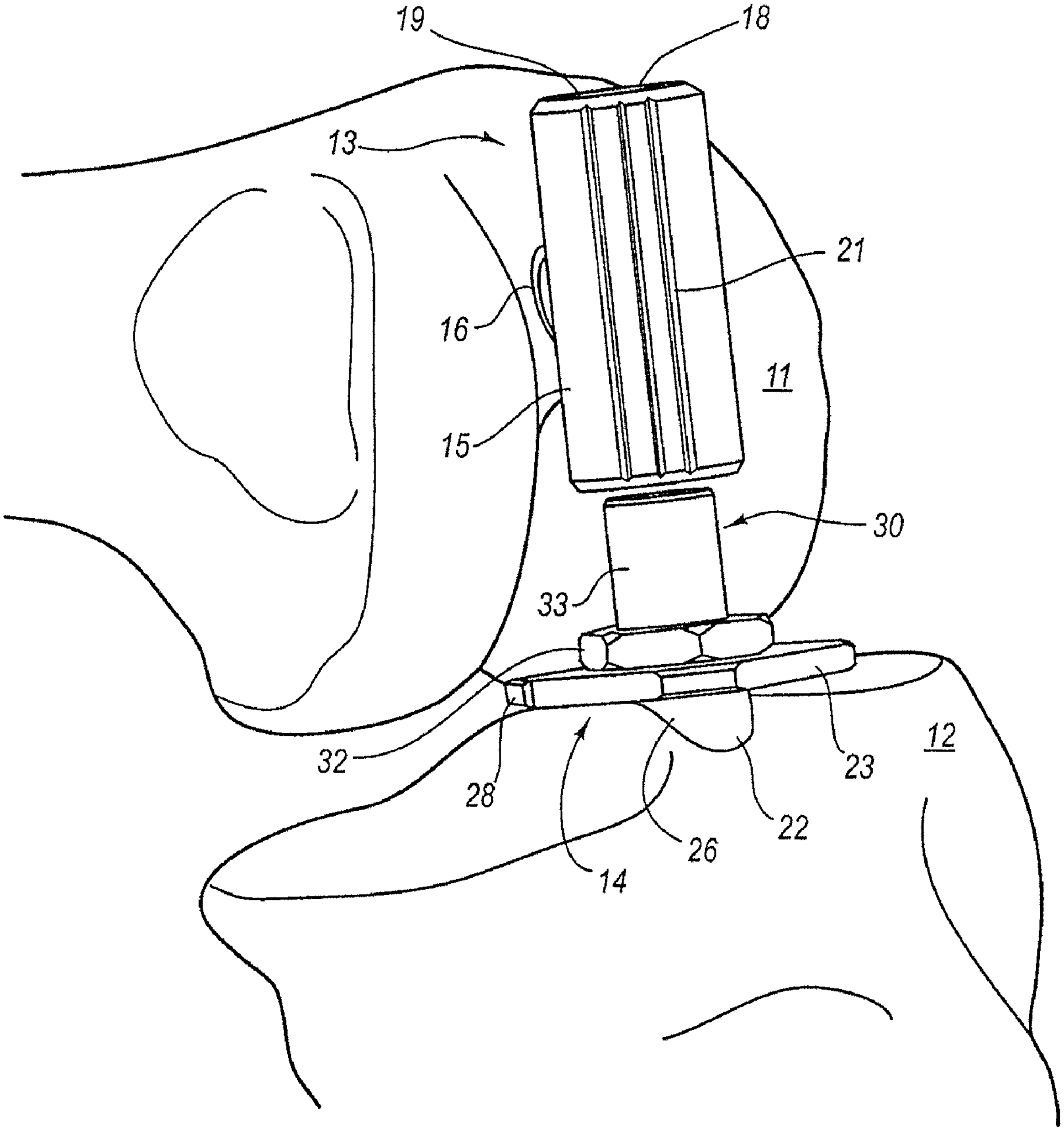
FIG. 5 is a perspective view of a bushing extending from an extension bolt of a representative embodiment of the described assembly, wherein the extension bolt is coupled to the tibial IM rod of FIG. 1.
Figure 6:
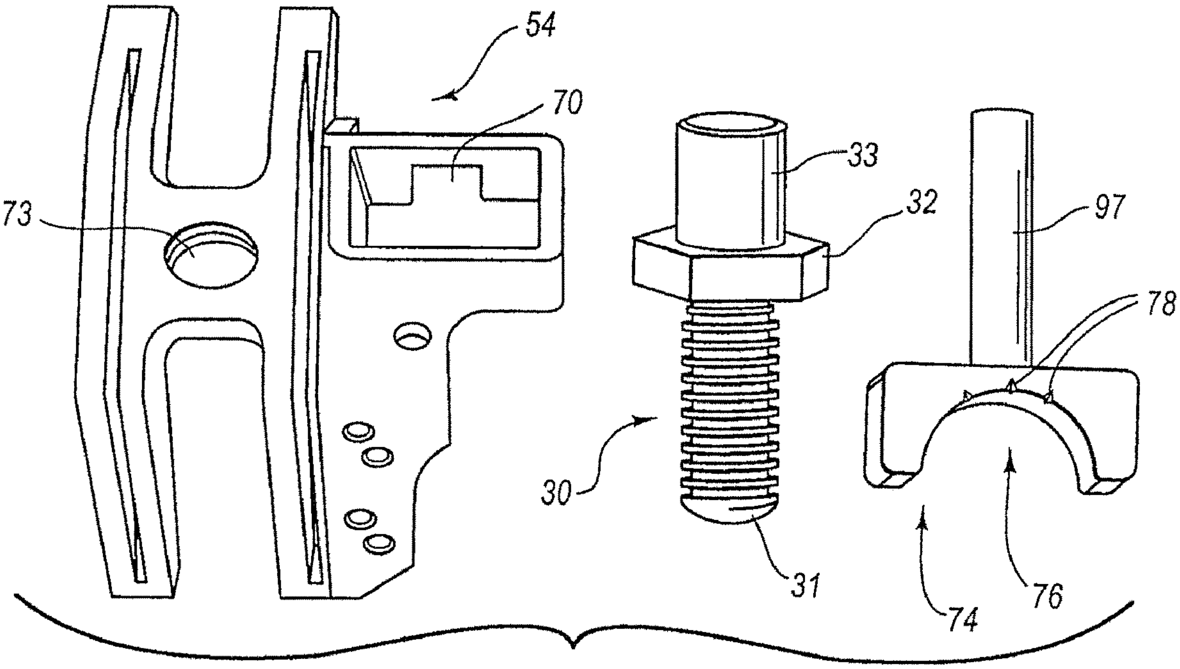
FIG. 6 is a perspective view of the extension bolt of FIG. 5 and of a tibial angulation guide and a flexed knee cutting guide of the described assembly, in accordance with a representative embodiment.

A threaded opening 29 extends into the tibial mount 23 and provides a coupling attachment for the flexion bolt 30, which includes a threaded shaft 31, a hex flange 32 and a bushing 33, as shown in FIGS. 5 and 6. The threaded shaft 31 has a plurality of threads and extends away from the hex flange 32, while the bushing 33 is a smooth, cylindrical shaft that extends opposite the threaded shaft from the other side of the hex flange 32. The hex flange 32 is shaped to allow gripping by a torque or other wrench to provide motivation for advancement of the threaded shaft 32.

Figure 7:
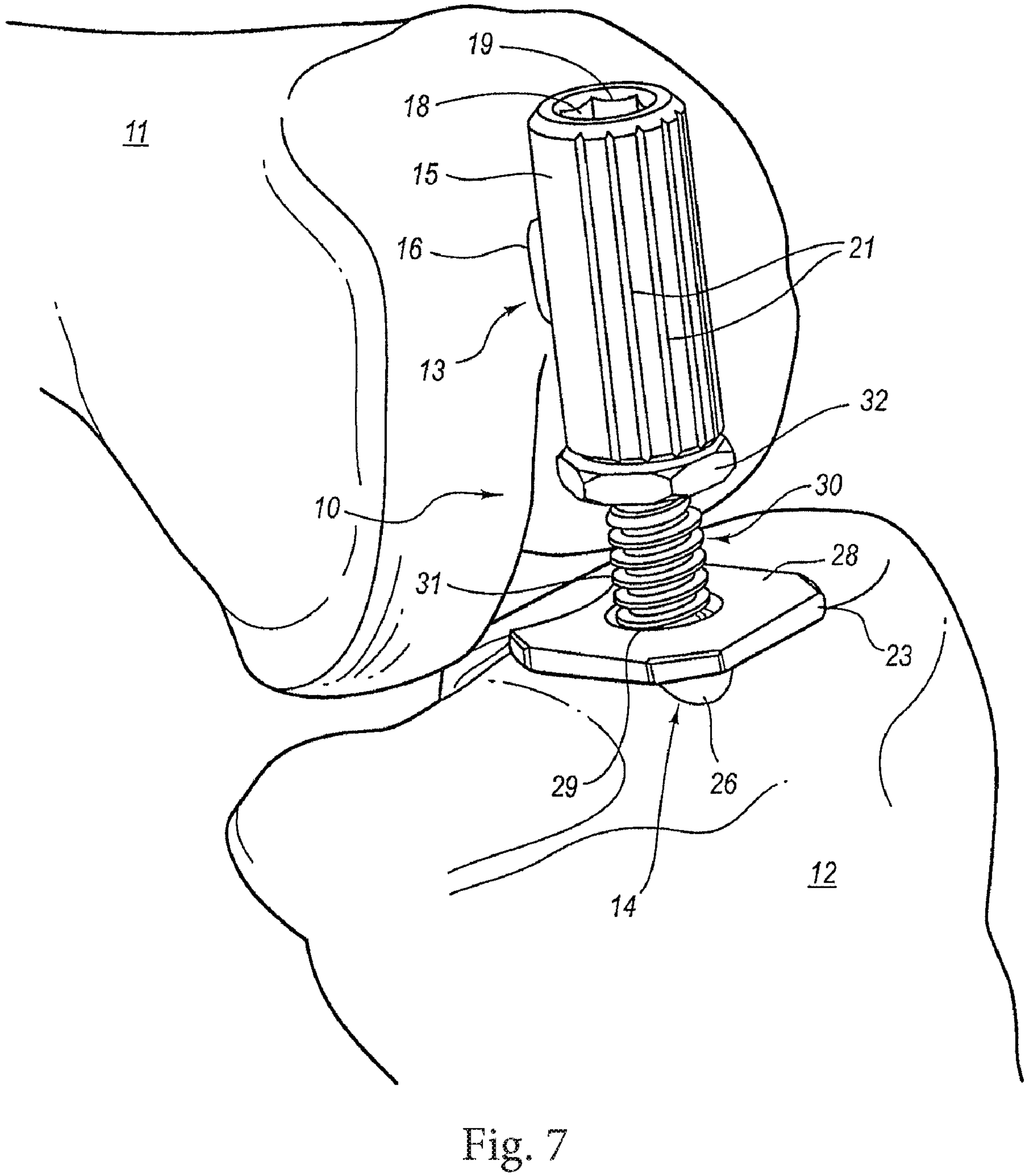
FIG. 7 is a perspective view of the bushing and IM rods of FIG. 5, wherein the bushing of the extension bolt is advanced to connect the IM rods.

The threaded shaft 31 is configured to be advanced into the threaded opening 29 of the tibial mount 23 until it is flush with the plateau flange 28 thereby positioning the bushing 33 at its lowest profile position, as shown in FIG. 5. This position allows the femur 11 and femoral mount 15 extending therefrom to be slipped into position above the bushing 33. Then, the torque wrench is used to reverse the advancement of the threaded shaft 31 until the bushing 33 engages the cylindrical portion 20 of the central opening 18 in the femoral mount 15, as shown in FIG. 7. Advancement is reversed until a pre-selected torque measurement is reached on the torque wrench, or adequate tension of the ligamentous structure is obtained. Once the appropriate ligament tension is obtained, this torque value is recorded for comparison later in the technique. The resulting assembly emulates a static linkage of the femur and tibia with the knee in flexion (e.g., at 30°, 60°, or 90° of flexion or increments there between) from which the surgeon can reference subsequent resection instruments as described below.

Figure 8:
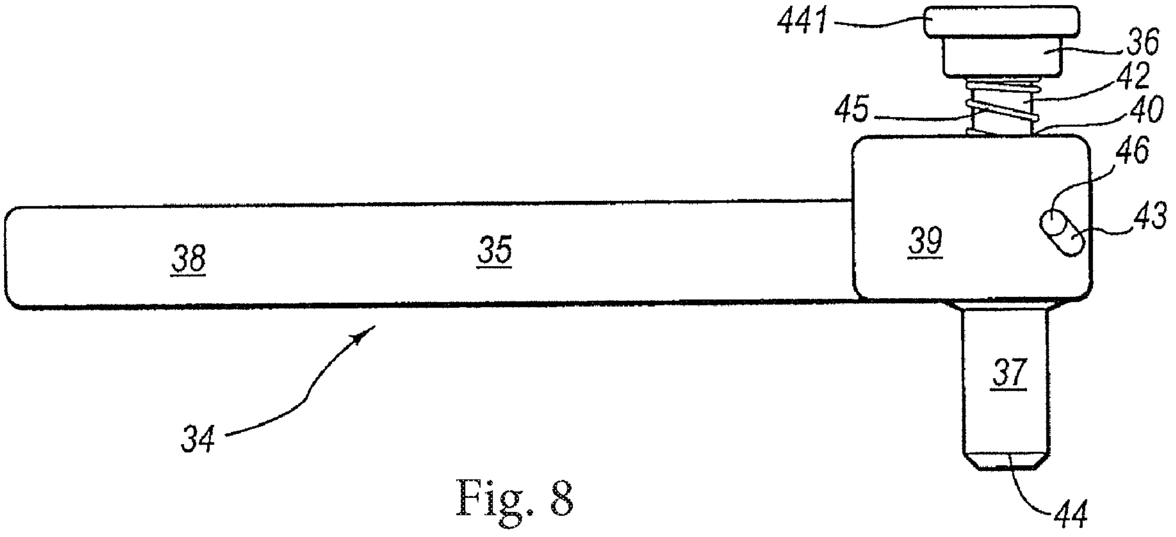
FIG. 8 is a side elevation view of a first locking mechanism of the described assembly, in accordance with a representative embodiment.
Figure 9:
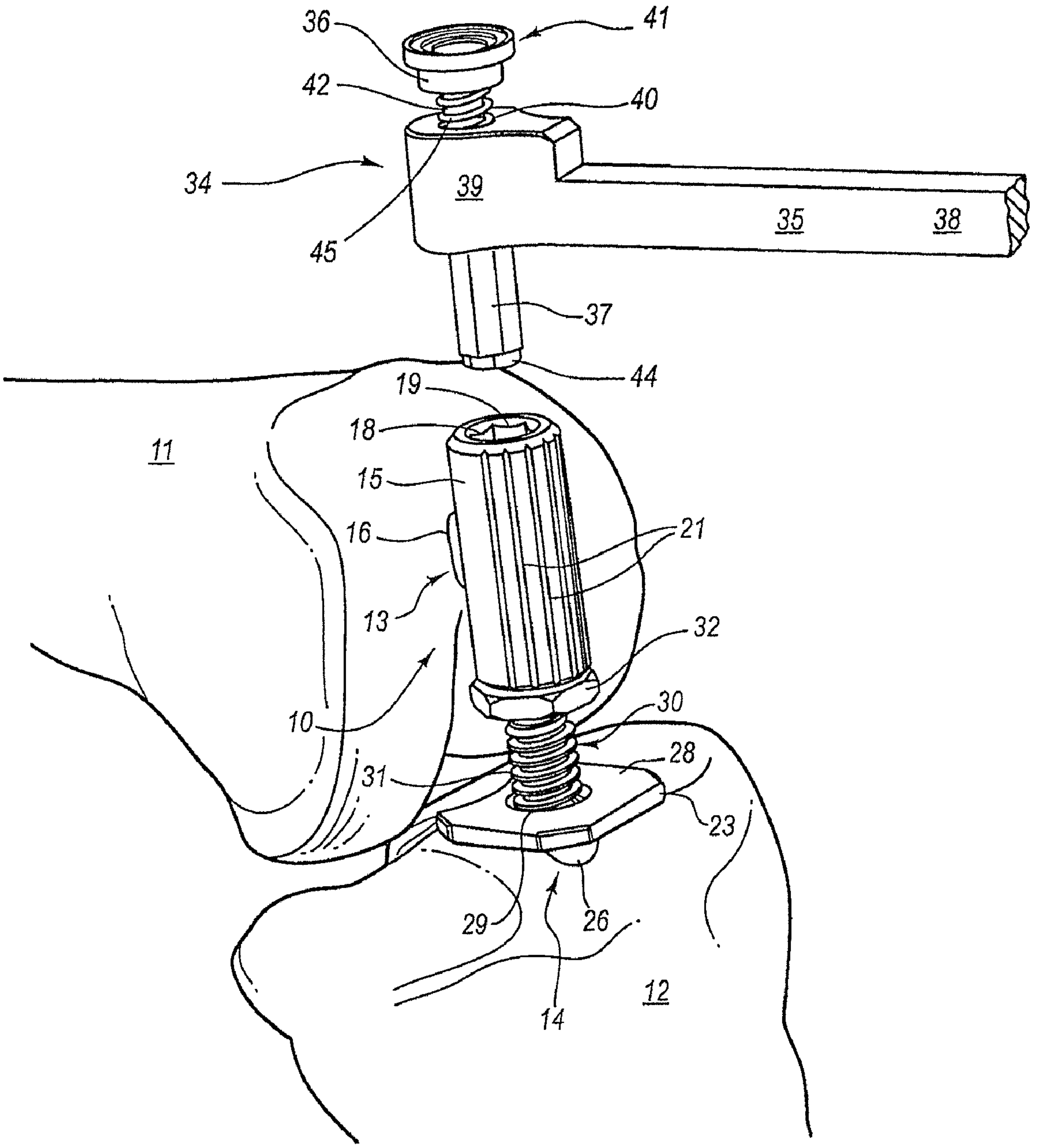
FIG. 9 is a perspective view of the first locking mechanism being connected to the assembled IM rods and bolt of FIG. 7, torqued to a desired load, in accordance with a representative embodiment.

Also included in the assembly 10 is a quick connect locking mechanism 34 that connects into the hex portion 19 of the central opening 18, as shown in FIGS. 8 and 9. Included in this embodiment of the locking mechanism are a static outrigger arm 35, a spring-biased plunger 36 and a static clocking extension 37 which emulates the anti-rotation feature 19, and in this instance has a hexagonal shape. The arm 35 has an elongate portion 38 and a rounded head portion 39. The elongate portion 38 of the arm 35 has a square cross-section and extends from the rounded head portion 39 which has a partially cylindrical shape with a pair of opposing flats at its ends. Extending from one of the flats of the rounded head portion is the hex extension 37. The hex extension 37 has a hexagonal cross-section configured to snugly fit within the hex portion 19 of the central opening 18 defined in the femoral mount 15. As shown in FIG. 8, defined in one rounded surface of the head portion 39 is a helically extending slot 43 which, as will be described below, guides motion of the plunger 36.

Defined through the rounded head portion 39 and the hex extension 37 is a cylindrical opening 40 through which the plunger 36 extends. In particular, the plunger 36 includes a thumb press 41, a shaft 42, a spring 45 and rotating extension 44 which emulates the anti-rotation feature 37, in this instance is a hex, but could be any non-cylindrical shape, such as square, triangle or ellipse, capable of limiting rotation. The thumb press 41 is positioned at one end of the plunger 36 and has the shape of a circular disk with ridges to promote pressing with a thumb. Subjacent the thumb press 41 is the spring 45 which is preferably in the shape of a coil and extends around the shaft 42 and between the thumb press and head portion 39 so as to bias them apart.

The shaft 42 includes a peg 46 that extends perpendicular to the shaft and into the helical slot 43 defined in the head portion 39, as shown in FIG. 8. Thus, depression of the thumb press 41 advances the shaft 42 within the opening 40 in the head portion 39, and also results in rotation of the shaft as the peg 46 fixed thereto helically travels in the helical slot 43. The hexagonal end 44 of the plunger 36 is fixed to the end of the shaft 42 opposite the thumb press 41, extends along a free end of the hex extension 37 and has a hexagonal shape and size matching that of the hex extension 37.

Figure 10:
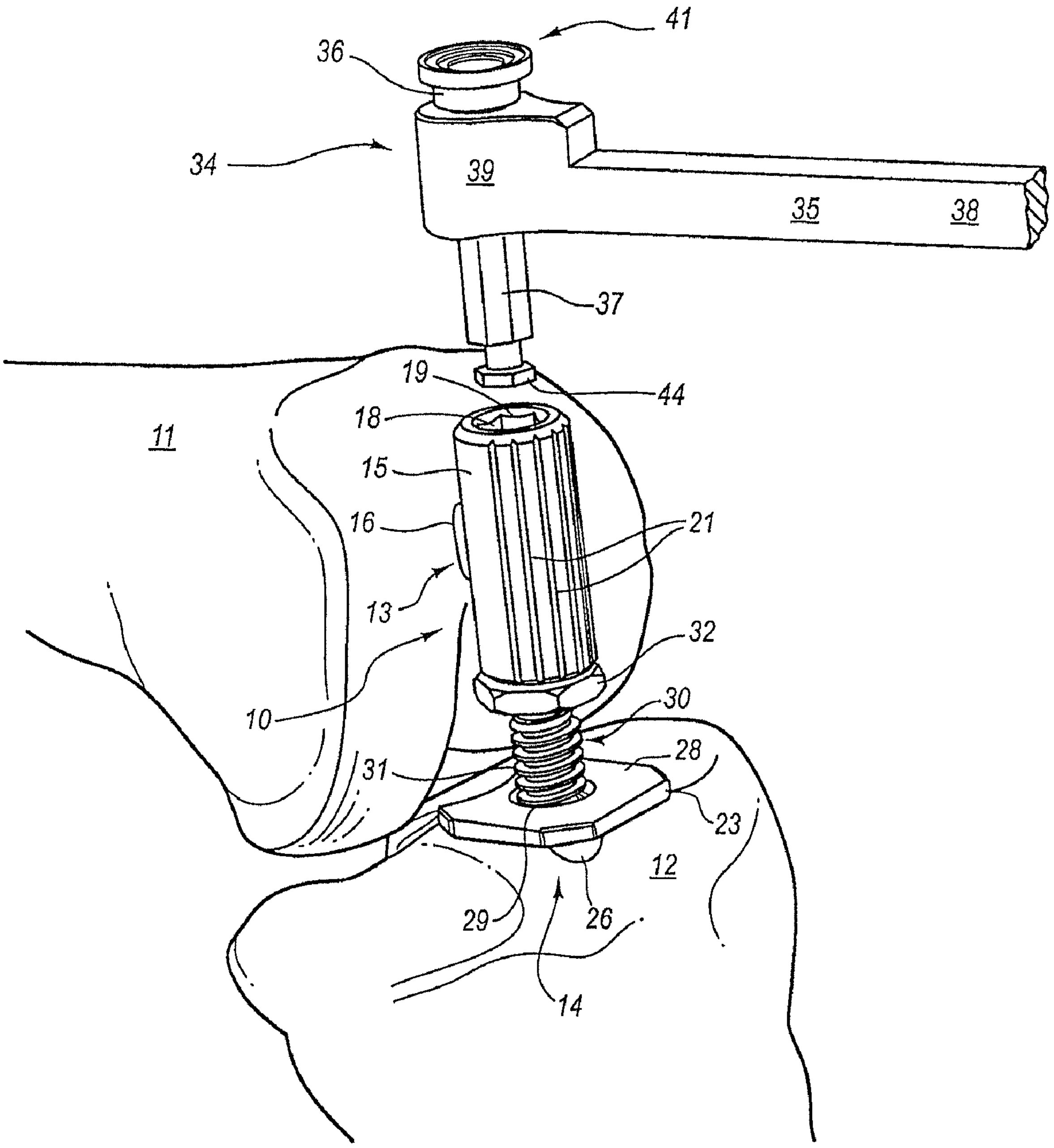
FIG. 10 is another perspective view of the first locking mechanism in the unlocked position, assembled IM rods and bolt of FIG. 9, torqued to a desired load, in accordance with a representative embodiment.
Figure 11:
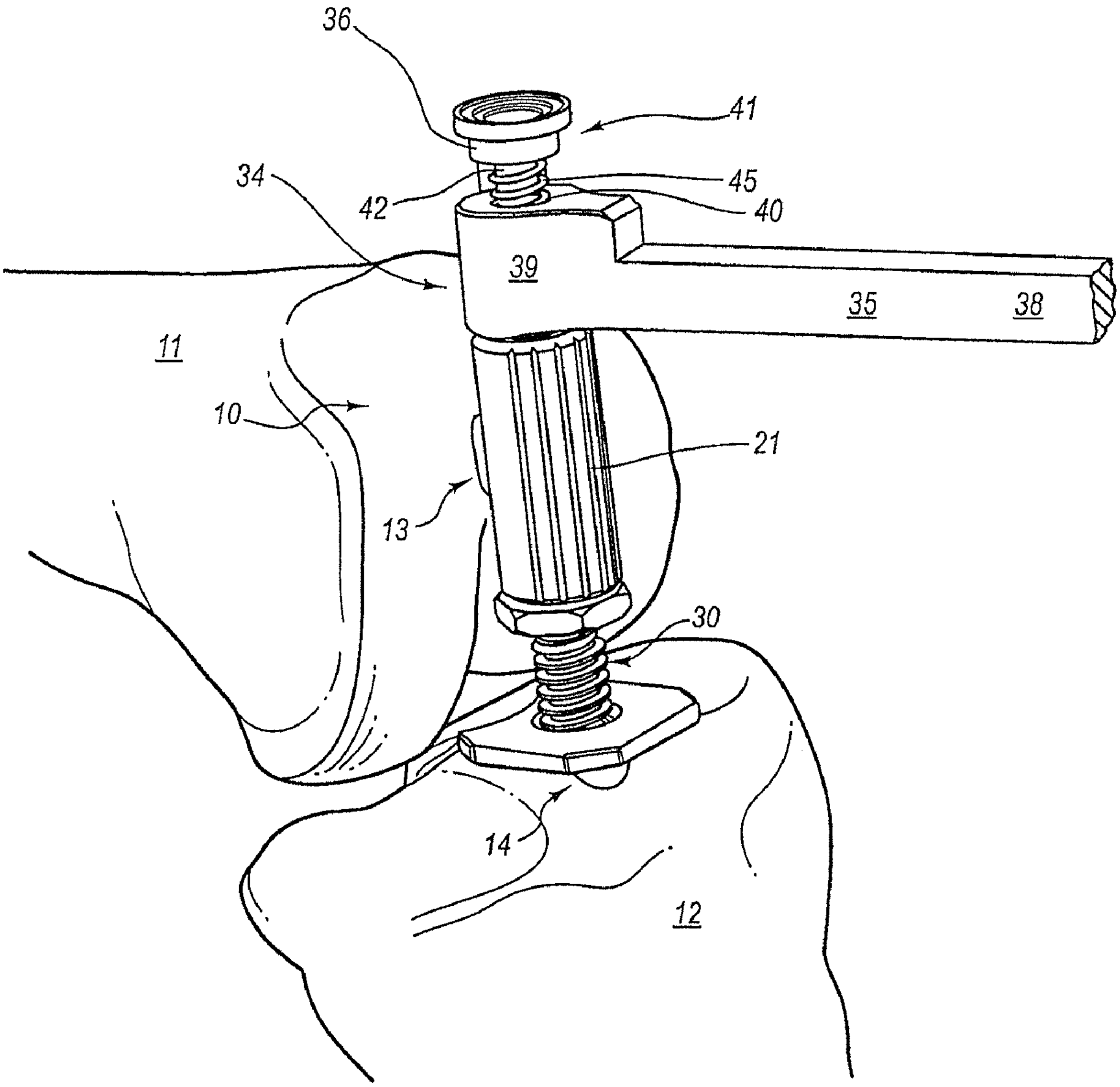
FIG. 11 is yet another perspective view of the first locking mechanism assembled and locked to the IM rods and extension bolt of FIG. 9, torqued to a desired load, in accordance with a representative embodiment.

Due to its connection to the shaft 42, depression of the thumb press 41 also causes rotation of the hexagonal end 44 of the plunger 36 until the flats of the hexagonal end match the orientation of the flats of the hex extension 37, as shown in FIG. 10. Matching of this orientation allows insertion of the hex extension 37 and the hexagonal end 44 into the hex portion 19 of the central opening 18 of the femoral mount 15, as shown in FIG. 11. Once the thumb press 41 is released, the spring 45 biases the thumb press, shaft 42 and hexagonal end 44 upwards, causing the flats of the hexagonal end to return to their non-matching, out-of-phase position (shown in FIG. 9) with respect to the flats of the hexagonal extension 37.

At this point, the hexagonal end 44 of the plunger 36 resides in the cylindrical portion 20 of the central opening 18 and, due to its non-matching position, cannot be withdrawn through the hex portion 19 of the central opening. As a result, the locking mechanism 34 becomes rotationally and translationally locked with respect to the femoral mount 15 and the femoral IM rod 13. Once locked in place, the arm 35 of the locking mechanism 34 extends anteriorly outward from the femoral mount 15 and the condyles of the femur 11. Notably, the combination of the relatively narrow femoral mount 15 and narrow, elongate structure of the arm 35 allows passage through relatively small surgical approach openings, facilitating use of the assembly 10 with less invasive procedures. For example, a modified mid-vastus, medial mid-vastus or sub-vastus approach could be used with a small 8-10 cm cut which allows avoidance of a release of the quadriceps from the anterior tibia.

Figure 12:
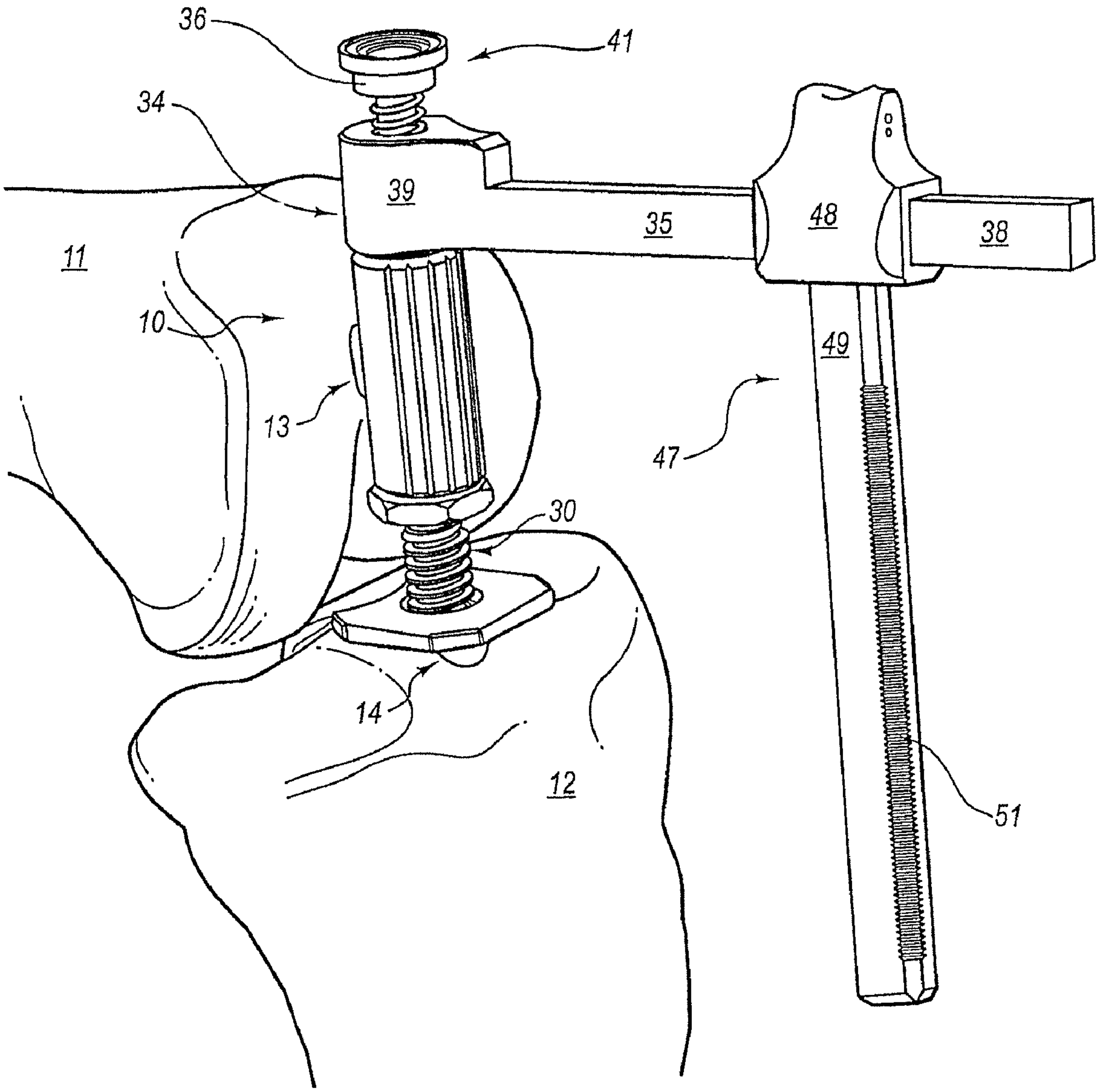
FIG. 12 is a perspective view of a flexion guide support member of the assembly of the described assembly connected to the first locking mechanism of FIG. 11, in accordance with a representative embodiment.

Also included in the assembly 10 of the illustrated embodiment of the invention is a flexion guide support member 47 which is supported by the locking mechanism 34. Included in the flexion guide support member is a slider member 48 and a ratchet bar 49. The slider member defines a rectangular opening 50 which is sized and shaped to allow the slider member to be supported by, and slide along, the rectangular cross-section of the arm 35 of the locking mechanism 34. This motion allows the ratchet bar 49, which is attached to the slider member 48, to move toward and away from the knee joint. The slider member 48 is preferably shaped to have finger grips (e.g., the tapered portion of the illustrated slider member) and may also include some type of a pin or locking assembly to resist, but not prohibit its sliding relative to the arm 35. The ratchet bar 49 itself is also rectangular shaped in cross-section and, when assembled, extends distally from the arm 35 of the locking mechanism 34, as shown in FIG. 12. The ratchet bar 49 also includes a pair of chamfered corners supporting a plurality of adjacent ratchet grooves 51 extending along the length of the ratchet bar.

Figure 13:
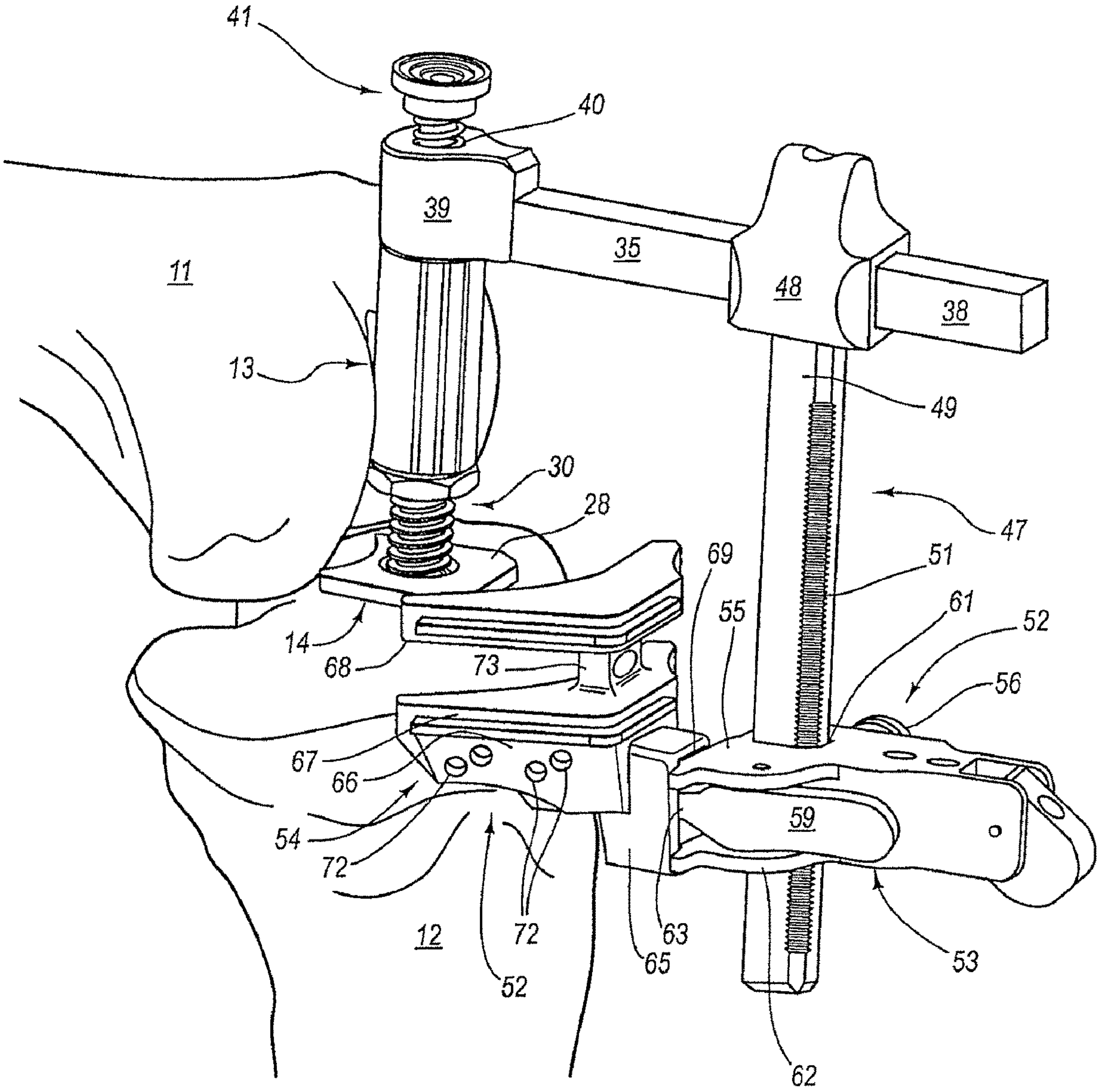
FIG. 13 is a perspective view of a flexed knee cutting guide assembly of the assembly of the described assembly connected to the flexion guide support member of FIG. 12, in accordance with a representative embodiment.
Figure 14:
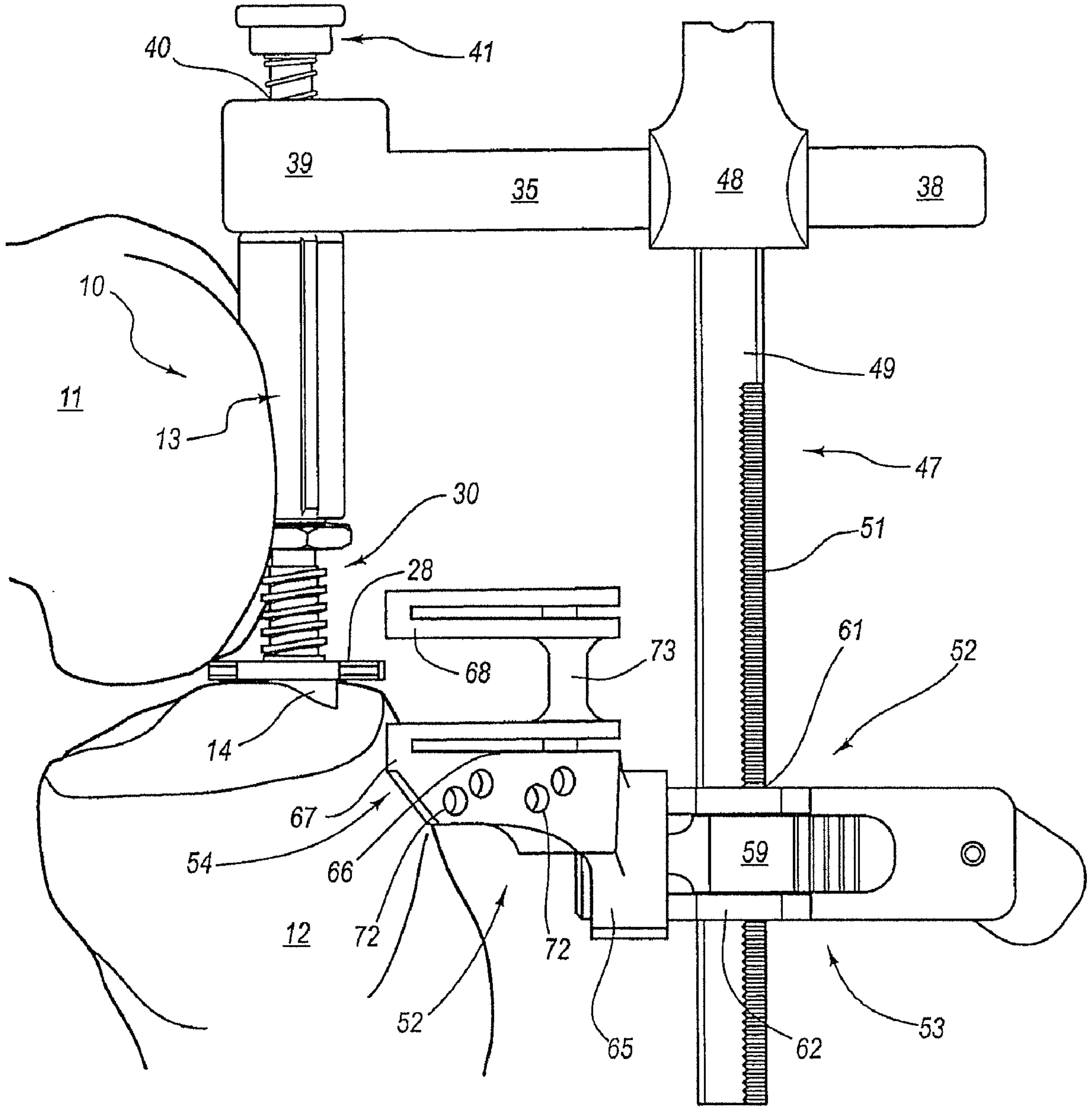
FIG. 14 is a side elevation view of the assembly of FIG. 13.
Figure 15:
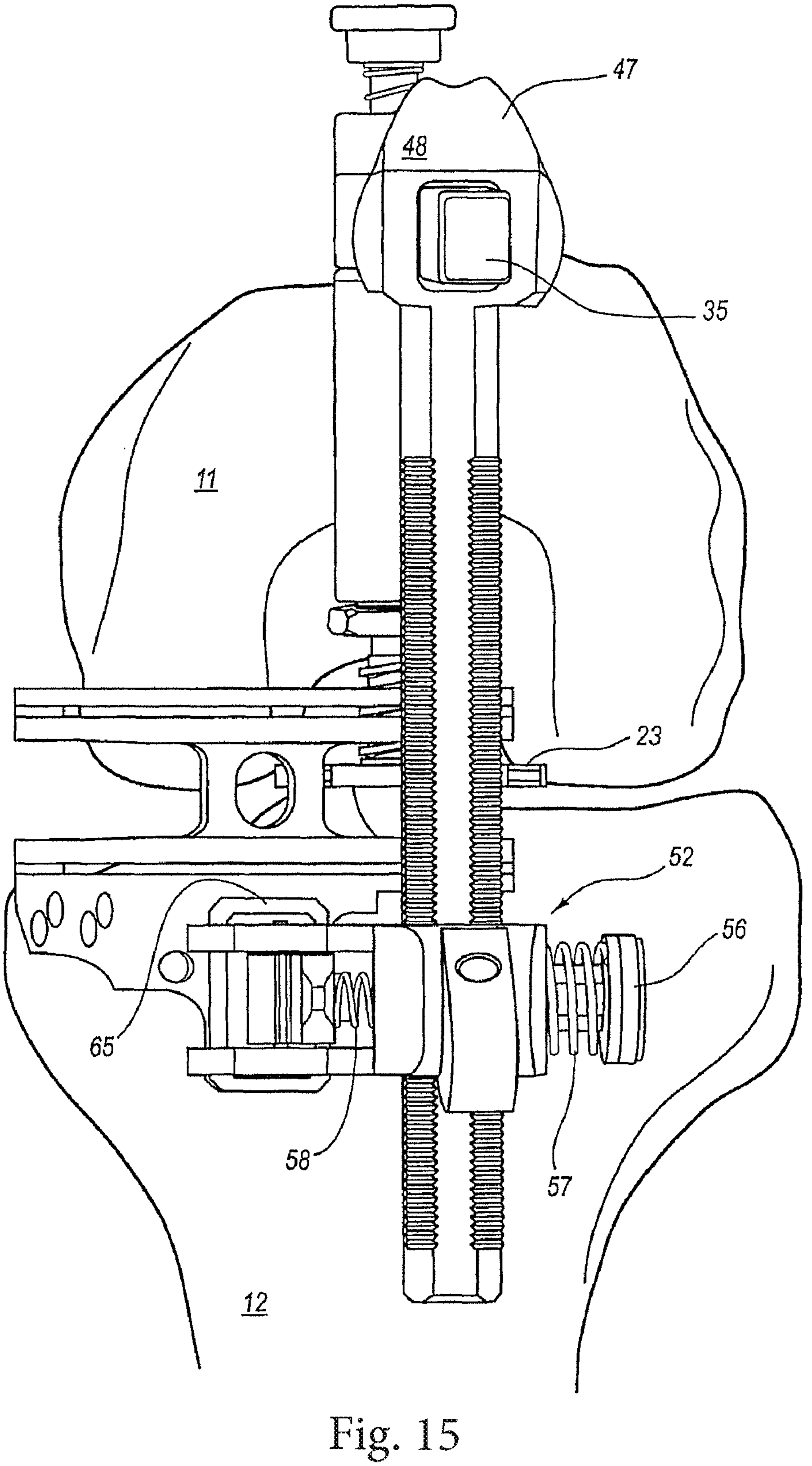
FIG. 15 is a front or anterior elevation view of the assembly of FIG. 13.
Figure 16:
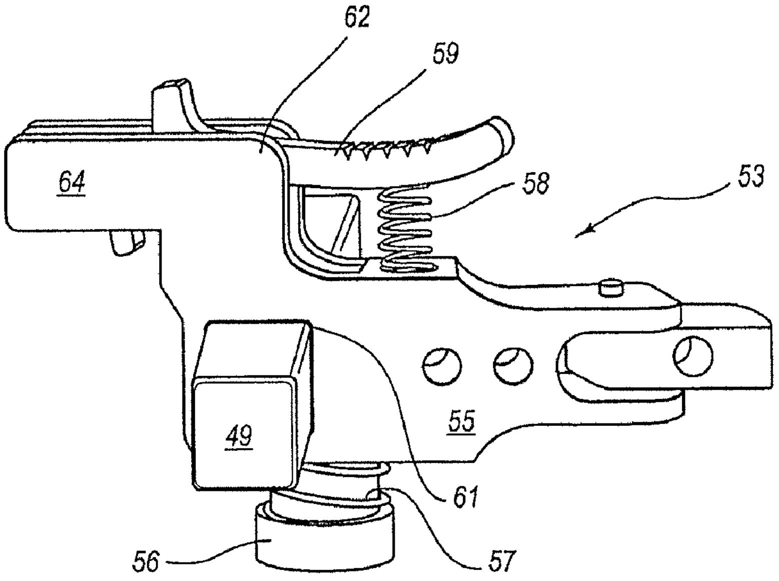
FIG. 16 is a perspective view of a quick release mechanism of the flexed knee cutting guide assembly of FIG. 13, in accordance with a representative embodiment.

The assembly 10 also includes a flexed knee cutting guide assembly 52 that attaches to the flexion guide support member 47, as shown in FIGS. 13, 14 and 15. The flexed knee cutting guide assembly 52 includes a quick release mechanism 53 and a cutting guide 54. The quick release mechanism 53 includes a body 55, a draw pin 56, first and second springs 57, 58, a locking lever 59 and a locking pin 60. As shown in FIG. 16, the body 55 defines a rectangular opening 61 which allows the body to be slid over the rectangular cross-section of the ratchet bar 49. In addition, the body 55 includes a side opening into which the draw pin 56 extends so that its end engages the ratchet grooves 51. In particular, the first spring 57 biases the draw pin into a position normally engaging the ratchet grooves so as to lock the draw pin, and hence the body 55, into a particular position on the slider member 48. The locking pin 60 extends through the body and through the draw pin 56 to secure the draw pin 56 and prevent it from disassembly.

Figure 17:
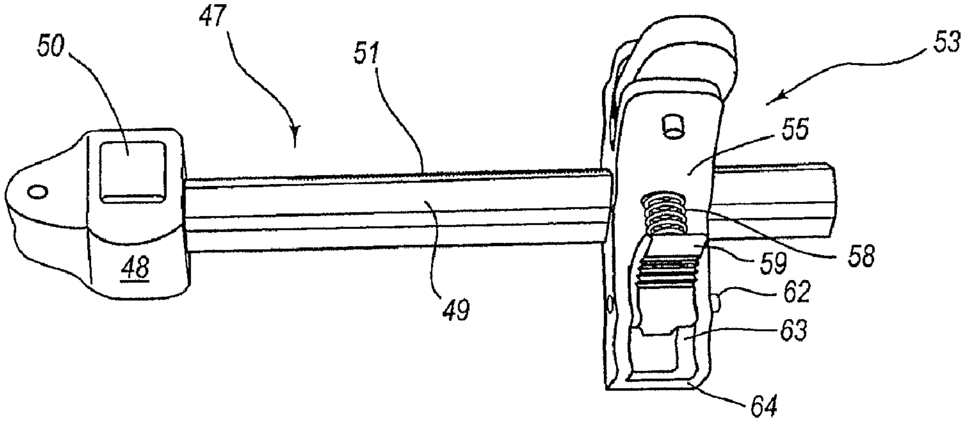
FIG. 17 is a perspective view of the quick release mechanism of FIG. 16 and the flexion guide support member of FIG. 12, in accordance with a representative embodiment.

The body 55 additionally includes a clevis 62 that extends outwards from the opposite side of the body from the draw pin 56 and which supports rotation of the locking lever 59 about its middle portion. As well shown in FIG. 17, the locking lever has a curved finger grip biased outward from the body 55 by the second spring 58 and the opposite end of the locking lever includes a tapered tongue 63 which, as will be described below, engages the cutting guide 54 so as to lock the quick release mechanism 53 thereto. Extending away from the clevis 62, opposite the locking lever, is an engagement member 64 of the body 55. The engagement member 64 has a rectangular cross-section and, in the assembled condition shown in FIG. 13, extends into a connection with the cutting guide 54.

Figure 18:
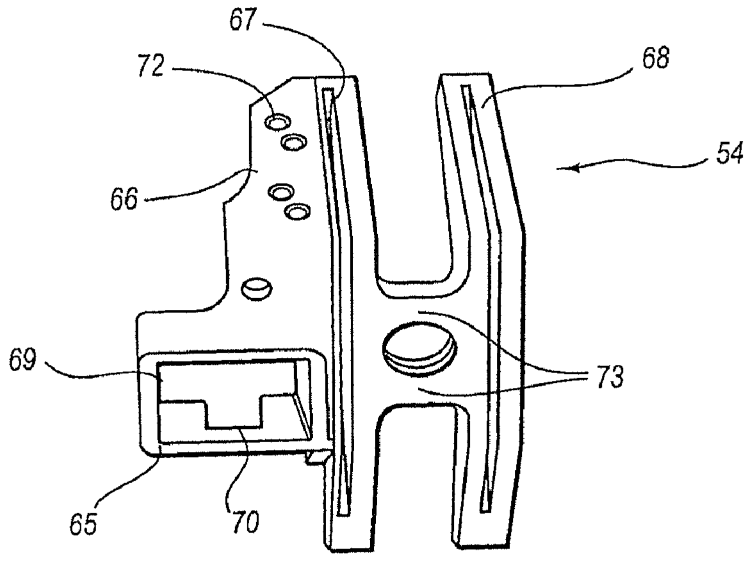
FIG. 18 is a perspective view of a flexed knee cutting guide of the flexed knee cutting guide assembly of FIG. 13, in accordance with a representative embodiment.

As shown in FIG. 13, the cutting guide 54 extends posteriorly (when assembled) from the quick release mechanism 53 and includes a mounting portion 65, a k-wire guide or fixation pin portion 66, a cross pin portion 71, a proximal tibial cut guide portion 67 and a posterior condylar femoral cut guide portion 68. The mounting portion 65 defines a rectangular opening 69 that is sized and shaped to slidably receive the engagement member 64 of the body 55 of the quick release mechanism 53. The mounting portion 65 also defines a notch 70 in one of the sidewalls of the rectangular opening 69, as shown in FIG. 18. The notch 70 is sized, shaped and positioned to receive the tapered tongue 63 of the locking lever 59 when the locking lever is under the bias of the second spring 58, as shown in FIG. 15. Release of the cutting guide 54 is easily accomplished by depressing the free end of the locking lever 59, overcoming the bias of the second spring 58 and disengaging the tapered tongue from the notch 70 of the mounting portion 65.

The fixation pin (or k-wire) guide portion 66, the tibial cut guide portion 67 and the femoral cut guide portion 68 each have a crescent shape that extends in a medial-lateral direction around the anatomical curvature of the anterior-medial or anterior-lateral tibia (depending upon which cut is being made), as shown in FIG. 13. The fixation pin guide portion 66 is adjacent the mounting portion 65 and defines a plurality of fixation pin holes 72 that extend in a posterior direction at an angle so as to guide fixation pins (used to fix the cutting guide 54 before release of the other components of the assembly 10) into the thickest anterior portions of cortical bone on the tibia 12. Although less preferred, the number and orientation of the fixation pin holes could be varied depending upon the firmness of the connection desired, size and morphology of the tibia 12, etc.

Figure 19:
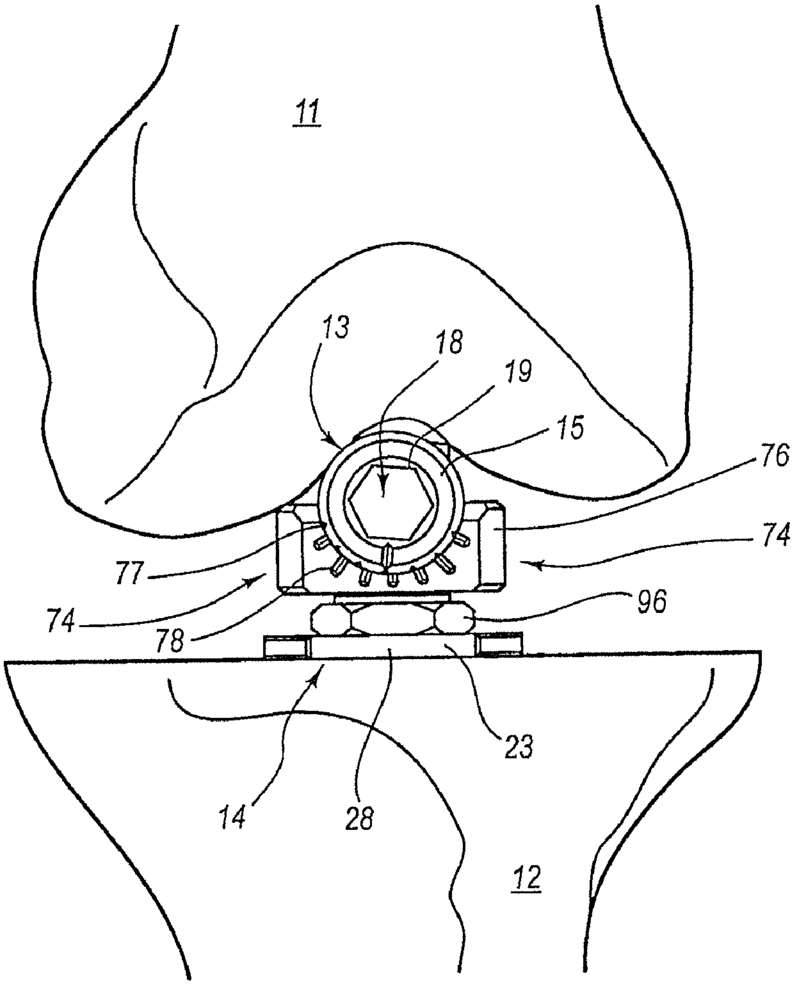
FIG. 19 is a front elevation view of a tibial angulation guide of the described assembly extending between the femoral and tibial IM rods of FIG. 1, coupled with an extension bolt, in accordance with a representative embodiment.

The tibial cut guide portion 67 is positioned adjacent the fixation pin guide portion 66 and defines a slot for guiding the tibial cut. The slot extends along the length of the crescent shape of the guide portion 67 and generally has a parallel orientation with respect to the tibial plateau. However, the resection plane defined by guide portion 67 may vary in posterior slope (sagittal plane angularity) and varus/valgus (coronal plane angularity), depending on the desired position and preference of the surgeon for the cutting guide 54. An example of such a cut is illustrated in FIG. 19, wherein the tibia has a flat planar cut extending in the anterior-posterior and medial-lateral planes on the proximal end of the tibia 12. The femoral cut guide portion 68 is proximally spaced from the tibial cut guide portion 67 by a pair of connection flanges 73 so as to bridge the knee joint compartment. Similar to the tibial cut guide portion 67, the femoral cut guide portion 68 defines a slot that extends along the length of the crescent shape. However, because the knee is in flexion, the cut is guided through the posterior of the condyles of the femur 11.

An advantage of the components of the assembly 10 for positioning cuts with the knee in flexion, including the femoral mount 15, the tibial mount 23, the flexion bolt 30, the locking mechanism 34, the flexion guide support member 47 and the flexed knee cutting guide assembly 52, is their usability with relatively non-invasive, narrow cuts in the anterior soft tissues of the knee (and with a retracted patella). Generally, as can be seen in FIGS. 14 and 15, the assembled components for making the cuts in knee flexion are relatively narrow as they extend out of the joint space in a U-shape, while at the same time providing a firm connection for supporting the cutting guide 54, a quick assembly and release of the components and accurate positioning of the flexed knee cutting guide. Considering the cutting guide 54 by itself (which can be positioned inside of the capsular incision), the width of this component is small compared to conventional cutting guides, for example, within a range of up to 4 to 5 cm thereby allowing their use with minimally invasive approaches to the knee joint.

The assembly 10 also includes instrumentation configured to guide cuts with the knee in extension (i.e., with the tibia and femur generally aligned, or at 0° of flexion), as shown in FIGS. 19-29. For knee extension, both the femoral IM rod 13 and the tibial IM rod 14 remain in place, as shown in FIG. 19. However, instead of attachment of the tibial mount 23 to the tibial IM rod 14, a tibial angulation guide 74 is attached to the tibial IM rod. The tibial angulation guide 74 includes a gauge block 76 and a post 97 which fits into an extension bolt 96 (similar to the flexion bolt 30, but without the bushing 33). The extension bolt 96 also has a hex flange 75. Alternatively, a separate gauge block 76 may be employed with a shaft (as shown in FIG. 6) that extends into an opening in the bushing 33, allowing removal of the bolt 30 to be avoided.

Figure 20:
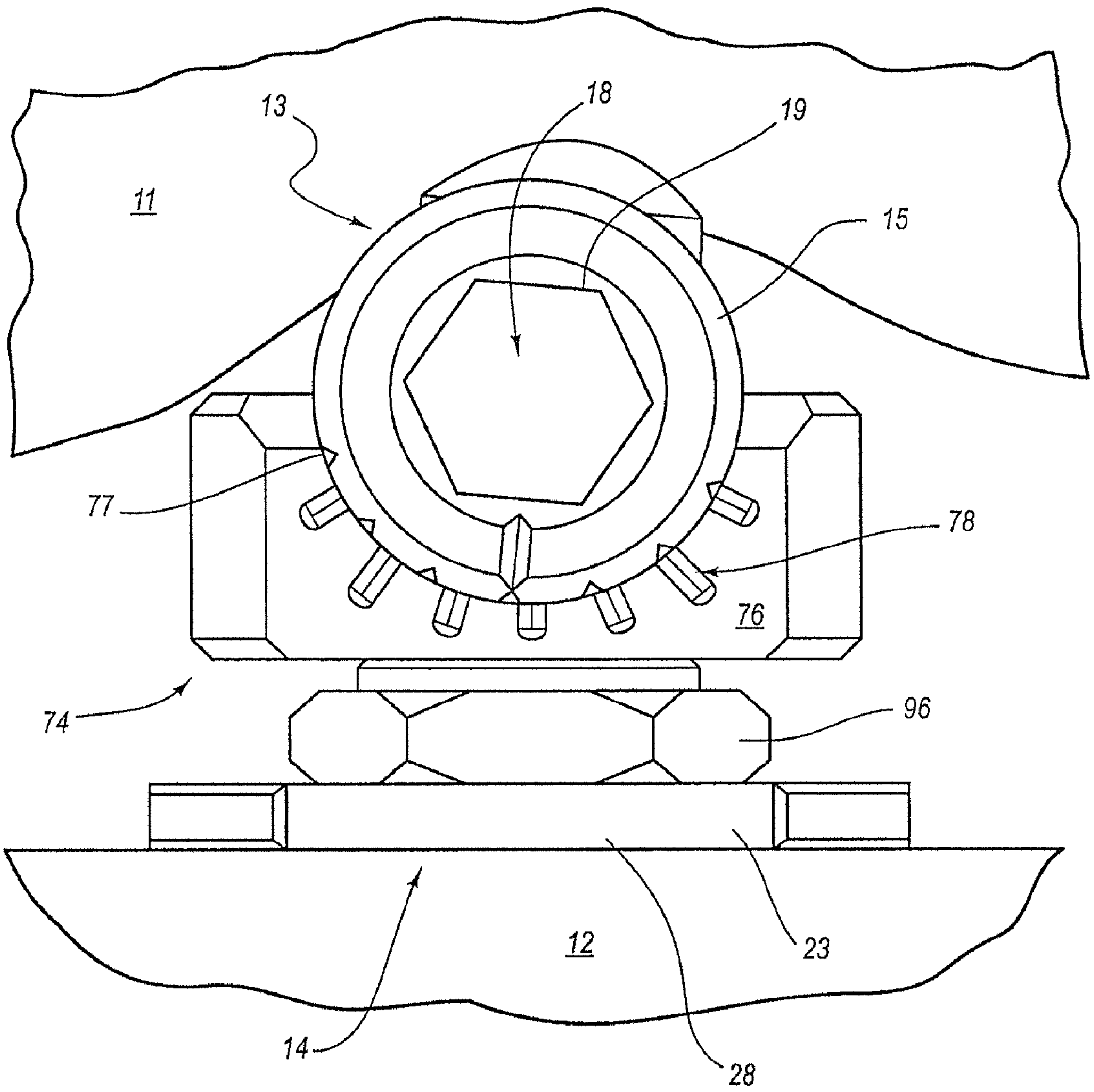
FIG. 20 is an enlarged view of the IM rods and tibial angulation guide of FIG. 19, in accordance with a representative embodiment.
Figure 21:
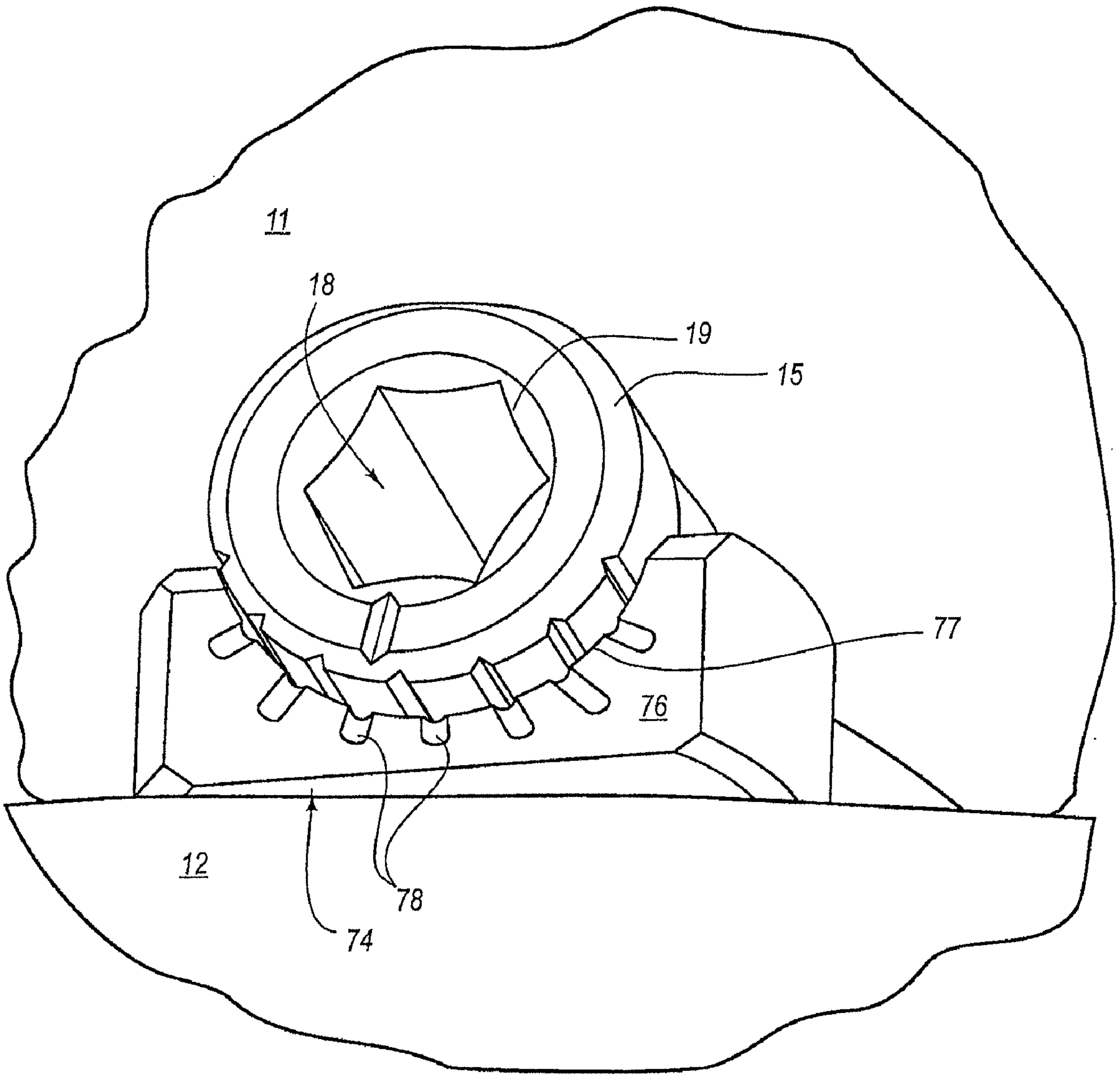
FIG. 21 is an enlarged perspective view of the IM rods and tibial angulation guide of FIG. 19, in accordance with a representative embodiment.

Regardless, gauge block 76 extends upward from the plateau flange 28 of the tibial mount 23 when the threaded shaft of the extension bolt 96 extends into the threaded opening 29 and defines an arc surface 77 and a plurality of gauge marks 78 defined on its anterior surface, as shown in FIGS. 19-21. The arc surface 77 is shaped and sized to receive the outer surface of the cylindrically shaped femoral mount 15 and allow the femoral mount 15 to rotate in the varus-valgus direction and slide in the anterior-posterior direction therein. These motions are left free so as to not over-constrain the femur 11 and tibia 12, but still promote anterior-posterior alignment of the instruments and rotational position selection, for better positioning of the tibial and femoral cuts. Other variations and combinations of shapes of the femoral mount 15 and tibial angulation guide 74 could be employed to allow these ranges of motion, such as by reversing the shapes of the gauge block 76 (it having a cylindrical shape) and the femoral mount 15 (it having the arc shape), by having a rounded shape between two plates, extending the angulation readings away from the instrument assembly, etc., and still be within the purview of the present invention.

Adjustment of the relative proximal-distal positioning of the femur 11 and the tibia 12 is accomplished, similar to the technique in the flexion position, by adjusting the rotation of the hex flange 75 of the extension bolt 96 with a torque wrench. This motion advances or retracts the threaded shaft of the tibial extension bolt 96 into and out of the threaded opening 29 in the tibial mount 23 and advances the tibial angulation guide 74 toward the femoral mount 15. Preferably, the femur 11 and tibia 12 are distracted until the torque wrench has a reading similar to that for the knee in flexion to ensure that the joint is not overly tight in knee extension. With respect to the torque wrench and the amount of joint space, the torque wrench may be equipped with an extender that extends the length of the wrench, has hex-shaped jaws at its end and is relatively thin or low profile. If this is the case, the torque measurements may be adjusted to compensate for the additional length of the extender. In either case, the objective is to match the torque value obtained when the instrument construct constrained the knee in some degree of flexion, in this instance 90° of flexion or increments there between, and torque the bolt to a similar torque measurement that was reached on the torque wrench in the previous step, or until adequate tension of the ligamentous structure is obtained.

Referring again to FIGS. 20 and 21, the gauge marks 78 of the gauge block 76 radiate outward from the center of rotation of the femoral mount 15, starting at the outer surface of the femoral mount, and are positioned on the anterior surface of the gauge block. The gauge marks 78 of the gauge block 76 are configured to match up with gauge marks 21 of the femoral mount 15 (as shown by the arrow) to indicate a valgus angle of the tibia 12 with respect to the femur 11. Generally, the valgus angle should be within a range of 3 to 7 degrees, or even 2 to 9 degrees, depending upon the knee's morphology, surgeon preference, etc.

Figure 22:
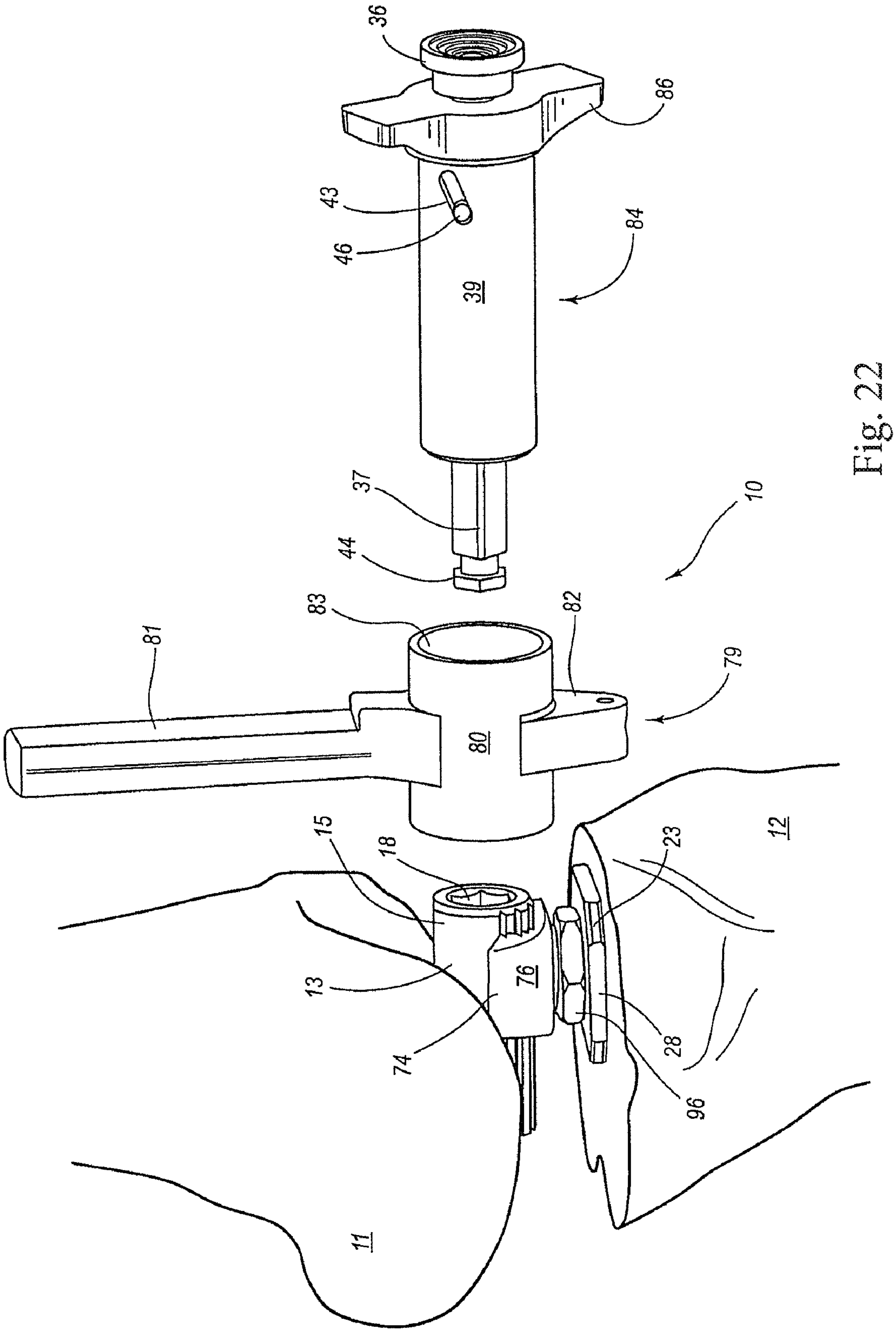
FIG. 22 is a perspective view of a second locking mechanism and extension guide support member of the described assembly being assembled to the femoral IM rod of FIG. 1, in accordance with a representative embodiment.
Figure 23:
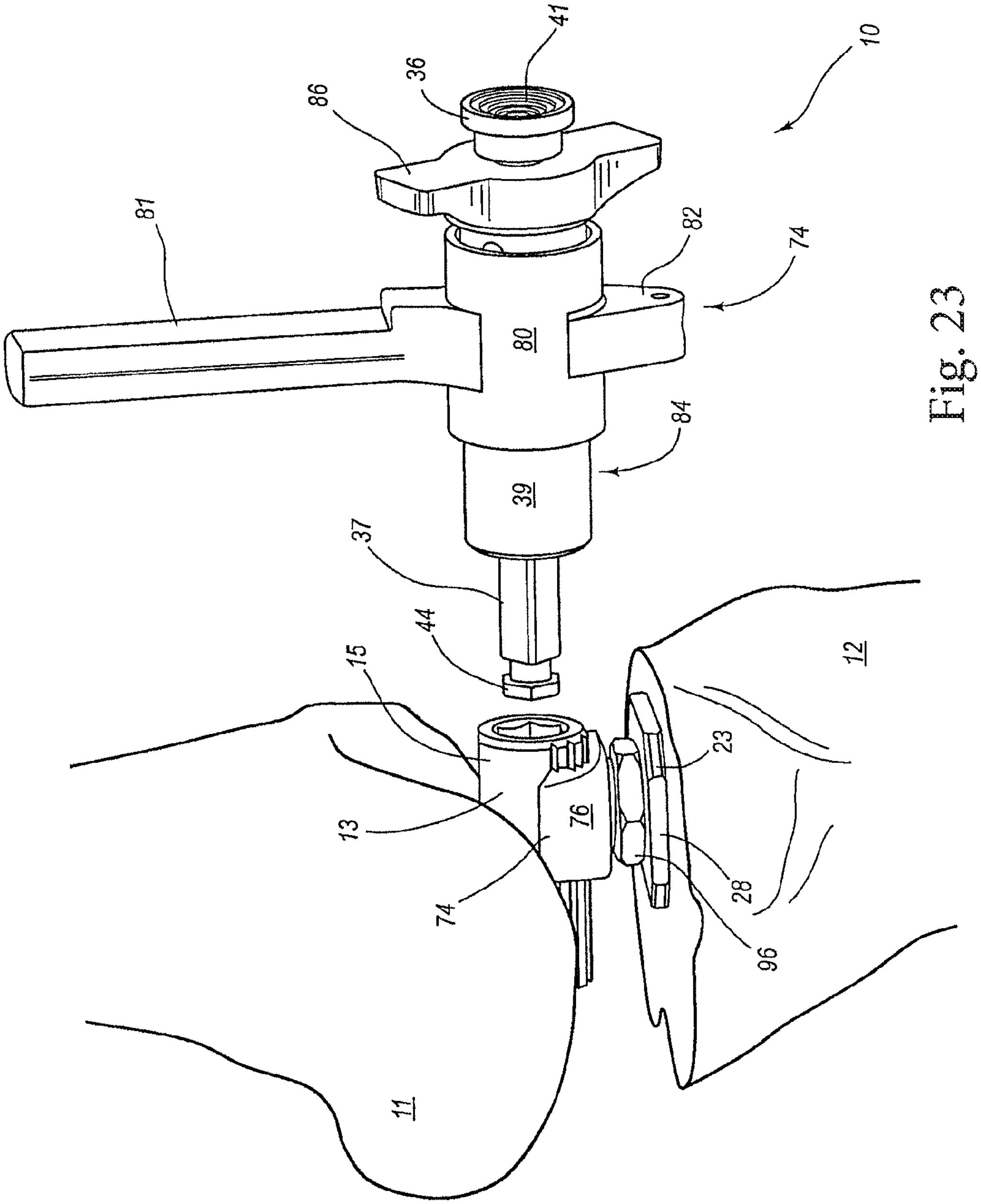
FIG. 23 is an enlarged perspective view of the assembly of the extension guide support member of the present invention to the second locking mechanism of FIG. 22, in accordance with a representative embodiment.

Once the angulation and proximal-distal positioning of the tibia 12 with respect to the femur 11 has been adjusted, an extension guide support member 79 is attached to the femoral mount 15 using a second locking mechanism 84, as shown in FIGS. 22 and 23. Generally, the second locking mechanism 84 includes the plunger 36 (and its components including hexagonal end 44), hex extension 37 and helical slot 43 which are similarly numbered as they share a similar function with the same components of the first locking mechanism 34. The second locking mechanism 84 differs in that the head portion 39 is somewhat longer, is cylindrical and lacks the elongate portion 38 of the arm 35. Also, the second locking mechanism 84 includes a grip flange 86 positioned adjacent the plunger 36 to facilitate a finger grip when depressing the plunger. Regardless, the hexagonal end 44 has the same rotating motion that facilitates quick attachment of the end of the second locking mechanism 84 to the femoral mount 15.

The extension guide support member 79 includes a mounting portion 80, a support arm 81 and a fixation flange 82. The mounting portion 80 has a cylindrical shape with a cylindrical opening 83 extending there through that is configured to slidably receive the second locking mechanism 84, but is not rotationally constrained by said second locking mechanism 84. Extending away from one side of the mounting portion 80 is the support arm 81 which is an elongate structure with a T-shaped cross section. Extending away from the other side of the mounting portion 80 is an additional flange 82 that acts as a housing for a mechanism, in this case a ball and spring 85, to provide some resistance to rotation of the extension guide support member 79 with respect to the second locking mechanism 84.

Also included in the illustrated embodiment of the assembly 10, is an extended knee cutting guide 87 that is supported by the extension guide support member 79 during positioning, as shown in FIGS. 24-29. The extended knee cutting guide 87 includes a mounting portion 88, a fixation pin (or k-wire) guide portion 89, a femoral cut guide portion 90 and a reference lever 91. The mounting portion 88 is generally centered in a body portion of the extended knee cutting guide 87 and defines a channel 92 that has a cross-sectional shape matched to the T-shaped cross-section of the support arm 81. The matching shapes allow the extended knee cutting guide 87 to slide in the proximal-distal direction along the support arm 81.

Figure 25:
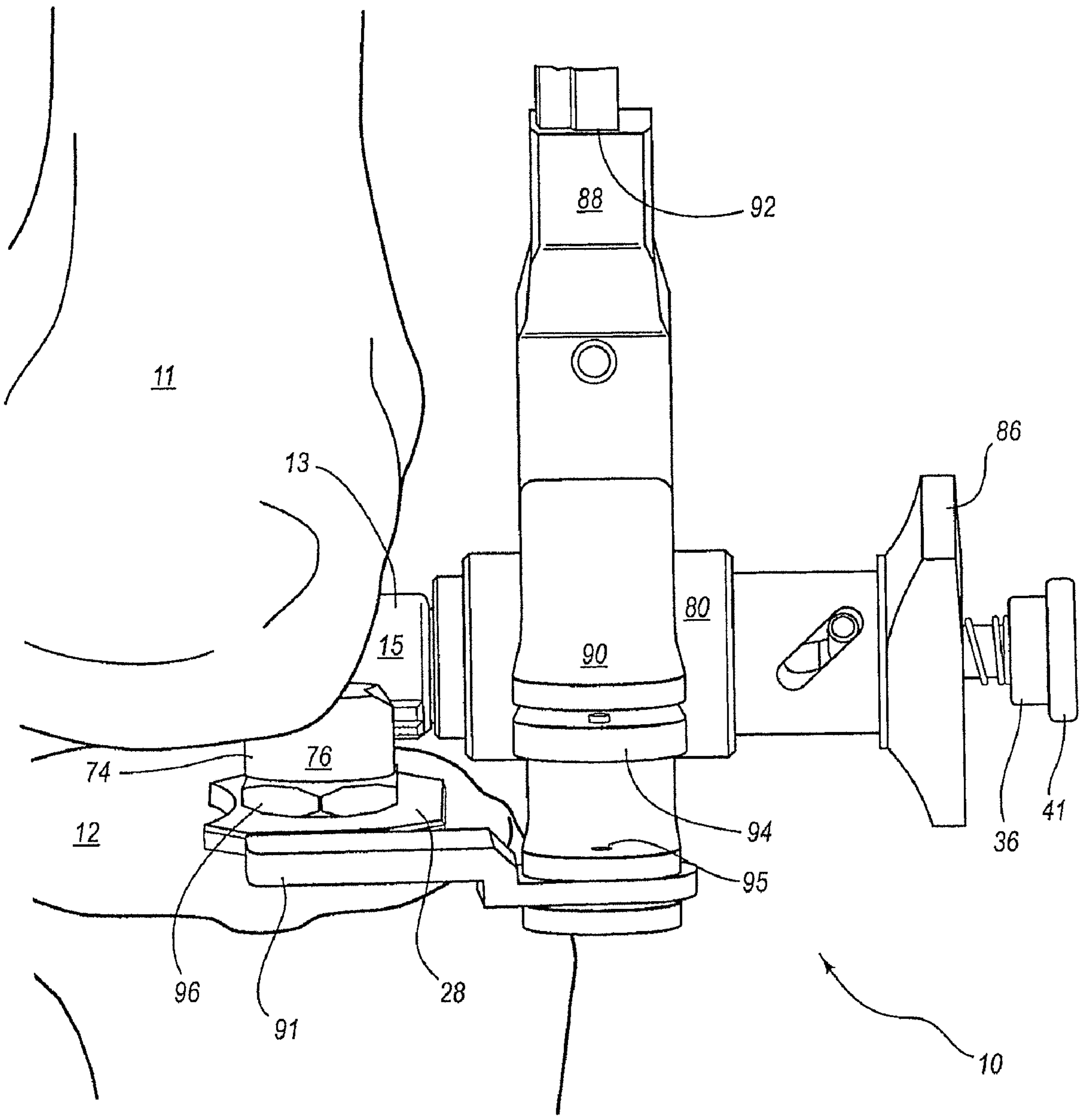
Figure 26:
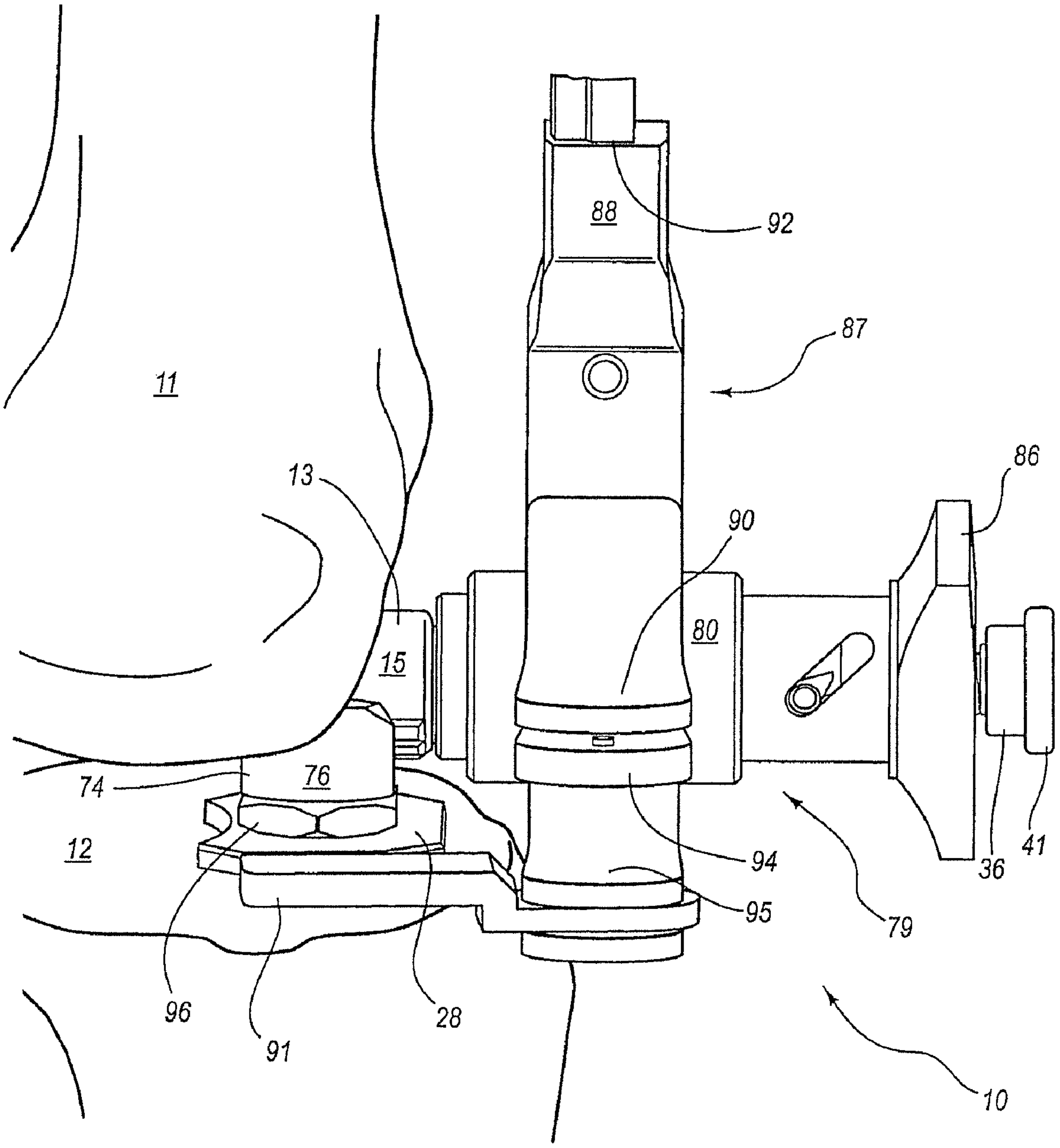

The fixation pin guide portion 89 defines a plurality of k-wire (or other type of fastener, e.g., screws, nails, etc.) holes 93 that allow fixation using fixation pins after positioning of the extended knee cutting guide 87. The holes 93 are positioned on medial and lateral sides of the anterior femur when positioned so as to allow fixation to relatively thick cortical bone, as shown in FIG. 25. As with the k-wire holes 72, the k-wire holes 93 can be oriented at various angles or selectively positioned to guide fasteners into and through larger lengths of denser bone on the femur 11.

The femoral cut guide portion 90 extends either laterally or medially for a uni-compartmental reconstruction (as with the illustrated embodiment), or in both directions for a full resection of the femoral condyles. Notably, the guide portion 90 extends distally in the shape of a U that fits around the second locking mechanism 84 when the extended knee cutting guide 87 is in place, as well shown in FIG. 29. Regardless, the guide portion 90 extends distally from the k-wire guide portion 89 and then laterally or medially to define a guide slot 94. The guide slot 94 is of sufficient width to allow passage of cutting instruments or blades but still promote a relatively straight or planar resection. Notably, extension medially allows the laterally shifted patella to be avoided in a medially oriented approach to the knee joint compartment.

Figure 24:
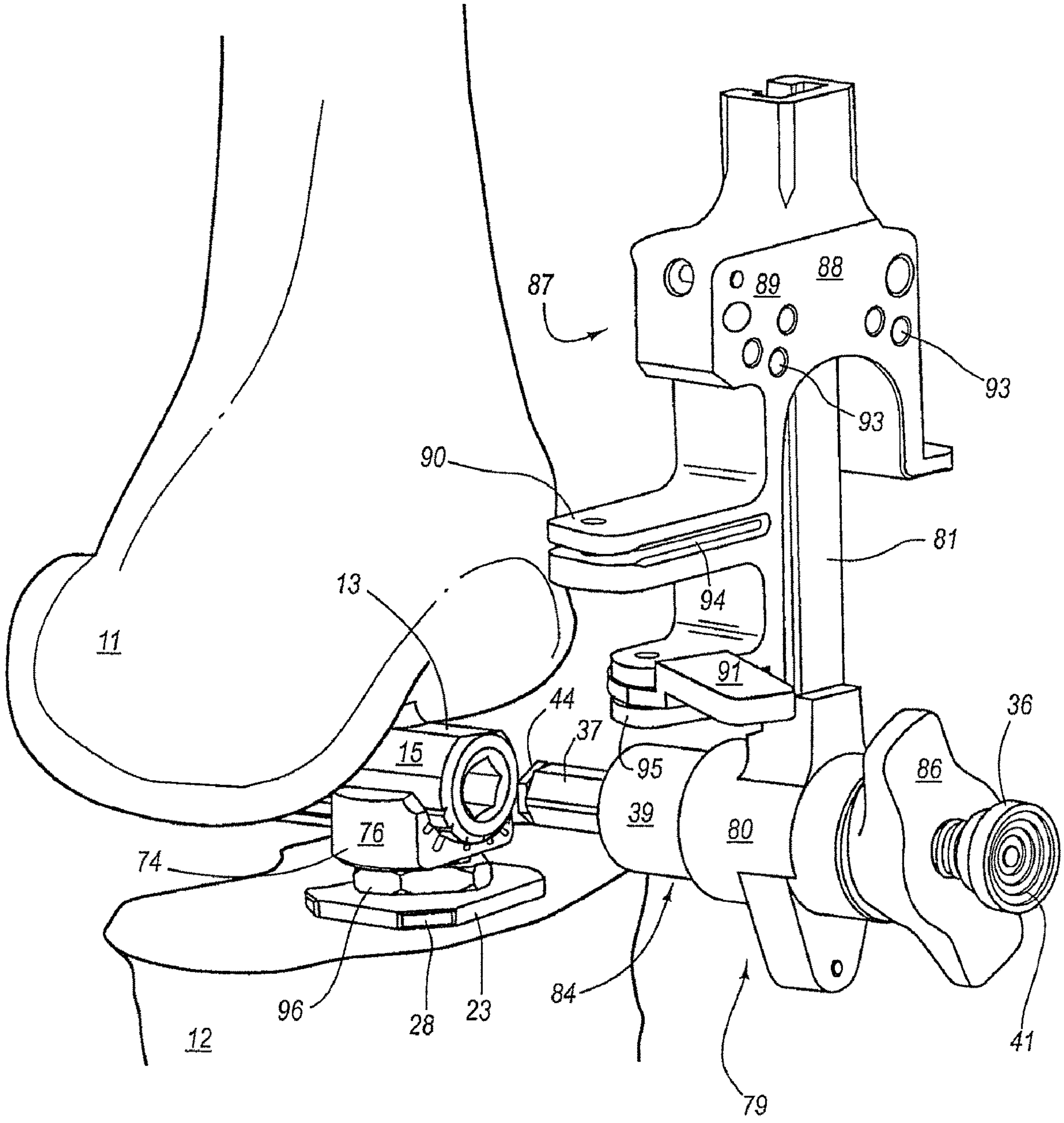
FIG. 24-26 are various a perspective views of an extended knee cutting guide of the assembly of the described assembly attached to the extension guide support member and second locking mechanism of FIG. 22, and the femoral IM rod of FIG. 1, in accordance with some representative embodiments.
Figure 27:
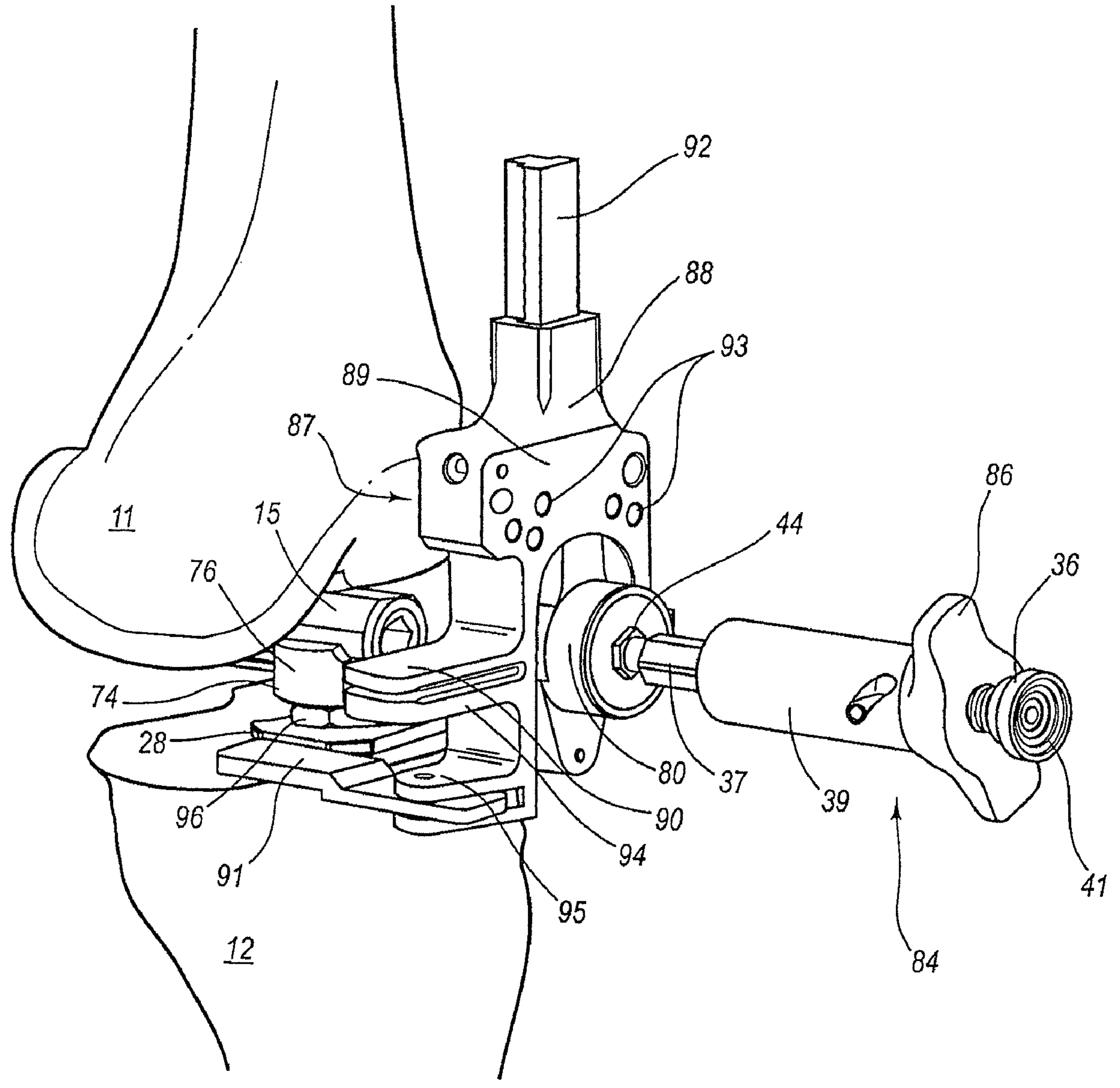
FIG. 27 is a perspective view illustrating disassembly (in accordance with some embodiments) of the second locking mechanism of FIG. 22, from the femoral IM rod of FIG. 1, once the extended knee cutting guide is fixed in position to the distal femur.
Figure 28:
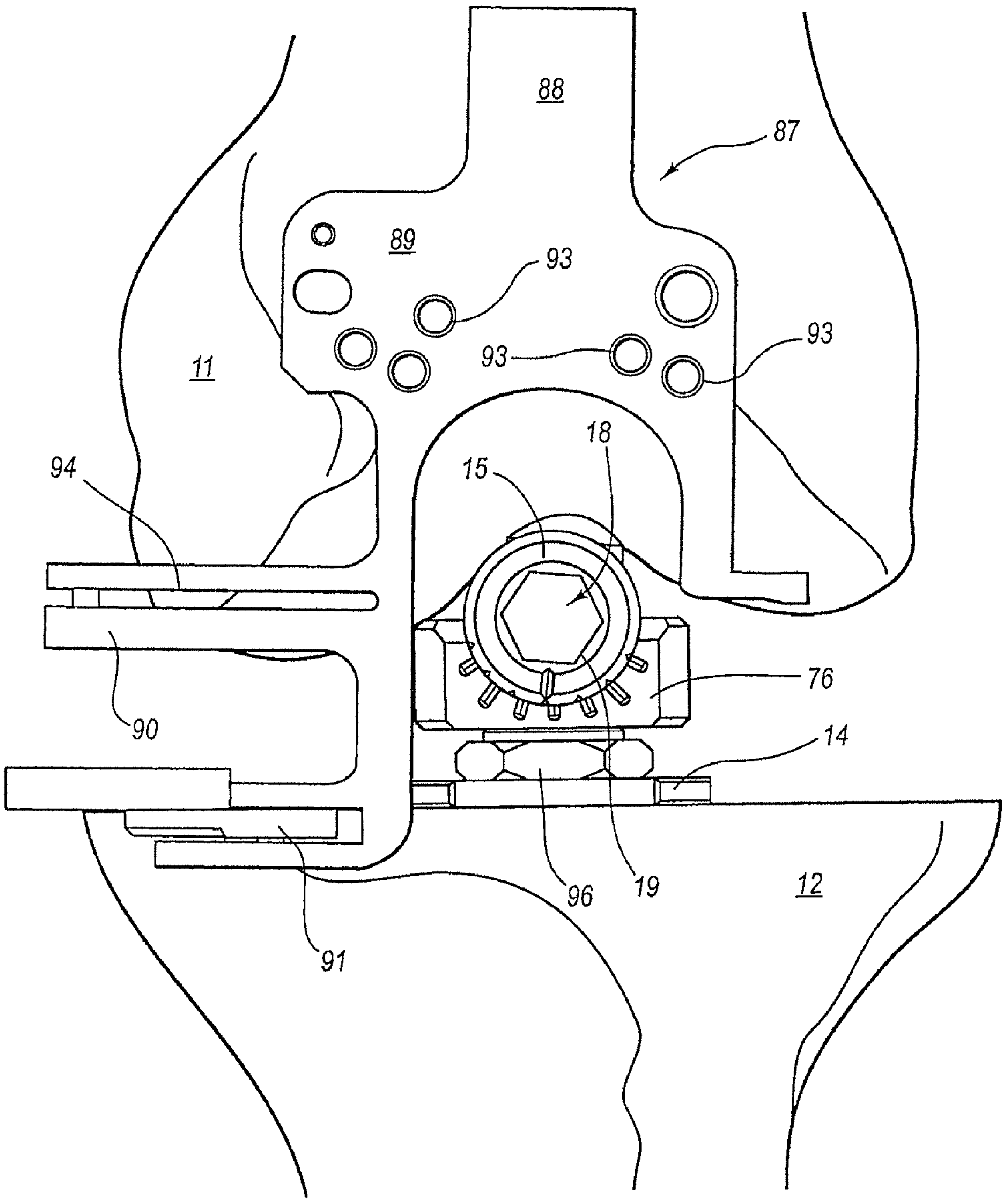
FIG. 28 is a front elevation view of the extended knee cutting guide of FIG. 24, in accordance with a representative embodiment.
Figure 29:
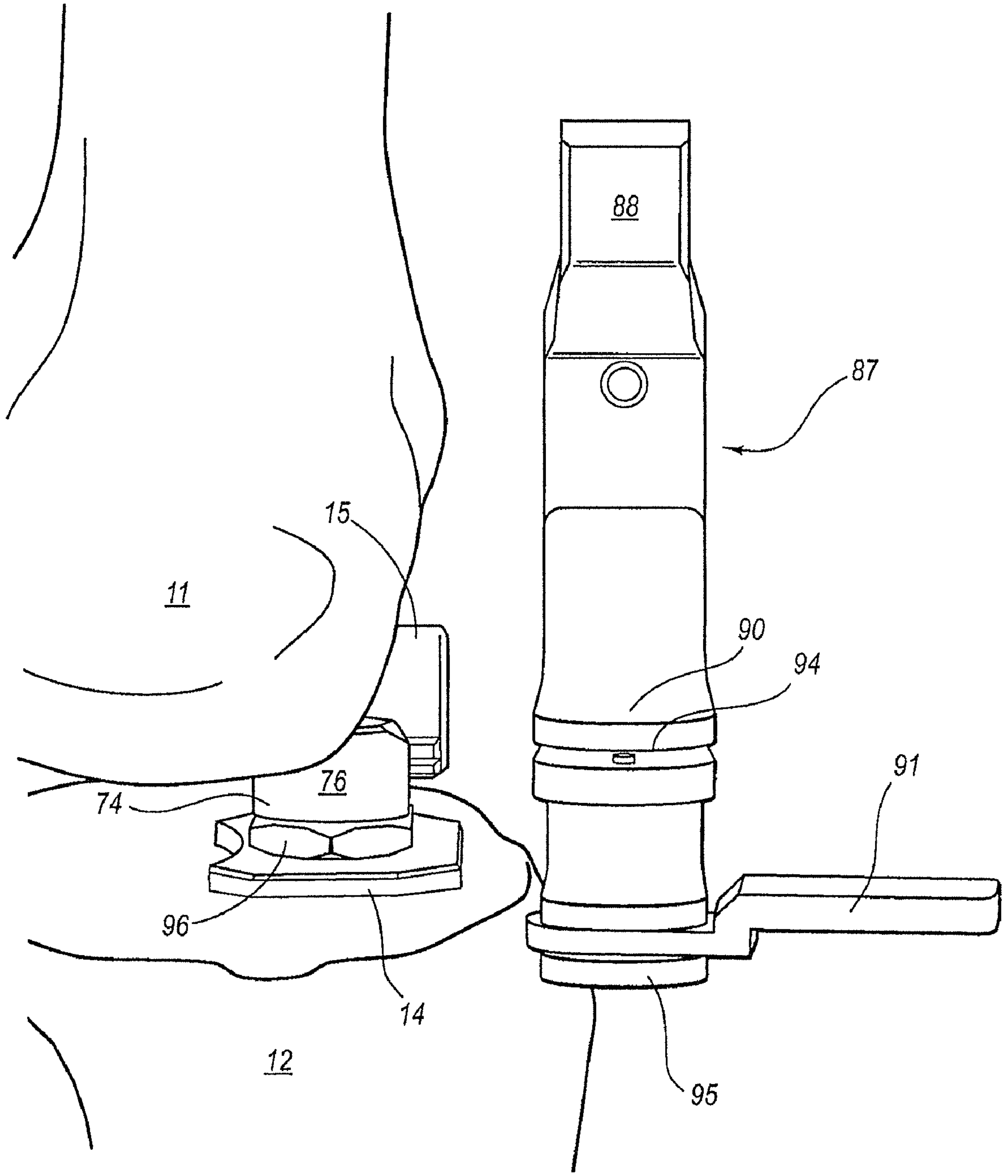
FIG. 29 is a side perspective view of the extended knee cutting guide of FIG. 24, in accordance with a representative embodiment.

Extending further distally from the femoral cut guide portion 90 is a portion of the extended knee cutting guide 87 that defines a clevis 95 that rotationally supports the reference lever 91. The reference lever extends laterally or medially and rotates in an anterior-posterior direction to allow positioning in the joint compartment, as shown in FIGS. 24 and 25. The reference lever 91 has a broad, flat distal surface that is configured to rest against the flat tibial cut and a flat lateral surface is configured to abut the side surface of the plateau flange 28. These surfaces provide a stop for the distal movement of the extended knee cutting guide 87 along the support arm 81 of the extension guide support member 79. With the reference lever 91 and the second locking mechanism 84 in place, fixation pins can be inserted through the pin holes 93 in the guide portion 89 to fix the femoral cut guide portion 90 to the femur 11. This allows removal of the extension guide support member 79, as shown in FIGS. 27, 28 and 29.

Advantageously, the components for positioning the cuts with the knee in extension, including the extension bolt 96, tibial angulation guide 74, the extension guide support member 79 and the extended knee cutting guide 87 are configured for passage through an anterior and medial approach to the knee compartment due to the narrow width and profile of the components. For example, as shown in FIG. 25, the posterior portion of the second locking mechanism 84 and the reference lever 91 would pass through the incision and exhibit the aforementioned narrowness and low-profile. Preferably, the width of this component is small compared to conventional cutting guides, for example, within a range of up to 4 to 5 cm thereby allowing their use with minimally invasive approaches to the knee joint.

Figure 30:
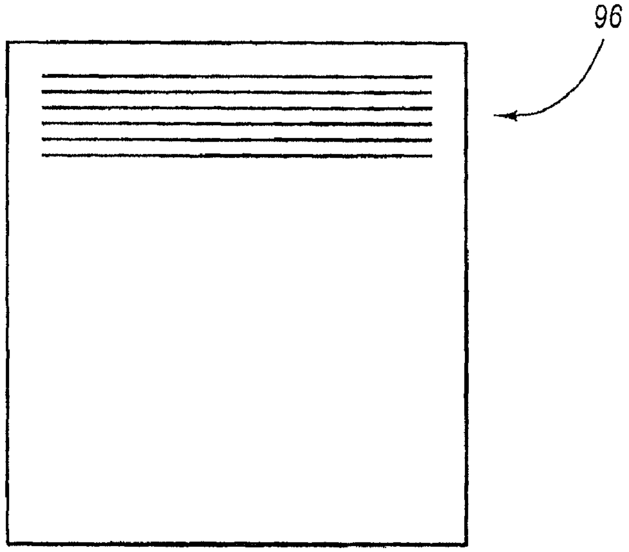
FIG. 30 is a plan view of an L-shaped cutting block of the described assembly, in accordance with a representative embodiment.
Figure 31:
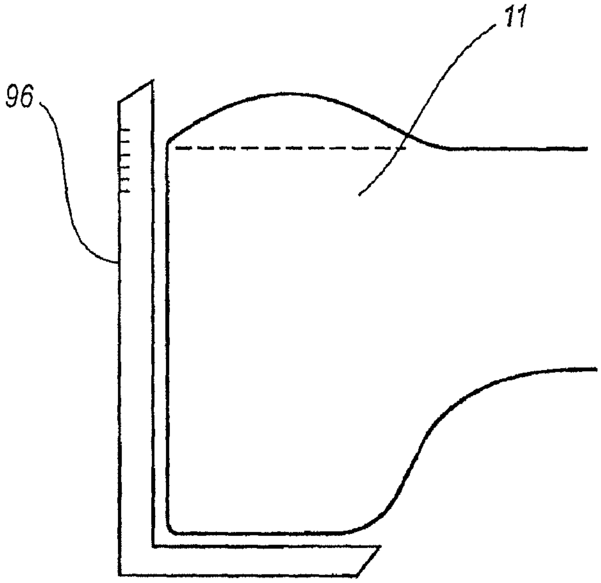
FIG. 31 is a side elevation view of the L-shaped cutting block of FIG. 30 being used to cut an anterior condyle of a femur, in accordance with a representative embodiment.

After these initial cuts, further cuts can then be made using the initial cuts as a reference. As shown in FIGS. 30 and 31, an L-plate 99 is employed to abut the posterior and distal flat surface of the femur 11 to guide an anterior cut. Chamfer cuts (anterior and posterior) can be made using a chamfer cut block and other finishing cuts can be references from the initial cuts made using the assembly 10 of the present invention. Additional description of these finishing cuts can be found in U.S. patent application Ser. No. 10/794,188 filed on Mar. 5, 2004, entitled "Reference Mark Adjustment Mechanism for a Femoral Caliper and Method of Using the Same," which is hereby incorporated herein by reference.

Figure 32:
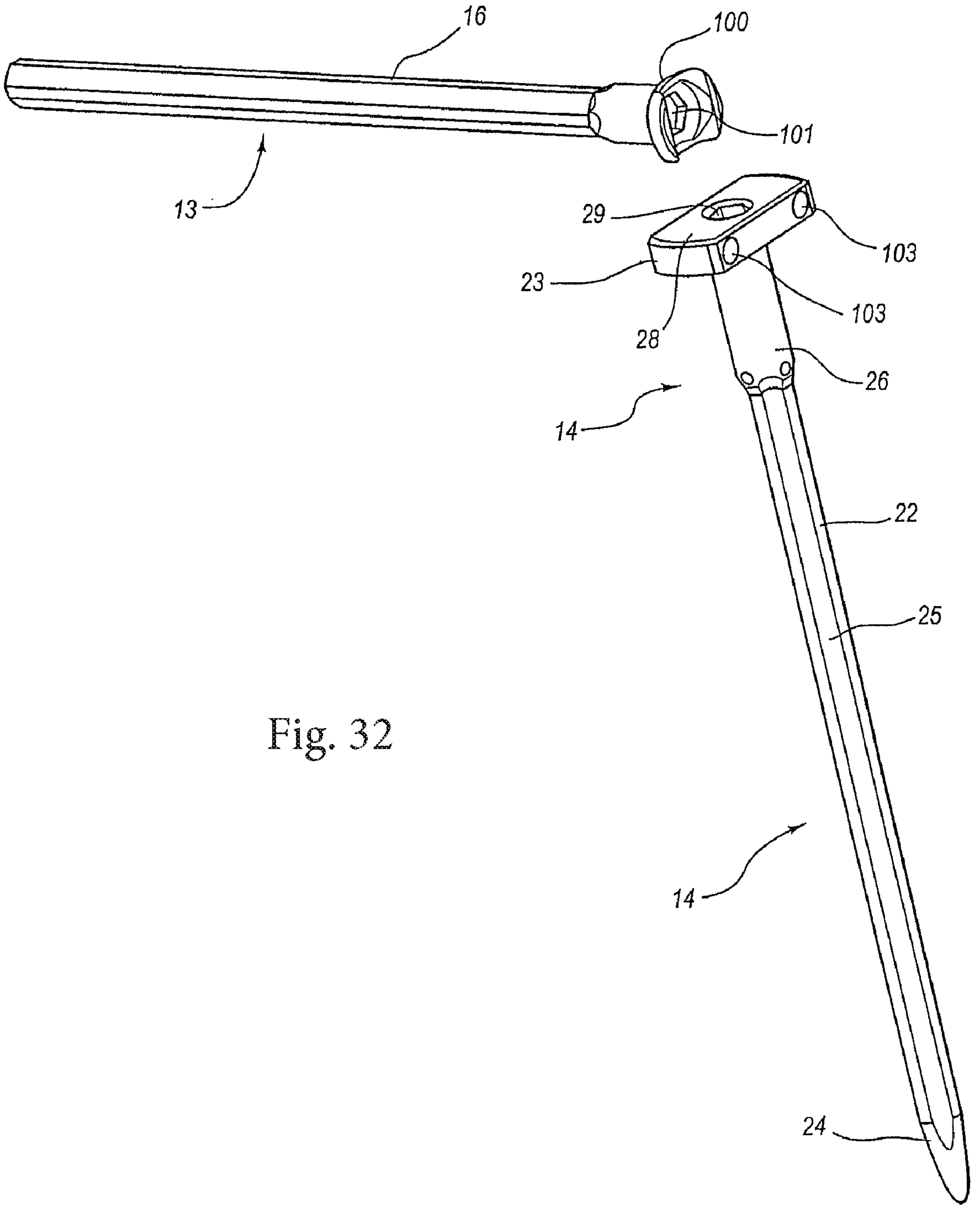
FIGS. 32-40 show various modular options of the described assembly that promote quick assembly and facilitate minimally invasive intra-operative use, in accordance with some representative embodiments.
Figure 33:
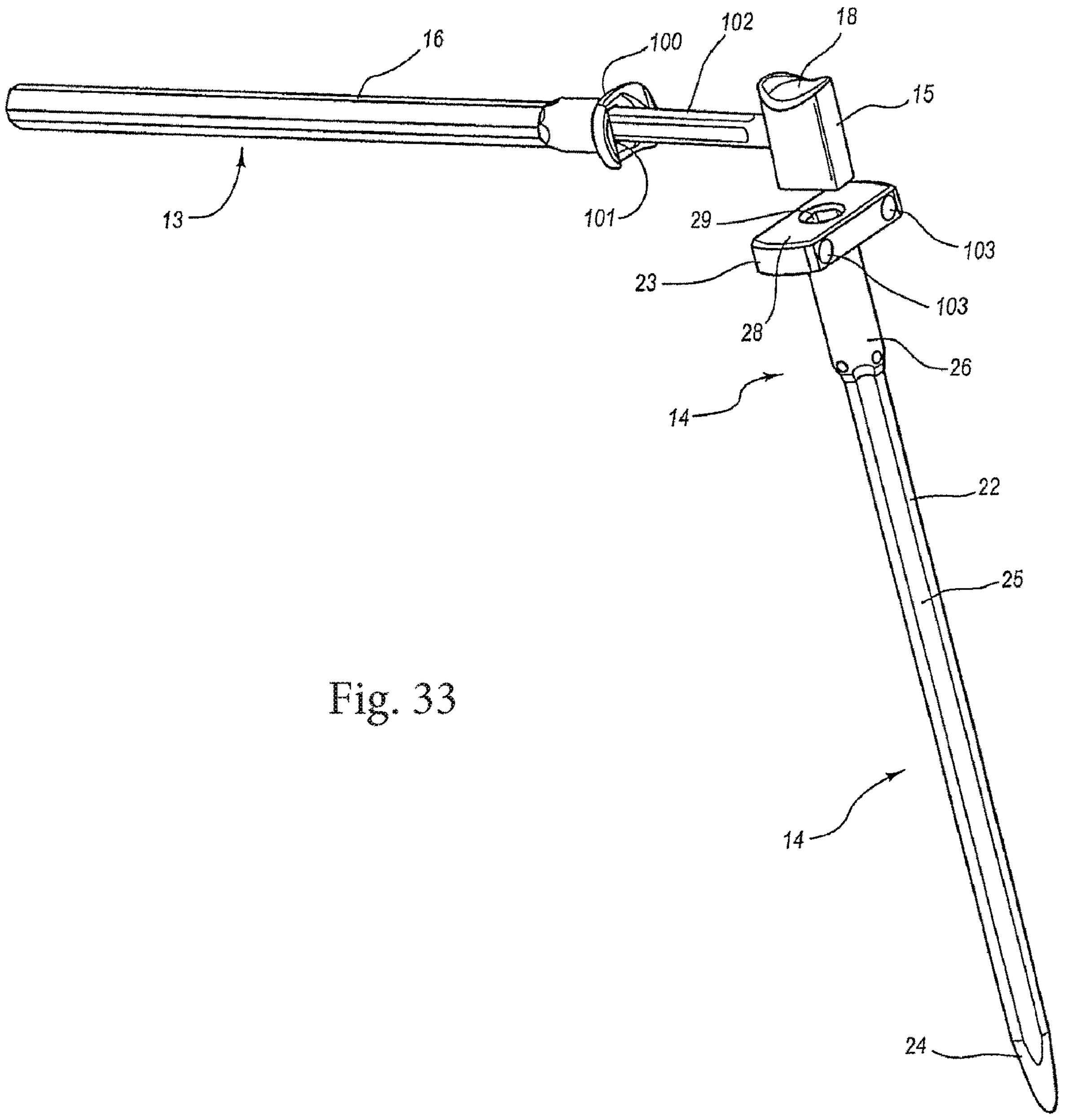

In another embodiment of the present invention, as shown by FIGS. 32 through 40, the assembly 10 includes additional modular options to promote quick assembly. As shown in FIG. 32, the femoral IM rod 13 includes a secondary femoral mount 100. The secondary femoral mount 100 has a saddle or crescent shape that extends laterally and distally from a central attachment to the distal end of the main shaft 16 of the femoral IM rod 13. Defined in the inner, convexly curved surface of the saddle is an opening 101 that is configured to receive a femoral mount rod 102 that supports the femoral mount 15, as shown in FIG. 33.

Figure 34:
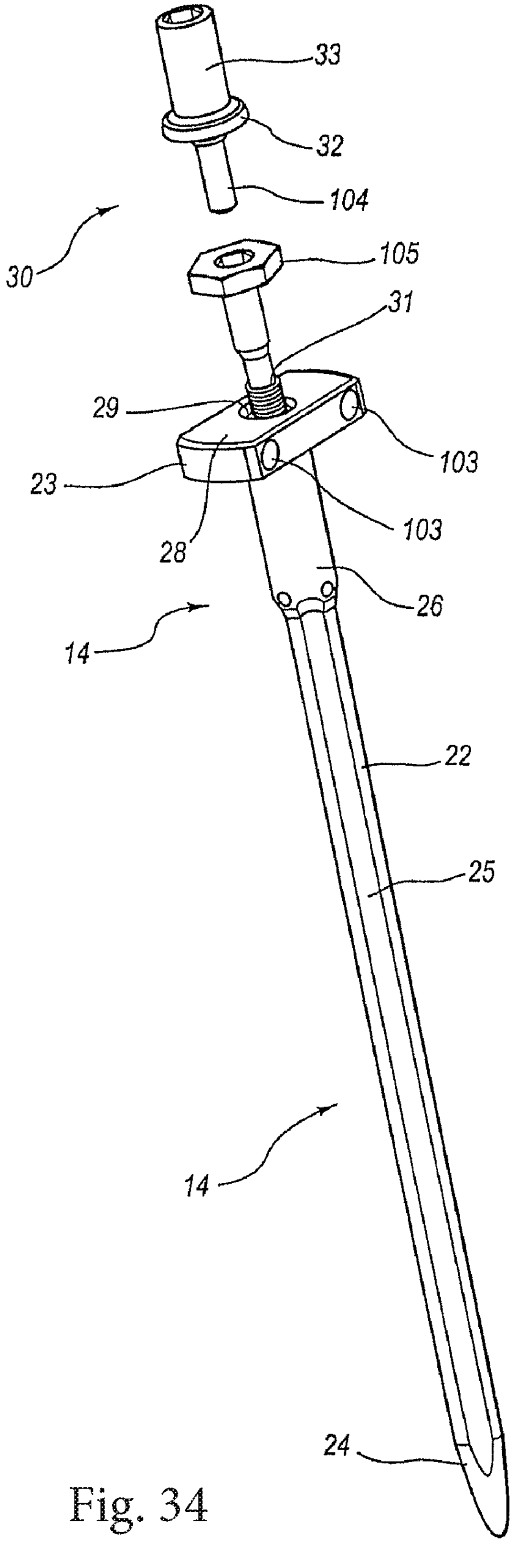
Figure 35:
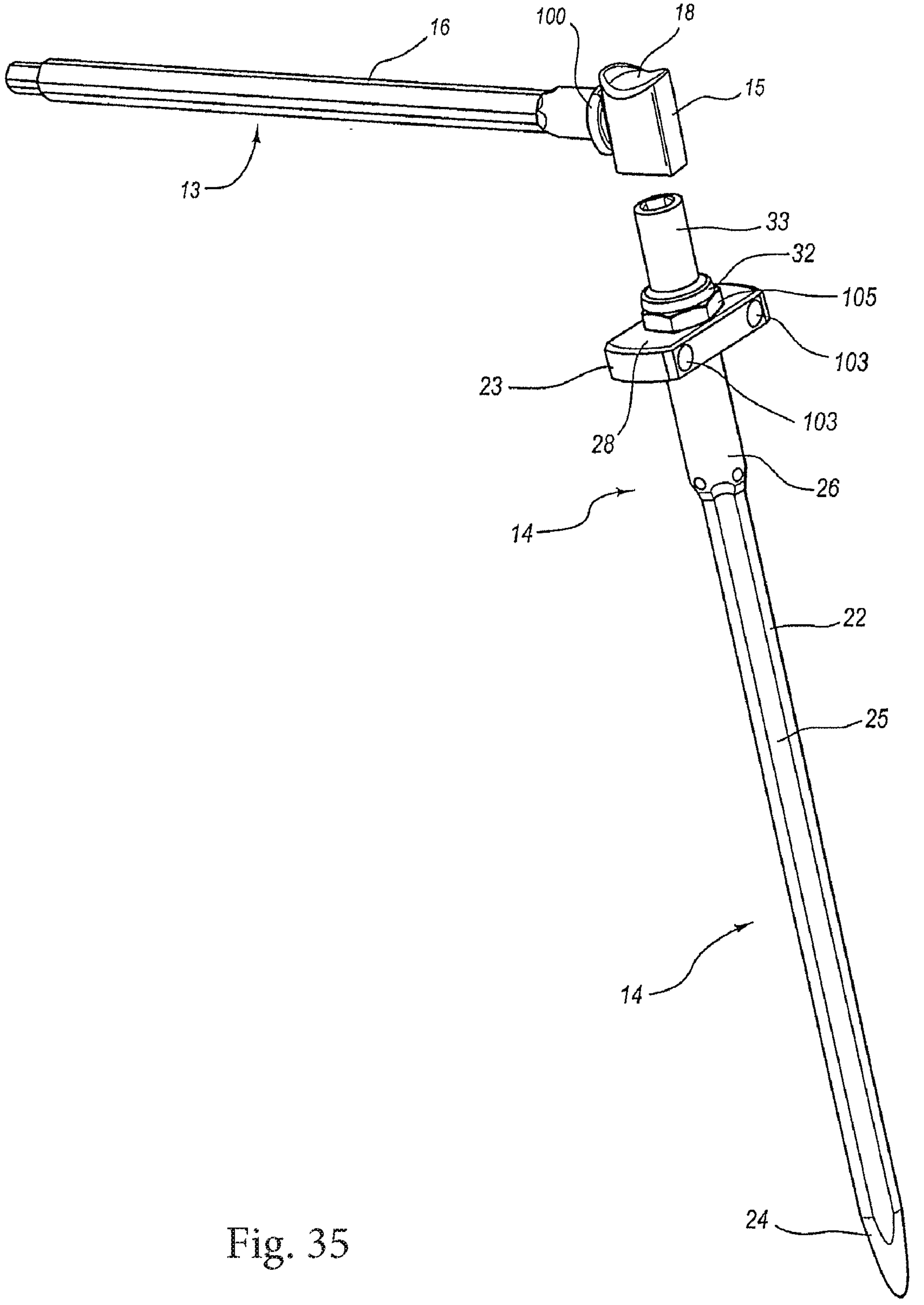
Figure 36:
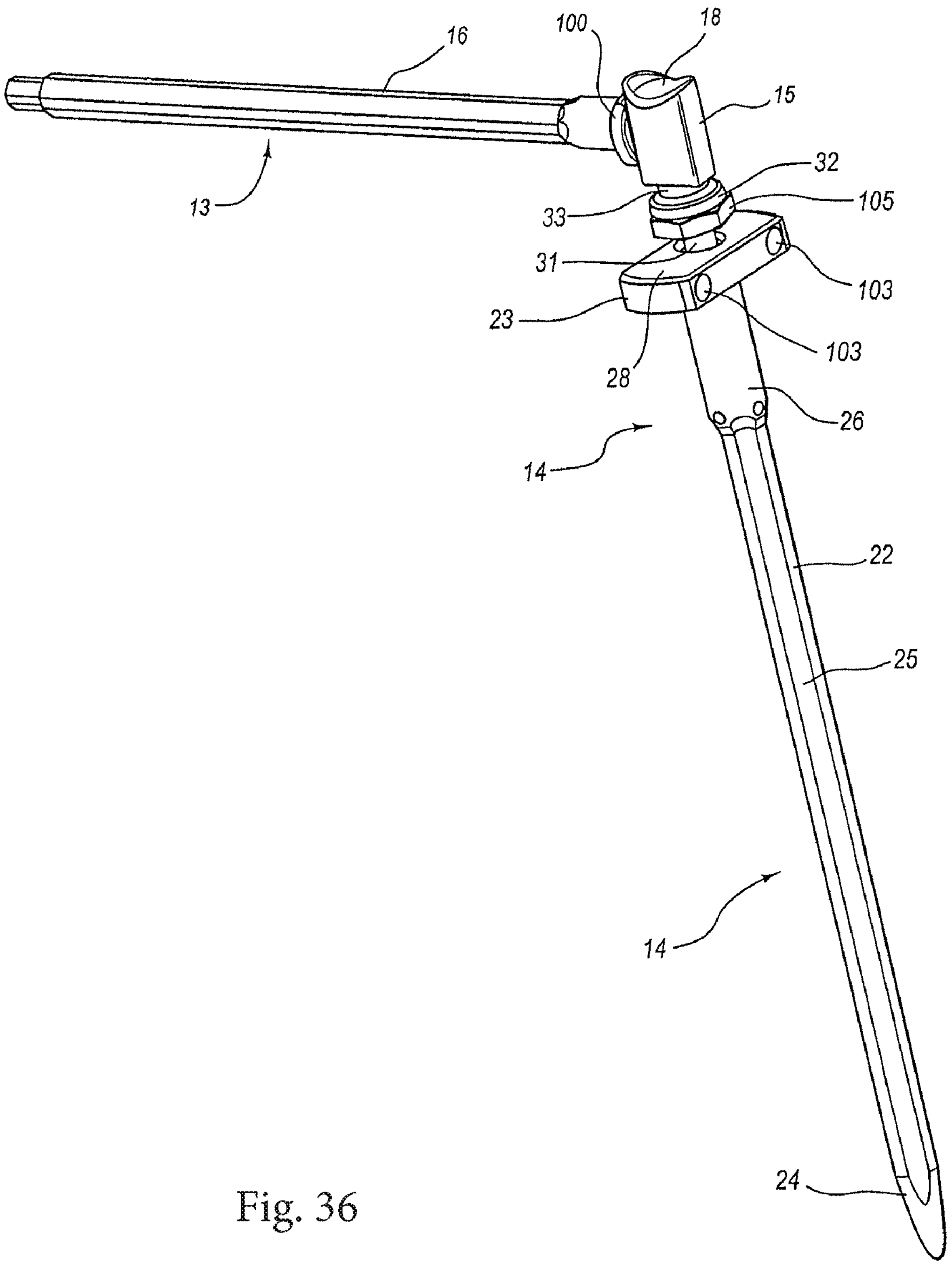

Referring again to FIG. 32, the tibial IM rod 14 includes a modified version of tibial mount 23 supported by the shaft 22. In particular, the plateau flange 28 of the tibial mount 23 has a widened rectangular shape that extends laterally outward from the threaded opening 29. Defined at the anterior side of the plateau flange 28 are a pair of guide mount openings 103 that extend posteriorly into the plateau flange. As shown in FIG. 34, the flexion bolt 30 may also be further modularized by providing a post 104 for mounting the bushing 33 and hex flange 32 within a central opening defined in a hex-head bolt 105 that includes the threaded shaft 31 extending from its head 105. FIGS. 35 and 36 show the assembly of the femoral mount 15 and tibial mount 32, along with tightening adjustment by elevation of the hex head bolt 105.

Figure 37:
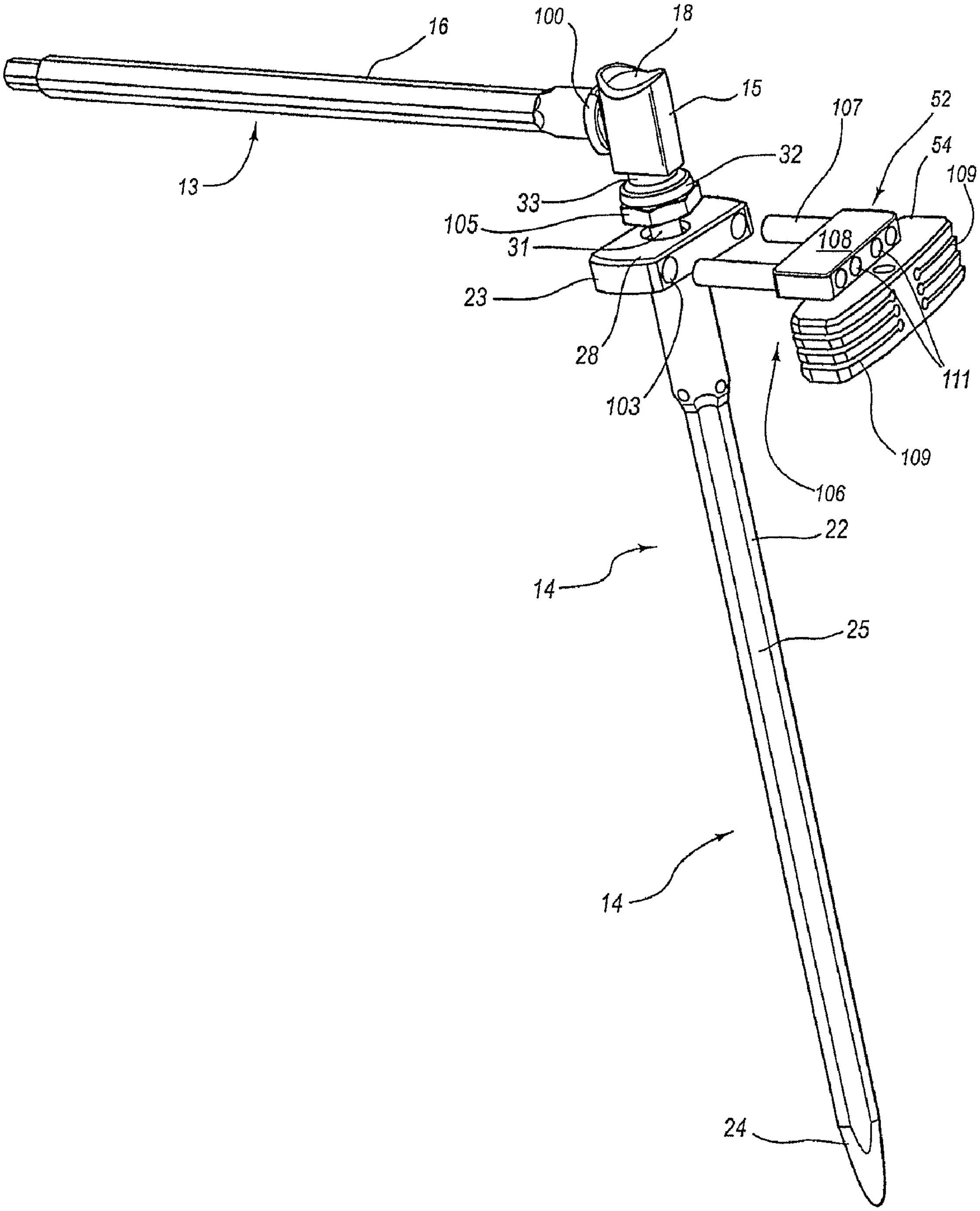

As shown in FIG. 37, the assembly 10 also includes a flexed knee cutting guide assembly 52 that includes a flexed knee cutting guide 54 and a direct mount 106. The direct mount includes a pair of posts 107 that are spaced apart and extend from a mounting block 108. The spacing and size of the posts 107 are configured to extend into the guide mount openings 103 defined in the plateau flange 28. Mounting block 108 can be coupled to tibial mount 32, such as by hermetically sealed magnets 111. The flexed knee cutting guide 54 is attached to and extends distally from the mounting block 108. The flexed knee cutting guide defines a selection of slots 109 for guiding tibial and femoral cuts.

The posterior femoral cut can be accomplished by turning the flexed knee cutting guide assembly 52 upside down or by using another block which would be a modification of the upside down cutting guide assembly 52 where the cutting guide 54 and selection of slots 109 is moved toward the posts 107 and therefore, closer to the posterior femoral condyles of the knee. The selection of slots 109 of cutting guide assembly 52 can be as shown with the slots attached centrally or could be open centrally and attached along both sides of the cutting guide 54.

Figure 38:
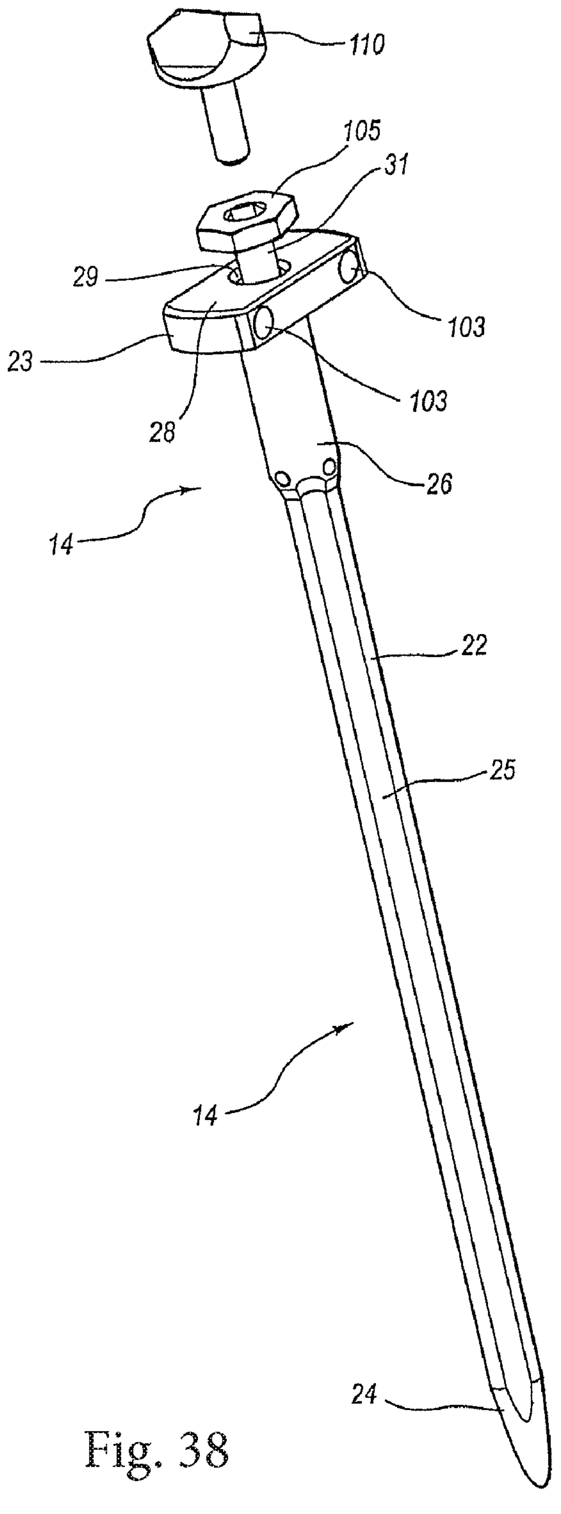
Figure 39:
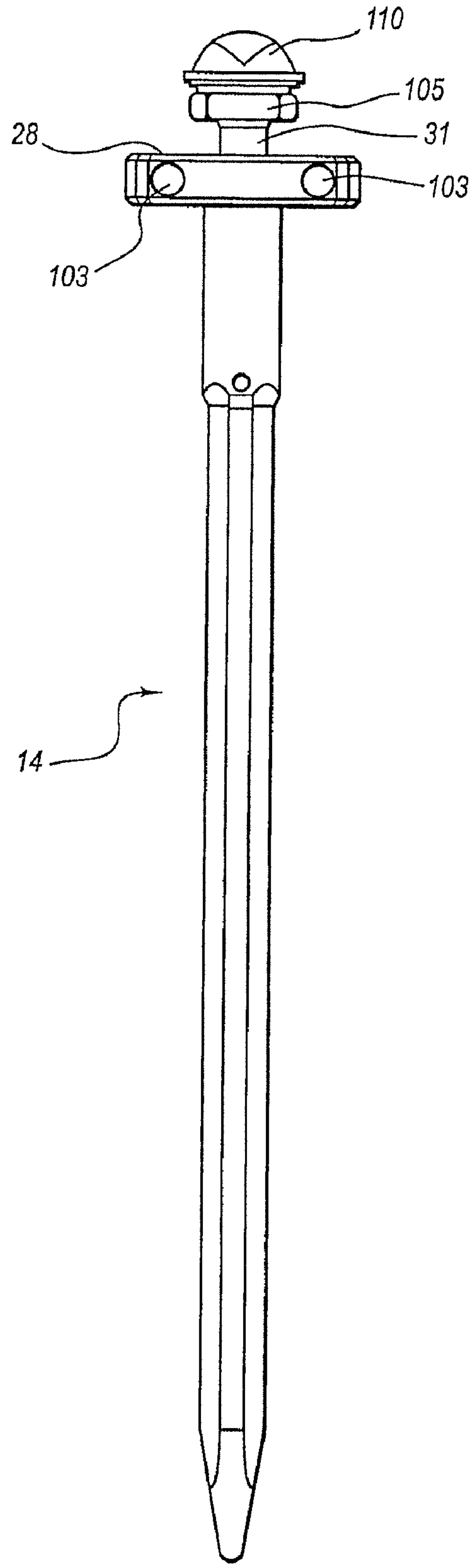
Figure 40:
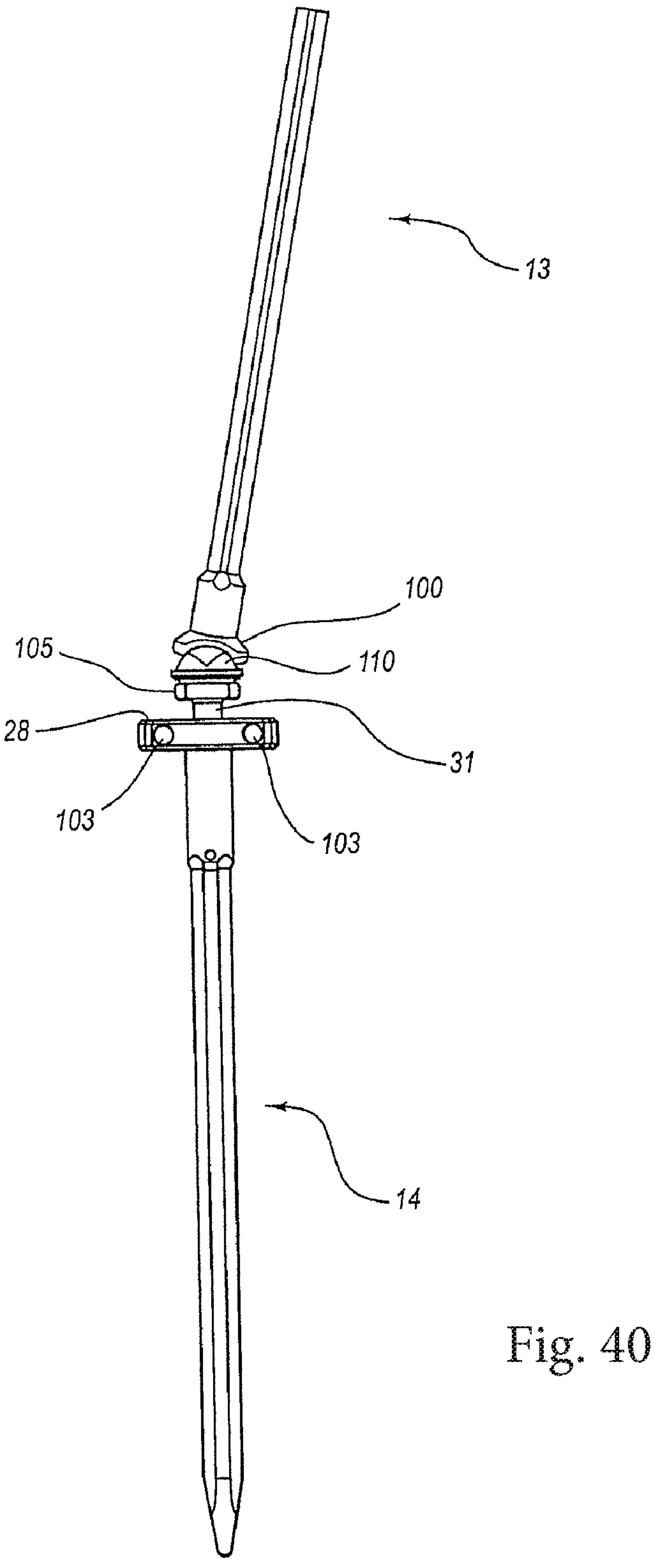

As shown in FIGS. 38 and 39, the tibial IM rod 14 may also include a valgus adapter member 110 or a modified version of femoral mount 15 that has its own post that is configured to insert into the central opening of the hex head bolt 105. As shown in FIG. 40, the valgus adapter member 110 has a convex shape that is configured to extend into the concave shape of the secondary femoral mount 100. This mating allows varus-valgus angulation to position the cuts when the knee is in extension, similar to the first embodiment disclosed above. Extended knee cutting guides can be mounted similar to the flexed knee cutting guide via posts 107.

The assembly 10 of the present invention has many advantages. It provides a relatively narrow and low profile collection of locking components that securely attach cutting guides to tibial and/or femoral IM rods. This provides a robust guide to reference cuts being made to the tibia and the femur with an approach to the joint that minimizes invasiveness. Further, many of the components, such as the first and second locking mechanisms 34, 84 and the quick release mechanism 53, facilitate quick assembly, easy adjustment and quick disassembly for improved efficiency. The use of the bolts 30 and 96 or 105 and the tibial angulation guide 74 or valgus adapter member 110 allow the tibia and femur to be distracted under a matching amount of torque in flexion and extension to ensure a better fit for the tibial and femoral knee replacement components throughout a range of flexion. Also, the tibial angulation guide allows the surgeon to adjust the amount of valgus angulation of the tibia as desired to match the anatomy of the patient.

Figure 41:
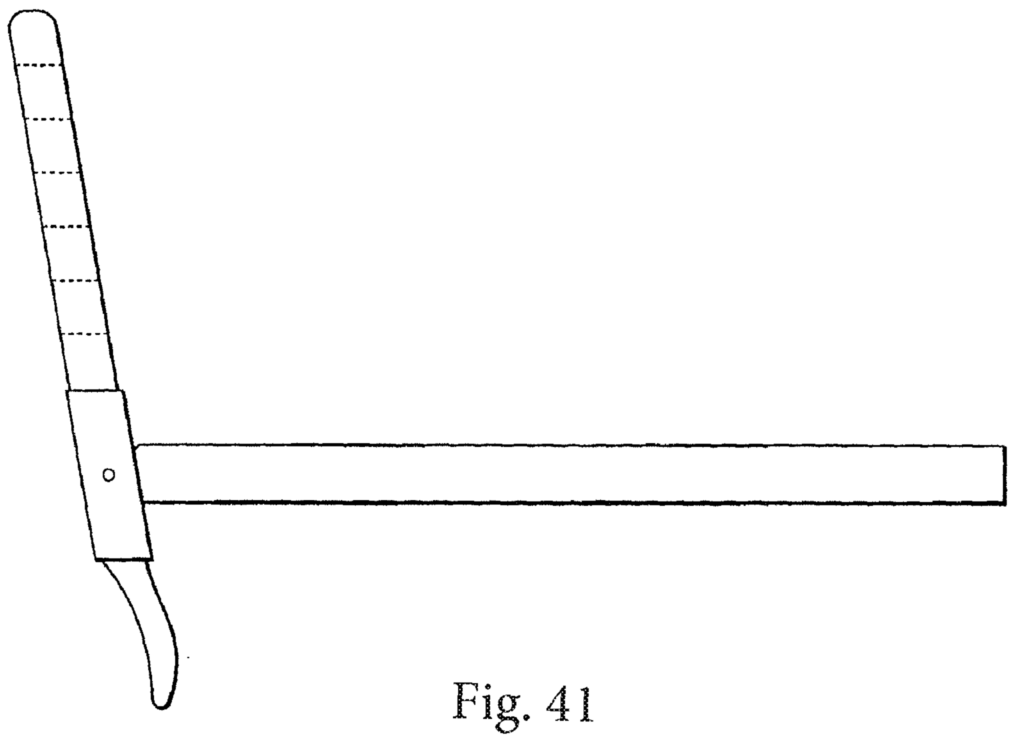
FIG. 41 shows a hinged retractor, in accordance with a representative embodiment.

As shown in FIG. 41, in another embodiment of the present invention a modified femoral mount rod 102 and femoral mount 15 with a hinge mechanism attaching mount 15 to the femoral mount rod 102 could be used with a retractor rod placed thru the hole 18 in the femoral mount 15 and guided posterior to the tibia thus providing a fulcrum and lever arm for the retractor to displace the tibia forward or anterior to allow exposure for placement of the tibial component of the total knee arthroplasty after the bone cuts have been made. Since the IM rods fix rigidly to the bone, other retractors could also be attached to the Guide Assembly to facilitate knee exposure during the knee surgery.

Figure 42A:
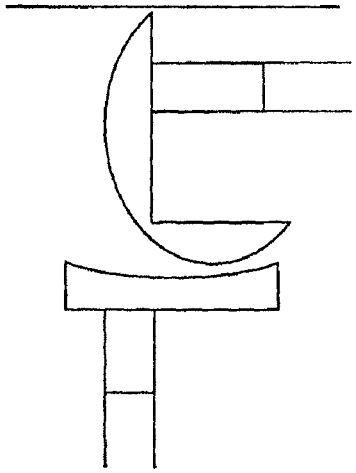
FIGS. 42A-42E shows mini-trial components, in accordance with some representative embodiments.
Figure 42E:
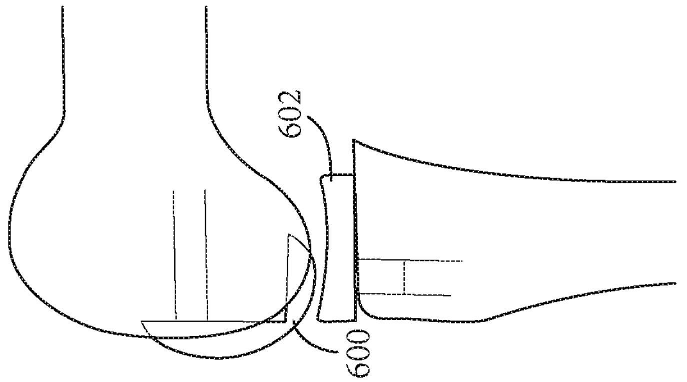
Figure 42D:
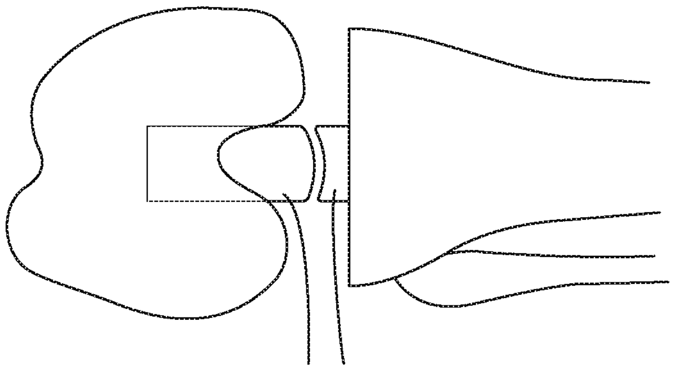
Figure 42C:
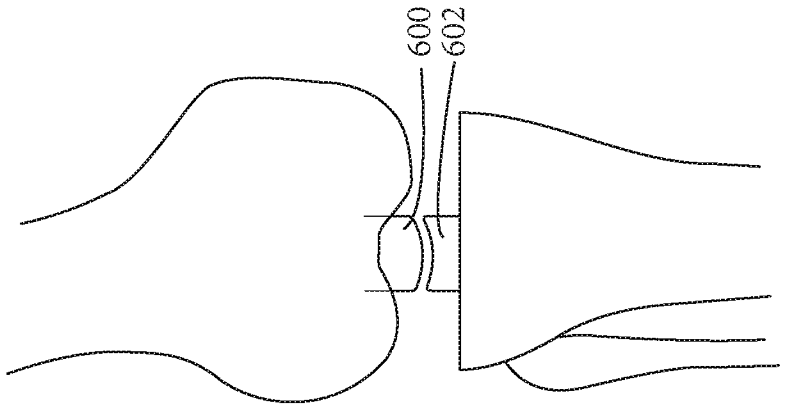
Figure 42B:
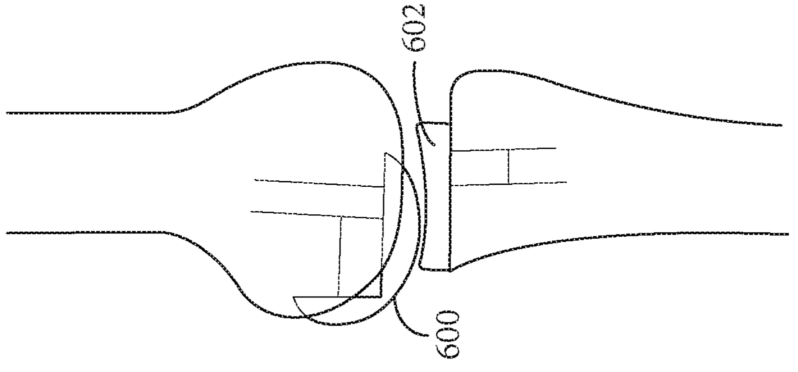

As shown in FIG. 42A, in another embodiment of the present invention mini-trial components or trial components which are smaller but shaped with identical (or substantially identical) thickness and radii to the actual knee arthroplasty implants, designed to fit in holes 101 of femoral IM rod 13 and 29 of tibial IM rod 14 and articulate in the center portion of the knee could be used to check alignment and ligament stability prior to placement of the actual final knee arthroplasty implants. This design of a centrally placed mini-knee arthroplasty implant system could become a stand-alone total knee arthroplasty. One advantage of this embodiment of the present invention is that the smaller instruments take up less space. The mini-trial femoral component could be designed with cutting surfaces or slots for making the chamfer cuts and other finishing cuts, thus eliminating the need for a chamfer cut block and L-plate 99 shown in FIGS. 30 and 31.

Additionally, while such trial components can comprise any suitable component or characteristic, FIGS. 42B-42E show that in some embodiments, the trail femoral implant 600 comprises a convex rounded surface that is configured to articulate against a concave or recessed surface of the trial tibial component 602. Additionally, in some embodiments, one or more components of the trial tibial component and the trial femoral component are selectively adjustable via any suitable adjustment mechanism to change a gap between the femur and tibia (e.g., distally, posteriorly, and/or otherwise).

Moreover, such trial components (centrally placed gap balancers and/or spacers) can be used with any other suitable component described herein, including, without limitation, with the spacers 500 discussed below.

Figure 43:
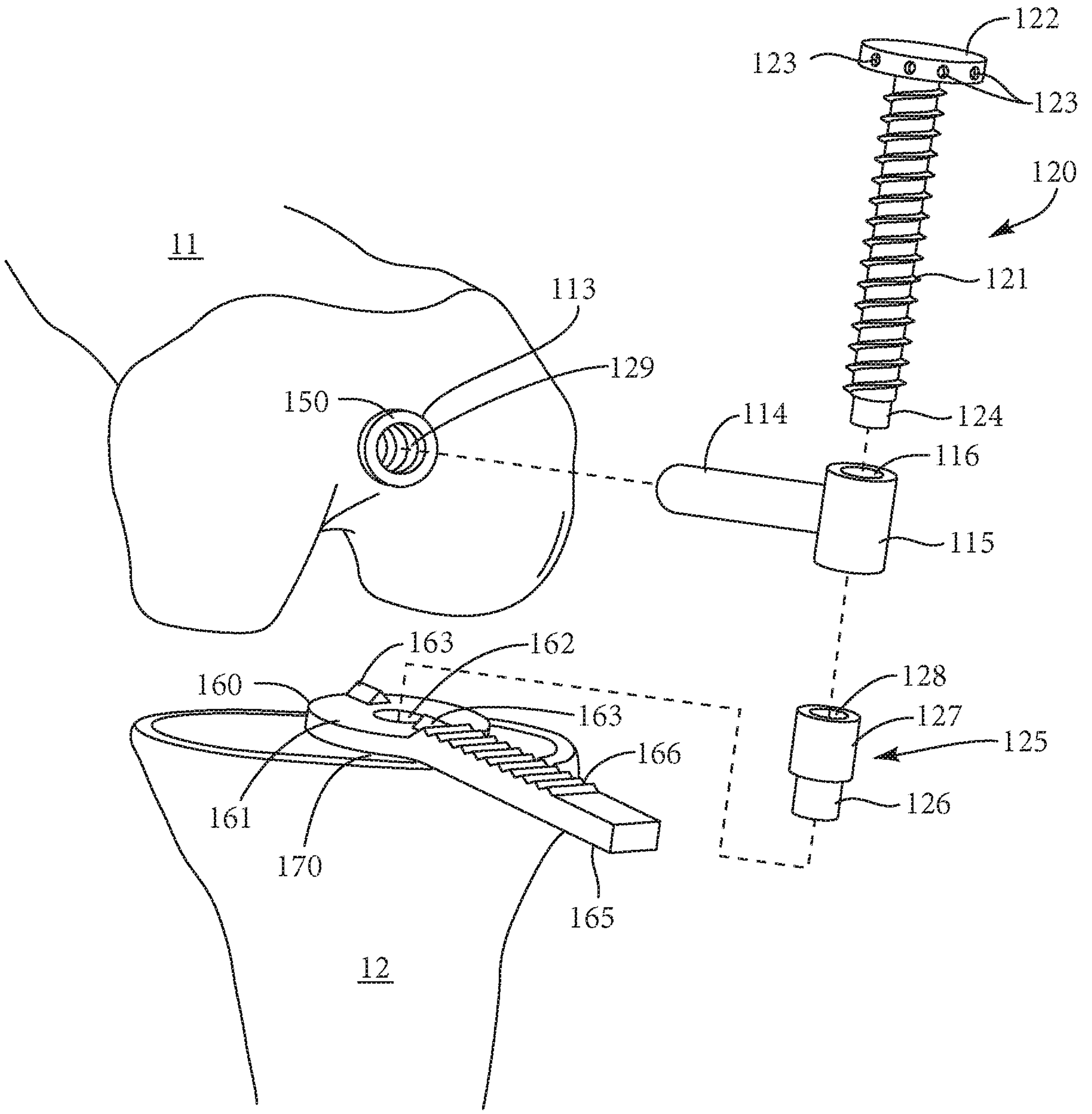
FIG. 43 shows an exploded view of an embodiment of the described assembly for resection in knee flexion.
Figure 44:
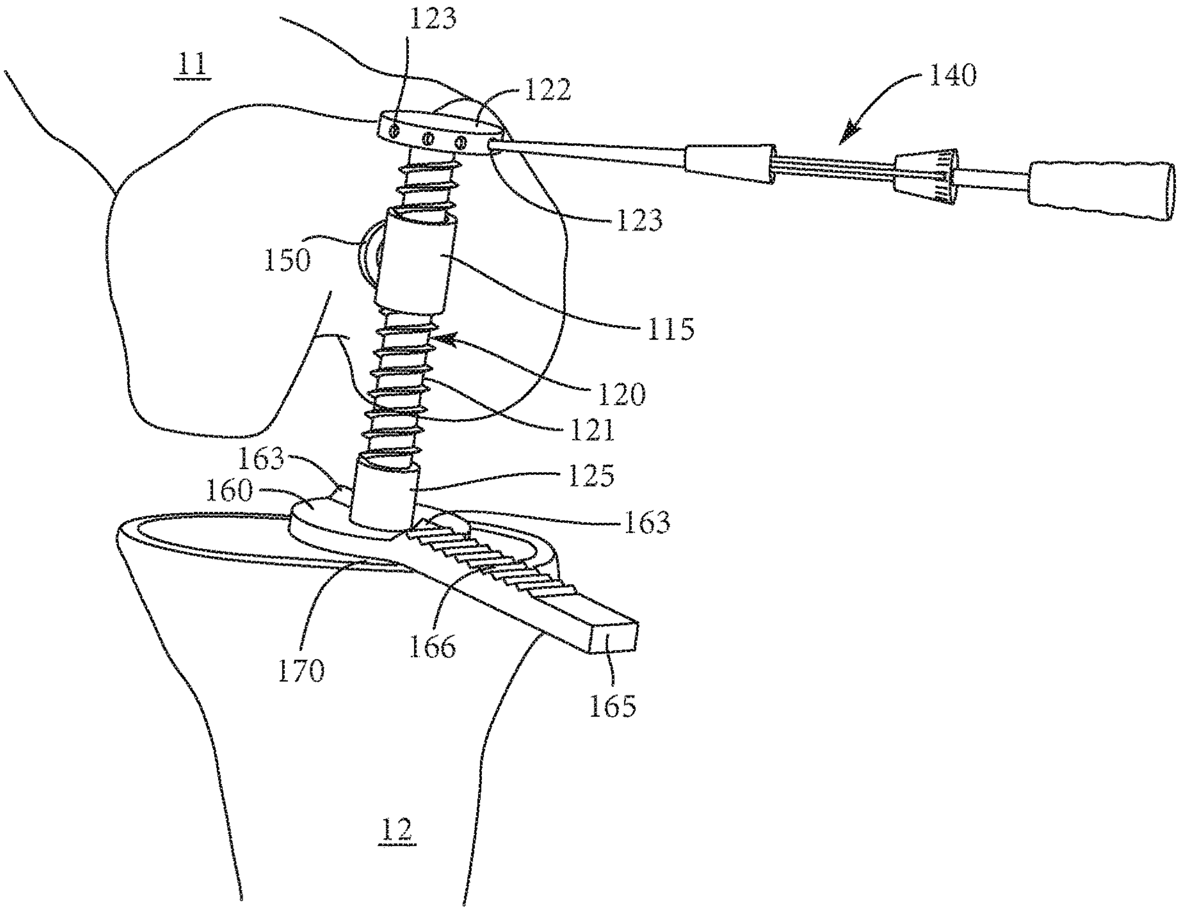
FIG. 44 shows a perspective view of the assembled embodiment of FIG. 43.
Figure 45:
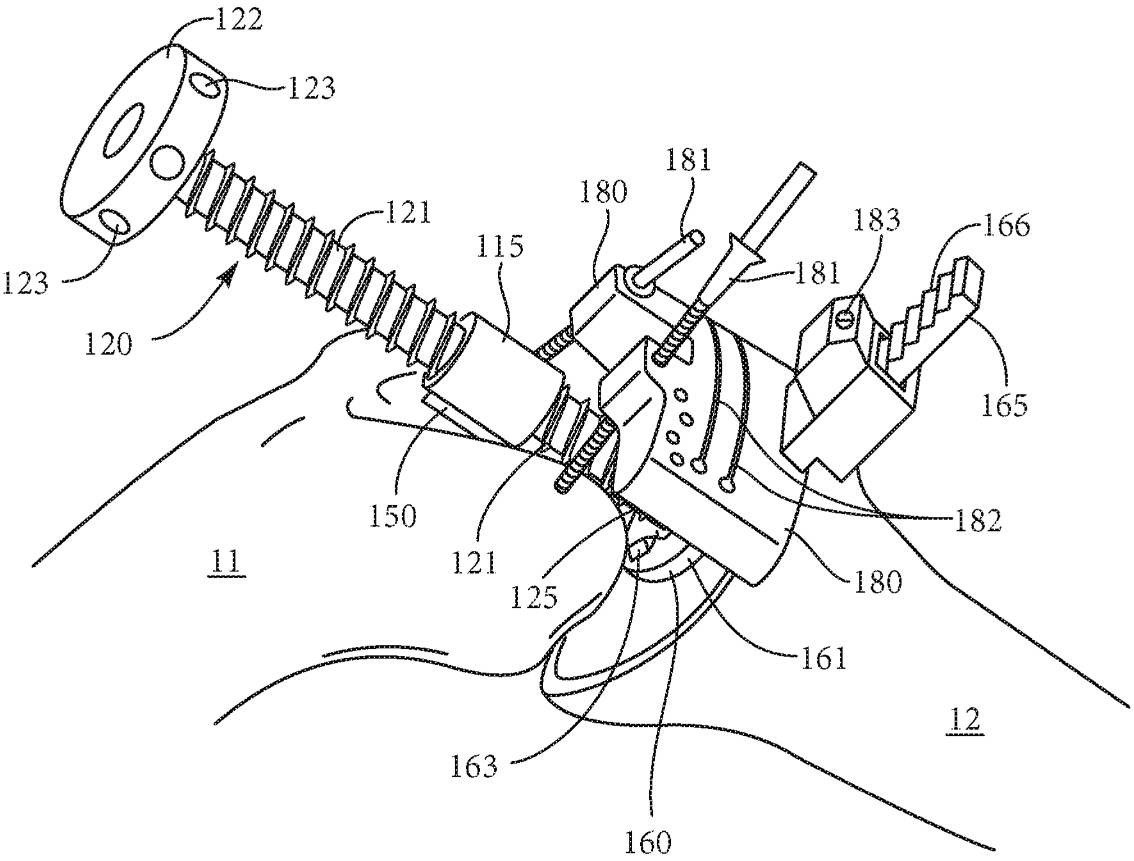
FIG. 45 shows a perspective view of the described assembly having the cutting block attached and secured, in accordance with a representative embodiment.
Figure 46:
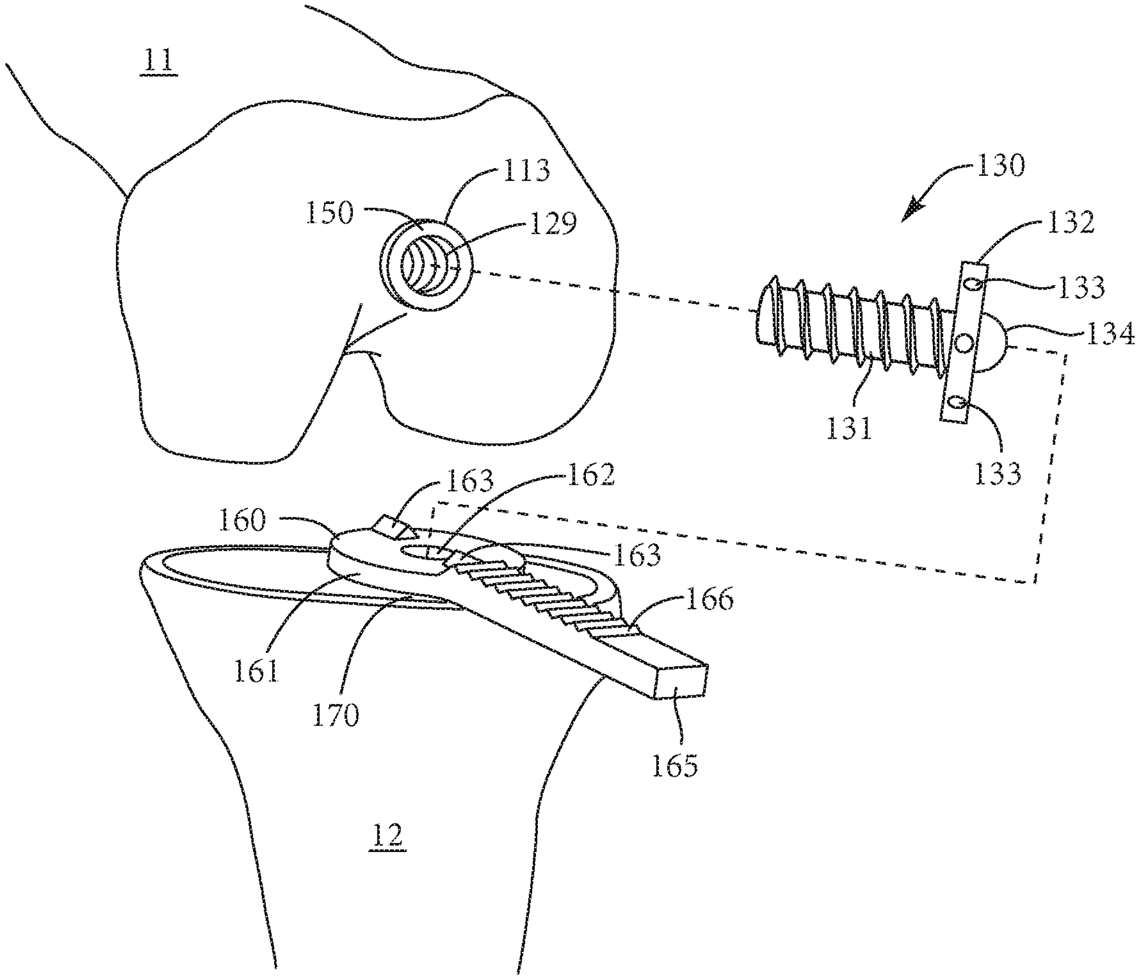
FIG. 46 shows an exploded view of an embodiment of the described assembly for resection in knee extension.
Figure 47:
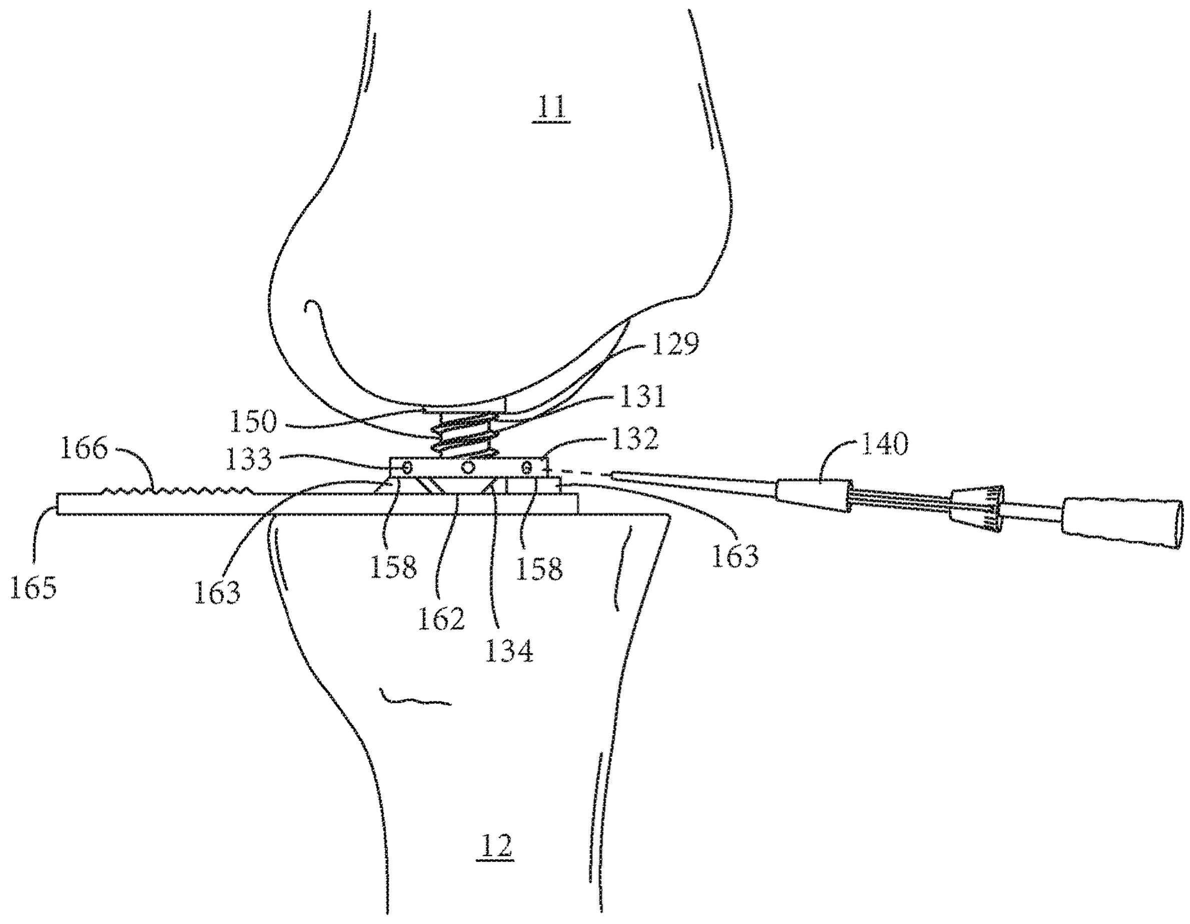
FIG. 47 shows a side view of the assembled embodiment of FIG. 46.
Figure 48:
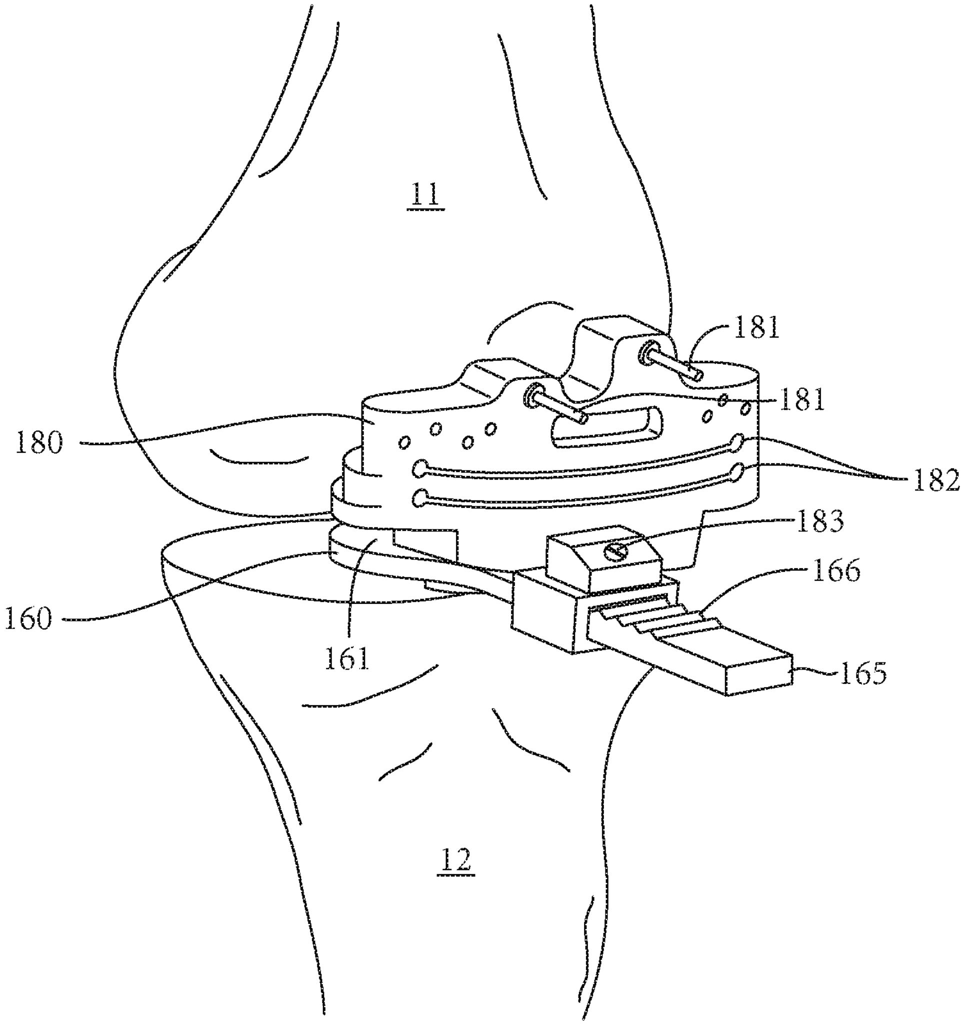
FIG. 48 shows a perspective view of a representative embodiment of the described assembly having the cutting block attached and secured.

Referring now to FIGS. 43-48, another embodiment of the present invention is shown. Specifically, FIGS. 43-45 illustrate an implementation of the current invention for resecting a patient's knee in flexion, and FIGS. 46-48 illustrate an implementation of the current invention for resecting a patient's knee in extension. The femoral mount 150 of the femoral IM rod 113 of each embodiment comprises a planar flange that is substantially inset, and flush with the insertion site of the femur 11. In one embodiment, a rongeur is used to prepare the distal femur for a 3/8 inch drill entry. Following insertion of the drill, a planar is then used to clear the remaining bone from the insertion site and to provide a recessed surface into which the femoral mount 150 is seated. A threaded opening 129 extends into the femoral mount 150 and provides a coupling attachment for an extension bolt 130, which includes a threaded shaft 131, a circular flange 132 with mounting holes 133, and a centralizing ball 134, as shown in FIGS. 46 and 47. Additionally, the threaded opening 129 provides a mounting channel into which a non-threaded post 114 of a threaded barrel 115 is inserted. The interaction between the non-threaded post 114 and the threaded opening 129 sufficiently retains the threaded barrel 115 within the femoral IM rod 113 and permits axial rotation of the threaded barrel 115 relative to the IM rod 113. Axial rotation is desirable to permit limited movement of the surgical tool relative to the natural physiology of the patient's knee. As such, the threaded barrel 115 is permitted to rotate and facilitate the natural alignment of the patient's knee throughout the tensioning process, as described below.

The threaded barrel 115 comprises a non-threaded post 114 perpendicularly coupled to an outer surface of a threaded opening 116. The threaded opening 116 extends through the threaded barrel 15 and provides a coupling attachment for a flexion bolt 120. The flexion bolt 120 includes a threaded shaft 121, a circular flange 122 with mounting holes 123, and a non-threaded tip 124. The threaded shaft 121 compatibly threads through the threaded opening 116 such that the non-threaded tip 124 exits and extends beyond the threaded barrel 115. The circular flange 122 is perpendicularly attached to the threaded shaft 121 opposite the non-threaded tip 124. The flange 122 is circular and generally disk-shaped having a plurality of mounting holes 123 evenly spaced around the circumferential edge of the flange 122. The mounting holes 123 are sized and configured to compatibly receive a torque wrench 140 or other device for turning the flexion bolt 120. In accordance with some embodiments (e.g., as illustrated in FIGS. 43 and 44, the described device allows for changes in varus-valgus angulation of the knee joint when the tibia and femur are tensioned with respect to each other when the knee is in flexion.

The current embodiment further comprises a tibial tensioning adapter 160. The tibial tensioning adapter 160 is stably supported by the tibial IM rod 170 and positioned generally perpendicular to the main shaft of the tibial IM rod 170. The tibial tensioning adapter 160 comprises a base member 161 and a resection block guide 165. The base member 161 is generally planar and disc-like, having a centrally located opening 162 that extends into the main shaft of the tibial IM rod 170. A bushing 125 is further provided to compatibly seat within the opening 162. The bushing 125 comprises a post portion 126 having a first diameter, and a sleeve portion 127 having a second diameter and an opening 128. The diameter of the post portion 126 is selected to compatibly insert within the opening 162 of the base member 161, while the diameter of the sleeve portion 127 is selected to be greater than the diameter of the opening 162. As such, the sleeve portion 127 rests on the upper surface of the base member 161 and is prevented from inserting into the opening 162. The opening 128 of the sleeve portion 127 is non-threaded and sized to compatibly receive the non-threaded tip portion 124 of the flexion bolt 120. Additionally, the interaction between the post 126 and the opening 162 does not utilize threads thereby allowing the bushing 125 to freely rotate within the opening 162 of the tibial tensioning adapter 160, and allowing the non-threaded tip 124 of the flexion bolt 120 to freely rotate within the opening 128 of the bushing 125. These freely rotating interactions prevent rigid structuring or position of the surgical tools thereby further permitting the natural physiology of the patient's knee to be maintained during the tensioning and resection processes. Thus, the flexion bolt 120, the threaded barrel 115, and the bushing 125 are combined with the femoral mount 150 and the tibial tensioning adapter 160 to apply tension to the patient's knee preparatory to performing the desired resections.

The base 161 further comprises a pair of spacers 163 forming a portion of the base member upper surface. The spacers 163 are generally pyramid shape and linearly configured on opposing sides of the opening 162. The spacers 163 are provided to create a gap between the circular flange 132 of the extension bolt 130 and the upper surface of the base member 161, as shown in FIG. 47. The pyramidal shape of the spacers 163 permits limited radial movement of the extension bolt 130 relative to the base member 161. This limited movement is desirable to accommodate the natural physiology of the patient's knee throughout the tensioning process, described below in connection with FIGS. 46 and 48.

The resection block guide 165 is fixedly coupled to an edge surface of the base member 161 and extends outwardly therefrom. The block guide 165 is generally aligned with the spacers 163 and positioned to extend outwardly from the anterior surface of the knee. The block guide 165 further comprises a plurality of notches 166 occupying an upper surface of the guide 165. The notches 166 span a portion of the upper surface and provide a coupling attachment for a resection block 180, as shown in FIGS. 45 and 48. The notches 166 further provide a plurality of reference points or positions by which to gauge the position of the resection block 180.

Referring now to FIG. 44, an embodiment of the assembled invention is shown. Once the surgical device is assembled, a torque wrench 140 is inserted into a hole 123 of the circular flange 122 and the flexion bolt 120 is rotated. Alternatively, in one embodiment the flexion bolt 120 is initially rotated by hand until the femur 11 begins to lift away from the tibia 12. The torque wrench 140 is then utilized to further rotate the flexion bolt 120 to a desired tension. This will typically result in a final tension of about 10-20 in/lbs. The amount of tension will differ for each patient based on individual physiology, injury, and ligament viscoelasticity of the knee. Once the final tension in flexion has been attained, the final amount of tension placed on the ligaments in is recorded for future reference.

Figure 44A:
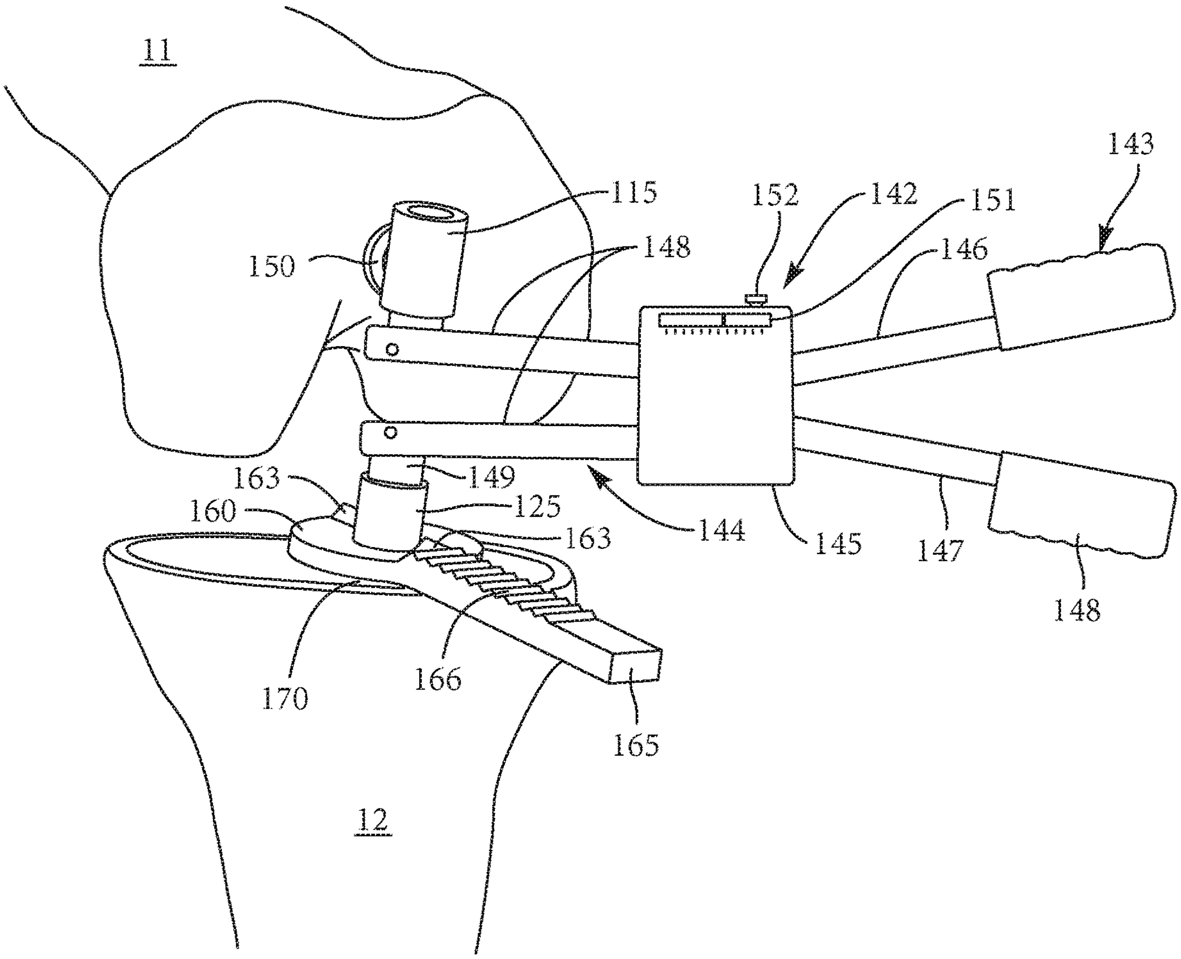
FIG. 44A shows a perspective view of a representative embodiment of the described assembly having a ratcheting device in place of the flexion bolt.

Referring now to FIG. 44A, an embodiment of the assembled invention is shown. In this embodiment, the flexion bolt 120 is substituted with a ratcheting device 142. The ratcheting device 142 generally comprises a handle portion 143, a biasing portion 144, and a gear box 145. The biasing portion 144 of the ratcheting device 142 is interposed between the threaded barrel 115 and the bushing 125. The handle portion 143 is then actuated to cause the biasing portion 144 to lift the femur 11 away from the tibia 12. The gear box 145 converts the motion, or actuation of the handle portion 143 to change the position of the biasing portion 144 and separate the knee joint.

The handle portion 143 may include any configuration whereby a physician may manipulate the handle portion 143 to actuate the biasing portion 144 of the device 142. For example, in one embodiment the handle portion 143 comprises a pair of opposing levers 146 and 147, each having a grip 148 at a distal end and extending into the gear box 145 at a proximal end. The biasing portion 144 of the device 142 is actuated by gripping the handle portion 143 and squeezing, such that the pair of opposing levers 146 and 147 is brought to a proximal position. The action of the opposing levers 146 and 147 manipulates the gear box 145 causing the biasing portion 144 to move away from a proximal position. Additionally, in one embodiment the gear box 145 includes a release for returning the biasing portion 144 to a proximal position.

In another embodiment, the handle portion 143 comprises a single shaft having a handle at the distal end, and extending into the gear box 145 at the proximal end. In this embodiment, the biasing portion 144 of the device 142 is actuated by rotating the handle portion 143 in a clockwise or counterclockwise direction. The rotating action of the handle portion 143 manipulates the gear box 145 causing the biasing portion 144 to move away from, or towards a proximal position. In one embodiment, the gear box 145 further includes a pawl or other device for maintaining the biased position of the biasing portion 144 during use. As such, a physician may actuate the device 142 to separate the knee to a desired position or tension, and then maintain the tension hands-free.

The biasing portion 143 may include any configuration capable of mounting into the threaded barrel 115 and the bushing 125. For example, in one embodiment the biasing portion 143 includes a pair of jaws 148 having a first end for engaging the threaded barrel 115 and the bushing 125, and having a second end extending into the gear box 145. In another embodiment, the first end further includes a jointed connector 149 for engaging the threaded barrel 115 and the bushing 125. The jointed connector 149 permits the pair of jaws 148 to separate the knee joint, yet provide limited movement of the knee joint to accommodate the natural physiology of the patient's knee throughout the tensioning process.

The gear box 145 may include any configuration of gears compatible with the handle portion 143 and the biasing portion 144 to achieve controlled separation of the knee joint. The gear box 145 may also include any means for limiting or measuring the tension placed on the knee joint. For example, in one embodiment the gear box 145 further comprises a tension meter 151 whereby the tension placed on the knee joint, by the ratcheting device, 142 is displayed. In another embodiment, the gear box 145 further comprises an adjusting screw 152 whereby the maximum allowed tension of the ratcheting device 142 is set. In this embodiment, a physician adjusts the adjusting screw 152 to a desired tension. Once set, the physician actuates the ratcheting device 142 to separate the knee joint. When the desired tension is achieved, further tensioning by actuation of the ratcheting device 142 is prevented, thus maintaining the desired tension for the knee. While the apparatus shown in FIG. 44A can perform any suitable function, in some embodiments, FIG. 44A shows that the ratcheting device 142 (and/or any other suitable device) allows for changes in the varus-valgus angulation between the tibia 12 and the femur 11 to occur when the two bones are in tension with respect to each other (e.g., when the knee joint is in flexion and/or extension).

Referring now to FIG. 45, the resection block 180 is attached to the resection block guide 165 and slid into position against the anterior surface of the femur 11. The resection block 180 is secured to the resection block guide 165 by tightening a set screw 183 against the notches 166 of the guide 165. The resection block 180 is then secured to the femur 11 via a plurality of screws 181. Once the resection block 180 is secured in position, the flexion bolt 120 is removed from the surgical tool assembly and the cutting guides 182 of the resection block 180 are used to resect the exposed distal surfaces of the lateral and medial condyles.

Referring now to FIGS. 46-48, an implementation of the current invention is provided for operation in knee extension. Referring to FIG. 46, the extension bolt 130 is shown prior to being interposed between the femoral mount 150 and the tibial tensioning adapter 160. The extension bolt 130 generally comprises a threaded shaft 131, a circular flange 132 and a centralizing ball 134. The threaded shaft 131 is configured to compatibly thread within the threaded opening 129 of the femoral mount 150. The circular flange 132 is perpendicularly attached to the threaded shaft 131 and interposed between the threaded shaft 131 and the centralizing ball 134. The flange 132 is disk shaped having a plurality of mounting holes 133 evenly space around the circumferential edge of the flange 132. The mounting holes 133 are sized and configured to compatibly receive a torque wrench 140 or other device for turning the extension bolt 130.

The centralizing ball 134 comprises a hemi-spherically shaped surface that is sized and configured to partially insert within opening 162 of the tibial tensioning adapter 160. As such, the centralizing ball 134 partially engages the opening 162 yet remains sufficiently free to provide axial rotation between the femur 11 and the tibia 12. The interface between the centralizing ball 134 and the opening 162 further ensures accurate alignment of the femoral mount 150 with the tibial tensioning adapter 160. Radial rotation is further provided to the femur 11 and the tibia 12 due to the interface 158 between the circular flange 132 and the spacers 163, as previously discussed and as shown in FIG. 47. Thus, the extension bolt 130 provides both alignment and limited free adjustment to the femur 11 and tibia 12 during the tensioning and resection procedures.

In one embodiment, the extension bolt 130 is first coupled to the femoral mount 150 by threading the threaded shaft 131 into the threaded opening 129 of the femoral mount 150, with the knee in flexion, as shown in FIG. 46. The extension bolt 130 is maximally inserted into the threaded opening 129 to minimize the distance between the femur 11 and the tibia 12. The knee is then brought into extension and the centralizing ball 134 is inserted into opening 162, as shown in FIG. 47. A torque wrench 140 is then utilized to rotate the extension bolt 130 and apply tension the knee. The torque wrench 140 is inserted into a hole 133 of the circular flange 132 and turned to gradually remove the extension bolt 130 from the threaded opening 129. In one embodiment, the physician immobilizes the resection block guide 165 to prevent rotation of the tibia 12 during rotation of the extension bolt 130. The physician continues to turn the extension bolt 130 until the desired tension is placed on the ligaments of the knee. Alternatively, a ratcheting device (see FIG. 44A) may be used with the knee in extension to place the desired tension on the ligaments of the knee. In one embodiment, the final tension in extension is equal to the final tension in flexion. In another embodiment, the final tension in extension is different than the final tension in flexion.

As illustrated in FIGS. 46 and 47, some embodiments of the described systems are configured to allow the femur 11 and tibia 12 of a knee joint to rotate with respect to each other in order to change a varus-valgus angulation of the knee joint when the knee joint is under tension. Thus, in some embodiments, the described systems allow for proper tension, gap balancing, and varus-valgus angulation to be achieved relatively easily and quickly during full or partial knee replacement.

Referring now to FIG. 48, the resection block 180 is attached to the resection block guide 165 and slid into position against the anterior surface of the femur 11, as discussed above in connection with FIG. 45. Once positioned, the resection block 180 is secured to the femur 11 with screws 181 and the anterior surfaces of the lateral and medial condyles are resectioned.

In another embodiment, since the guide assembly is fixed rigidly to the bone and left in place during the essential steps of the knee preparation, computer assisted guides are attached to the guide assembly instruments thus facilitating computer assisted total knee replacement. In other embodiments of the present invention, the guide assembly instruments are modified for use in a partial or uni-compartmental knee arthroplasty procedure.

In some embodiments, the Guide Assembly Instruments can be modified for use with short IM rods or a tibial platform instead of an IM rod for extramedullary knee preparation.

In some embodiments, the Guide Assembly holds a patient's leg in place. This decreases the need for medical assistants to hold the patient's leg.

Figure 49:
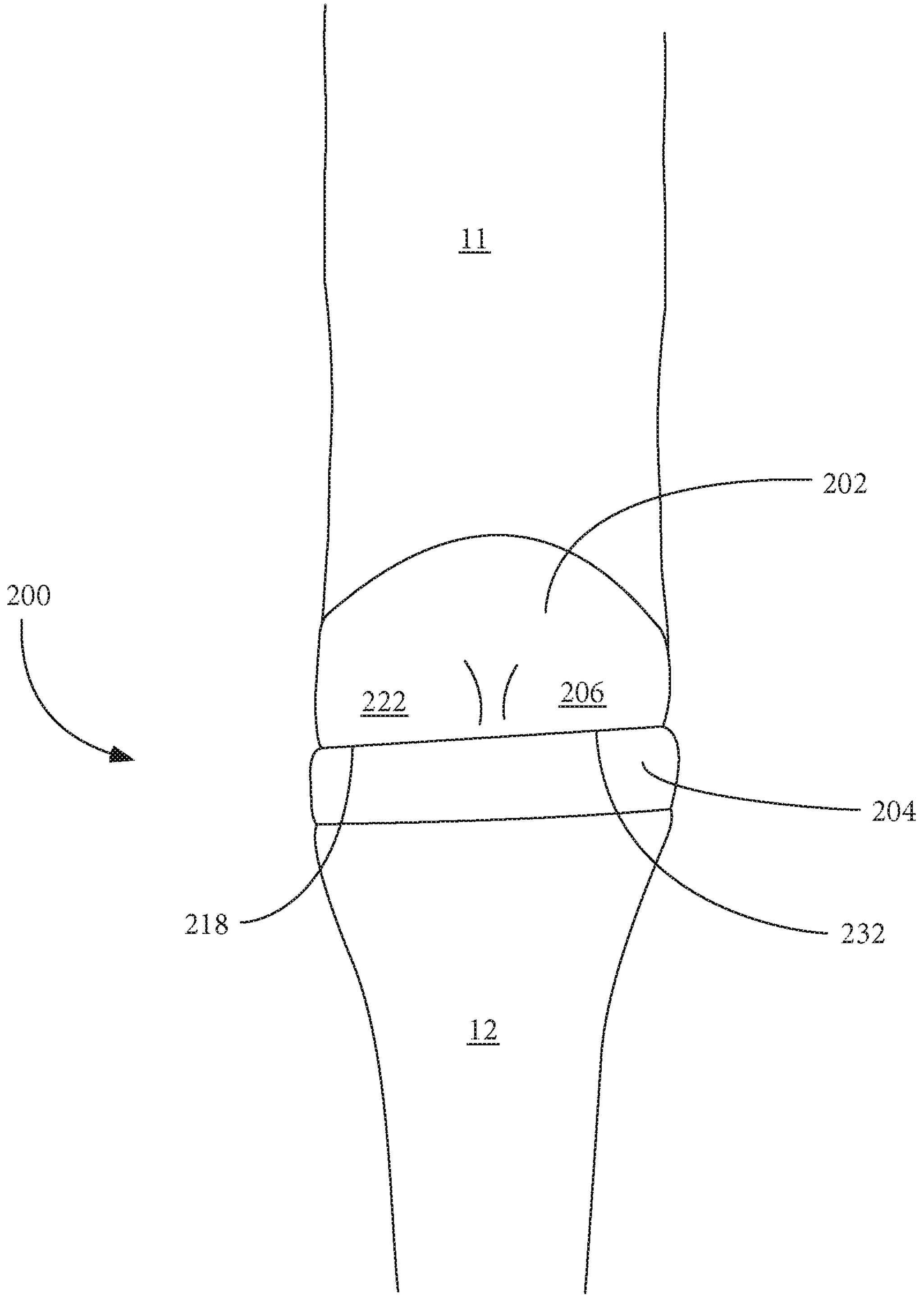
FIG. 49 shows a perspective front view of a resectioned knee having been fitted with a knee prosthesis, in accordance with a representative embodiment.
Figure 50:
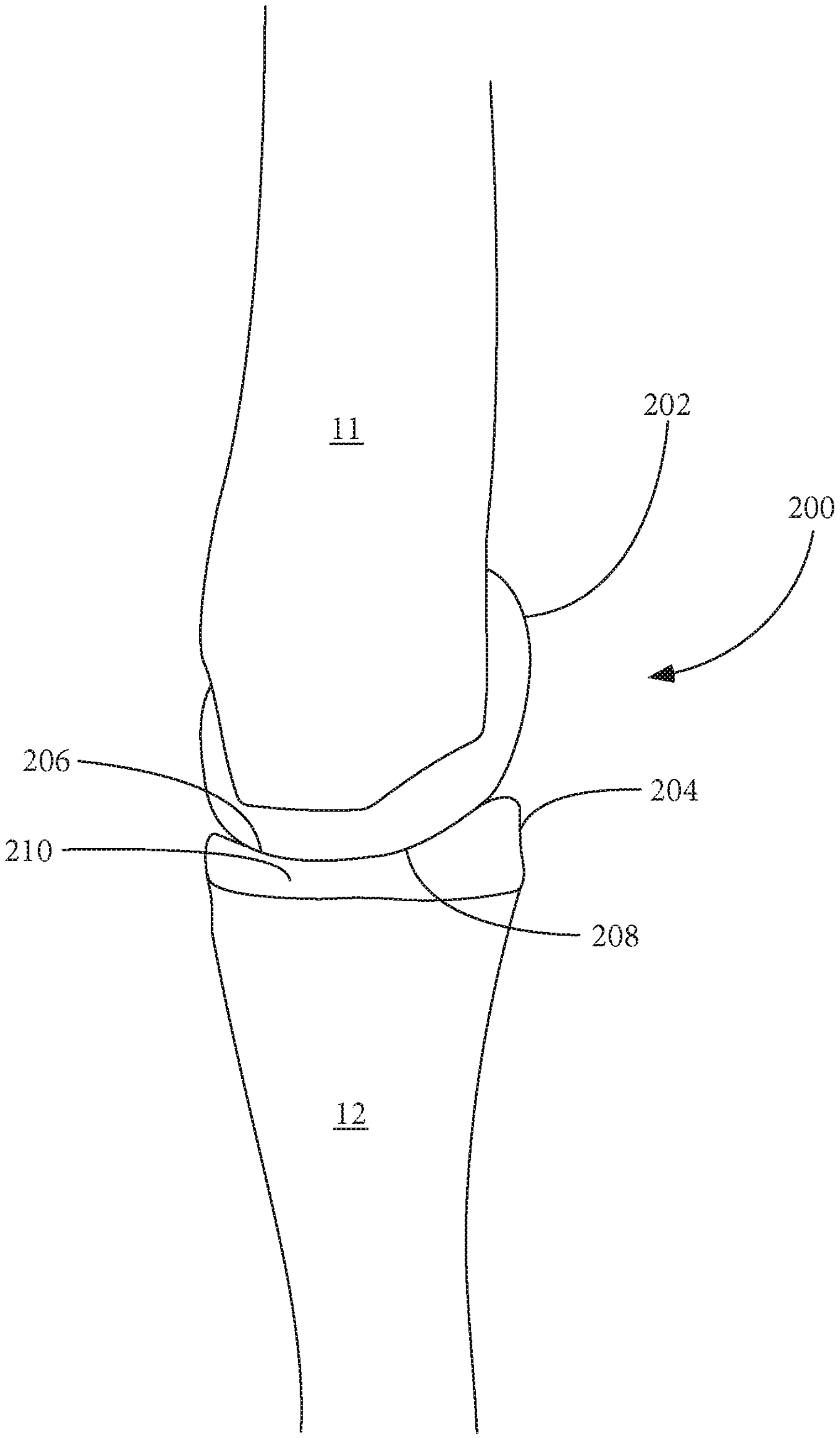
FIG. 50 shows a side view of the embodiment of FIG. 49.

Following a completed resection of the patient's knee joint, the resectioned portions of the femur 11 and the tibia 12 are replaced by a knee prosthesis or implant 200, such as shown in FIGS. 49 and 50. The knee implant 200 generally comprises a femoral component 202 and a tibial component 204. Although the instruments of the invention can be used with any type of knee prosthesis 200, the instruments are particularly well-suited for use in accurately resecting the knee for receipt of a knee prosthesis that employs a constant radius throughout the primary range of flexion, such as Wright Medical Technology, Inc.'s ADVANCE® medial pivot knee implant. The features and characteristics of constant radius knee prostheses are well known to those of skill in the art, but have not previously been used with knee tensioning resection instruments. As will be described below, a synergistic and previously unappreciated effect is obtained by using the tensioning instruments in combination with prior art constant radius knee implants. It is anticipated that the end result of this synergistic combination will be greater overall accuracy in the implantation of constant radius knee implants, with resulting improvements in clinical outcomes.

One of the benefits of a properly designed and implanted constant radius knee prosthesis is that it provides the patient with constant ligament tension throughout the primary range of flexion. As discussed herein, the use of the instruments of the invention to resect the knee while under optimum tension helps insure accurate placement of the knee implant components. The combined use of tensioning instruments and constant radius knee implants improves the likelihood of achieving constant ligament tension throughout the primary range of flexion. Various embodiments of knee implants that incorporate a constant radius are discussed in the following prior art documents, which are incorporated herein by reference: U.S. Pat. Nos. 7,261,740; 6,013,103; 6,013,103; 5,824,100; 5,330,533; 5,326,361; 5,314,482; 5,219,362; 5,133,758; 4,085,466; German Patent Application 3,314,038 A1.

Figure 51:
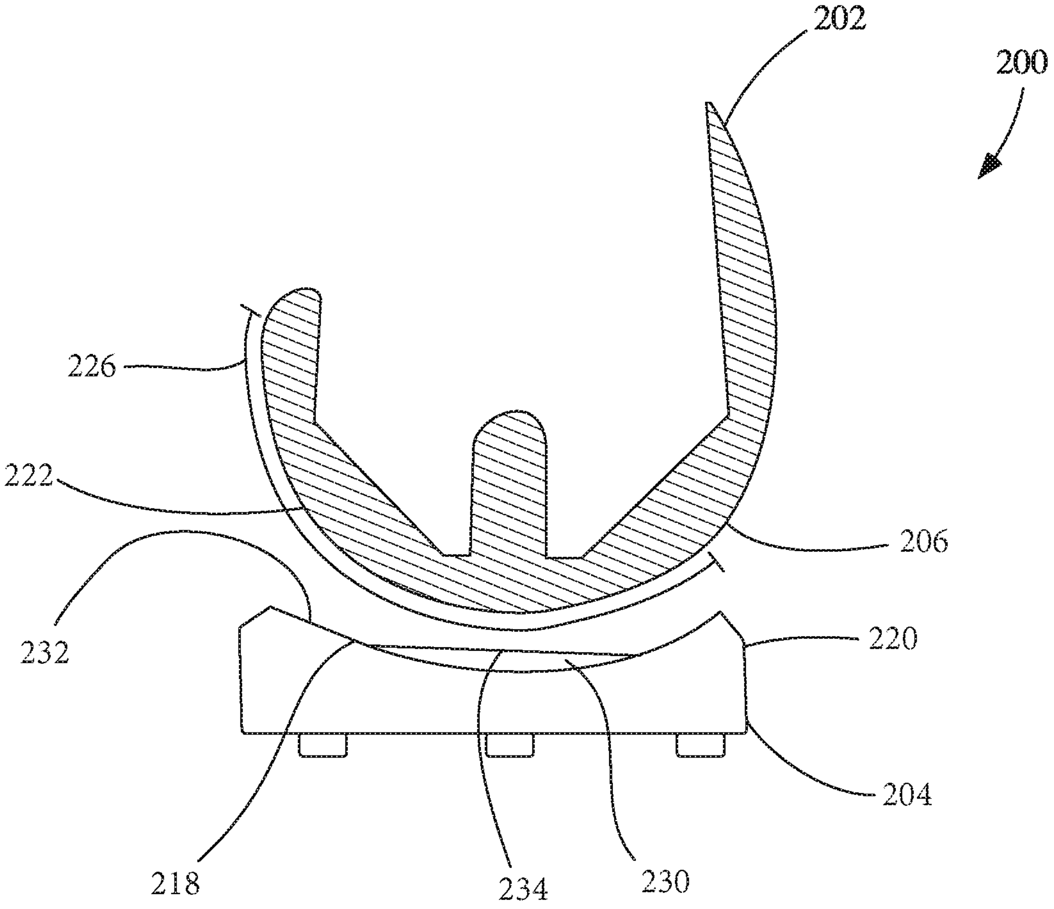
FIG. 51 shows a partially cross-sectioned view of a representative embodiment of a knee prosthesis.

In the prior art ADVANCE® Medial Pivot knee implant, the femoral component 202 has a spherical condyle 206 on the medial side. As indicated in FIG. 51, in the sagittal or A-P plane, the medial femoral condyle 206 has a constant radius 226 over at least the primary range of flexion, which extends from about 0 degrees in extension to about 90 degrees in flexion, depending on the patient. The lateral femoral condyle 222 also has an A-P constant radius 226 throughout the primary range of flexion. The medial side of the tibial base 204 of the ADVANCE® Medial Pivot knee has a shallow spherically concave bearing surface 232, which is sized to closely receive the medial femoral condyle 206 in a ball-and-socket manner. The lateral side of the tibial base 204 is generally in the form of an elongated arcuate trough 230. These features allow the medial femoral condyle 206 to pivot in the medial tibial bearing 232 during flexion, while simultaneously permitting the lateral femoral condyle 222 to translate posteriorly in the lateral tibial bearing 218. This action is designed to mimic the function of the natural knee, in which the medial femoral condyle exhibits less rollback than the lateral condyle during motion. Features and characteristics of the ADVANCE® Medial Pivot knee are discussed in greater detail in U.S. Pat. Nos. 5,964,808 and 6,013,103, which are incorporated herein by reference. Although the ADVANCE® Medial Pivot knee implant is an exemplary implant design for optimizing and complementing the use of the tensioning instruments of the invention, other constant radius knee implant designs can be used to similar or equal effect.

One of the drawbacks of prior art knee instruments is that overstuffing or under filling the joint sometimes occurs, with resulting tightness or laxity, respectively, in the ligaments. As discussed above, use of the tensioning instruments to resect with the knee tensed in the extended position allows the user to make a balanced extension gap resection when compared with the tensed resections made with the knee previously positioned in flexion. The resection cuts are made off of a single reference point, the single reference point being the desired amount of tension. The use of equal flexion and extension gaps automatically balances the mid-flexion gap at all points in between. By then implanting a constant radius knee implant onto the resectioned knee, the surgeon effectively transfers the optimum tension obtained by the tensioning instruments to the constant radius knee implant, resulting in a stable, smoothly functioning knee throughout at least the primary range of flexion. In mechanical terms, the tensioning technique preloads the bearing, the bearing being the constant radius knee implant.

In contrast, if a conventional J-curve or varying radius knee implant is used with the tensioning technique, rather than a constant radius implant, it becomes necessary to vary the cuts instead of using an equal flexion and extension gap. The use of a varying radius knee implant thus necessarily complicates the process and the use of the instruments.

In addition to the aforementioned components and characteristics of the described systems and methods, in some embodiments, the described systems and methods are configured to be used with one or more robots, robotic arms, laparoscopic devices, and/or other automated devices. Indeed, in accordance with some embodiments, the described systems and methods are used to provide a desired tension to a knee joint and an automated device (e.g., the MAKO™ robotic arm produced by Stryker of Kalamazoo, MI USA and/or any other suitable robotic and/or automated assembly) is then used to resect one or more portions of bone in the knee joint. In such embodiments, the automated device can make the cuts in any suitable manner. Indeed, in some embodiments, the automated device uses one or more cutting guides 54, femoral cut guide portions 90, flexed knee cutting guide assemblies 52, and/or any other suitable components that are configured to direct a cutting tool. In some other embodiments, however, the automated device is configured to make desired cuts in the knee joint without the use of the described cutting guides or guide/resection blocks.

As another example of a suitable modification, some embodiments of the described apparatuses and systems are configured to maintain tension in one or more ligaments of the knee joint throughout a range of motion of the joint. In this regard, in some embodiments, one or more components of the described systems and methods are changed between adjusting tension in the knee joint in flexion (e.g., as shown in FIGS. 7-15, 33-37, and 43-45) and in extension (e.g., as shown in FIGS. 9-19, 38-40, and 46-48).

In some other embodiments, however, the described systems and methods comprise one or more articulated connectors that comprise part of and/or that extend between a femoral component (e.g., the femoral IM rod 13, the femoral mount 15, the secondary femoral mount 100, the opening 129 in the femoral mount, and/or any other suitable femoral component), a tibial component (e.g., the tibial IM rod 14, the tibial mount 23, the plateau flange 28, the tibial tensioning adapter 160, the hole 162 in the tensioning adapter, and/or any other suitable tibial component), the tensioning assembly (e.g., the flexion bolt 30, the extension bolt 96, the gauge block 76, the bushing 33, the valgus adapter member 110, the flexion bolt 120, the threaded barrel 115, the bushing 125, the ratcheting device 142, the extension bolt 130, and/or any other suitable component that is used to increase and/or decrease tension in a knee joint), and/or any other suitable component of the described systems and methods).

Figure 52A:
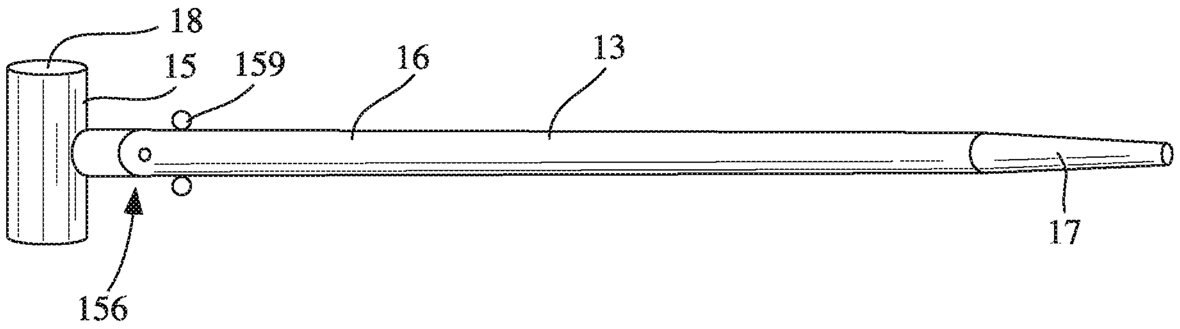
FIGS. 52A-52C illustrate some representative embodiments of articulated connectors.
Figure 52B:
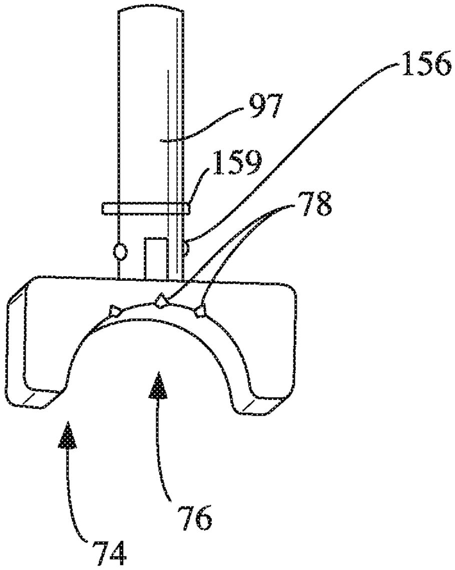
Figure 52C:
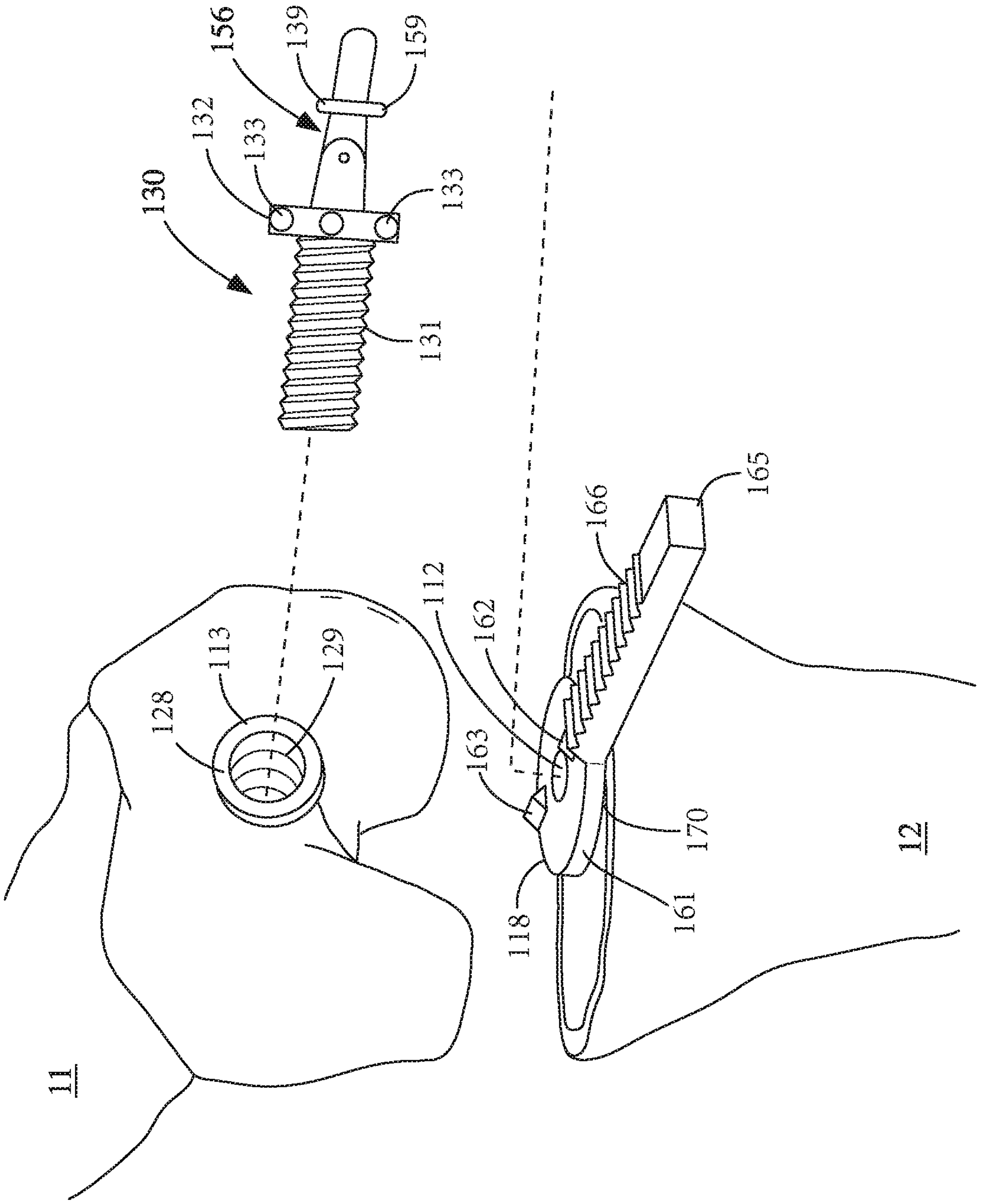

By way of non-limiting illustration FIG. 52A shows that, in some embodiments, the femoral IM rod 13 is configured to comprise a joint 156 that allows the femoral mount 15 to pivot so that a knee joint comprising such a rod can be moved through a range of motion without requiring different components to be used in extension and flexion. In another non-limiting illustration, FIG. 52B shows that, in some embodiments, the guide block 76 comprises a joint 156 that allows it to pivot so that a knee joint comprising such a block and a femoral mount 15 (e.g., as shown in FIG. 1) can be moved through a range of motion without requiring different components to be used in extension and flexion. In still another non-limiting illustration, FIG. 52C shows an embodiment in which the extension bolt 130 comprises a joint 156 that allows the bolt to pivot so that a knee joint comprising such a bolt and the tibial tensioning adapter 160 can be moved through a range of motion without requiring different components to be used in extension and flexion (e.g., an extension bolt and a flexion bolt).

Where the described systems and methods comprise one or more articulated connectors, the connectors can have any suitable component or characteristic. By way of example, the articulated connectors can comprise any suitable type of joint, including, without limitation, one or more pivot joints, ball joints, hinge joints, universal joints, prismatic joints, rotoide joints, and/or other suitable joints that allow the knee joint to move through a range of motion when such connectors are disposed in the joint and coupled to one or more components of the described apparatuses and systems. As another example, some embodiments of the articulated connectors comprise one or more stops (e.g., ridges, rings, protuberances, and/or other stops 159) that are configured to retain a sufficient amount of the connectors outside of the femur and/or tibia to allow a portion of each connector (and hence the knee joint comprising the connector) to move through a range of motion without undesirable impingement on another object (e.g., bone, a femoral component, a tibial component, etc.). In still another example, some embodiments of the articulated connectors comprise one or more detents, locks, locking mechanisms, limits, clamping mechanisms, and/or other position retaining mechanisms that allow the connectors to be selectively moved from and/or be retained in desired positions.

Bone Milling

With reference now to the described bone milling technology, some embodiments of the present invention relate to the use of instruments for guiding preparation of a knee for resection, as well as for guiding preparation of a knee for installation of an implant during an arthroplasty. In particular, some embodiments relate to a system for guiding a milling tool along a specific axis to provide an aperture of a desired depth.

Figure 53:
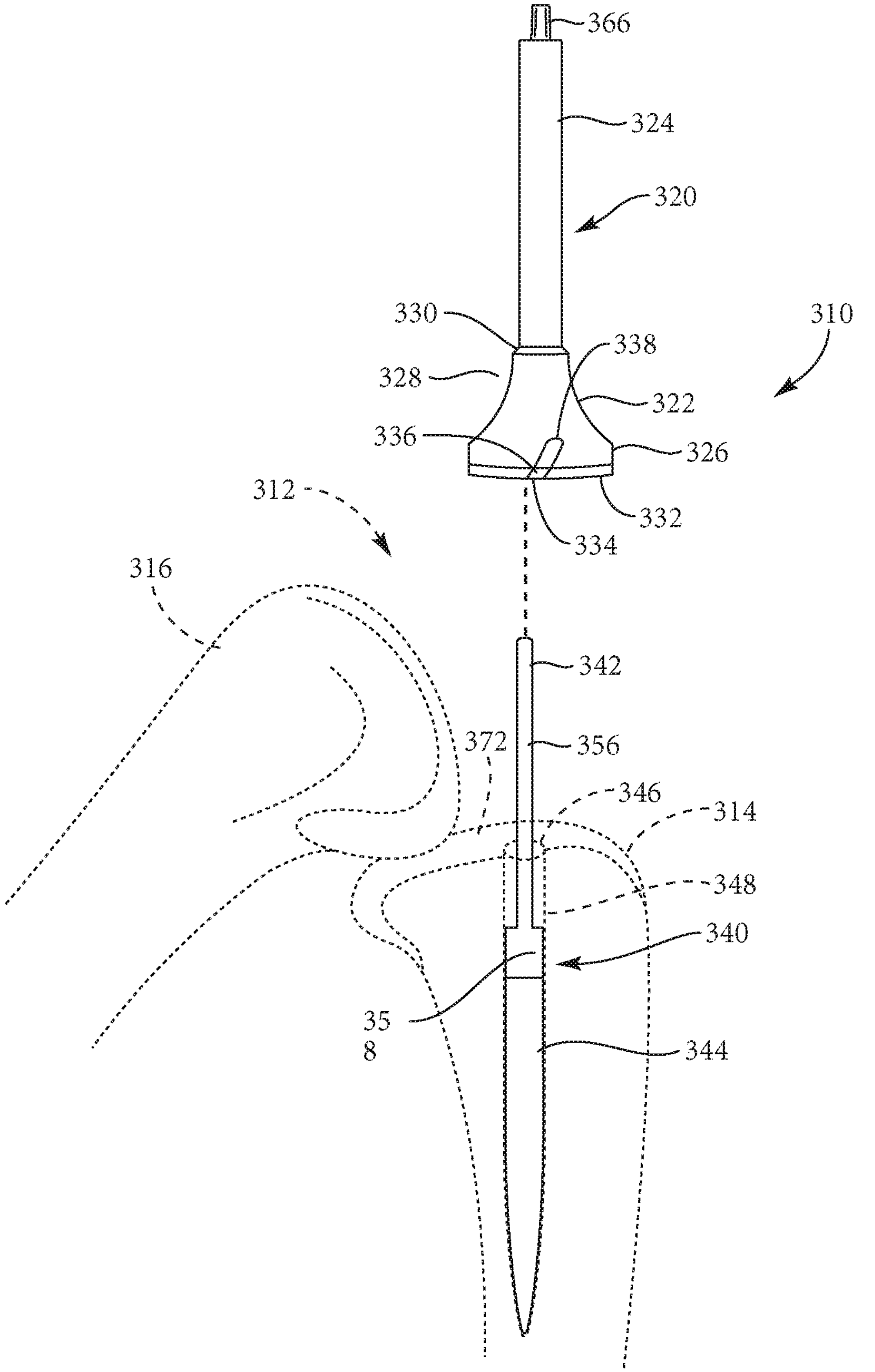
FIG. 53 is a side view of a representative embodiment of a bone milling system having a portion thereof being inserted into a knee, shown in phantom.

Referring now to FIG. 53, a perspective view of an implementation of the current invention is shown as positioned within a knee 312 in flexion, shown in phantom. The bone milling device 310 comprises a milling bit 320 and a guide rod 340. The bone milling device 310 generally comprises surgical metal materials that are compatible with surgical applications, such as surgical steel, titanium, aluminum, and alloys thereof. However, one of skill in the art will appreciate that other non-metallic materials, such as Teflon and nylon, may be incorporated into the current invention within the scope of the present disclosure. For example, in one embodiment a Teflon coating is applied to opposing surfaces of the bone milling device 310 to reduce friction.

Figure 54:
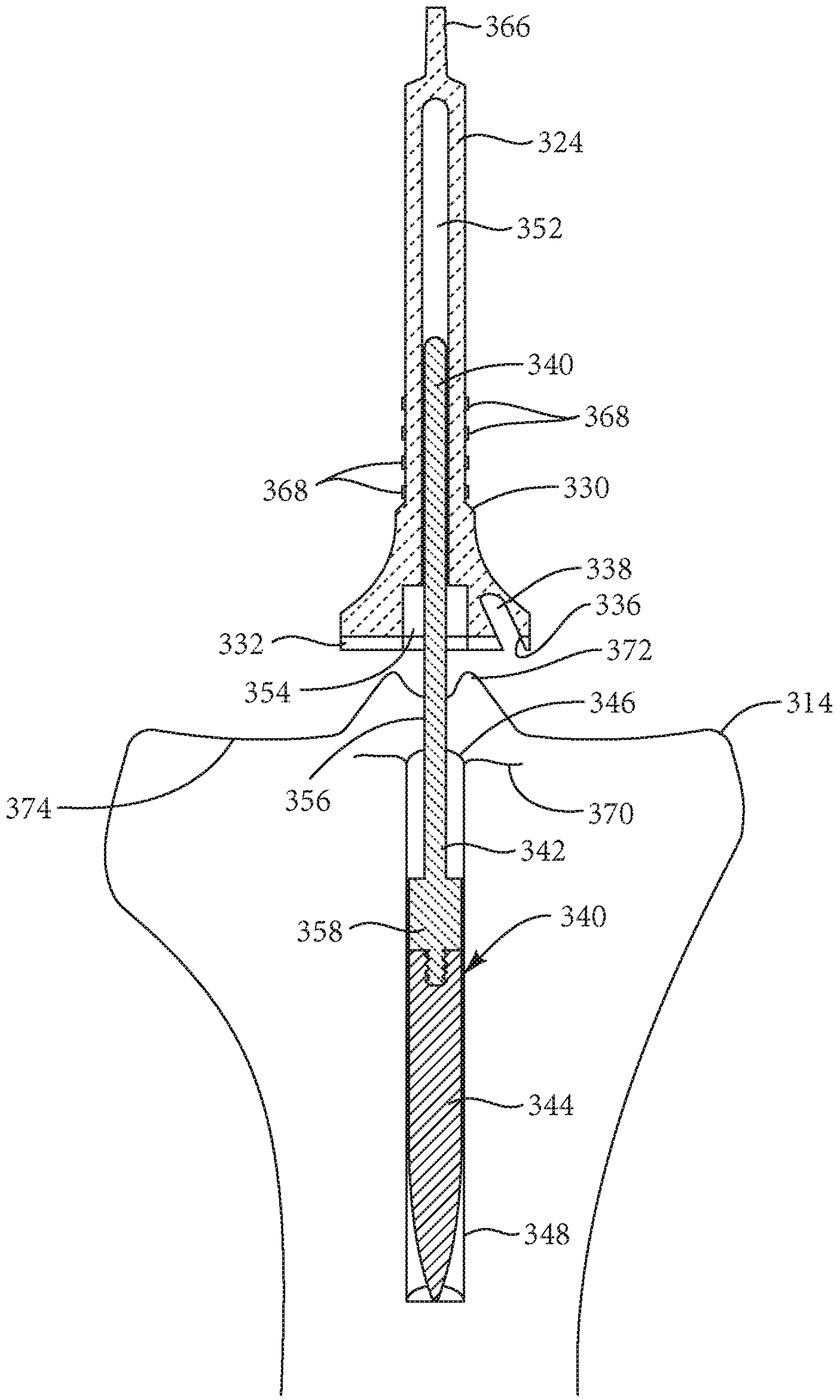
FIG. 54 is a cross-sectioned view of a representative embodiment of the present system prior to milling an aperture in the tibia.
Figure 55:
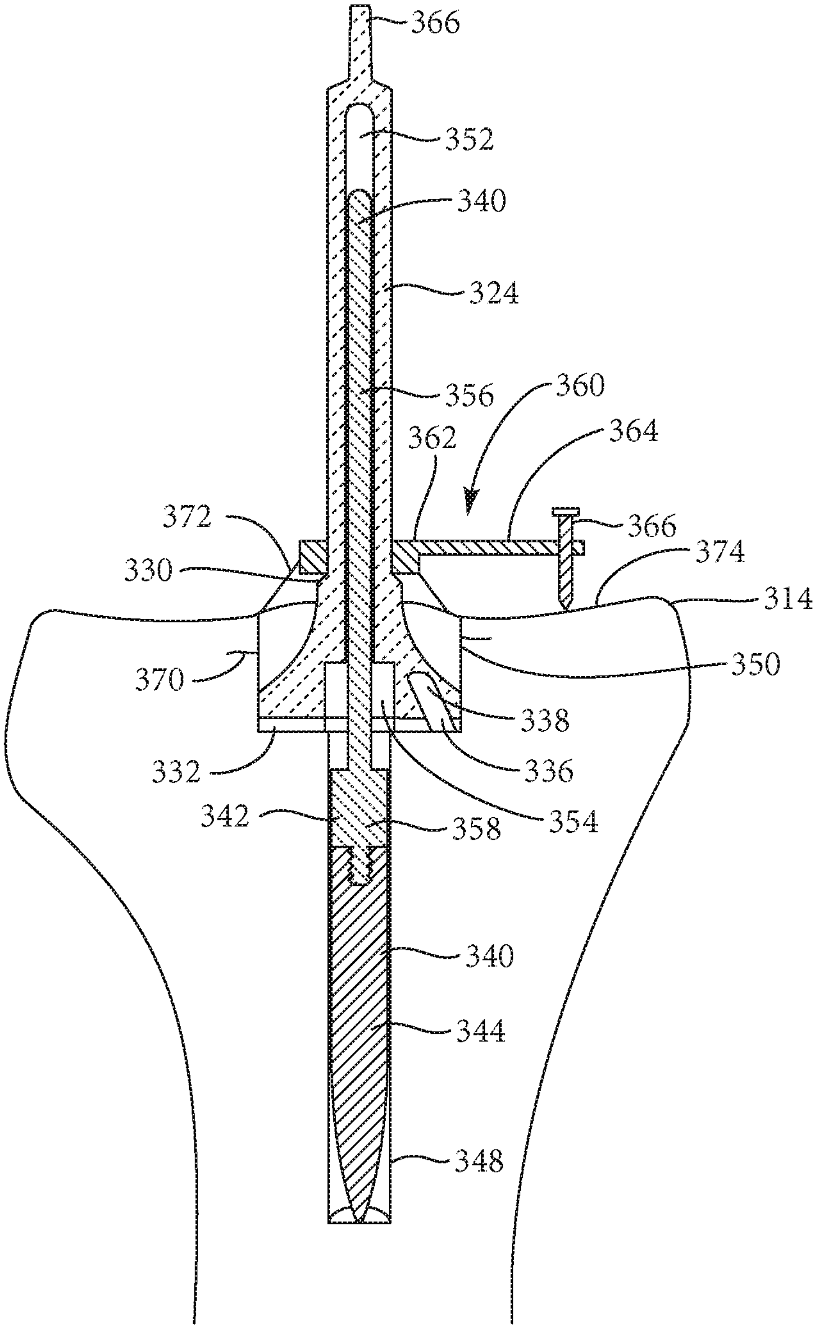
FIG. 55 is a cross-sectioned view of a representative embodiment of the present system following milling of the aperture, demonstrating use of a depth gauge, in accordance with a representative embodiment.

Referring now to FIGS. 53-55, the milling bit 320 comprises a cutting head portion 322 and a shaft portion 324. The cutting head portion 322 is generally bell-shaped having a wider base 326 and a narrower, tapered top 328 that joins the shaft portion 324. In some implementations of the current invention, a ledge or stepped surface 330 is interposed between the cutting head portion 322 and the shaft portion 324 to support a depth gauge 360, as shown in FIG. 55. The shaft portion 324 further comprises a shank 366 for coupling the milling bit 320 to a drill or other device for rotating the bit 320.

The cutting head portion 322 further comprises a removable blade 332. The removable blade 332 is generally disk shaped having a cutting edge 334 and a window 336. The cutting edge 334 is provided to cut through the bone to create the aperture 350, while the window 336 is provided to remove the cut bone debris from the aperture 350. In this manner, the aperture 350 is both cut and cleared by the milling bit 320. The cutting head portion 322 further includes a window 338 that aligns with the window 336 of the removable blade 332. As such, bone debris is entirely removed from the cutting head portion 322 of the milling bit 320 and does not interfere with the ability of the milling bit 320 to form the aperture 350.

The milling bit 320 further comprises a cavity 352 extending through the central core of the shaft portion 324 and the cutting head portion 322. The cavity 352 is closed on one end and includes an opening 354 in the cutting head portion 322 of the bit 320. The cavity 352 comprises a diameter that is adapted to rotatably receive a portion of the guide rod 340. The tolerance between the cavity 352 and the guide rod 340 permits the bit 320 to freely rotate around the guide rod 340 yet controls and limits the movement of the bit 320 relative to the axis of the guide rod 340. As such, the interaction between the cavity 352 and the guide rod 340 ensures that the angle of the aperture 350 is parallel to the angle of the guide rod 340.

The guide rod 340 is inserted or anchored within a portion of the bone 314 that is to receive the aperture 350. Typically, the bone 314 is predrilled to provide an access or opening 346 into the intramedullary (IM) canal 348 of the bone. The pre-drilling procedure is common to the area of orthopedic medicine. Following this procedure, a first end 344 of the guide rod 340 is inserted into the opening 346 and positioned within the IM canal 348 such that a portion of the second end 342 of the guide rod 340 extends outwardly from the opening 346.

In one embodiment, the first and second ends 344 and 342 of the guide rod 340 are threadedly coupled to form the guide rod 340. As such, the first end 344 of the guide rod 340 may threadedly receive a plurality of compatible surgical devices. For example, in one embodiment the second end 342 of the guide rod 340 is removed, following creation of the aperture 350, and replaced with another surgical instrument needed to complete the arthroplasty procedure.

The second half 342 of the guide rod 340 comprises a post portion 356 and a base 358. The base 358 is threadedly coupled to the first end 344 and generally comprises the same diameter as the first end 344. The post portion 356 extends outwardly from the base 358 and is substantially positioned exterior to the IM canal 348. As previously discussed, the diameter of the post portion 356 is selected and adapted to rotatably insert within the cavity 352 of the milling bit 320. In one embodiment the diameter of the base 358 is made greater than the diameter of the post portion 356 so as to increase the surface area of the guide rod 340 in contact with the IM canal, yet still provide the post portion 356 with a diameter compatible with the cavity 352. In another embodiment, the base 358 and the first end 344 further include fluted outer surfaces to enhance contact with the IM canal 348 and prevent rotation of the guide rod 340 within the IM canal 348.

The depth and positioning of the guide rod 340 within the IM canal is selected to permit the milling bit 320 to precisely cut the aperture 350 to a desired depth. The accuracy of the depth of the aperture 350 is a crucial element of any arthroplasty procedure. As such, the milling device 310 further comprises means for accurately determining the depth of the aperture 350. For example, in one embodiment the outer surface of the shaft portion 324 comprises a plurality of annular reference marks 368. The reference marks 368 provide a visual indication of the depth of the removable blade 332 relative to various physiological references on the bone being cut. In an embodiment where the aperture 350 is being cut into the tibia 314, the required depth of the aperture 350 is either 2 mm below the normal level 370 of the bone, 13 mm below the tibial spines 372, or 10 mm below the lateral side 374. Thus, the reference marks 368 are observed relative to the physiological references 370, 372 and 374 to determine the depth of the aperture 350. Where the aperture is being cut into another bone, such as the femur 316, other boney references are used, as known in the art.

In another embodiment, a depth gauge 360 is placed over the shaft portion 324 of the bit 320 and supported by the stepped surface 330. The depth gauge 360 includes a base 362, an arm 364 and a pin 366. The base 362 further includes an aperture having a diameter to rotatably receive the shaft portion 324 of the bit 320. The arm 364 extends outwardly from the base 362 so as to position the pin 366 beyond the aperture 350. In one embodiment, the arm 364 further comprises a joint to adjust the length of the arm 364. In another embodiment, the arm 364 further comprises a set screw to adjust and lock the pin 366 to a desired position relative to the arm 364. In yet another embodiment, a plurality of depth gauges 360 is provided to accommodate various physiological references on the bone being cut.

The depth gauge 360 provides a physical indication of the depth of the removable blade 332 relative to the various physiological references, as previously discussed. In one embodiment, the depth gauge 360 is seated against the stepped surface 330 and the arm 364 and the pin 366 are adjusted to be in alignment with the desired physiological reference 374. Additionally, the height of the pin 366 is set relative to the physiological reference to produce an aperture 350 of a desired depth. Thereafter, the depth gauge 360 is held in place and prevented from rotating while the bit 320 is rotated to form the aperture 350. Once the pin 366 touches the physiological reference 374, the bit 320 is removed from the aperture 350, having achieved the desired depth.

Figure 56:
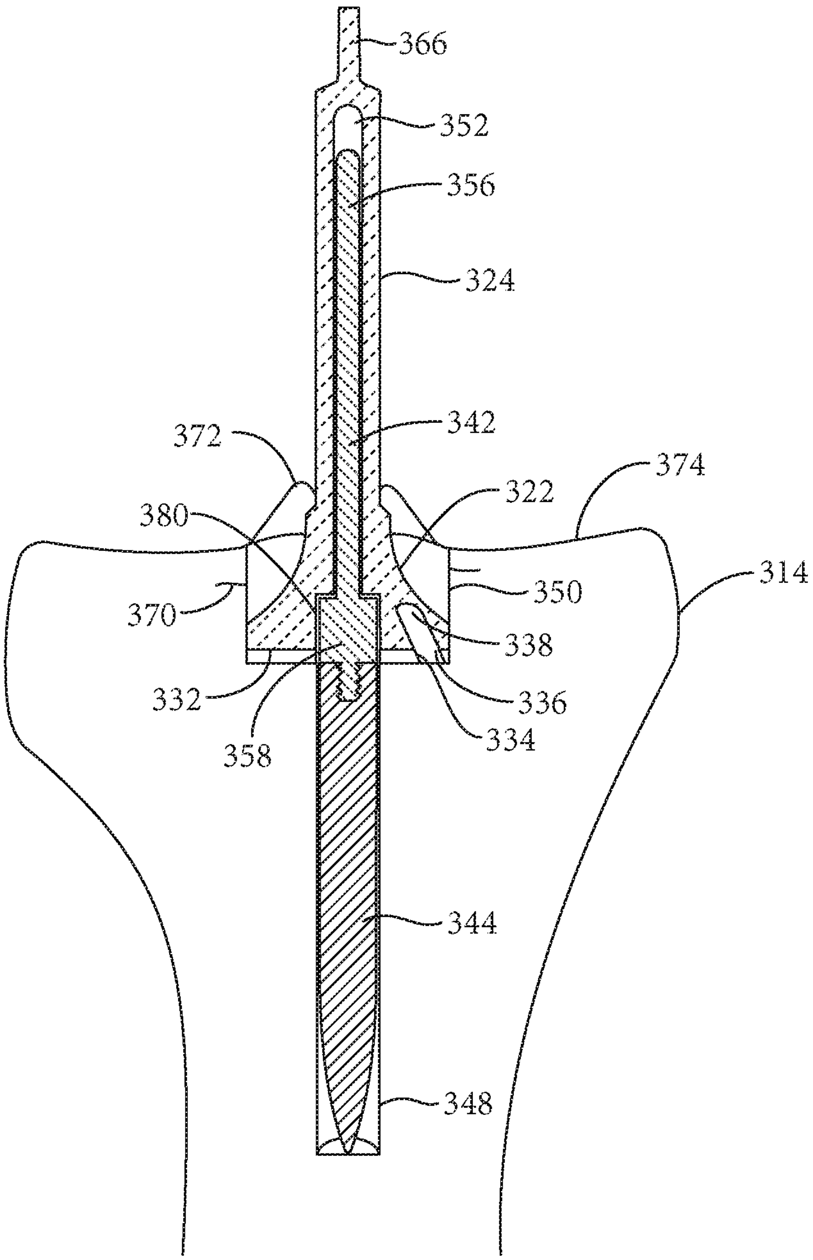
FIG. 56 is a cross-sectioned view of a representative embodiment of the present system following formation of the aperture.

Referring now to FIG. 56, another method for accurately cutting the aperture 350 to a desired depth is shown. In this method, the desired aperture 350 depth is attained by cutting into the bone 314 until the cutting bit 320 contacts the base 358 of the guide rod 340. This method requires that the base 358 of the guide rod 340 be accurately positioned within the IM canal 348 relative to the cutting edge 334 of the blade 332. Therefore, the blade 332 cuts and descends into the bone 314 along the guide rod 340 until the point at which the cutting head 322 contacts the base 358. Once contact between the cutting head 322 and the base 358 occurs the milling bit 320 is removed from the aperture 350. In one embodiment, the cutting head portion 322 of the milling bit comprises a recessed compartment 380 having a diameter adapted to compatibly and rotatably receive the base 358 of the post portion 356. Thus, in this embodiment the depth of the base 358 is set within the IM canal 348 such that when the base 358 fully engages the recessed compartment 380, the cutting edge 334 of the blade 332 is positioned accurately at the desired depth of the aperture 350. While several different methods have been discussed, one of skill in the art will appreciate that various other methods and apparatuses may be successfully combined with the milling device 310 to achieve the desired results.

Figure 57:
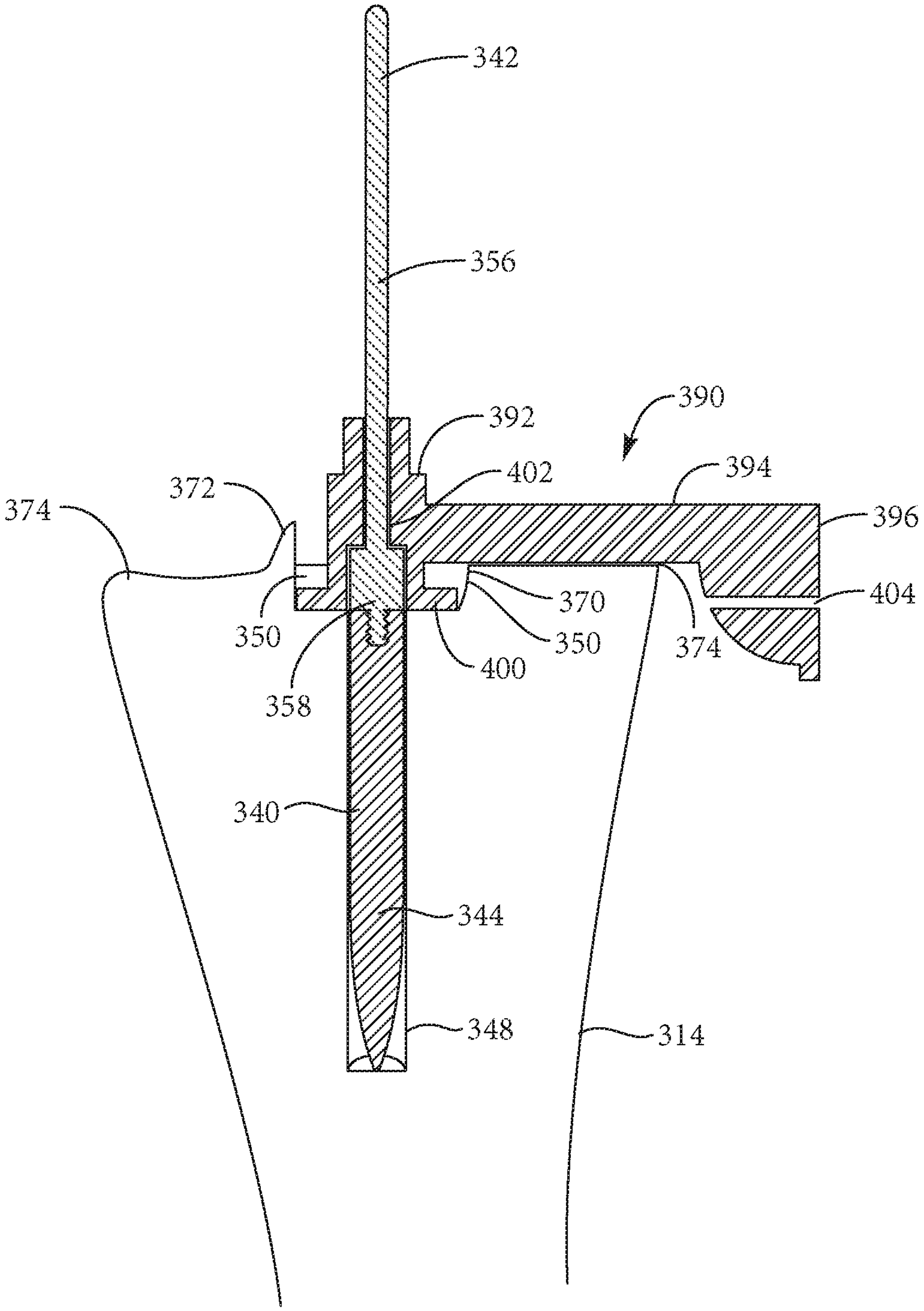
FIG. 57 is a cross-sectioned view of a representative embodiment of the present system incorporating a resection block.

Referring now to FIG. 57, the tibia 314 is shown following formation of the aperture 350 and prior to resection. Once the aperture 350 is provided, the guide rod 340 may be further utilized to assist in completing the arthroplasty procedure. For example, in one embodiment a resection block 390 is positioned over the guide rod 340, via a channel 402, and seated within the aperture 350. The resection block 390 comprises a base 392, an arm 394, and a cutting guide block 396. The base further comprises a flange portion 400 having a diameter equal to the diameter of the aperture 350. Additionally, the base 392 includes a channel 402 having contours and dimensions adapted to compatibly engage the post portion 356 and the base 358 of the guide rod 340. As such, the resection block 390 accurately seats within the aperture 350 and is steadied by the interposing and complimentary surfaces of the guide rod 340.

Figure 57A:
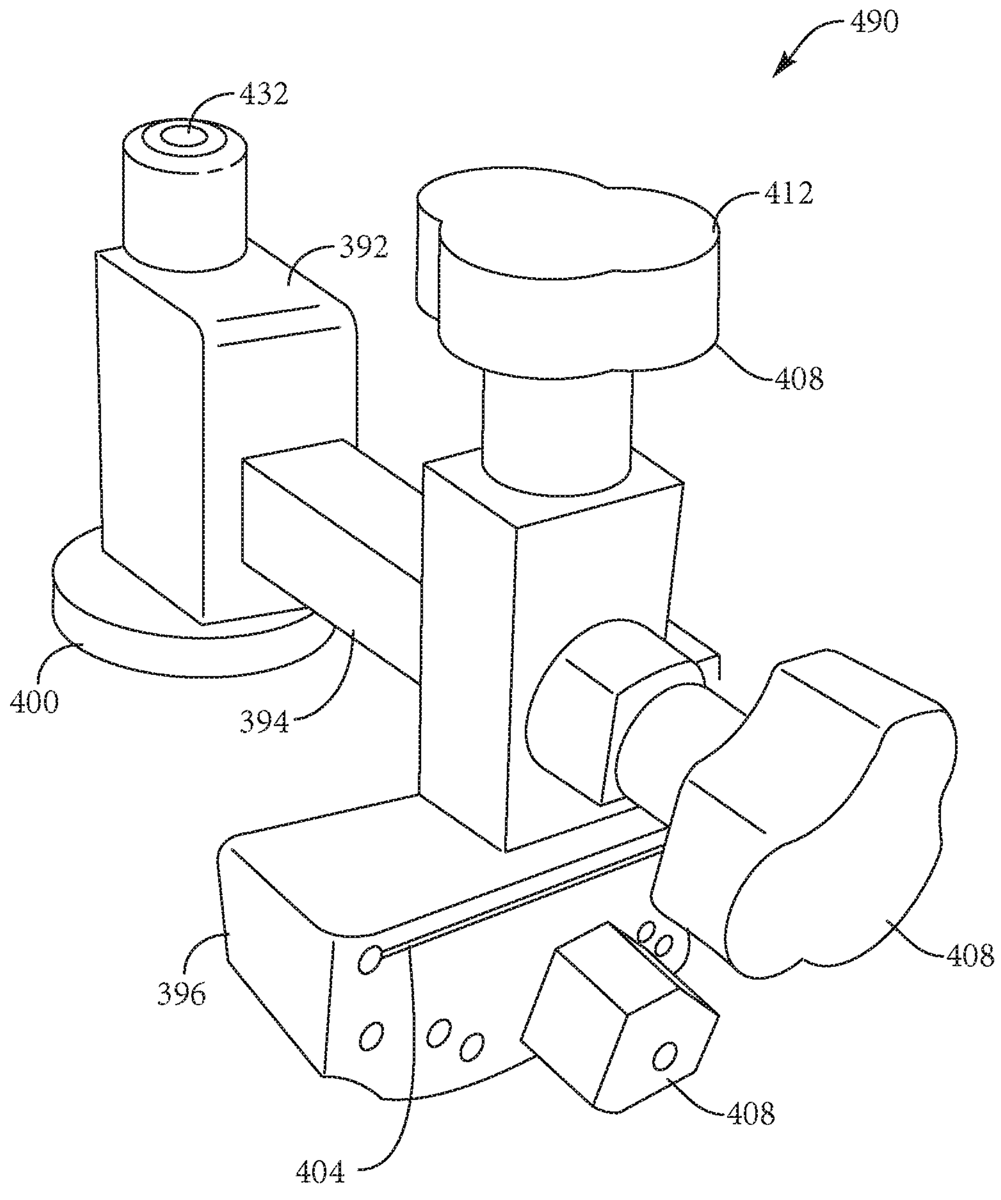
FIG. 57A is a perspective view of a representative embodiment of the resection block having a plurality of adjustments and/or apertures.

The arm 394 of the resection block 390 is attached to the base 392 at a height equal to the lateral side 374 of the bone 314. As such, the arm 394 clears the surface of the bone 314 and extends laterally from the base 392 beyond the aperture 350. In one embodiment, the resection block 490 further includes a plurality of adjustments 408 to position the arm 394 relative to the depth and location of the aperture 350 as required by the individual, physiological features of the bone 314 undergoing the arthroplasty, as shown in FIG. 57A. Thus, one resection block 390 may be infinitely adjusted and adapted for use with any procedure as required.

The cutting guide block 396 is attached to the end of the arm 394 opposite the base 392. The cutting guide block 396 is positioned such that a saw blade (not shown) may be inserted through the slot 404 to resect the bone 314 to the depth of the aperture 350. In one embodiment, the resection block 390 further includes a plurality of adjustments 412 to position the cutting block guide 396 relative to the depth and location of the aperture 350 as required by the individual, physiological features of the bone portions 370, 372, and 374 undergoing resection, as shown in FIG. 57A. In some implementations of the current invention, the cutting block guide 396 further comprises a plurality of apertures for attaching the cutting block guide 396 to the bone 314 via fasteners. In other implementations, a plurality of adjustments permits removal of the cutting block guide 396 from the arm 394. Therefore, in one embodiment the cutting block guide 396 is first positioned on and attached to the bone 314 with fasteners to ensure accurate positioning. Following attachment, the cutting block guide 396 is then removed from the remainder of the resection block 390 and the resections are made. As such, the resections are made accurately and efficiently with minimal componentry.

In another embodiment, instrumentation for performing the femoral cuts is inserted into and/or referenced from the final depth of the aperture 350. Since the depth of the aperture 350 is the final level for the tibial cuts, all femoral cuts may be accurately referenced from the depth of the aperture 350. As such, the aperture 350 provides a sufficient and relatively non-invasive reference point for the tibia 314. Once the femoral cuts are made, the remaining uncut portions of the tibia 314 are then exposed and easily accessible for resection. In another embodiment, tensioning devices are combined with the guide rod 340, the resection block 390, and the aperture 340 to tension the knee 312 as part of the resection procedure. Tensioning devices and procedures as taught in U.S. patent application Publication, Ser. No. 11/349,772, entitled GUIDE ASSEMBLY FOR GUIDING CUTS TO A FEMUR AND TIBIA DURING A KNEE ARTHROPLASTY, filed Feb. 8, 2006 (now U.S. Pat. No. 7,927,336), and U.S. patent application Ser. No. 12/191,245, entitled SYSTEMS AND METHODS FOR GUIDING CUTS TO A FEMUR AND TIBIA DURING A KNEE ARTHROPLASTY, filed Aug. 13, 2008 (now U.S. Pat. No. 8,303,597), may be easily combined with the present device 310, and are incorporated herein by reference, in their entirety. Modifications to the instrumentation and bone 314 are discussed in connection with FIG. 57B, below.

Figure 57B:
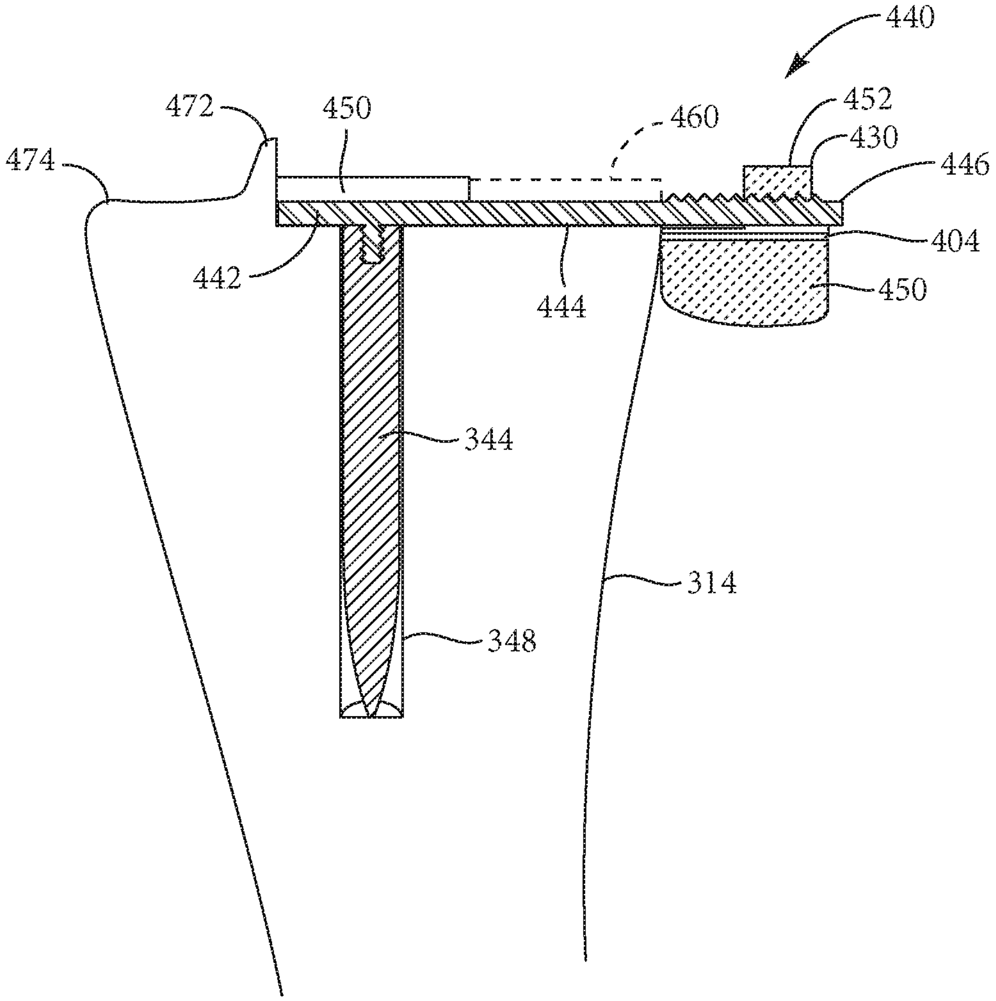
FIG. 57B is a cross-sectioned view of a representative embodiment of a resection block system coupled to a portion of a guide rod.

Referring now to FIG. 57B, an implementation of a resection block is shown as combined with the first end 344 of the guide rod 340. In this embodiment, the post portion or the second end 342 of the guide rod 340 is removed from the first end 344 and replaced with a resection block system 440. The resection block system 440 includes an integrated base 442 and arm 444, as well as a sled-style cutting guide block 450. The base 442 is disk-shaped having a diameter slightly less than the diameter of the aperture 350. The arm 444 extends laterally outward from the base 442 in the same plane as the base 442. As such, a portion 460 of the bone 314 must be removed to provide a pathway for the arm 444. In one embodiment, a rongeur or other surgical device is used to remove the bone portion 460 to create the pathway. Once the bone portion 460 is removed, the first end 344 of the guide rod 340, with the attached system 440, is repositioned within the IM canal 348. The cutting guide block 450 is then slid over the distal end 446 of the arm 444 and positioned against the bone 314. At this point, the cutting guide block 450 is securely attached to the bone via fasteners and the required resections are made via the slot 404. In one embodiment, the cutting guide block 450 further includes means for releasing the guide block 450 from the arm 444 while the guide block 450 is fastened to the bone 314. For example, an upper portion 452 of the guide block 450 may be adapted to be removable thereby releasing the lower, fastened half of the block 450 from the remainder of the system 440.

In an alternate embodiment, the cutting guide block 450 is first slid over the distal end 446 of the arm 444 so that the slot 404 of the guide block 450 aligns with femur 316 rather than with the tibia 314. In this configuration, the guide block 450 is positioned, relative to the depth of the aperture 350, to make the femoral cuts. Thus, the aperture 350 of the tibia 314 acts as a reference point to accurately make the femoral cuts. Once the femoral cuts have been made, the guide block 450 is removed and repositioned to make the tibial cuts, as previously discussed.

Figure 58:
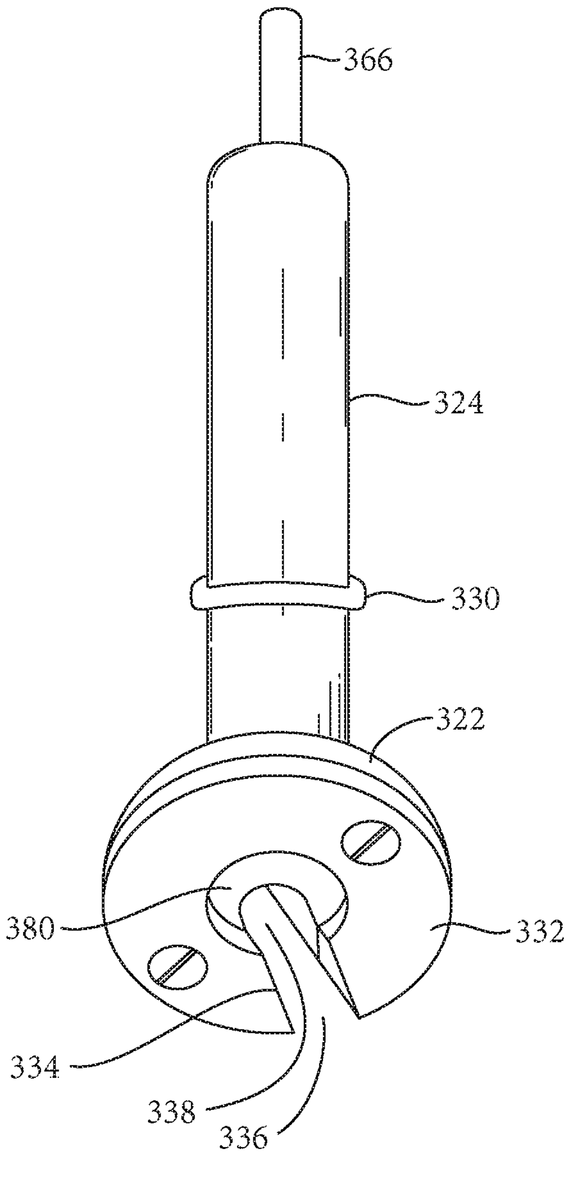
FIG. 58 is a perspective view of a representative embodiment of a milling bit.
Figure 59:
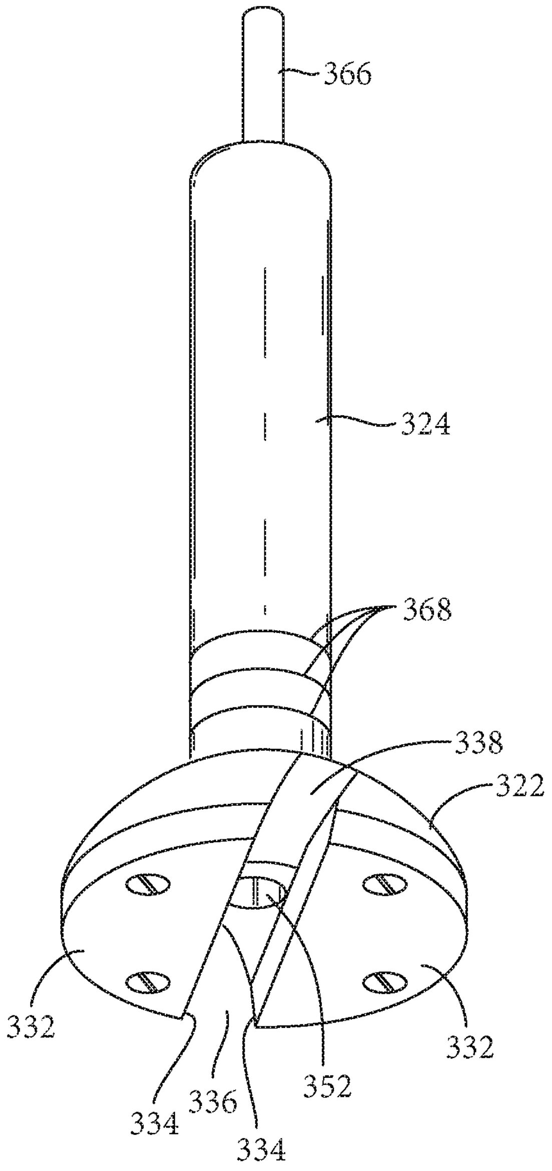
FIG. 59 is a perspective view of a representative embodiment of the milling bit.

Referring now to FIGS. 58 and 59, various perspective views of implementations of the milling bit 320 are shown. Of particular note are the various configurations of removable blades 332. The removable blade 332 is attached to the cutting head portion 322 via a set of screws 410. As such, the blade 332 is easily removed from the bit 320 to allow sharpening and/or replacement of the blade 332. As shown in FIG. 58, some implementations of the removable blade 332 include a single window 336 and a single cutting edge 334. As shown in FIG. 559, some implementations of the removable blade 332 include multiple windows 336 and multiple cutting edges 334.

Figure 60:
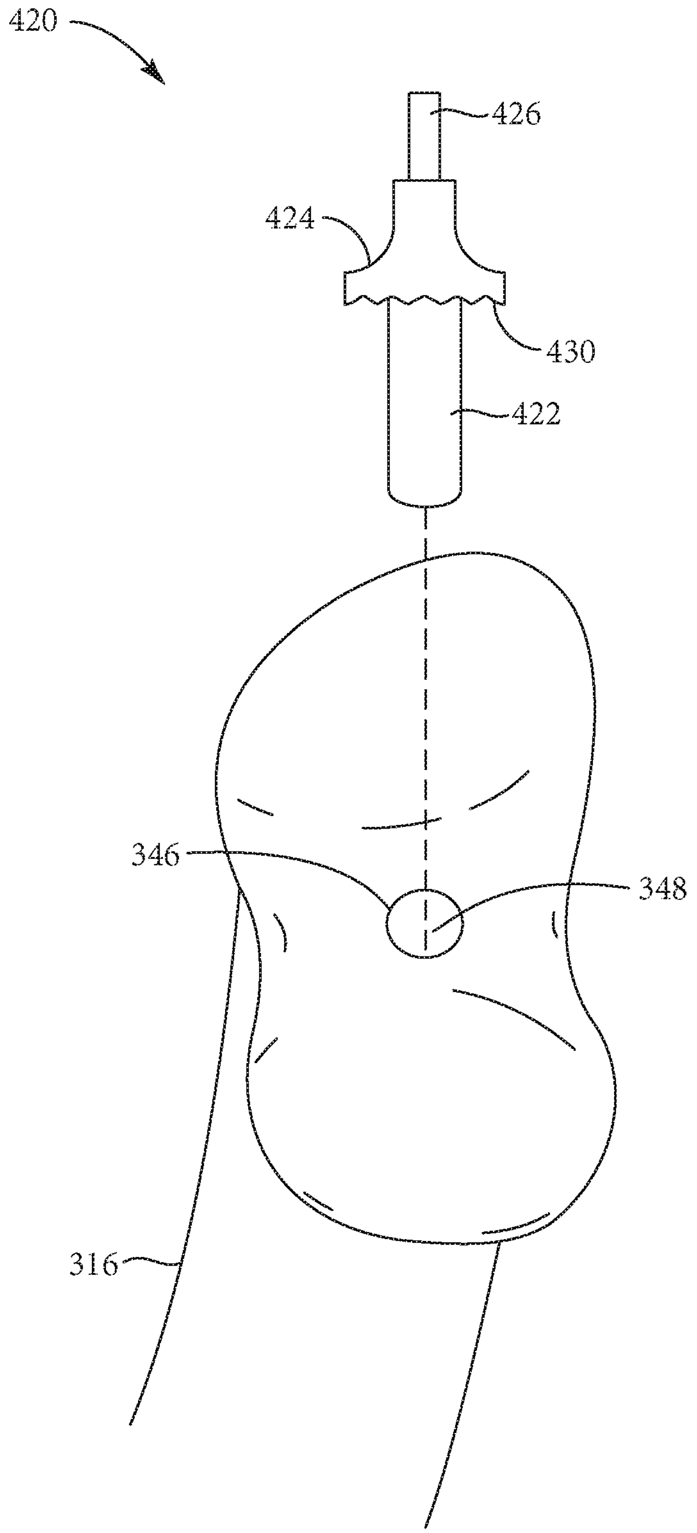
FIG. 60 is a perspective view of a representative embodiment of a bone milling device as embodied in a singular unit.

Referring now to FIG. 60, an implementation of a bone milling device 420 is shown. Unlike the previously discussed bone milling device 310, the present device 420 combines all of the elements of the bone milling device 310 into a singular unit 420. The bone milling device 420 comprises a guide rod 422, a cutting head portion 424, and a shank 426. The guide rod 422 is sized and adapted to rotatably insert within the opening 346 of the bone 316. The guide rod 422 thereby aligns and directs the cutting head portion 424 into the opening 346 of the bone 346. The shank 426, as previously discussed, couples the milling device 420 to a drill (not shown) or other means for rotating the milling device 420.

The cutting head portion 424 includes a plurality of annularly situated cutting teeth 430. Unlike the cutting edge 334 of the previous embodiments, the cutting teeth 430 provide a corrugated surface of sharpened edges that extend radially outward from the guide rod 422. Thus, the cutting teeth 430 contact and grind the adjacent surfaces of the opening 346 to level or knock down any inconsistent features or ridges of the bone 316 surface. As such, the cutting teeth 430 provide a uniform surface having a diameter equal to the diameter of the cutting head portion 424. The milling device 420 is useful where a level and consistent bone surface is required adjacent to the opening 346. In some implementations of the milling device 420, the cutting head portion 424 includes a plurality of cutting edges and windows to form an aperture in the bone 316.

Figure 61:
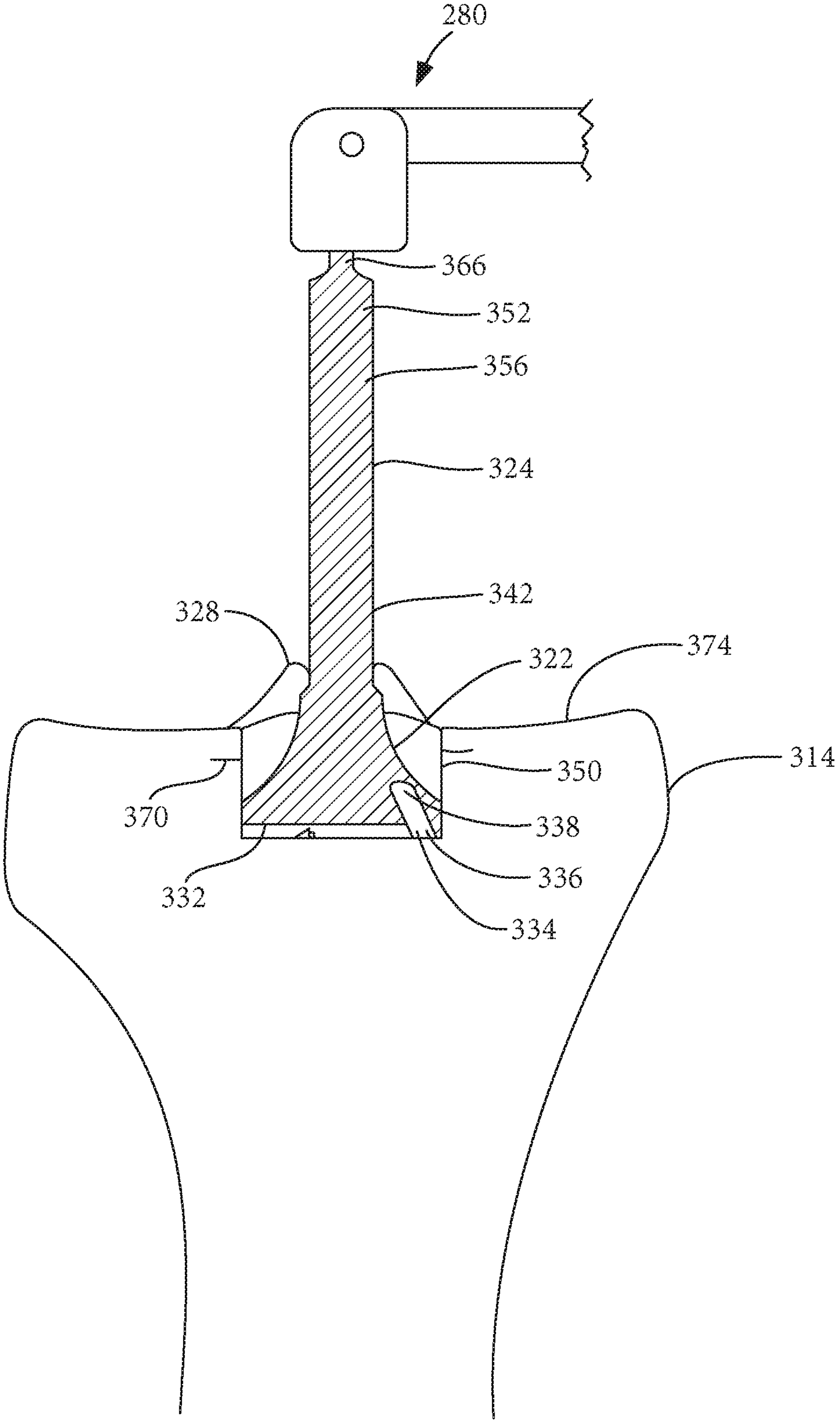
FIG. 61 illustrates a side view the bone milling device being used with an automated device in accordance with some embodiments.

While the described systems and methods for using the bone milling device 310 can be modified in any suitable manner, in some embodiments, the bone milling device is operated by one or more robots, robotic arms, laparoscopic devices, and/or other automated devices. In such embodiments, the automated device can cut make cuts in the tibia and/or femur with or without the use of a guide rod (e.g., guide rod 340, guide rod 422, etc.). Indeed, in some embodiments, the automated device is able to stabilize the knee and to use the bone milling device to cut portions of the tibia and/or femur without the use of a guide rod that extends up into the bone milling device during resection.

Where an automated device (e.g., a robot arm comprising the described bone milling device 310 and/or any other suitable device) is used to cut a portion of the tibia and/or femur, the automated device can cut any suitable portion of the tibia and/or femur. Indeed, in some embodiments, the automated device 280 is configured to cut the aperture 350 into the tibia (see e.g., FIG. 61).

Although in some such embodiments, after the aperture has been cut in the tibia by the automated device 280, a person then uses a cutting device (e.g., a bone saw) to remove the bone around the periphery of the aperture 350 at the proximal end of the tibia down to a final depth of the aperture, in some other embodiments, the automated device uses the milling tool 310 (and/or any other suitable cutting tool) to remove the bone around the periphery of the aperture. In such embodiments, the automated device can remove the peripheral bone in any suitable manner, including, without limitation, by cutting from side to side across the proximal end of the tibia (e.g., with the milling device and/or any other suitable cutting tool); by lifting the milling tool (or other cutting device) between cuts and then forcing it distally into the bone around (and/or overlapping with) the aperture, down to the depth of the aperture; and/or in any other suitable manner that removes bone from the proximal end of the tibia to allow for implantation of a tibial prosthesis.

In some embodiments, the automated device 280 is further configured to use the milling tool 310 (and/or any other suitable cutting device) to make one or more cuts to the distal end of the femur. In some such embodiments, the diameter of the cutting head portion 322 of the milling tool is configured to be substantially equal to and/or greater than a medial-lateral width of each individual condyle that it will be used to cut. Accordingly, in some embodiments, when the milling tool is placed into contact with a portion (e.g., a center and/or other portion) of a femoral condyle and spun, the milling tool will cut a flat surface into the femoral condyle. Thus, in some embodiments, the automated device uses the milling tool (and/or any other suitable cutting device) to resect a distal portion of a femur's medial and/or lateral condyle to create one or more distal cuts on the femur. In some embodiments, the automated device is further configured to use (and the described methods further comprise using) the bone milling device (and/or any other suitable cutting device) to make an anterior chamfer cut, an anterior cut, a posterior chamfer cut, and/or any other suitable cut to one or both of the femur's condyles. Additionally, while the posterior cut can be made in any suitable manner, including, without limitation, through the use the automated device and the bone milling device, in some other embodiments, a surgeon cuts the proximal cut (and/or any other suitable cut or portion of a cut) manually (e.g., via a bone saw, a chisel, and/or in any other suitable manner). Again, while the automated device can use a guide rod (e.g., as discussed above) to make any cut, in some embodiments, the automated device is configured to perform its cuts without the use of a guide rod that extends into the milling tool. Additionally, while the automated device can be used with any of the assemblies illustrated in FIGS. 1-48 to balance a gap and/or obtain a desired tension between the tibia and femur, in some embodiments, the automated device (and/or another computer device) is configured to balance the gap between the tibia and femur without the use of any of the other tensioning components set forth herein.

Spacers and Tibial Baseplate System

In addition to the foregoing, some embodiments of the described systems and methods include one or more wedges, blocks, trial tibial components, and/or other spacers that are configured to be inserted in between the femur and the tibia (i.e., between the tibial baseplate (described below) and a portion of the femur) in a knee joint to apply tension to one or more of the knee joint's ligaments (e.g., the lateral collateral ligament, the medial collateral ligament, the posterior cruciate ligament, and/or any other suitable ligament, ligaments, tendons, muscles, and/or other tissues), to balance ligament (and/or tendon) tension in the knee joint, to properly align the tibia and/or femur for resection, to support and/or properly place a cutting guide block, to ensure that cuts are made in the proper place, to avoid varus and/or valgus angulation of the knee, to provide the knee with a natural feeling flexion and extension, and/or to otherwise prepare the knee joint for resection and/or implantation of one or more prostheses. Indeed, as it may be difficult to apply a proper amount of tension to multiple ligaments (for instance, to three or more) in a knee joint at a time, in some embodiments, the described spacers can help apply a desired amount of tension to each desired ligament in a knee joint to ensure the knee joint is properly balanced and/or aligned when the knee joint is in flexion and/or extension.

With respect to the spacers, the spacers can have any suitable characteristic that allows them to function as described herein. Indeed, the spacers can be any suitable shape, including, without limitation, being: wedge-shaped, block-shaped, rectangular-prismatic-shaped, prism-shaped, tubular-prism-shaped, cup-shaped, dish-shaped, disk-shaped, U-shaped, V-shaped, W-shaped, circular, semi-circular, pill-shaped, bean-shaped, shaped to roughly correspond to the shape of a proximal end of a tibia, substantially constant in thickness (or height), of a varying thickness or height, rounded at a posterior end, rounded at an anterior end, squared at an anterior end, substantially flat and/or squared at its anterior end, rounded at one or more corners, chamfered and/or rounded at one or more edges, symmetrical, asymmetrical, regular, irregular, polygonal, and/or any other suitable shape that allows them to be used to apply a desired tension to one or more ligaments in a knee and/or to maintain a desired gap in the knee.

In some embodiments, the spacer comprises a disc-like (or semi-disc-like), sheet-like, plate-like, dish-shaped, and/or other suitably shaped object. Additionally, while some embodiments of such a spacer comprise a flat face (e.g., a first surface, proximal surface, inferior surface, etc.) for contacting the proximal end of the tibia and/or a flat face (e.g., a second surface, a superior surface, etc.) for contacting the distal end of the femur in a knee joint, in some other embodiments, the first surface of the spacer (or the side that is to face the femur) comprises one or more depressions, indentations, concavities, fossas, and/or other recesses that are each configured to cradle or otherwise hold a: femoral condyle, resected portion of a distal end of a femur, and/or femoral component. Although some embodiments of the spacer comprise one flat face (e.g., the inferior surface) and an opposing face (e.g., the superior surface) defining a recess, in some other embodiments, the spacer comprises two opposing faces that each define a recess (not illustrated).

Figure 62A:
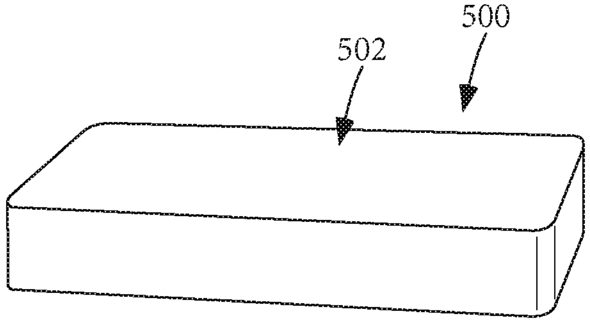
FIGS. 62A-62Z, 63A-63H, 64A-64D, and 65A-65I illustrate various embodiments of the described systems and methods.
Figure 62B:
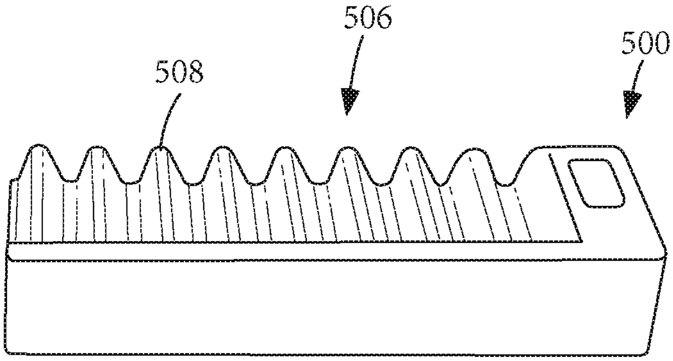
Figure 62C:
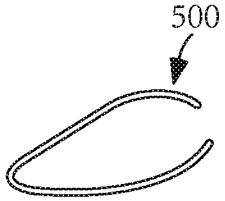
Figure 62D:
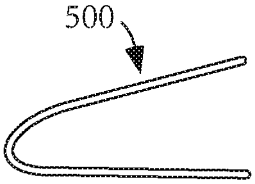
Figure 62E:
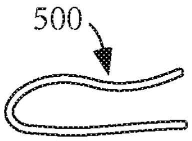
Figure 62F:
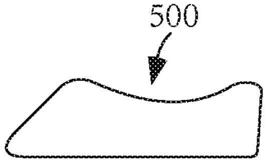
Figure 62G:
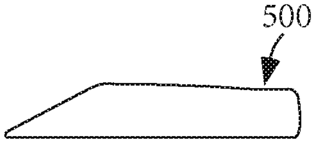
Figure 62H:
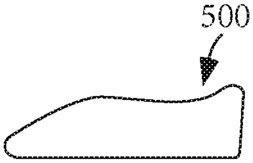

In other examples of suitable spacer shapes, FIGS. 62C-62E show that, in some embodiments, the spacer 500 comprises a strip of material (e.g., a leaf spring, a piece of resilient plastic, a flat strip of material having a ribbon shape that is bent, and/or any other resilient suitable material) that is formed into a U-shape, a V-shape, a wedge shape, a wedge shape having a recessed surface for cradling the femur (see e.g., FIG. 62E), and/or any other suitable shape that allows it to act as a spacer, and to apply pressure (e.g., as a spring and/or any other suitable type of biasing force), between a tibia and a femur when the spacer is disposed in the knee joint.

Figure 62I:
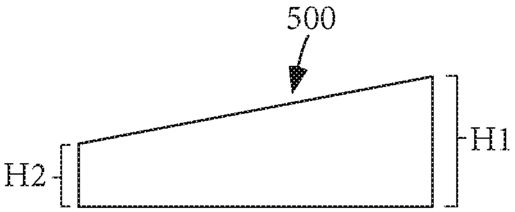
Figure 62J:
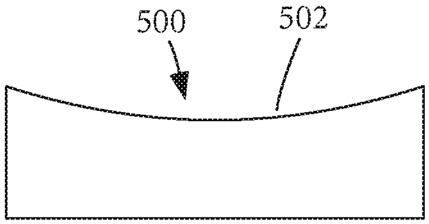
Figure 62K:
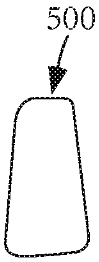
Figure 62L:
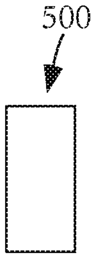
Figure 62M:
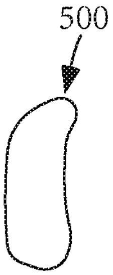
Figure 62N:
Figure 62O:
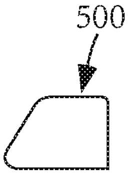
Figure 62P:
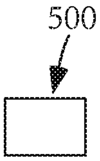
Figure 62Q:
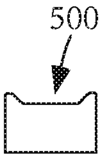
Figure 62R:

In still other examples of suitable spacer shapes, FIGS. 62F-62J illustrate some embodiments in which the spacer 500 has (from a side view) a wedge shape (see e.g., FIG. 62I), a wedge portion and a portion configured to cradle a distal portion of a femur (see e.g., FIG. 62F), a wedge portion and a plateau portion to support the distal portion of the femur (see e.g., FIGS. 62G and 62H), and/or a portion that is configured to cradle the distal portion of the femur and/or femoral component (see e.g., FIG. 62J, which illustrates one embodiment of the spacer 500 when viewed from a side or an embodiment of the spacer when viewed from its anterior or posterior end).

In still other examples of suitable spacer shapes, the spacer 500 can have any suitable shape when viewed from a top or bottom view that allows the spacer to function as intended. In this regard, FIGS. 62K-62N illustrate some non-limiting examples of plan views of some embodiments of the spacer 500 (e.g., embodiments having a substantially trapezoidal (or corn-kernel) shape, rectangular shape, curved shape, and/or iron-face shape, respectively). Additionally, while the spacer 500 can have any suitable profile from an end and/or side view, FIGS. 62O-62R illustrate some non-limiting embodiments of spacer 500 profiles (e.g., as viewed from an anterior end of the spacers, or an end that is configured to be placed adjacent to an anterior portion of a knee).

Figure 62T:
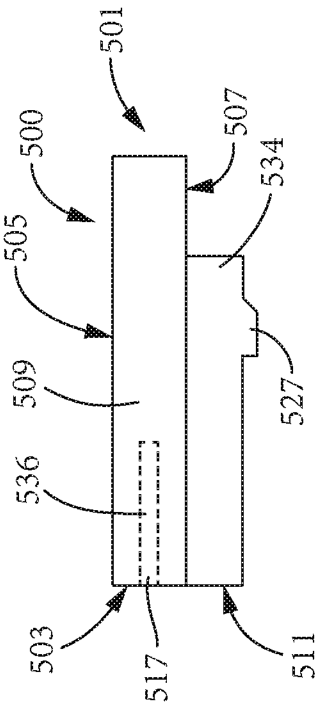
Figure 62S:
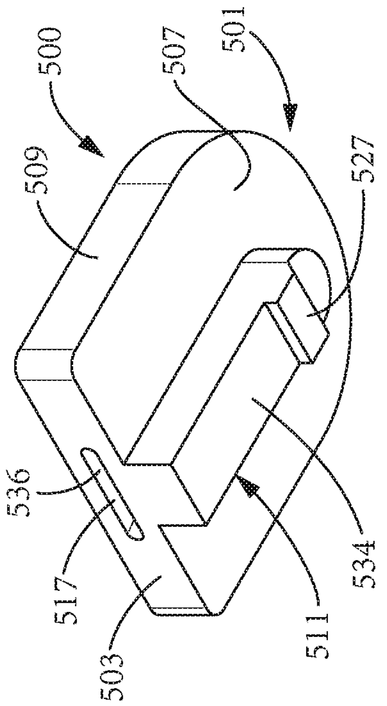
Figure 62U:
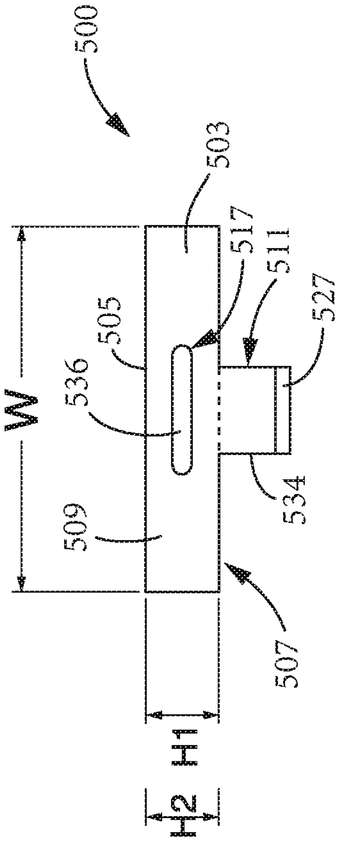
Figure 62V:
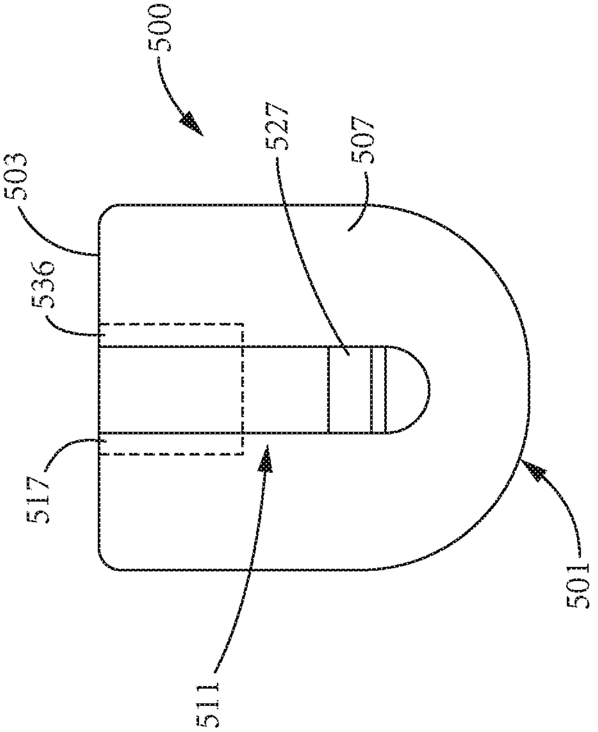
Figure 62X:
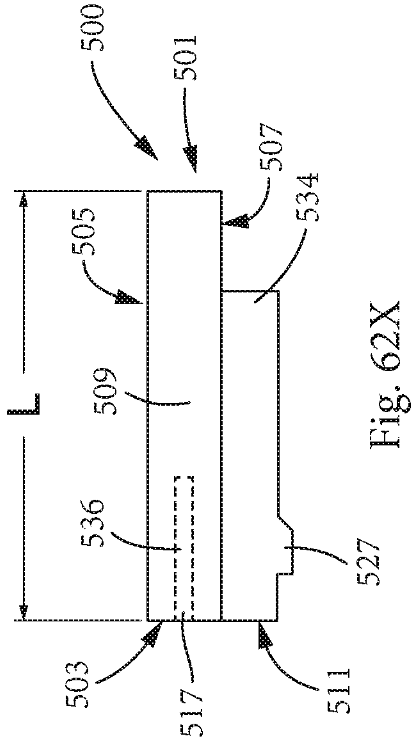
Figure 62W:
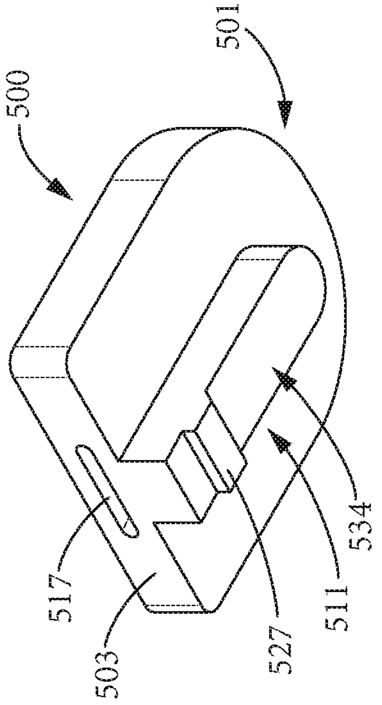
Figure 62Y:
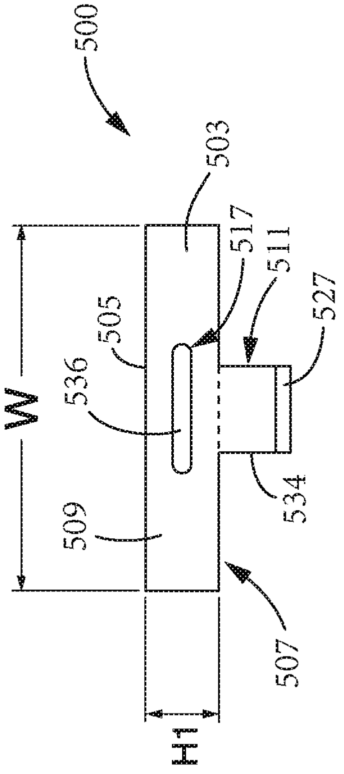
Figure 62Z:
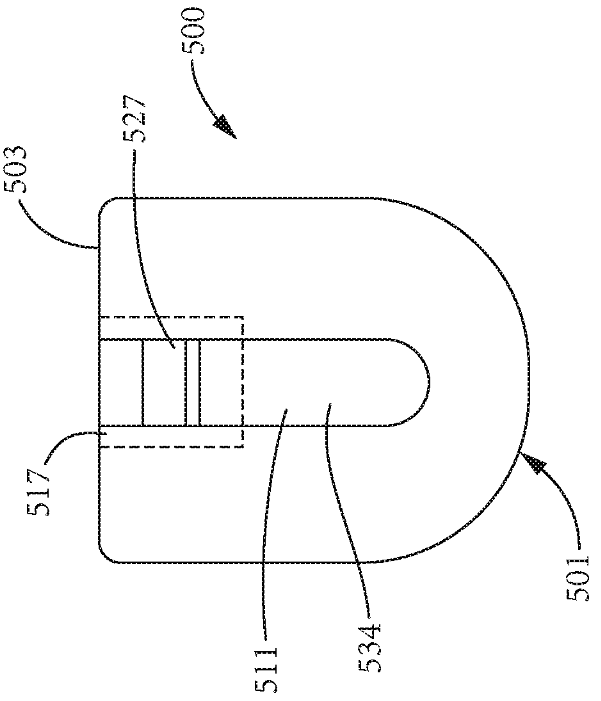

In some additional examples of suitable spacer 500 shapes and characteristics, FIGS. 62S-62Z show some embodiments in which the spacer 500 optionally comprises one or more: posterior ends 501 having any suitable shape (e.g., a rounded shape to help the spacer match and/or not gouge into one or more anatomical contours in the knee joint and/or for any other suitable purpose); anterior ends 503 having any suitable shape (e.g., being rounded, being substantially flat (as shown in FIG. 62S), and/or being any other suitable shape); proximal, superior, or first surfaces 505 having any suitable shape (e.g., being: rounded, substantially flat (as shown in FIGS. 62T and 62Y), concave, and/or having any other suitable shape); distal, inferior, or second surfaces 507 having any suitable shape (e.g., being: rounded, undulated, flat (as shown in FIGS. 62S and 62T), and/or having any other suitable shape); bodies 509 (e.g., as shown in FIG. 62X) having any suitable height H1 (e.g., a varying thickness or height and/or a substantially constant thickness or height H1 (as shown in FIGS. 62U and 62Y)); inferior spacer guides 511 (e.g., one or more recesses, rails, guides, paths, grooves, processes 534 (as shown in FIG. 62S), couplers, and/or other suitable component or components) that is configured to couple the spacer 500 to a tibial baseplate (discussed below) and/or any other suitable component; catches 515 (e.g., for selectively retaining the spacer in a position with respect to the tibial baseplate and/or any other suitable component), with the catch being disposed in any suitable location (e.g., posteriorly, as shown in FIG. 62S, and/or anteriorly, as shown in FIG. 62W); handle couplers 517 (e.g., openings 536), pressure sensors, and/or any other suitable feature or characteristic.

In yet additional examples of suitable shapes, FIGS. 76A-76H show some embodiments in which the spacer 500 is substantially cuboidal and/or prismatic in shape. In such embodiments, the spacer can have any suitable prismatic shape, including, without limitation, a substantially: rectangular, square, parallelepiped, trapezoidal, pyramidal (having a flattened and/or recessed top section), polygonal, elliptical, circular, rounded, symmetrical, asymmetrical, polygonal, irregular, and/or any other suitable prismatic shape. Indeed, FIGS. 76A-76H show some embodiments in which the spacers 500 are substantially rectangular prism shaped.

Figure 76A:
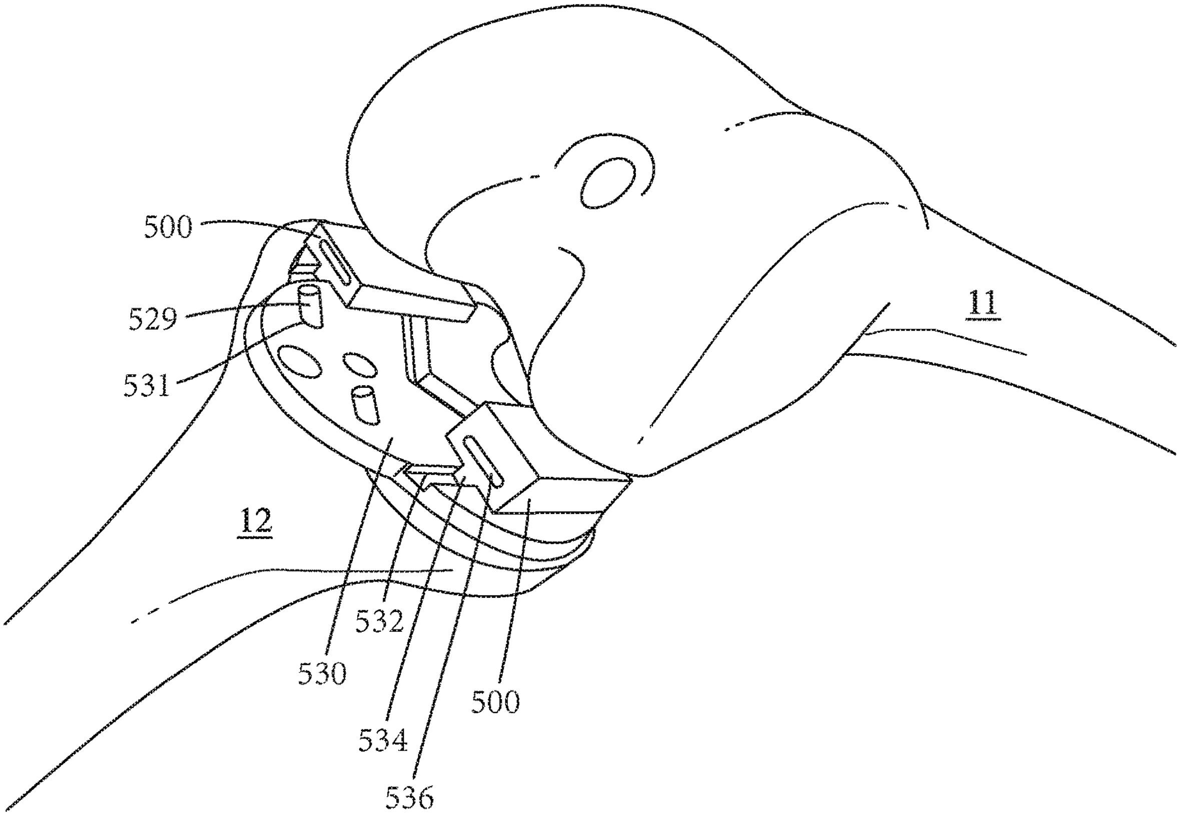
FIG. 76A depicts a perspective view of a knee joint in flexion comprising multiple spacers in accordance with a representative embodiment.
Figure 76B:
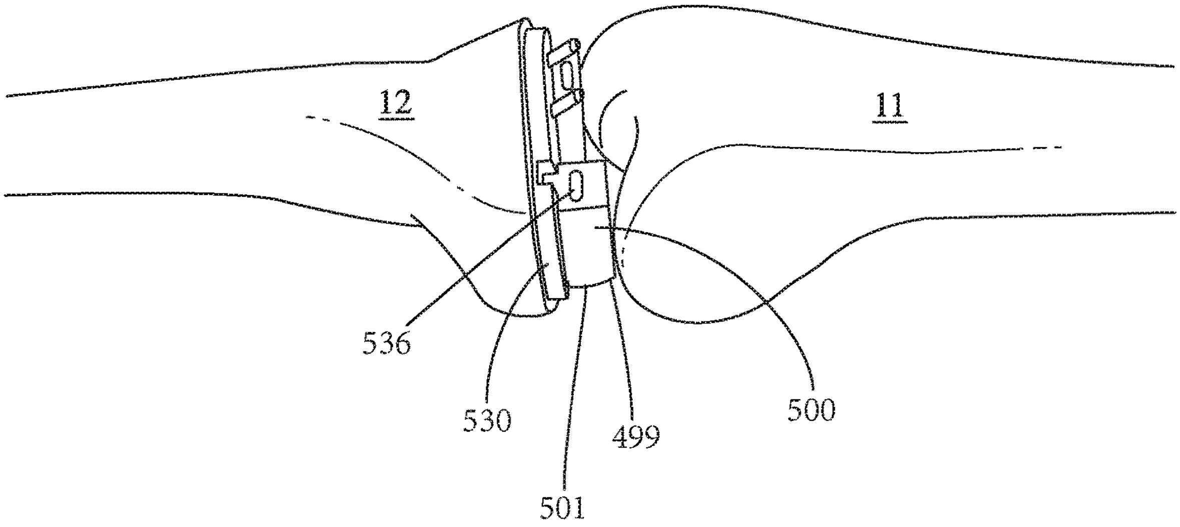
FIG. 76B depicts a perspective view of a knee joint in extension comprising multiple spacers in accordance with a representative embodiment.

In some embodiments, one or more ends, corners, and/or edges of the spacer 500 are angled, notched, rounded, curved, chamfered, wedge-shaped, pointed, narrowed, and/or otherwise shaped to help the spacer be inserted between the femur 11 and the tibia 12 relatively easily. By way of non-limiting illustration, FIG. 76B shows an embodiment in which a posterior end 501 of the spacer 500 (or an end of the spacer that is configured to be disposed posteriorly in the knee joint) is missing a corner and/or has a rounded or angled edge 499 (see e.g., FIG. 62S).

The spacer 500 can be any suitable size that allows it to apply a desired tension to one or more ligaments in the knee joint. In some embodiments, the spacer has a maximum height (e.g., a maximum distance that it is to separate the tibia (and/or tibial baseplate) from the femur and/or a femoral component; also referred to as H1, as shown in FIGS. 62I, 62U, and 62Y) of between about 1 mm and about 2.5 cm (or any subrange thereof). Indeed, in some embodiments, the spacer has a height H1 or a maximum height of between about 3 mm and about 16 mm (e.g., between about 4 mm and about 15 mm). Additionally, some embodiments include multiple spacers with a variety of maximum heights (e.g., for use in lateral and/or medial gaps, for use on patients of different sizes, and/or for any other suitable purpose). In this regard, although in some embodiments, the same sized spacers (or at least spacers of the same maximum H1) are used on both the lateral and medial sides of the knee joint, in some other embodiments (e.g., as shown in FIGS. 76A-76C, 76E, 76G, 76H, 78, and 79), the height of the spacers 500 vary between the lateral and medial sides. Thus, in some embodiments, the described systems and methods allow for asymmetrical spacer use (or for the use of different sized spacers on the lateral and medial sides of a knee joint).

While the spacer 500 can have any suitable minimum height (e.g., a minimum distance that it is to separate the tibia (and/or tibial baseplate) from the femur when the spacer is inserted between them in the knee joint; as referred to as H2, and as shown in FIG. 62I), in some embodiments, the spacer's minimum height is between about 0.1 mm and about 2.5 cm (or within any subrange thereof). Indeed, in some embodiments, the spacer has a minimum height H2 (e.g., to a lowest point of a depression in the superior surface of the spacer) of between about 2 mm and about 12 mm (e.g., between about 4 and about 10 mm). Additionally, in some embodiments, the spacers are made with a variety of minimum heights (e.g., for use in lateral and medial gaps, for use on patients of different sizes, and/or for any other suitable purpose). Moreover, in some embodiments (as described below), the spacer is configured to be modified to adjust its maximum and/or minimum height (via one or more springs, adjustment mechanisms, ratchets, stackable spacers, and/or in any other suitable manner). Although in some embodiments, the minimum height H2 is shorter than the maximum height H1, in some other embodiments (e.g., as shown in FIGS. 62U and 76A), the maximum height H1 and minimum height H2 of the spacer 500 are equal or at least substantially equal (e.g., the superior surface and the inferior surface of the spacer are both flat and run substantially parallel with each other).

The spacer 500 can be any suitable length that allows it to function as intended. Indeed, in some embodiments, the spacer has a length (e.g., a length of a portion of the spacer that is configured to be in contact with at least one of the femur, a femoral component, the tibia, and/or the tibial baseplate (discussed below) when the spacer is inserted between the tibia and femur) of between about 1 cm and about 12 cm (or any subrange thereof). Indeed, in some embodiments, the spacer has a length L between its anterior and posterior-most ends (e.g., as shown in FIG. 62X) that is between about 1 cm and about 4 cm long (or any sub-range thereof). For instance, some embodiments of the spacer have a length L that is about 3 cm±5 mm.

Moreover, in some embodiments, the spacer 500 has a width W (e.g., as shown in FIG. 62Y and/or a width of a portion of the spacer (e.g., between its lateral and medial-most edges) that is configured to be in contact with at least one of the femur, the femoral component, the tibial baseplate, and/or the tibia when the spacer is inserted there between) of between about 0.5 cm and about 12 cm (or any sub-range thereof). Indeed, in some embodiments, the spacer is between about 5 mm and about 3 cm wide (or any sub-range thereof). For instance, some embodiments of the spacer have a width W of about 2.5 cm±0.5 cm.

Additionally, the spacer's external surfaces can have any texture that allows the spacer 500 to function as intended. In some embodiments, the spacer includes one or more smooth surfaces that allow a portion of the femur, femoral component, tibial baseplate, and/or the tibia to articulate against the spacer or vice versa (e.g., as the knee joint is moved through its range of motion, as the spacer is slid into the knee joint, etc.). Indeed, in some implementations, a proximal or superior side of the spacer comprises a smooth articular surface that is configured to allow a distal end of the femur and/or a femoral component to articulate against it as the knee joint moves through a range of motion. Accordingly, in some such embodiments, the spacer is configured to be used to provide a desired tension throughout at least a portion of the knee's range of motion.

In some other embodiments, one or more portions of the spacer 500 comprise one or more non-smooth surfaces. Some non-limiting examples of such non-smooth surfaces include one or more surfaces comprising one or more roughened textures, spongiosa metals (and/or other material), knurled textures, barbs, ridges, processes, zig-zag surfaces, cog-like surfaces, porous cladding, external frames, spikes, catches 515, external matrices, pins, and/or any other suitable surfaces and/or components that are configured to help prevent the spacer from undesirably sliding out from between the femur or femoral component and the tibia or the tibial baseplate. In this regard, such non-smooth surfaces can be disposed on any suitable portion of the spacer (e.g., its superior surface, its inferior surface, its perimeter, etc.).

In one non-limiting illustration, while FIG. 62A shows an embodiment in which the spacer's proximal or superior face 502 is substantially smooth (e.g., to allow for the femur to articulate against it). Additionally, FIG. 62B shows an embodiment in which the distal or inferior face 506 of the spacer 500 (or the face that is configured to face the tibia and/or the tibial baseplate) comprises a plurality of ridges 508 that are configured to help prevent the spacer from sliding on the tibia and/or the tibial baseplate as the spacer is used. In some other embodiments, however, the proximal face of the spacer optionally comprises a spiked, ridged, knurled, and/or other roughened texture to help prevent the spacer from sliding with respect to the femur.

Although, in some embodiments (e.g., as shown in FIGS. 62F-62H and 62S-62Z), the spacer 500 comprises a single monolithic object (e.g., an object that is configured to rest directly on the tibia and/or on a tibial baseplate), in some other embodiments (e.g., as illustrated in FIGS. 63A-63E and 62C-62E), the spacer comprises one or more components that: couple together to form, are configured to be stacked to form, and/or are resiliently formed and/or coupled together as, the spacer. Indeed, in some embodiments, the spacer comprises a proximal portion that is configured to contact a distal portion of the femur and a distal portion that is configured to contact a proximal portion of the tibia (and/or a tibial baseplate, as discussed below) when the spacer is inserted into the knee joint.

In some embodiments in which the spacer 500 does not just consist of a single monolithic component, the spacer optionally comprises one or more springs and/or other biasing mechanisms that are configured to force the distal and proximal portions of the spacer apart so as to apply a consistent and/or constant pressure to (and/or to maintain the appropriate gaps in) the femur and the tibia when inserted into the knee joint. By way of non-limiting illustration, FIGS. 63A-63E show some non-limiting embodiments in which the spacer 500 comprises a proximal portion 510 and a distal portion 512 that are coupled together. Additionally (while not shown directly), some embodiments of the spacers are configured to be stacked on each other (e.g., as blocks, interlocking blocks, and/or in any other suitable manner).

In some embodiments, the spacer 500 further comprises one or more mechanisms for biasing the proximal portion 510 and the distal portion 512 apart. In this regard, the proximal and distal portions can be biased apart in any suitable manner, including, without limitation, through the use of one or more springs, elastomeric materials, rubber bands, and/or other resilient materials. By way of non-limiting illustration, FIGS. 63A-63D show some embodiments in which the spacer 500 comprises one or more springs 514.

In some embodiments, the spacer 500 is further configured to identify, quantify, and/or distinguish the pressure that it exerts on the tibia and/or the femur when the spacer is placed in between the two bones in a knee joint. In this regard, the spacer can be configured to determine and/or otherwise identify the pressure it places on the tibia and/or femur in any suitable manner. Indeed, in some embodiments, the spacer comprises one or more piezochromic polymers, pressure indicating pigments, pressure indicating coatings, scales, pressure transducers, gauges, differential pressure sensors, resistive sensors, capacitive sensors, optical sensors, MEMS sensors, and/or any other suitable pressure sensors. In this regard, some additional examples of such pressure sensors include, but are not limited to, one or more piezoresistive strain gauges, capacitive pressure sensors, diaphragm pressure sensors, electromagnetic pressure sensors, piezoelectric sensors, optical pressure sensors, potentiometric sensors, pressure gauges, and/or any other suitable pressure sensors.

By way of non-limiting illustration, FIGS. 63C-63G illustrate some embodiments in which the spacer 500 comprises one or more pressure sensors 516 and/or other indicators 520 that are configured to measure pressure that is applied to a distal end of the femur. In accordance with some such embodiments, when the spacer is inserted between the tibia and/or the femur, the knee joint is able to move through a range of motion (e.g., with the distal end of the femur articulating against the proximal portion 510 of the spacer)

such that tension in the knee joint (e.g., on the lateral and/or medial side of the knee) can be measured throughout the range of motion and not just when the knee is at 0 degrees and/or 90 degrees. Additionally, in some embodiments, a first spacer is placed at a lateral side of the knee joint and a second spacer is placed at a medial side of the knee joint such that pressure can be measured at the medial and lateral sides of the knee throughout a range of motion of the knee (e.g., to properly balance tension in the knee).

Where the spacer 500 comprises one or more pressure sensors 516, the sensors can communicate their sensor readings in any suitable manner, including, without limitation, wirelessly, via one or more wired connections (see e.g., a wired connection 518 in FIG. 63E), via an analog display and/or mechanism, via an LCD and/or other display on the spacer (or elsewhere), by changing their coloring, by changing their appearance, and/or in any other suitable manner. In some embodiments, however, the spacer is configured to communicate sensor readings via a wired connection. Accordingly, by limiting the hardware that is disposed in the spacer, the overall price of the spacer can be reduced while the lifespan of the spacer can, in some embodiments, be increased (or even reduced, for disposable spacers). In some other embodiments, however, the spacers comprise one or more pressure sensitive color changing pigments and/or piezoelectric sensors (e.g., such that the spacers are configured to be disposable).

Figure 63A:
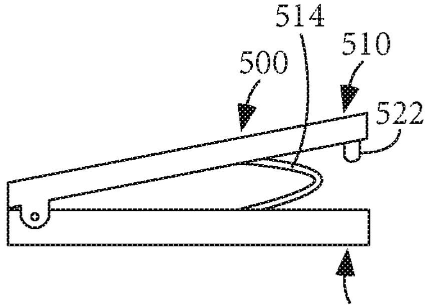

In some embodiments, instead of (or in addition to) having a pressure sensor, the spacer 500 uses one or more mechanical mechanisms to determine an amount of tension in the knee joint. Accordingly, in some embodiments, when a first spacer is placed in a lateral side of the knee joint and a second spacer is placed in a medial side of the knee joint, a practitioner and/or computer device can determine whether or not tension in the knee joint is balanced and/or is otherwise proper. In such embodiments, the spacer can comprise any suitable mechanical mechanism that is capable of indicating a tension and/or pressure in the knee joint. In this regard, FIGS. 63A, 63B, 63C, 63D, 63F, and 63H show some embodiments in which the spacer 500 comprises one or more springs 514 that are used to indicate a pressure exerted on the spacer. In such embodiments, the springs can be used to measure (and/or to otherwise indicate) pressure in the knee joint in any suitable manner. By way of non-limiting example, FIGS. 63C-63D show that, in some embodiments, the spacer 500 comprises a spring 514 and/or other resilient material and a gauge 520 that are configured to indicate a pressure and/or tension measurement.

In another non-limiting example, some embodiments of the spacer 500 are calibrated such that one portion of the spacer (e.g., the proximal portion 510, a stop, and/or any other suitable component) contacts another portion (e.g., the distal portion, a stop, and/or any other suitable component) when a set pressure is reached. By way of non-limiting illustration, FIGS. 63A and 63H show that, in some embodiments, the spacer 500 is configured to have a stop 522 contact the distal portion 512 of the spacer when a set amount of pressure is applied to the proximal portion 510 of the spacer.

Figure 63B:
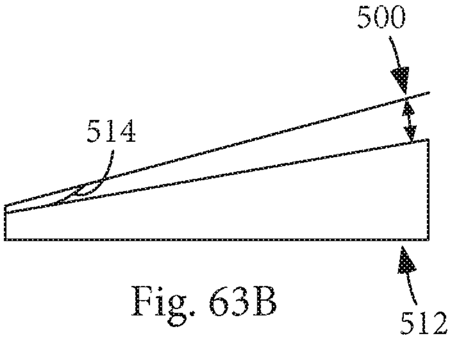
Figure 63C:
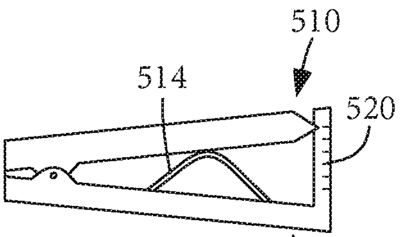
Figure 63D:
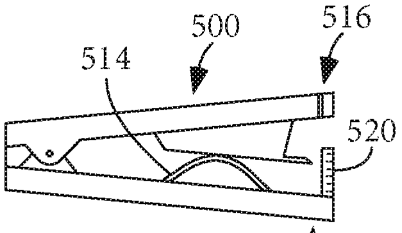
Figure 63E:
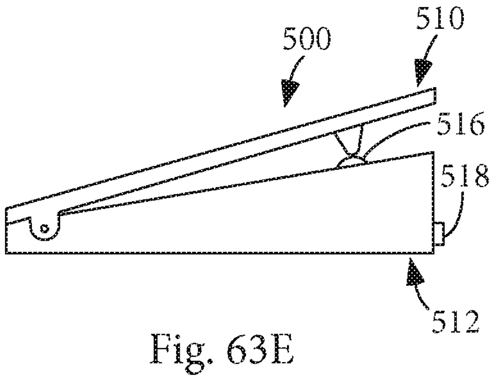
Figure 63F:
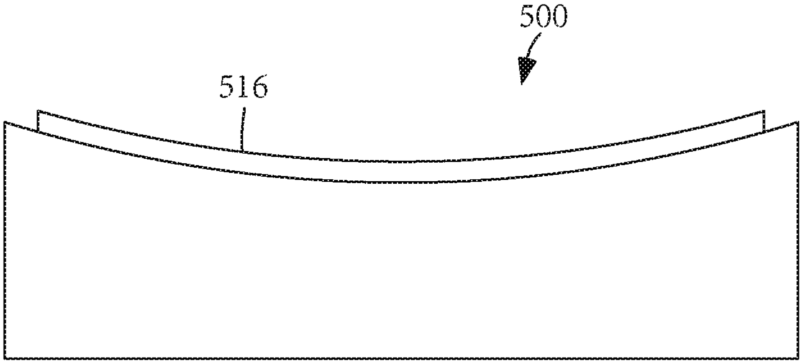
Figure 63G:
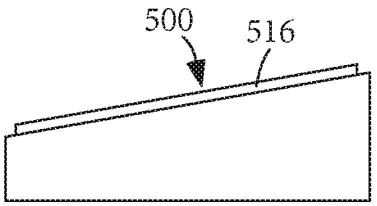
Figure 63H:
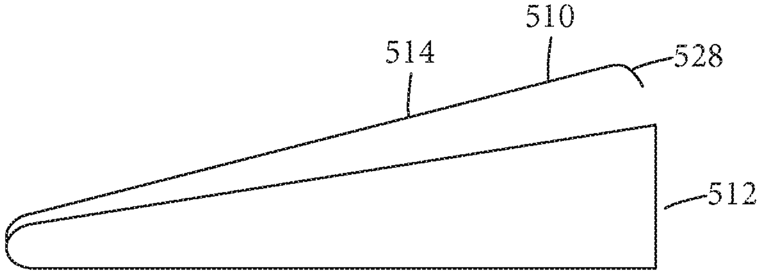

In another non-limiting illustration, FIG. 63B shows that, in some embodiments, the spacer 500 is configured to have the proximal portion 510 contact the distal portion 512 when a set amount of pressure is applied to the proximal portion 510 of the spacer. Additionally, the skilled artisan will recognize that, in accordance with some embodiments, when the proximal portion 510 of the spacer 500 in FIG. 63H is forced against the distal portion such that a portion of the proximal portion 510 (in addition to the stop 522) contacts the distal portion 512, more pressure is being applied to the spacer than desired (e.g., indicating that the knee is under more tension than desired).

In some embodiments in which the spacer 500 comprises one or more piezochromic polymers, pressure indicating pigments, and/or pressure indicating surfaces, a practitioner and/or computer device can identify when a pressure that is applied to a spacer is too high and/or not high enough. While this can be accomplished in any suitable manner, in some cases, when a practitioner inserts a spacer into the knee joint and the practitioner and/or a computer system (e.g., via the naked eye, via ultraviolet light, via a camera, via a sensor, and/or otherwise) determines that a portion of the spacer displays (or does not display, as the case may be) a certain coloring, the practitioner and/or computer know that such spacer is not appropriate in that circumstance.

In some knee arthroplasties, the gaps between the tibia and femur are different on the lateral and medial sides of the knee joint (e.g., in flexion and/or otherwise). Accordingly, in some embodiments, the spacers 500 are configured such that a different sized spacer is used on the medial and the lateral sides of the knee joint (e.g., as mentioned above). Indeed, in some embodiments, a taller spacer (or a spacer having a taller lateral side and/or a taller maximum H1 and/or minimum height H2) is used on the lateral side and a shorter spacer (or a spacer having a shorter medial side and/or a shorter maximum height and/or minimum height) is used on the medial side of the knee joint (or vice versa). In some embodiments in which a medial and a lateral spacer have different heights and in which one portion of the spacer is configured to contact another portion of the spacer when a desired pressure is obtained between the tibia and the femur, the differently sized spacers (and/or a spacer having differently sized medial and lateral portions) are calibrated to exert similar pressures, and to indicate (e.g., via the contacting of a first portion with a second portion of each of the spacers and/or otherwise) that the same desired pressure has been achieved in each side of the knee. Similarly, in some embodiments in which the spacers comprise a pressure sensitive material that changes color (and/or that otherwise function) based on pressure, the spacers are configured to exhibit the same coloration (and/or reading) when they are both subject to similar pressures.

The spacers 500 can each be configured to indicate that any desired amount of pressure has been achieved in the knee joint. In some embodiments, such a desired pressure can be between about 1 and about 40 inch pounds of force (or any sub-range thereof). Indeed, in some embodiments, a first portion of each spacer is configured to contact a second portion of each spacer, a spacer color is configured to change, a light is produced, a sound is made, and/or the spacer is otherwise configured to indicate (directly or indirectly) when a pressure between about 10 inch pounds and about 25 inch pounds (e.g., between about 15 and about 21 inch pounds) is applied to the spacers.

In some embodiments, the spacer 500 is configured to be used with any suitable conventional and/or novel method of joint arthroplasty. In some embodiments, one or more spacers are configured to be used to balance gaps between the tibia and femur, to apply desired tensions to tendons/ligaments in the knee joint, and/or to otherwise prepare the knee for resection and/or component implantation, without necessarily requiring any other bone spreaders, tensioning assemblies, and/or other devices to separate the tibia from the femur for gap and ligament balancing. By way of illustration, FIGS. 64A-64D illustrate some embodiments in which multiple spacers 500 are used to properly balance the knee joint in preparation for resection (e.g., by resting directly on the tibia and/or otherwise). In this regard, any suitable spacer can be used to balance the knee joint, including, without limitation, those spacers 500 shown in FIGS. 62A-63H, 65A-65I, and elsewhere herein.

In some other embodiments, however, one or more spacers 500 are configured to be used with one or more other apparatuses (i.e., one or more of the apparatuses, systems, and/or methods described herein) to prepare a knee for resection. Indeed, in some embodiments, one or more spacers are configured to adjustably couple to one or more of the components described herein, including, without limitation, to the tibial mount 23, the tibial tensioning adapter 160, the plateau flanges 28, the femoral mount 15, a cutting guide (e.g., cutting block, guide, cutting guide block, assemblies, etc., such as cutting accessories 52, 54, and 87), a tibial baseplate, a saw blade capture block, alignment rod block, gap resection block, and/or any other suitable component that allows the spacers to be selectively held in place while being disposed in the knee joint.

By way of non-limiting illustration, FIGS. 65F-65X, 66A-67C, and 76A-76H show that, in some embodiments, one or more spacers 500 are configured to couple in the knee joint via one or more tibial baseplates 530 and/or other tibial components (which can be for uni-compartmental and/or total knee replacements or arthroplasties). Additionally, FIGS. 66A and 66B and 67A-67C show that, in accordance with some embodiments, the spacers 500 are configured to couple to one or more tibial baseplates 530, tibial tensioning adapters 160, and/or other tibial components.

Where the spacers 500 are configured to couple to one or more of the described apparatuses and/or systems (e.g., to one or more tibial baseplates 530 and/or other tibial components), any of the spacers described herein (or modified versions thereof) can be coupled to such apparatuses and/or systems in any suitable manner, including, without limitation, via one or more mechanical engagements, frictional engagements, slides, guides, rails, magnets, grooves with one or more slidably mating objects, cables, by being configured to have one component rest on the other such that one component can be moved in medially, laterally, posteriorly, and/or anteriorly with respect to the other component, via one or more interlocking mechanisms, and/or via any other suitable spacer guide and/or coupling mechanism.

By way of non-limiting illustration, FIGS. 65F-65K, 65S-65W, 70-73C, and 76A show that, in some embodiments, the tibial component (e.g., tibial baseplate 530) comprises one or more slots or other recesses 532 (or spacer guides), and the spacers 500 each comprise one or more corresponding processes (or projections) 534 that are configured to mate (slidably and/or otherwise) with the slots. In some such embodiments, the tibial baseplate is configured to couple with one or more spacers of different size and/or having one or more other varied characteristics (e.g., on a lateral side and/or a medial side of the tibial baseplate). Accordingly, in some such embodiments, a user can readily place one or more baseplates on the tibia (e.g., by setting the baseplate on the tibia, connecting the baseplate to the tibia via one or more fasteners 529 (e.g., via hole 531) and/or in any other suitable manner) and then selectively place one or more different sized spacers on the baseplate until a proper balance and/or alignment is achieved in the knee joint. Of course, while FIGS. 65F-65I, 71A-75C, and 76A show some embodiments in which the tibial baseplate 530 defines one or more elongated recesses 532 (or spacer guides) and the spacers 500 comprises one or more elongated processes (or projections) 534, in some other embodiments, the tibial baseplate comprises one or more elongated projections and the spacers comprise one or more corresponding recesses and/or the tibial baseplate and the spacers are otherwise configured to couple with each other.

Where the tibial baseplate 530 comprises one or more grooves, recesses, rails, guides, and/or is otherwise configured to guide (and/or retain) one or more spacers to (or in) a desired position on the baseplate, the baseplate can comprise any suitable configuration that allows it to function in such a manner. Indeed, in some embodiments, the baseplate comprises one or more guides or couplings (e.g., grooves, rails, openings, etc.) that extend (and/or are disposed) in any suitable direction (e.g., in an anteroposterior direction, in a medial-lateral direction, at an angle, and/or in any other suitable direction with respect to the baseplate). For instance, FIGS. 65J and 73A show some embodiments in which the tibial baseplate 530 comprises two elongated recesses 532 that run substantially in an anteroposterior direction.

Figure 65I:
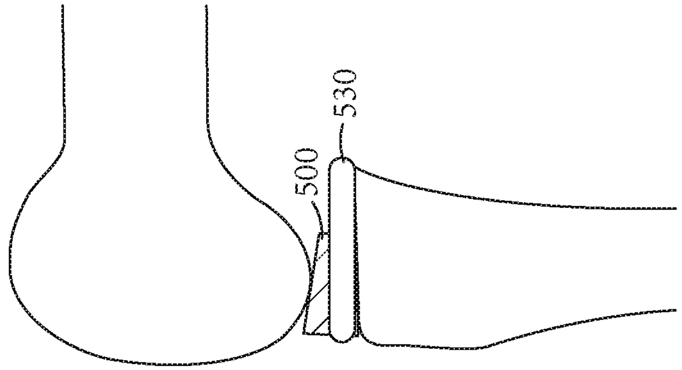
Figure 65H:
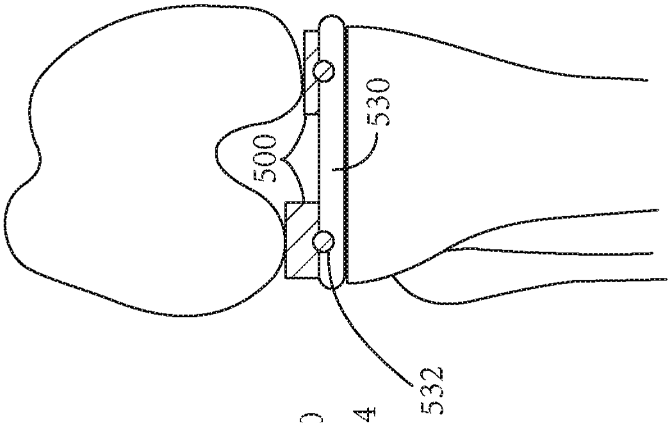
Figure 65G:
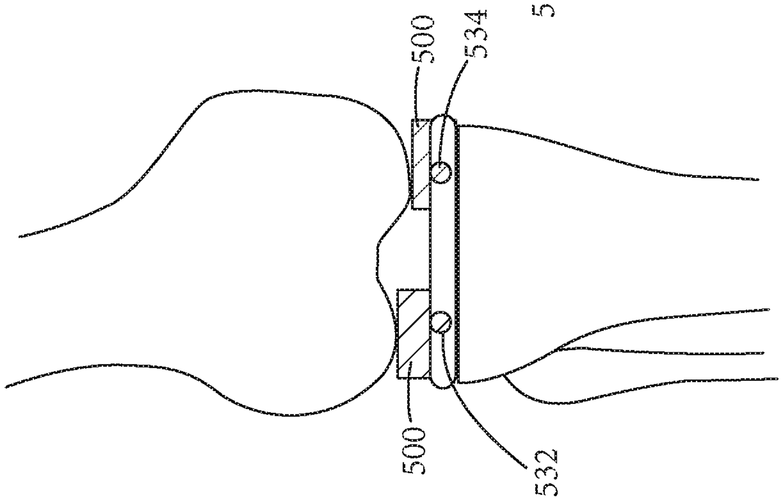
Figure 65F:
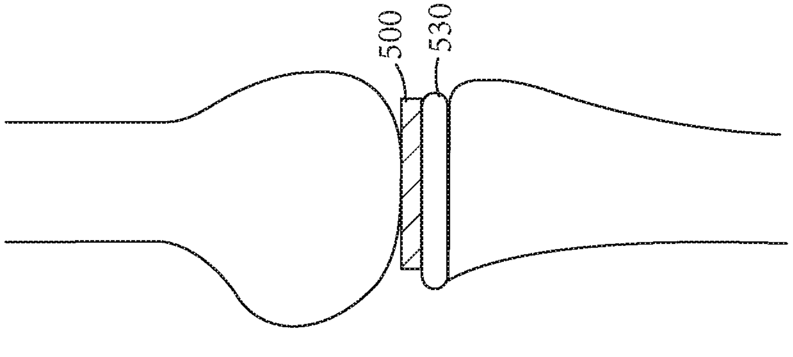
Figure 65J:
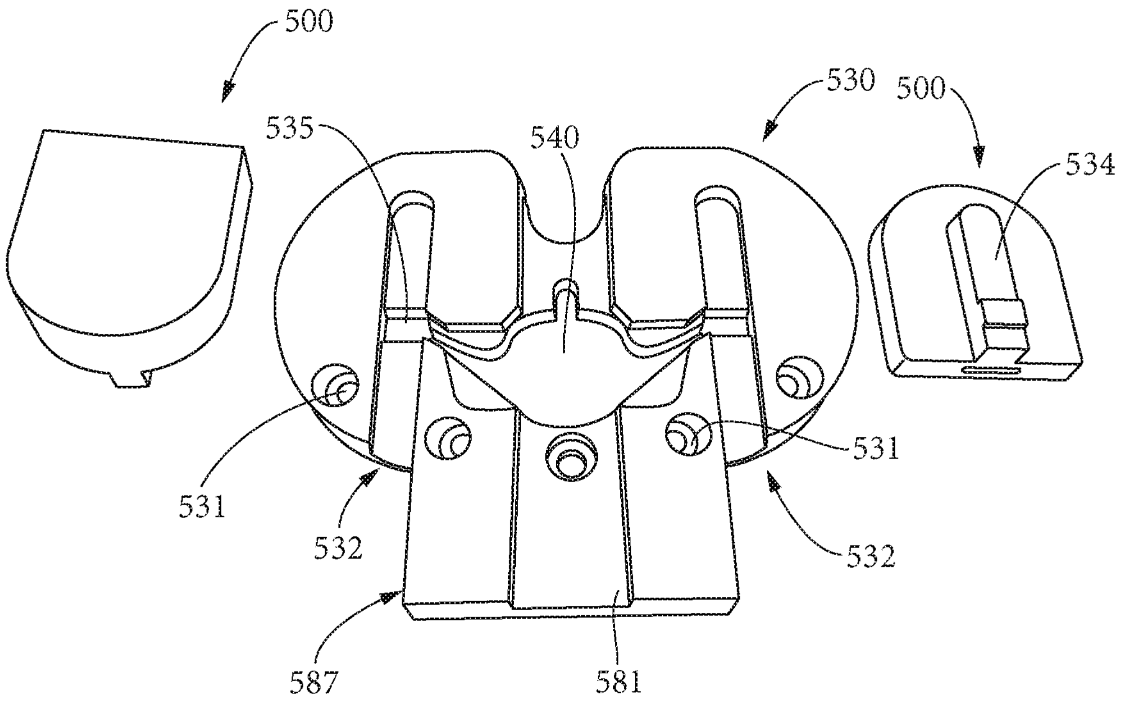
Figure 65K:
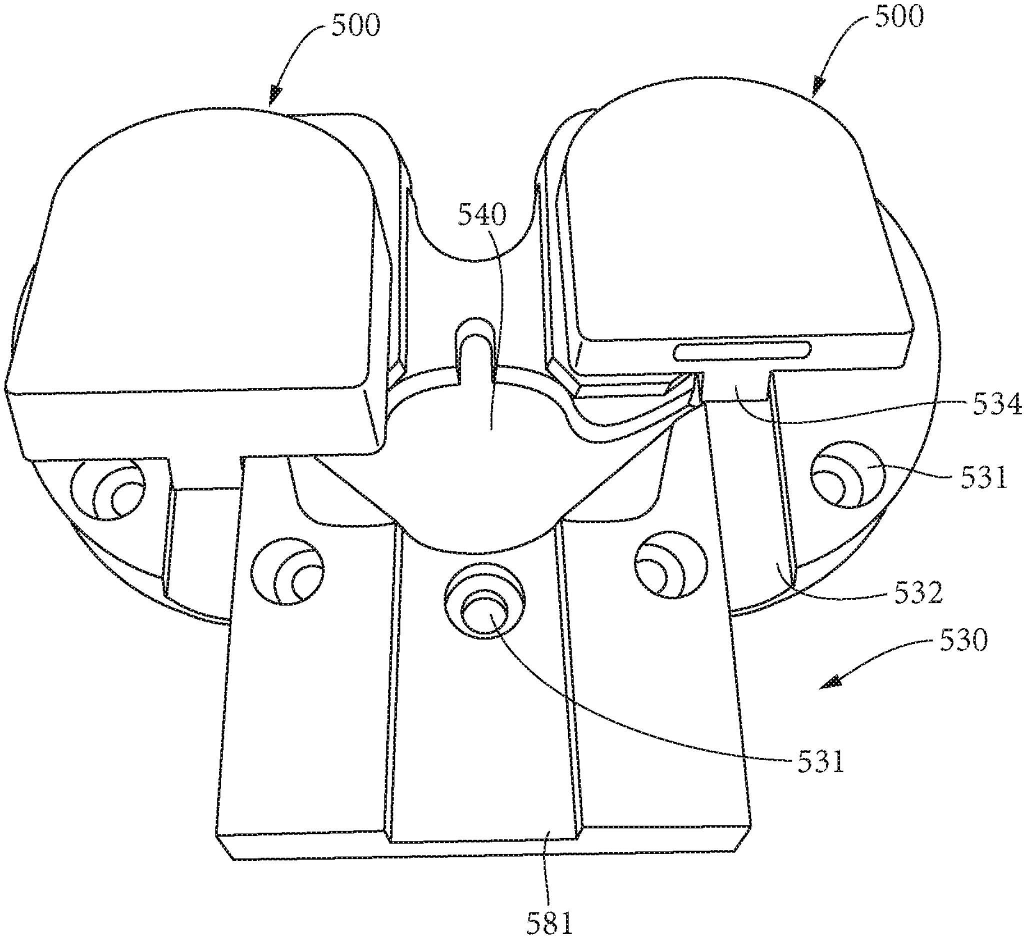
Figure 65L:
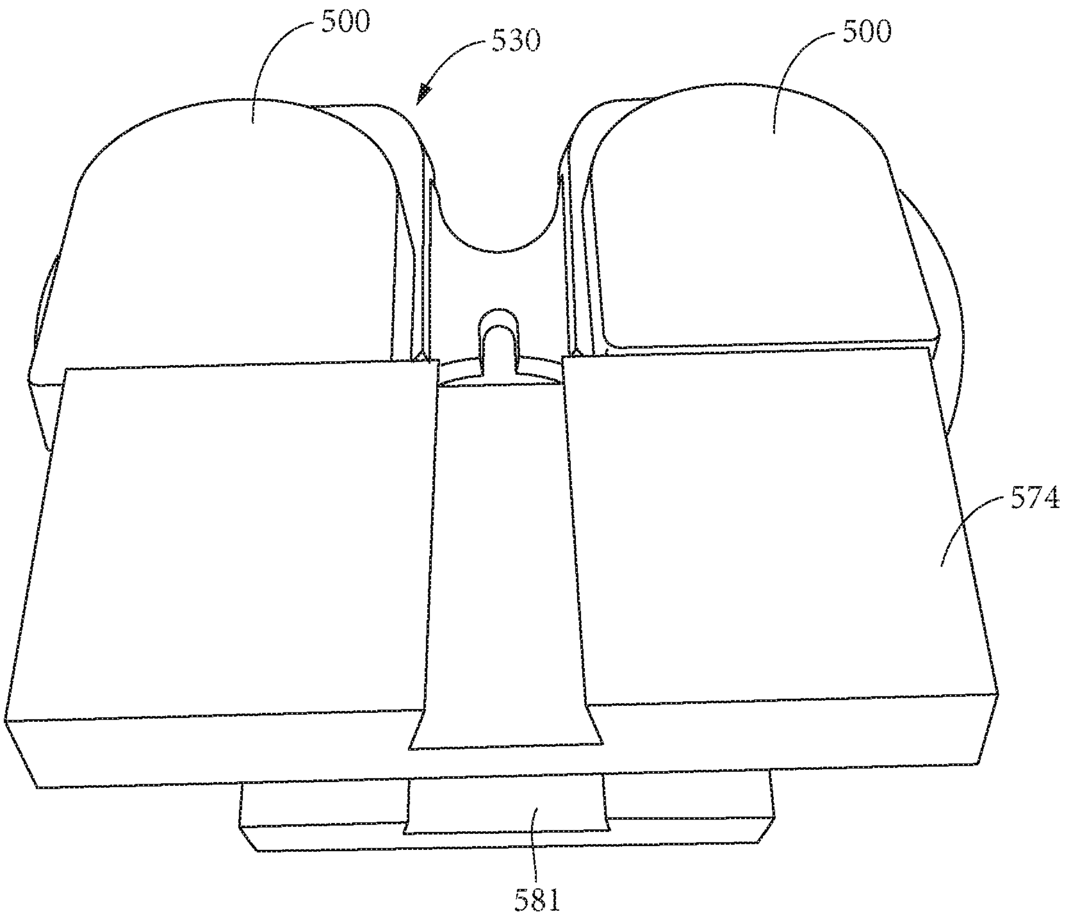
Figure 65M:
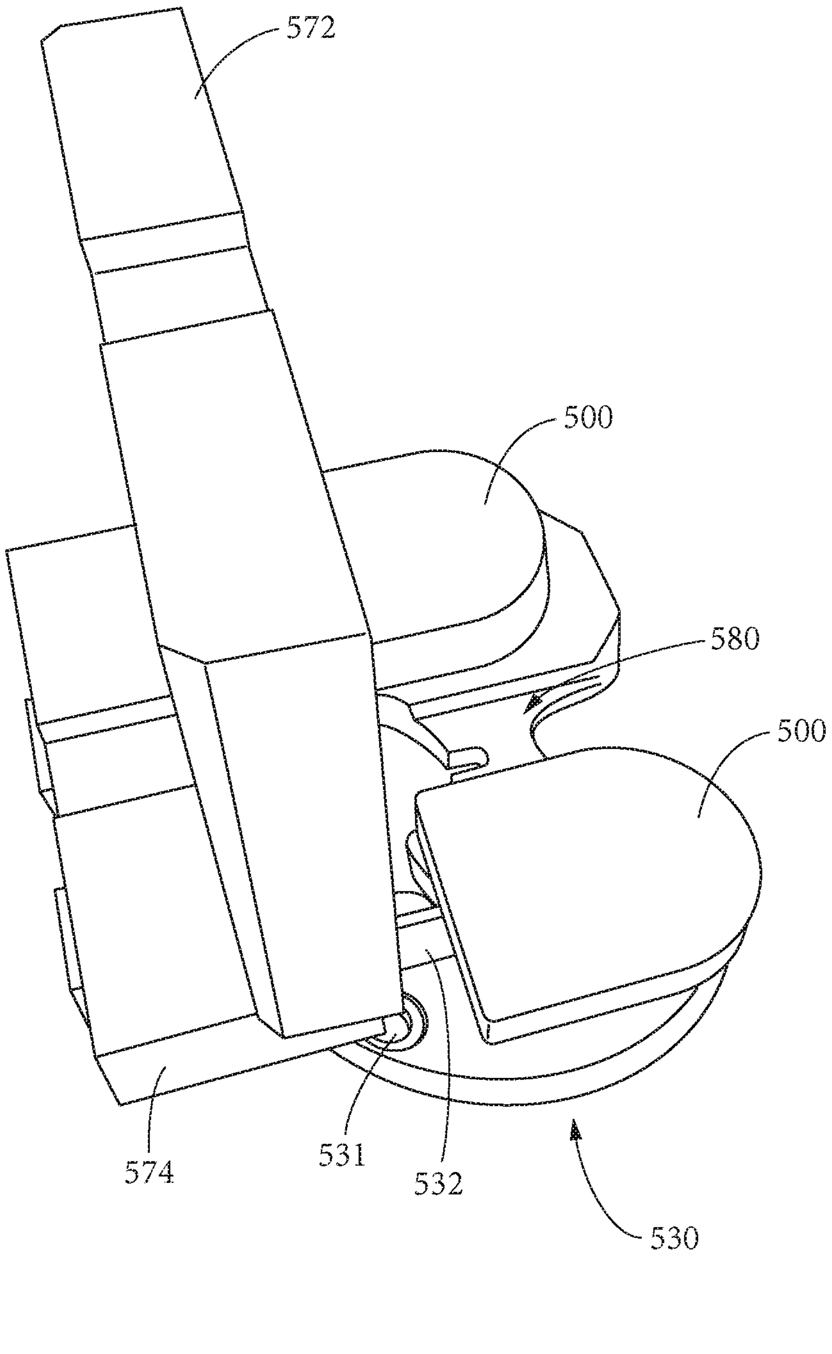
Figure 65N:
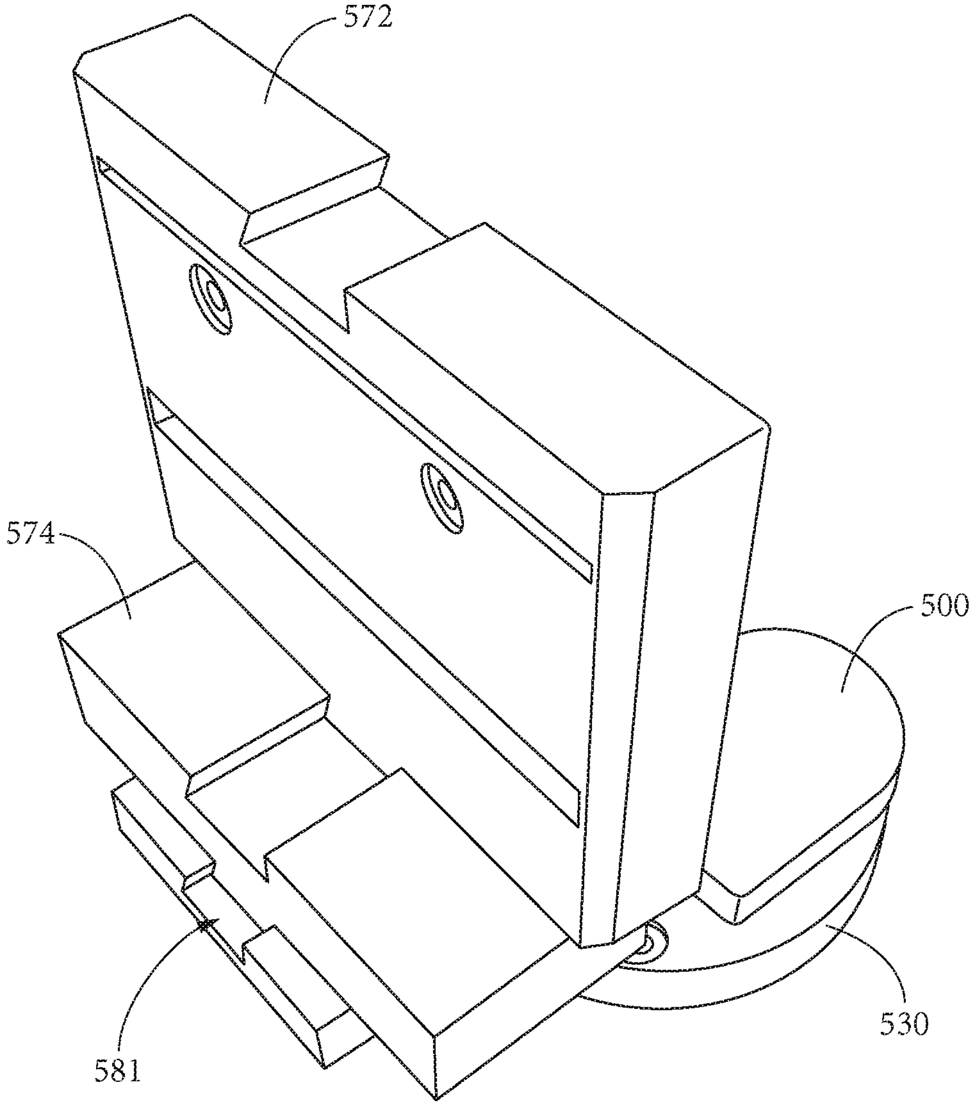
Figure 65O:
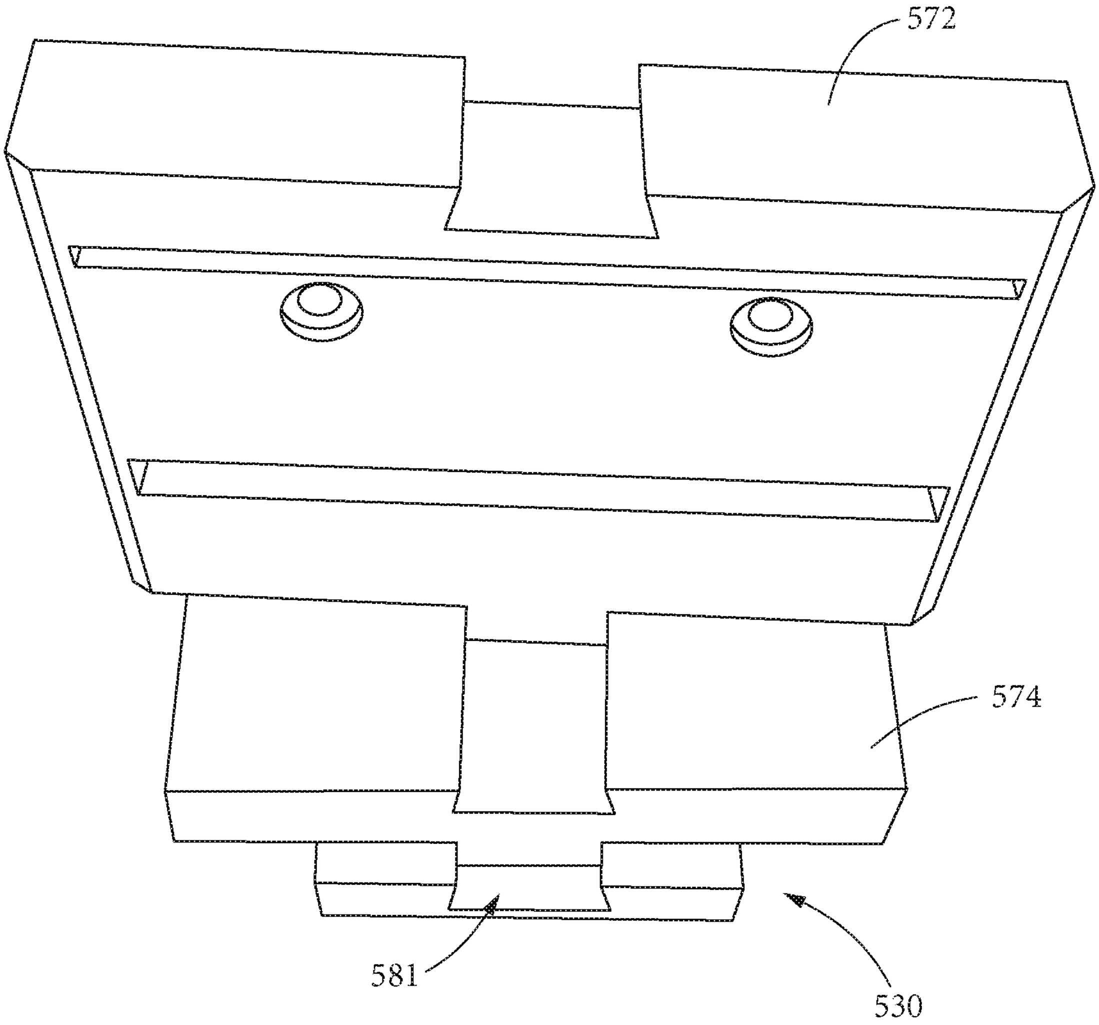
Figure 65P:
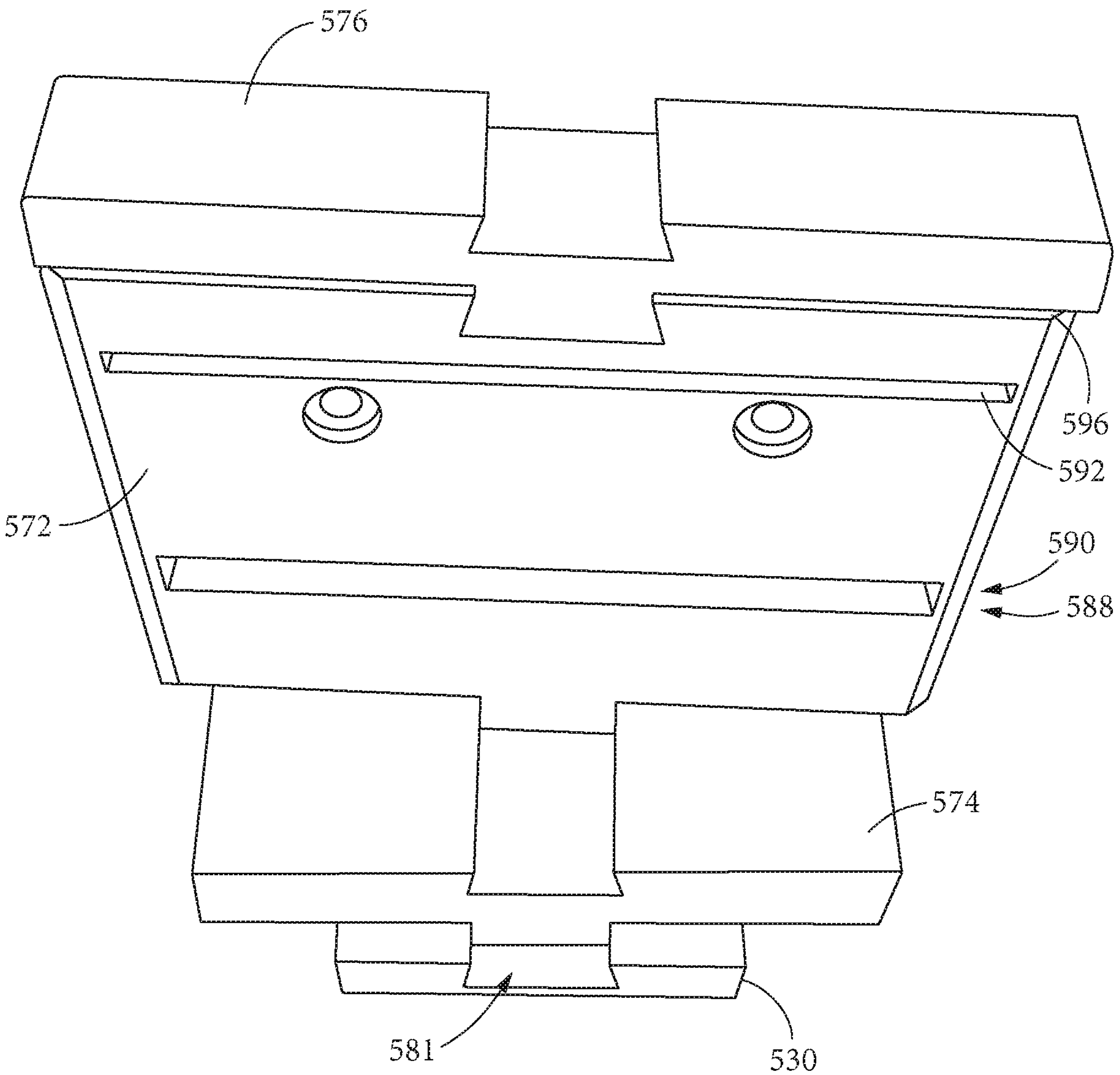
Figure 65Q:
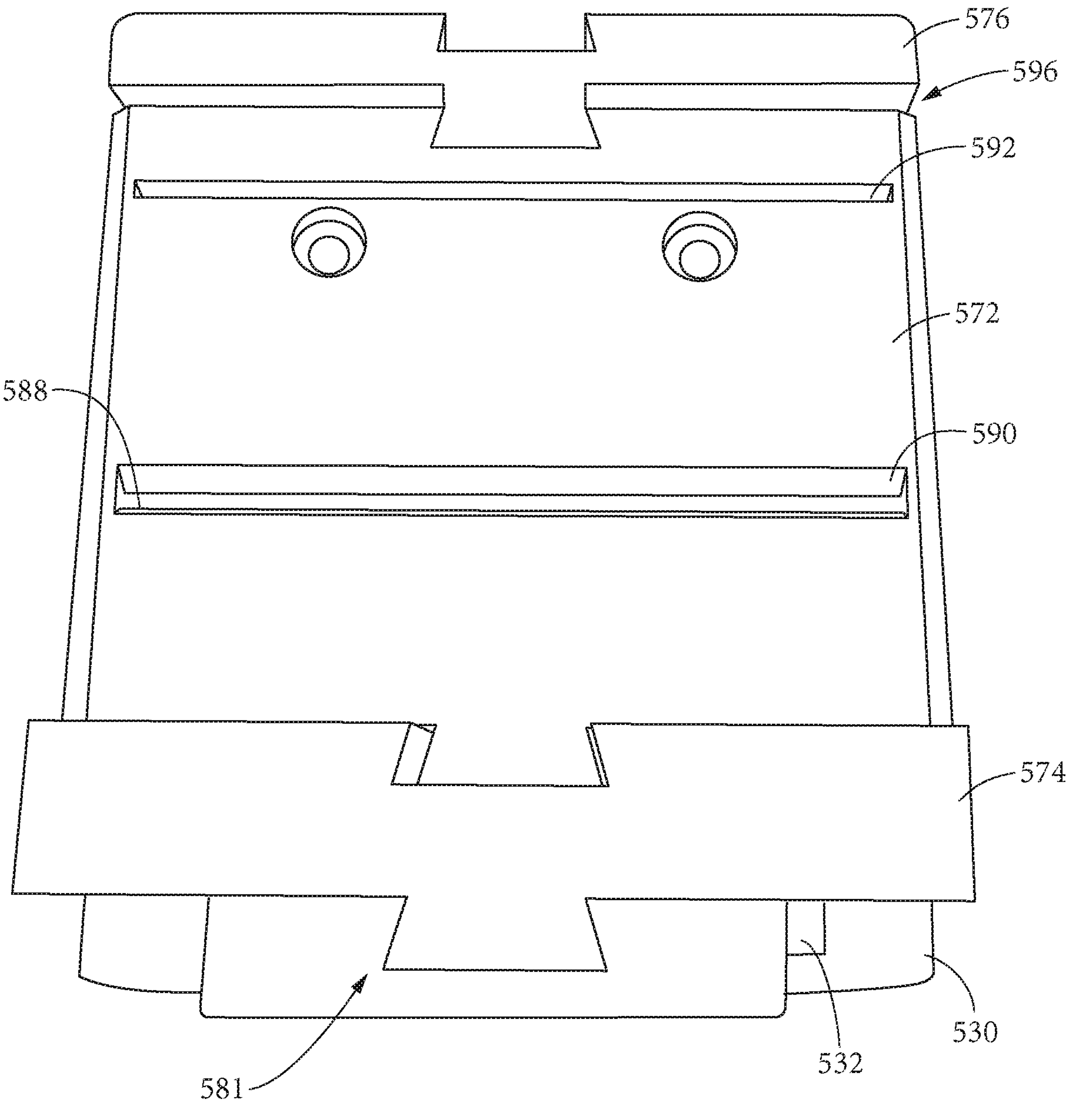
Figure 65R:
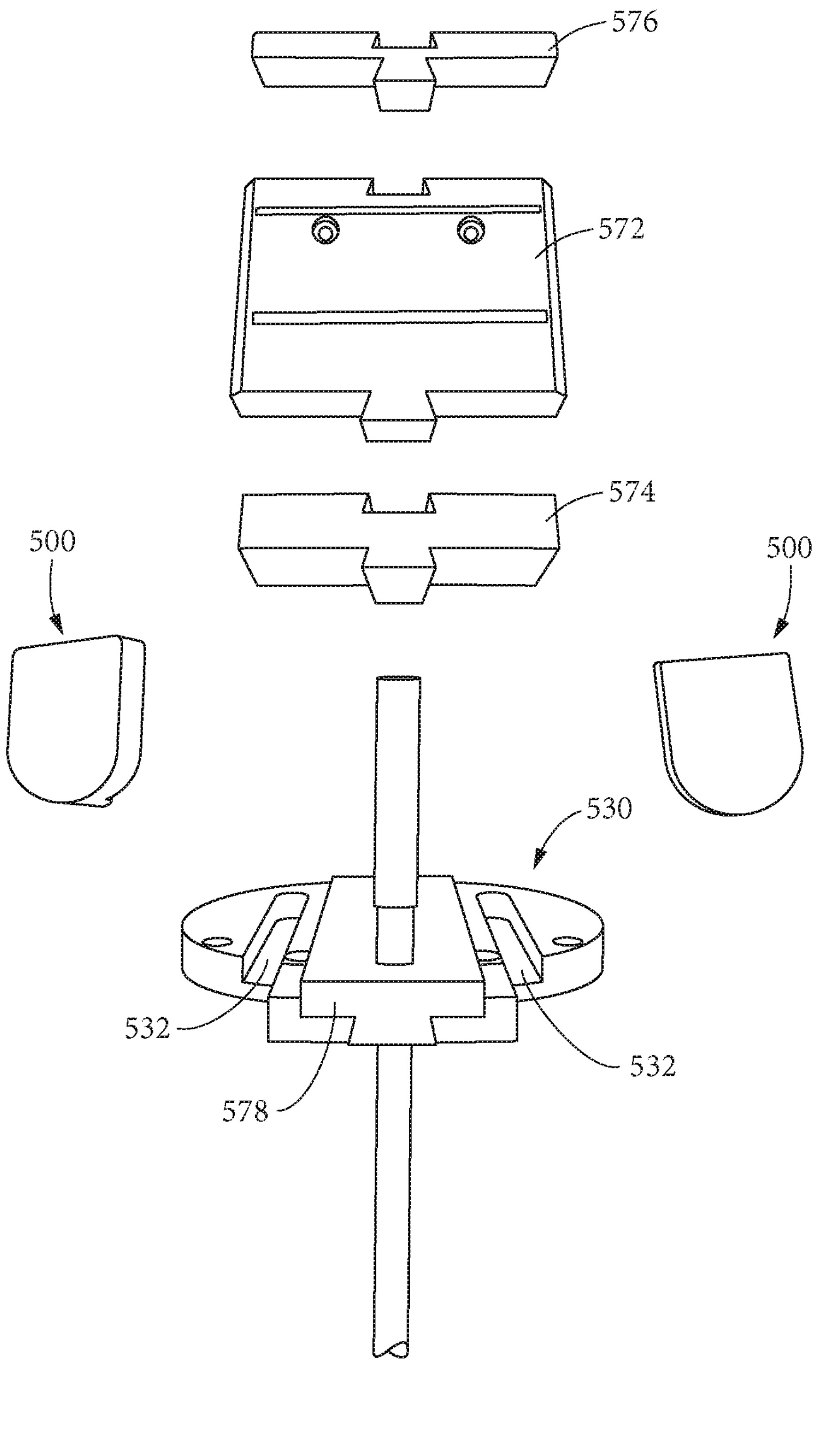
Figure 65S:
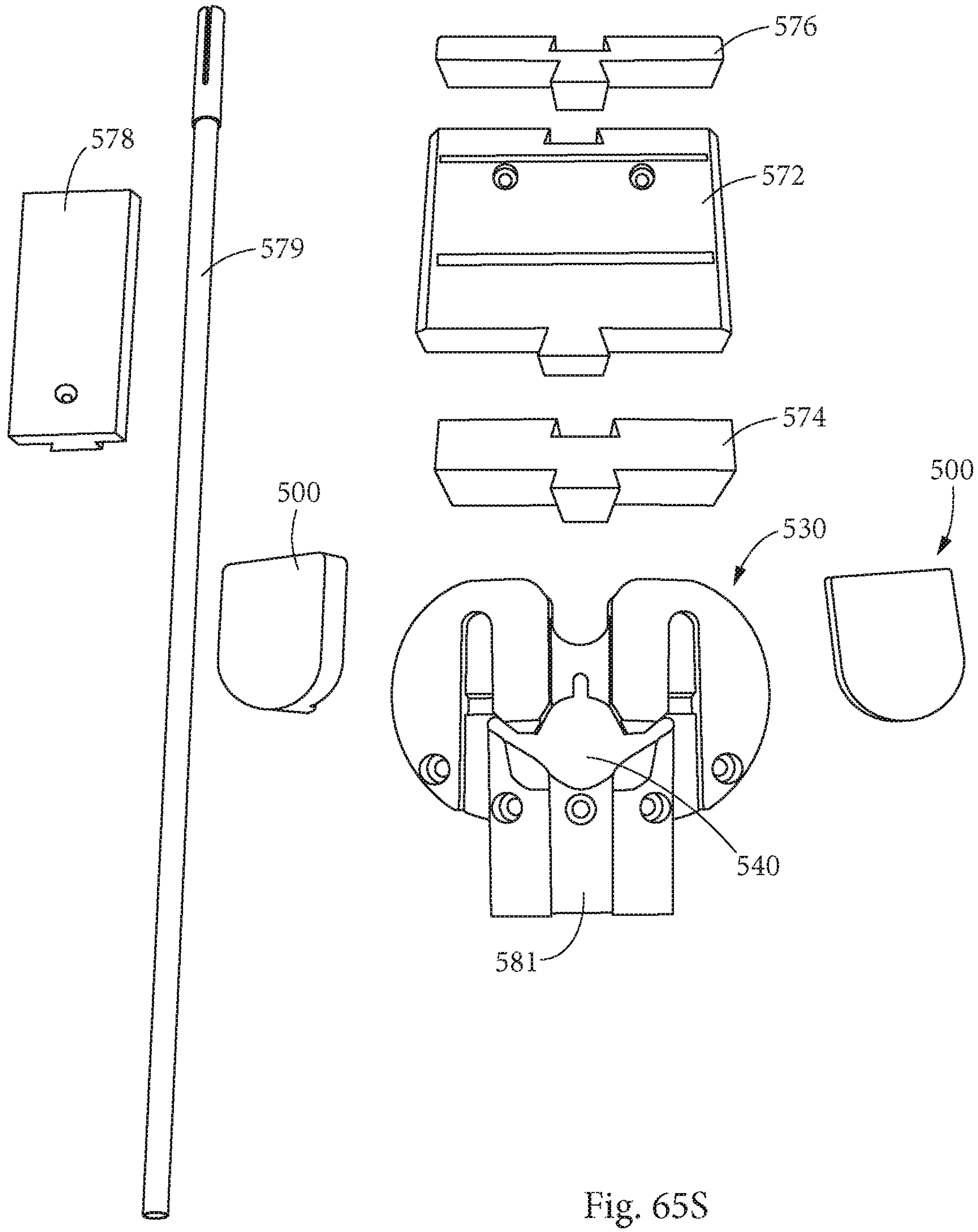
Figure 65U:
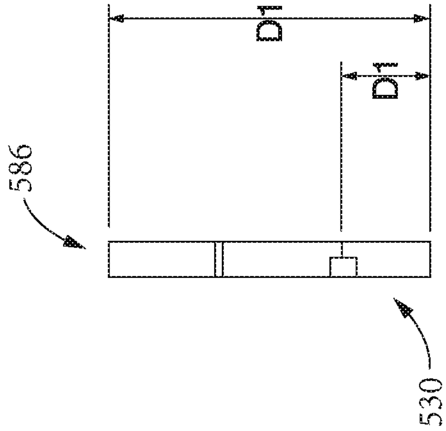
Figure 65T:
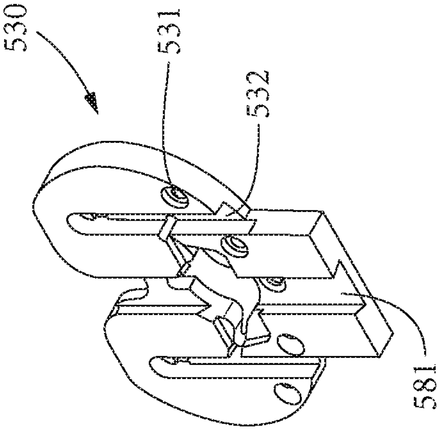
Figure 65W:
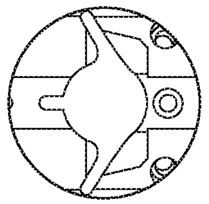
Figure 65V:
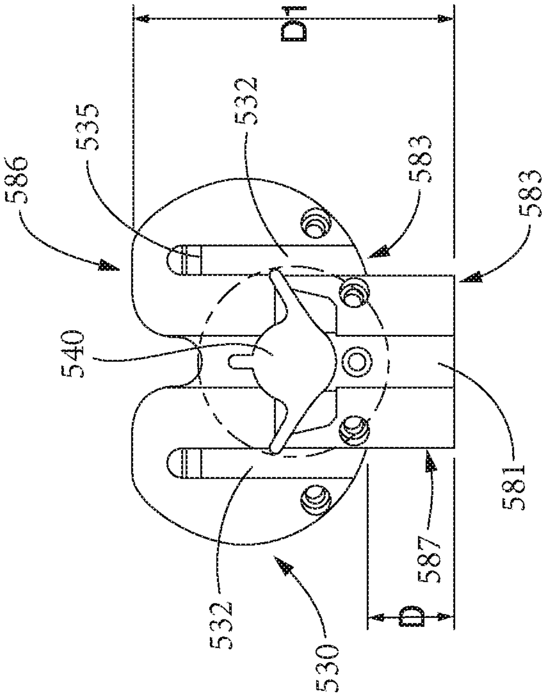
Figure 73B:
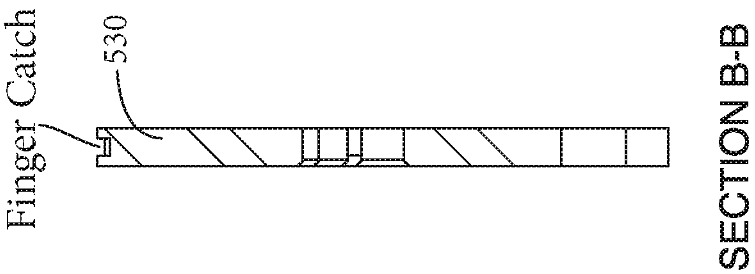
Figure 73C:
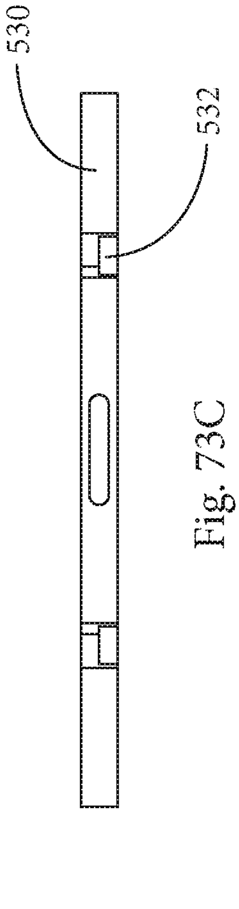
Figure 73A:
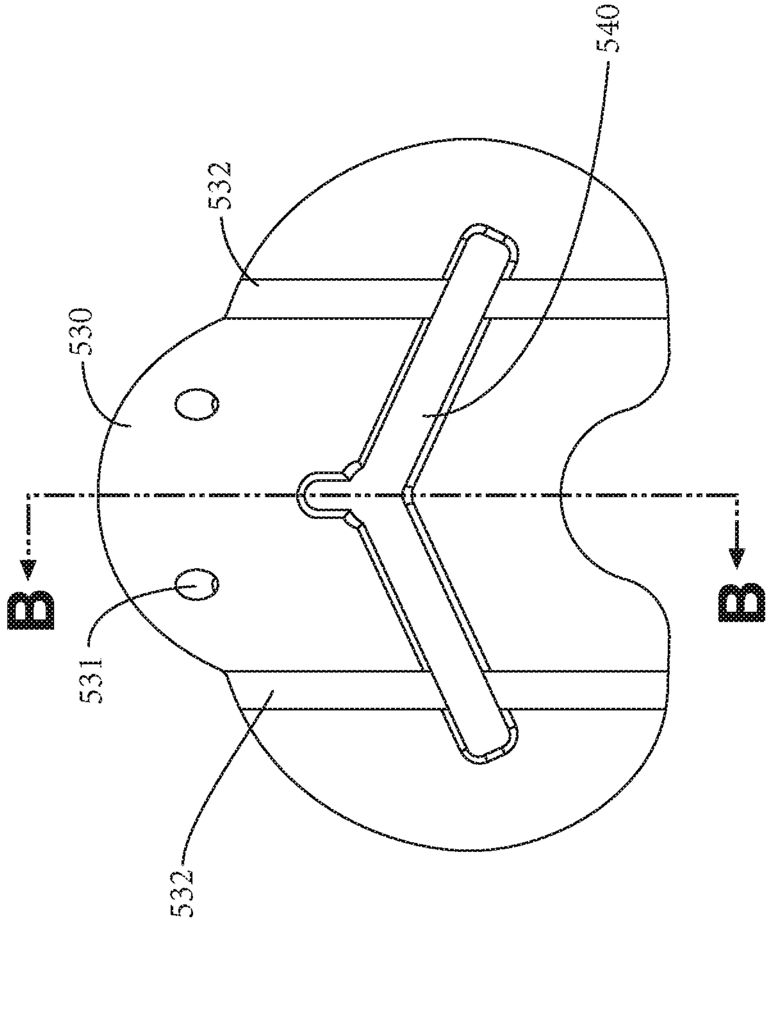

Additionally, while the various guides or couplings on the tibial baseplate 530 can have any suitable relationship to each other (e.g., being perpendicular to each other, being at an angle to each other, being disposed at the same or different heights on and/or in the tibial baseplate with respect to each other, and/or having any other suitable relationship), FIGS. 65J, 65V, and 73A shows that, in some embodiments, the tibial baseplate 530 comprises multiple elongated recesses 532 (or spacer, trial tibial component, elongated slots 581, and/or any other suitable guides or couplings) that run substantially parallel with one another.

In some embodiments, in which the spacer 500 is configured to couple to another object in the knee joint (e.g., the tibial baseplate 530), the spacer is configured to be adjustably moved to and/or selectively retained in one or more desired positions (e.g., via one or more catches, recesses, processes, projections, protuberances, adjustment mechanisms, clamps, pins, racks and pinions, locking mechanisms, ratchets, pawls, guides, slides, friction fittings, mechanical mechanisms, pressure from the knee joint, and/or other suitable mechanisms). By way of non-limiting illustration, FIGS. 65J and 65 show some embodiments in which the tibial baseplate 530 defines or more catches 535 or recesses that are configured to selectively capture a projection 527 (e.g., as shown in FIGS. 62V-62W). In this regard, such a recess and/or other catch can be disposed in any suitable location (e.g., on or in a superior surface 505, in and/or on an elongated recess 532, at an anterior portion, at a posterior portion, and/or in any other suitable location on the tibial baseplate).

By way of non-limiting illustration, FIG. 65J shows an embodiment in which the catch 535 is disposed adjacent to a midsection of a length of the elongated recess 532 (and/or at any other suitable portion of the spacer guide or recess 532). Additionally, FIG. 65V shows an embodiment in which the catch 535 is disposed towards a posterior end of the tibial baseplate 530. Accordingly, in some embodiments, the spacers are configured to be selectively pushed deeper into and/or to be removed from the knee joint and to be selectively retained in a desired position to change and/or maintain tension in the knee joint.

In some embodiments, the spacers 500 are configured to only be inserted and/or retracted from the tibial baseplate 530 from an anterior end of the baseplate. Indeed, in some embodiments, one or more of the spacer guides or elongated recesses (e.g., recess 532) are keyed (e.g., comprise a narrowed portion that is configured to capture a portion of a spacer coupler (e.g., the process 534) so as to allow the spacer to be slide into and/or removed from an anterior end portion of the tibial baseplate, while being captured so as to not be configured to be removed vertically from a portion of the spacer guide. Indeed, in some embodiments, the spacer guide (or elongated recess 532) comprises a dove-tail shaped groove, a circular groove (e.g., as shown at 532 in FIG. 66A), and/or any other suitably shaped groove. In contrast and as illustrated in FIGS. 65J, 65K, 65R, and 65W, in some embodiments, the spacer guide (e.g., elongated groove 532) is not keyed (or at least a portion of the guide is not keyed) such that the spacer guide can be selectively coupled to, and removed from, the spacer guide by vertically lifting and/or inserting the spacer guide coupler (e.g., the process 534) from and/or into the spacer guide.

Although some embodiments of the spacer 500 comprise no handle, some other embodiments, comprise one or more handles and/or handle couplers 517 that are configured to help a user readily manipulate the spacer—even when the spacer is disposed in the knee joint. In this regard, the handle can connect to the spacer in any suitable manner, including, without limitation, via one or more catches, recesses, hooks, eyelets, mechanical engagements, frictional engagements, magnetic engagements, threaded engagements, holes in the spacer that receive a portion of the handle, barbs, hooks, and/or in any other suitable manner. By way of non-limiting illustration, FIGS. 62S, 62T, 62W, 62X, 68A-68H, and 79 illustrate some embodiments in which the spacers 500 comprise one or more openings 536 that are configured to receive one or more portions of a handle 538. Accordingly, in some such embodiments, the handle can be used to push the spacer into a desired position in the knee joint, and the handle can then be removed to prevent it from encumbering the knee joint. Moreover, in some embodiments in which a portion of the spacer guide (e.g., elongated recess 532) is not keyed, the handle is configured to be used to pry and/or lean the spacer 500 (e.g., to disengage the projection 527 from the catch 535).

While, in some embodiments, the handle 538 is permanently coupled with a spacer 500, in some other embodiments, the spacer and its corresponding handle are configured to selectively couple to and/or decouple from each other in any suitable manner, including, without limitation, by having a projection at an end of the handle fit into an opening 536 at an anterior portion (and/or any other suitable portion) of the spacer, via one or more catches, one or more hooks, one or more hook-and-loop fasteners, one or more magnets and/or magnetic materials disposed in the handle and the spacer, and/or in any other suitable manner. Indeed, in some embodiments, an anterior portion of the spacer 500 defines an opening that is configured to receive a projection 539 (e.g., as shown in FIGS. 62S-62Z and 79) at an end of the handle. In some such embodiments, the handle's projection comprises a extension member (not shown) that is configured to extend into a corresponding opening in the recess of the spacer (e.g., when the handle is disposed at a certain angle) such that the handle can be used to pull the spacer from between the tibia and the femur.

In some embodiments, the spacers 500 are further configured to support and/or directly and/or indirectly couple with (and/or position) one or more cutting guides (e.g., cutting accessories 52, 54, and/or 87, femoral cutting guide blocks, saw blade capture blocks, gap resection blocks, and/or other suitable cutting accessories) to direct a cutting tool for resection of a portion of the knee joint. In such embodiments, the spacers can be used to support, couple with, and/or position the cutting guides and/or any other suitable components in any suitable manner, including, without limitation, through the use of one or more catches, mechanical engagements, frictional engagements, magnetic engagements, threaded engagements, rails, grooves, magnets, holes in the spacer that receive a portion of the cutting guide, coupling mechanism, and/or in any other suitable manner. By way of non-limiting example, in some embodiments, the spacers 500 comprise one or more openings 536 that are configured to receive (and/or one or more one or more processes that are configured to be received by) portions of a cutting guide (e.g., the flexed knee cutting guide 54 and direct mount 106 (as illustrated in FIG. 37) and/or other suitable cutting guide). In some other embodiments, FIGS. 65K-65Q show that (in some cases) the spacers 500 are configured to block and/or otherwise prevent a femoral cutting guide block 572, gap resection block 574, saw blade capture block 576, alignment rod block 578, and/or any other suitable accessory from being pushed or otherwise disposed too far posteriorly on the tibial baseplate 530.

Figure 76C:
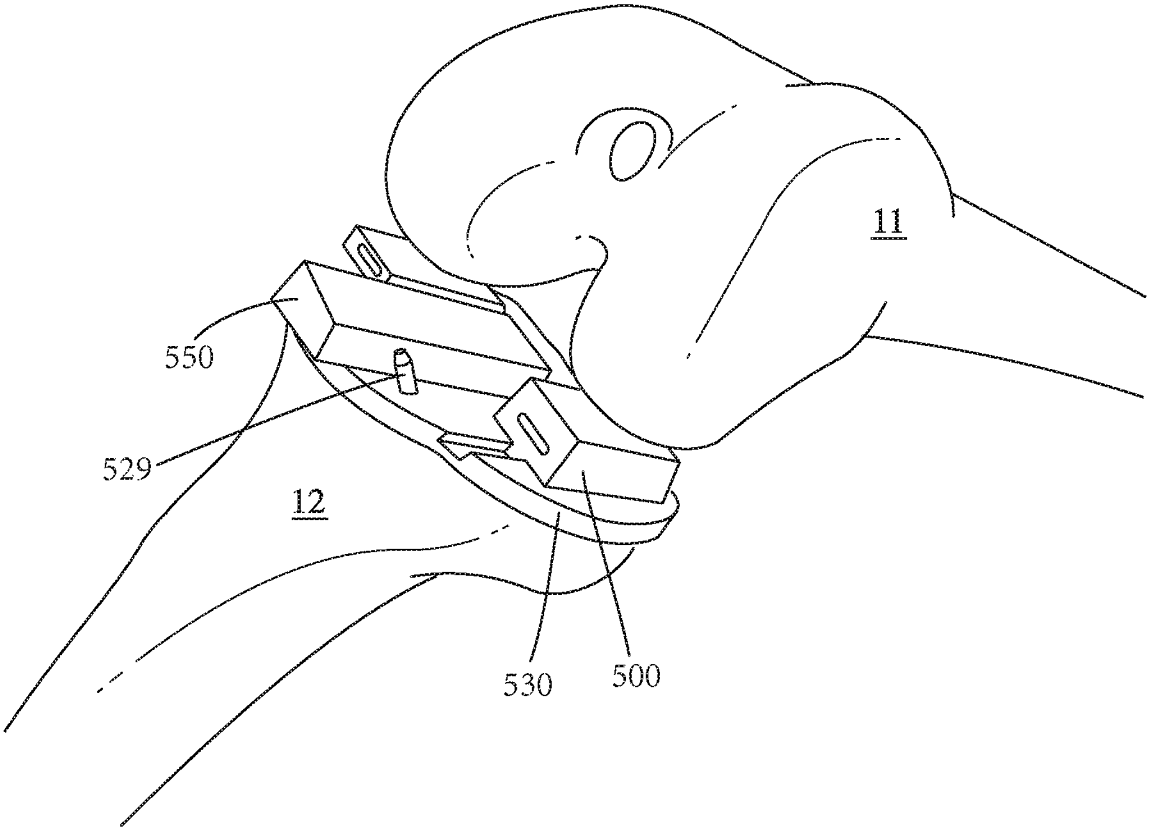
FIG. 76C depicts a perspective view of a knee joint in flexion comprising a cutting block reference spacer in accordance with representative embodiment.
Figure 76D:
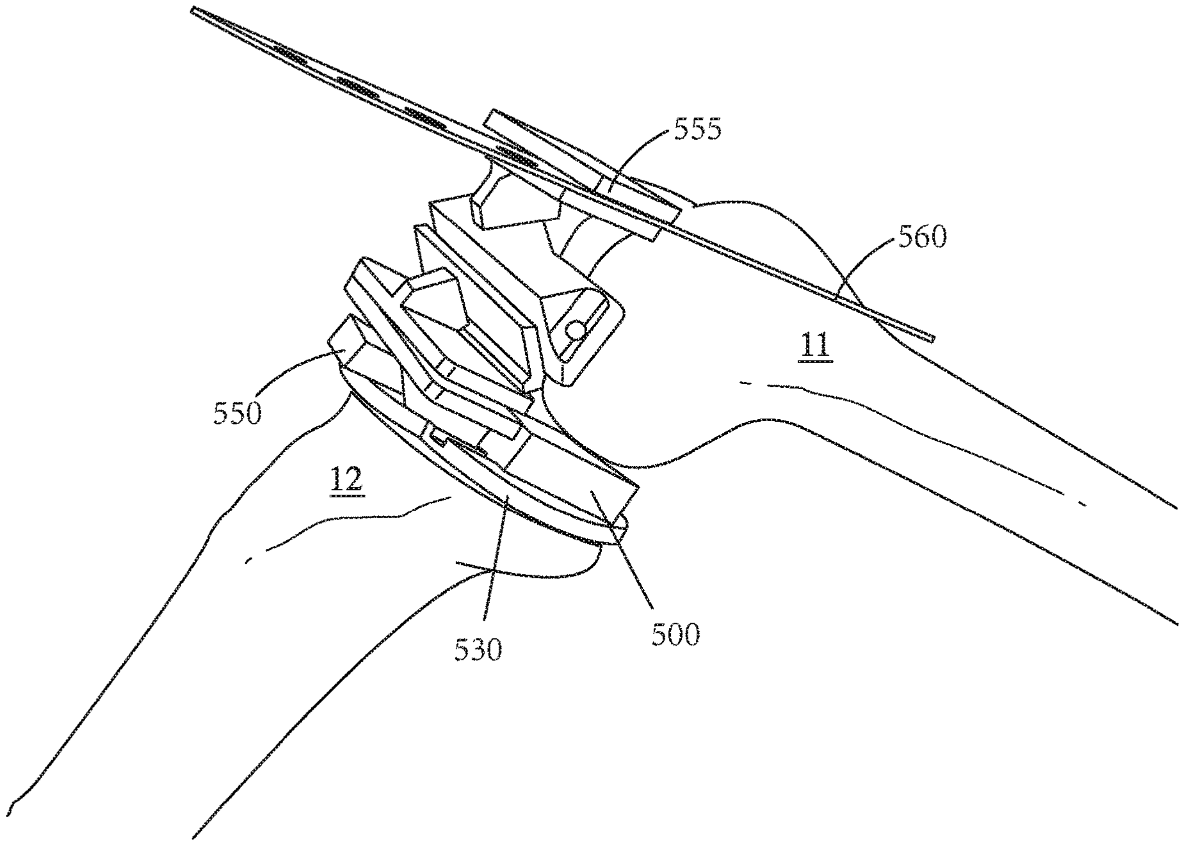
FIG. 76D depicts a perspective view of a knee joint in flexion comprising the cutting block reference spacer and a cutting block in accordance with representative embodiment.

In some embodiments, the described systems comprise one or more reference spacers that are configured to dispose the cutting block, guide, and/or any other suitable component, in the proper location. By way of non-limiting illustration, FIGS. 76C-76F show some embodiments in which one or more reference spacers 550 are disposed on the tibial baseplate 530 so as to support, couple with, and/or hold one or more cutting tool guides, blocks, and/or assemblies 555. In this regard, the reference spacers can be used in any suitable manner to ensure that the cutting assembly 555 is in the right position. For instance, FIG. 76D shows that, in some embodiments, the cutting assembly 555 is used with a gauge or marker (which may include a cutting blade) 560. In some such embodiments, different sized reference spacers 550 can be used until the marker 560 and/or another portion of the cutting assembly 555 is disposed in a desired location. In this regard, the reference spacers can be any suitable height, length, width, size, and can include any other suitable feature (e.g., handle opening 536, chamfered edge, etc.), as discussed above with respect to the spacers 500 (the references spacers being classified as spacers).

Where the described systems and methods optionally allow for the use of one or more reference spacers 550, such reference spacers can couple to the tibial baseplate 530, the cutting assembly 555 and/or any other suitable component in any suitable manner, including, without limitation, via one or more mechanical engagements, frictional engagements, magnets, slides, guides, rails, grooves with one or more slidably mating objects (e.g., via an elongated slot 581 in the tibial baseplate, as shown in FIG. 65K), cables, couplers, by being configured to have one component rest on the other such that one component can be moved in medially, laterally, posteriorly, and anteriorly with respect to the other component, by resting on the baseplate, and/or in any other suitable manner. By way of non-limiting illustration, FIG. 76C shows an embodiment in which the reference spacer 550 rests on the baseplate 530 and is at least somewhat held in position by one or more fasteners 529. Additionally, although some embodiments of the reference spacer 550 can selectively connect to and disconnect from the cutting assembly, FIG. 76D shows an embodiment in which the cutting assembly 555 rests on top of the reference spacer 550. In this regard, FIGS. 76D and 76F show that such a configuration can allow the reference spacer 550 (or reference spacers of a variety of sizes) to properly align the cutting assembly 555 when the knee joint is in flexion (e.g., as shown in FIG. 76D) and/or in extension (e.g., as shown in FIG. 76F).

Where one or more spacers 500 and/or 550 are disposed in the knee joint during resection, the spacers can be used in any suitable manner. Indeed, in some embodiments, the spacers are maintained in the knee joint until one or more distal, posterior, anterior, chamfer, and/or any other suitable cuts of the femoral condyles have been made completely. In some other embodiments, however, one or more spacers are inserted into the knee joint, and one or more partial cuts are made before the spacers are removed and the cuts are completed. In some embodiments, one or more spacers 500 are coupled to the tibial baseplate 530 when a posterior cut, a posterior chamfer cut, an anterior chamfer cut, an anterior cut, and/or any other suitable cut is made to the femur.

Figures 64A, 64B, 64C, 64D, 65A, 65B, 65C, 65D, 65E:
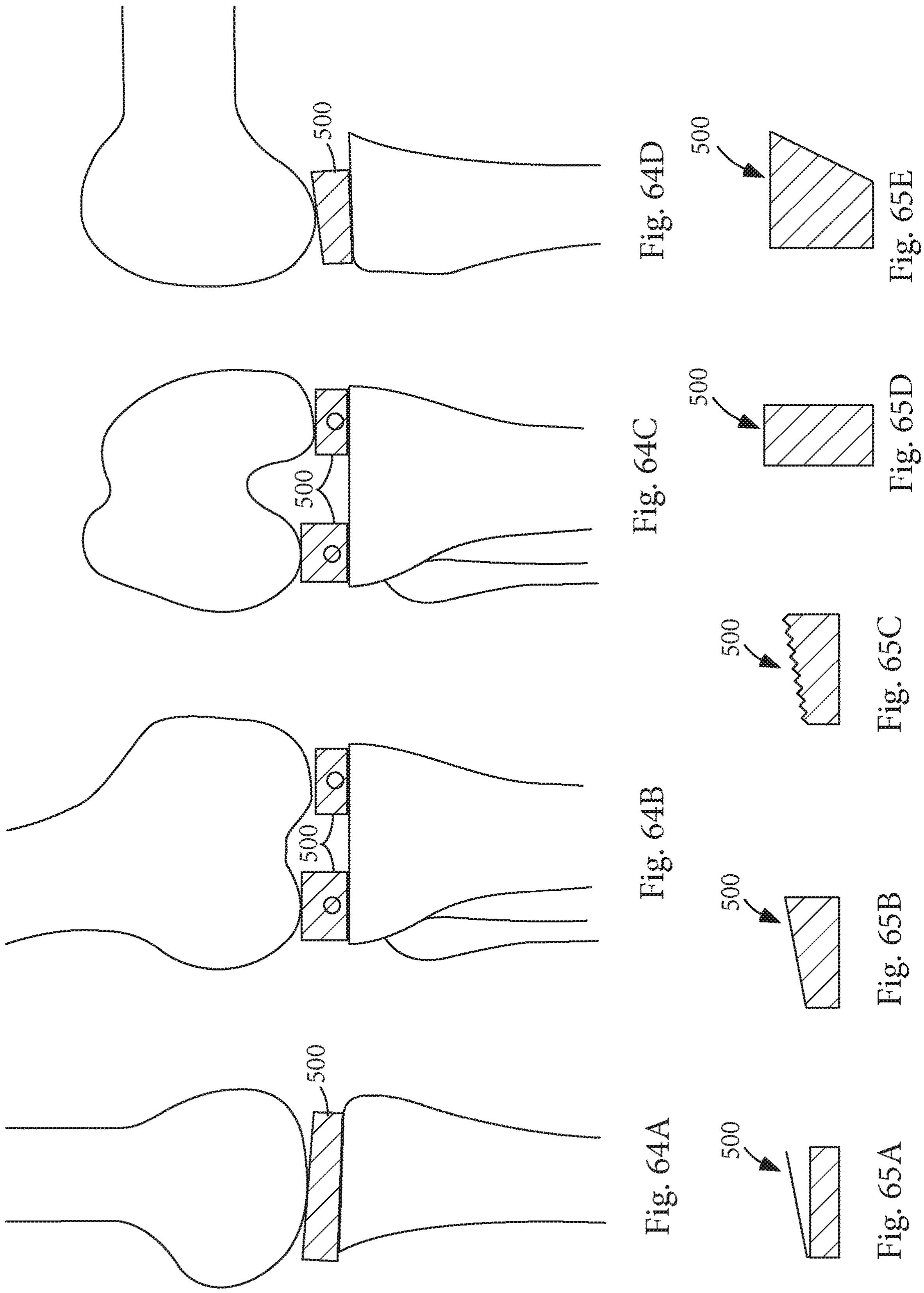

In some embodiments, a spacing height of one or more of the spacers is configured to be adjusted. In this regard, the spacing height of the spacers can be adjusted in any suitable manner, including, without limitation, by placing one spacer on top of another, adding one or more shims to a spacer, mechanically adjusting a spacer, and/or in any other suitable manner. Indeed, in some embodiments, one or more of the spacers 500 comprise a soft tissue retractor, lamina spreader, spreader, reverse plier, lever, and/or any other suitable device that is capable of being used to separate the femur 11 from the tibia 12 in the knee joint. Indeed, in some embodiments, one or more retractors (e.g., soft tissue and/or any other suitable type of retractors) are attached to any suitable portion of the described apparatuses and/or systems (including, without limitation, to one or more spacers 500, reference spacers 550, tibial mounts 25, tibial baseplates 530, femoral mounts 15, tibial IM rods 14, femoral IM rods 13, plateau flanges 28, secondary femoral mounts 100, tibial tensioning adapters 160, flexion bolts 30, extension bolts 96, gauge blocks 76, bushings 33, valgus adapter members 110, flexion bolts 120, threaded barrels 115, tibial components, femoral components, tensioning assemblies, ratcheting devices 142, gap resection blocks 574, femoral cutting block 572, saw blade capture blocks 576, alignment rod blocks 578, and/or any other suitable components). Accordingly, in some such embodiments, one or more retractors are coupled (e.g., permanently, selectively, adjustably, and/or otherwise) to one or more of the tibial baseplate, femoral mount, a femoral component, the tibial mount, a tibial component, a tensioning assembly, a cutting block, and/or any other suitable portion of the described apparatuses and/or systems to provide better exposure to the bones in the knee joint while the described systems and methods are in use. In one non-limiting example, FIG. 65E shows that, in some embodiments, the spacer 500 is configured to have a prominent lateral edge (e.g., at a proximal and/or distal portion) that is configured to serve with and/or as a lateral tissue retractor.

Figure 77A:
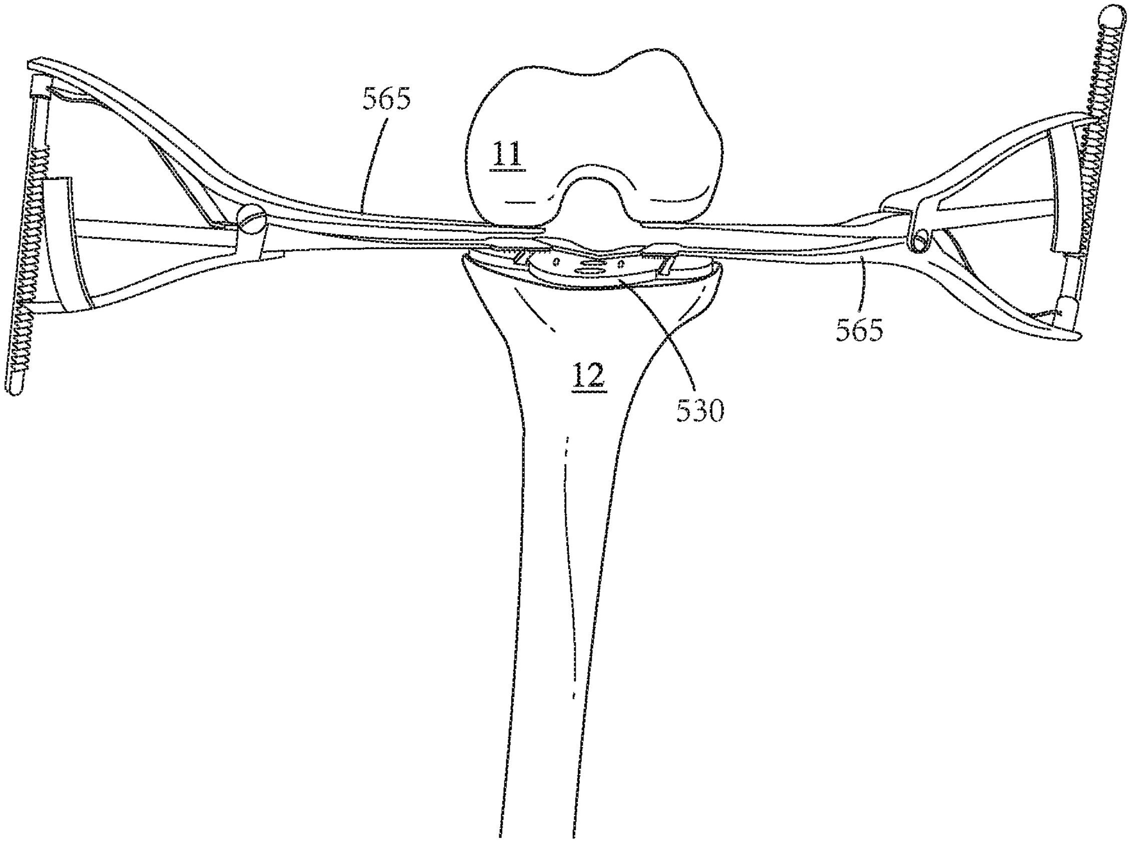
FIG. 77A depicts a front view of a knee joint in flexion comprising two lamina spreaders in accordance with a representative embodiment.
Figure 77B:
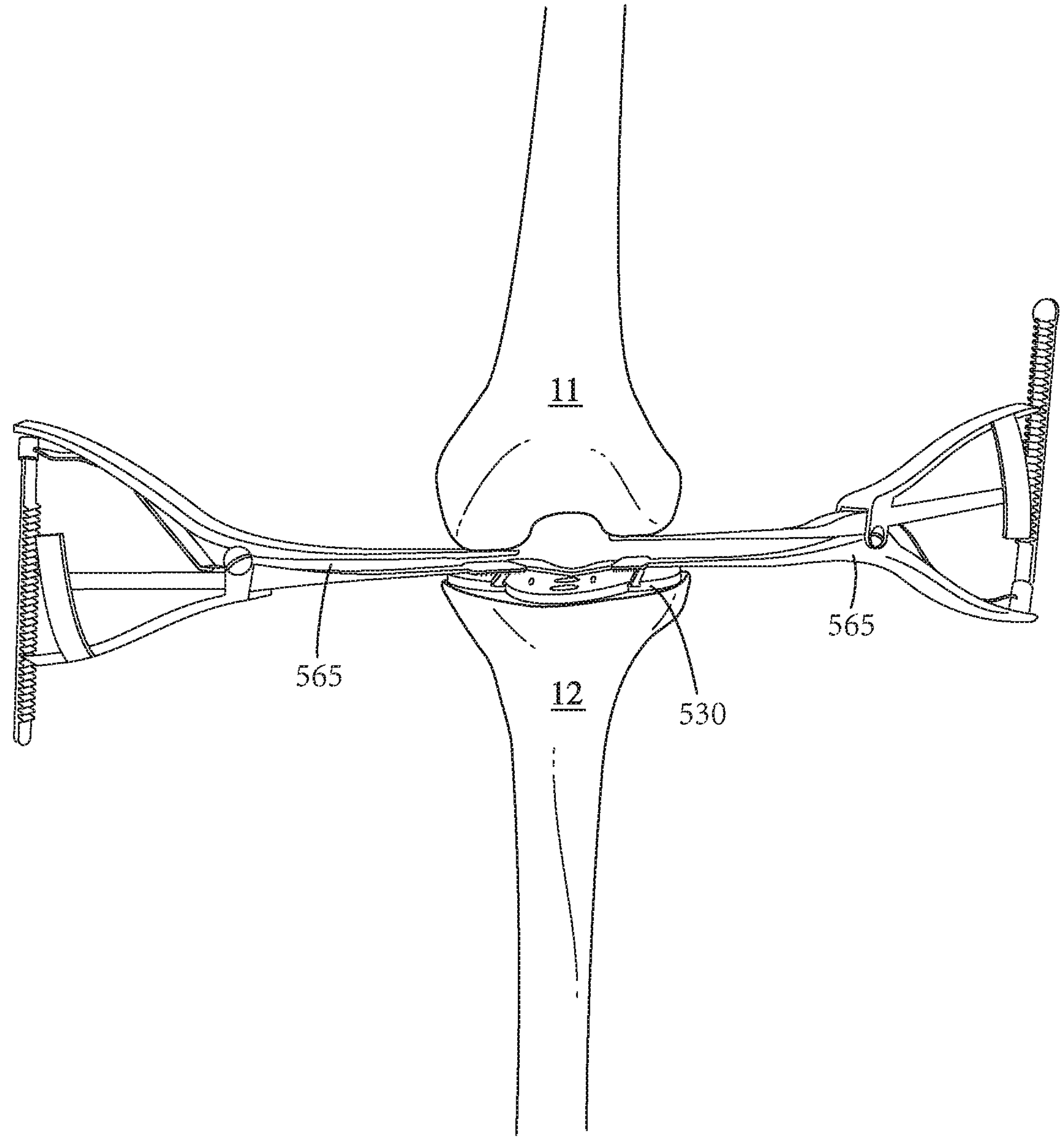
FIG. 77B depicts a front view of a knee joint in extension comprising two lamina spreaders in accordance with a representative embodiment.
Figure 77C:
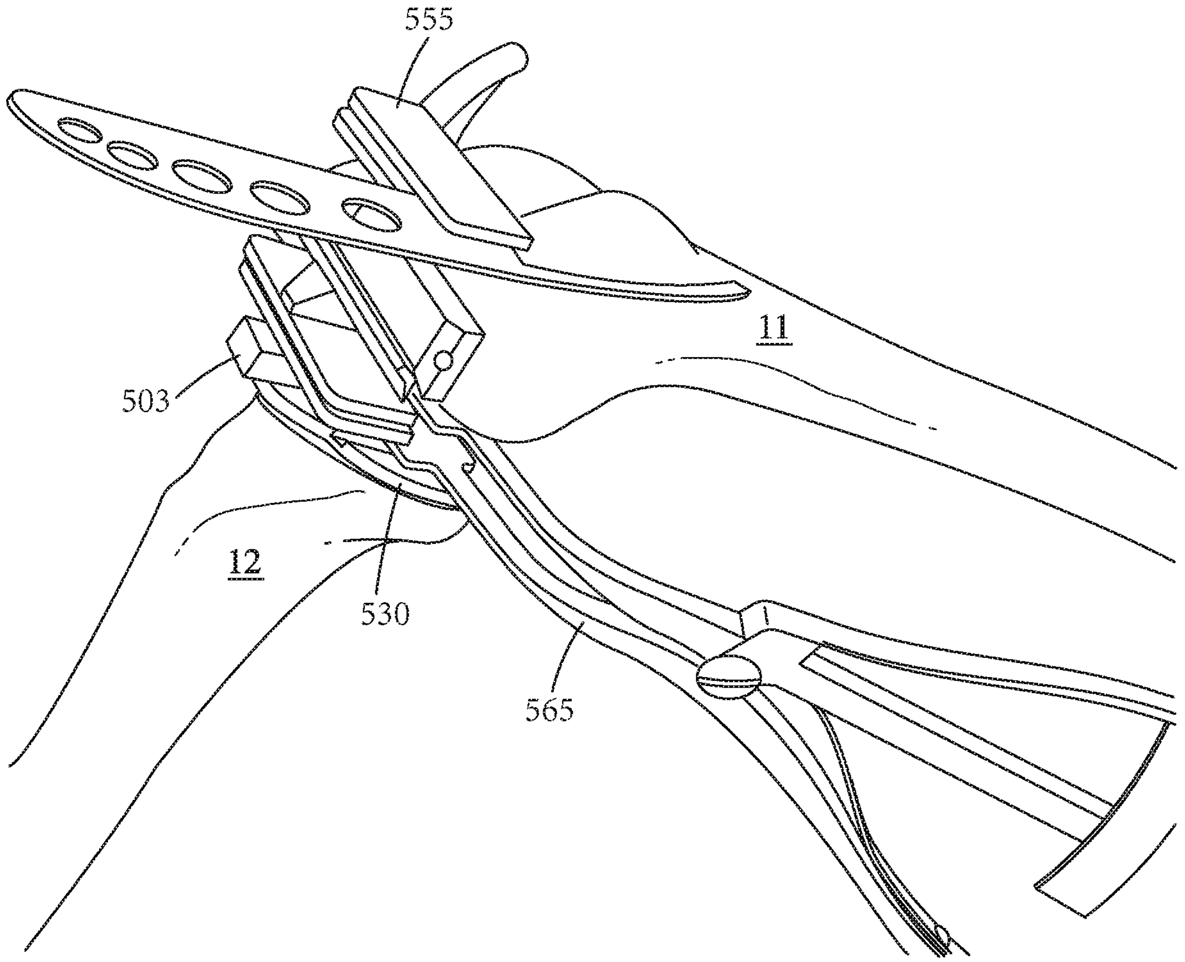
FIG. 77C depicts a side perspective view of a knee joint in flexion, the knee joint comprising two lamina spreaders, the cutting block reference spacer, and the cutting block in accordance with a representative embodiment.
Figure 77D:
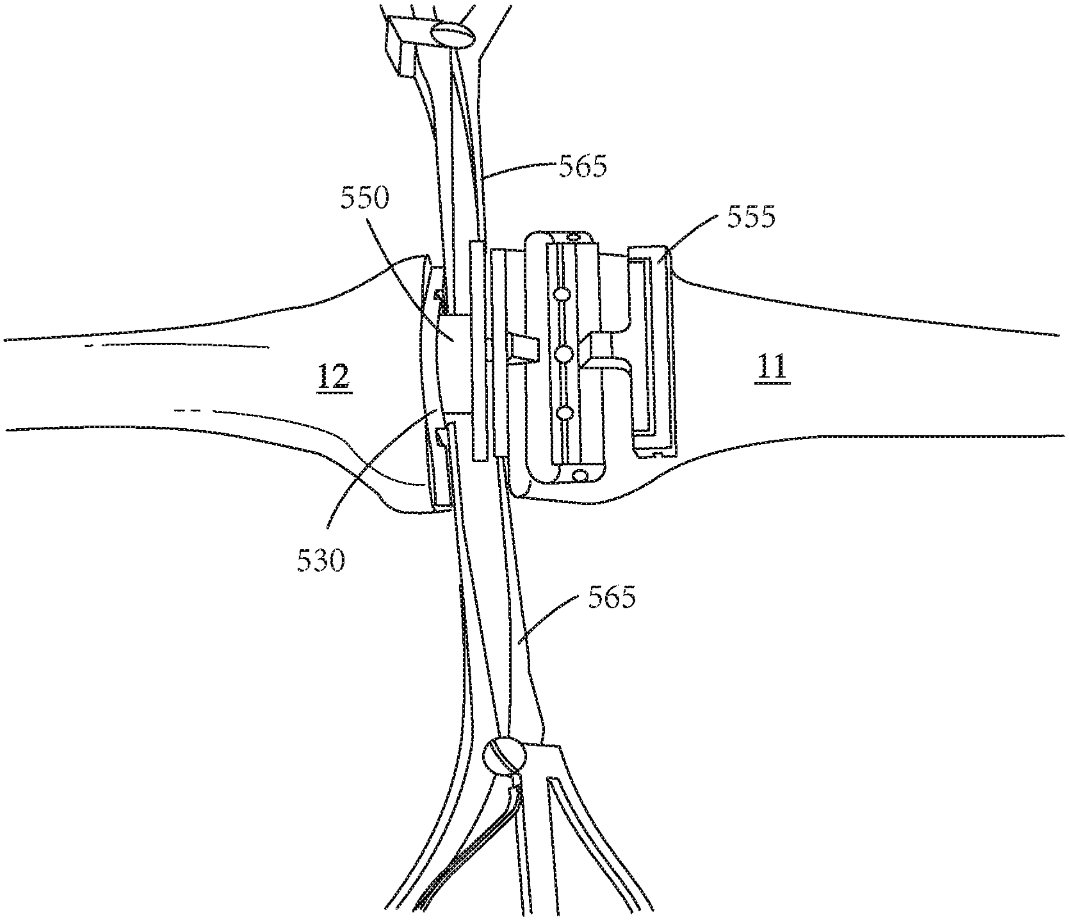
FIG. 77D depicts a side perspective view of a knee joint in extension, the knee joint comprising two lamina spreaders, the cutting block reference spacer, and the cutting block in accordance with a representative embodiment.
Figure 77E:
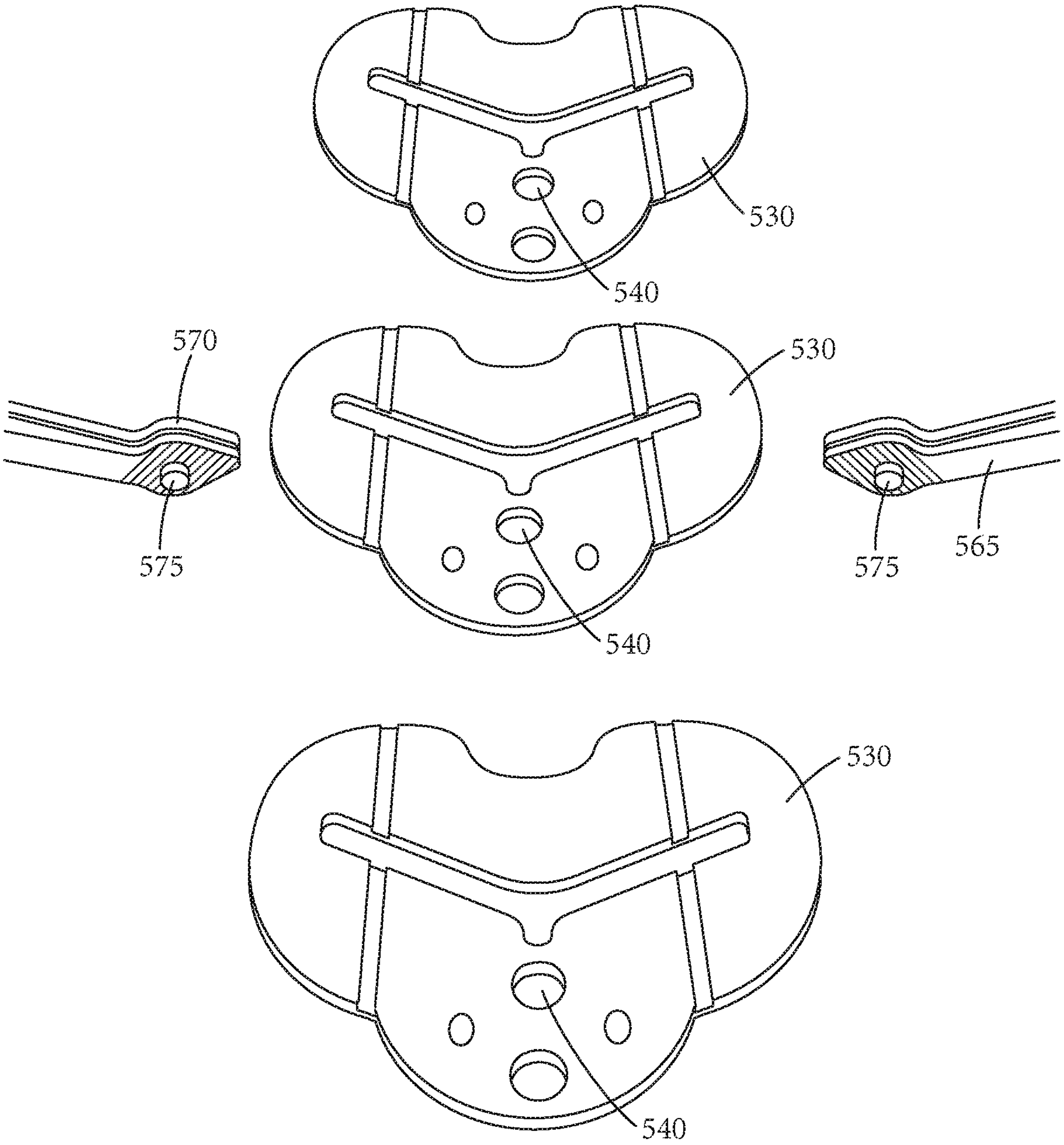
FIGS. 77E-77F depict a portion of a spreading device comprising a process that is configured to be received within a portion of the tibial baseplate in accordance with some representative embodiments.
Figure 77F:
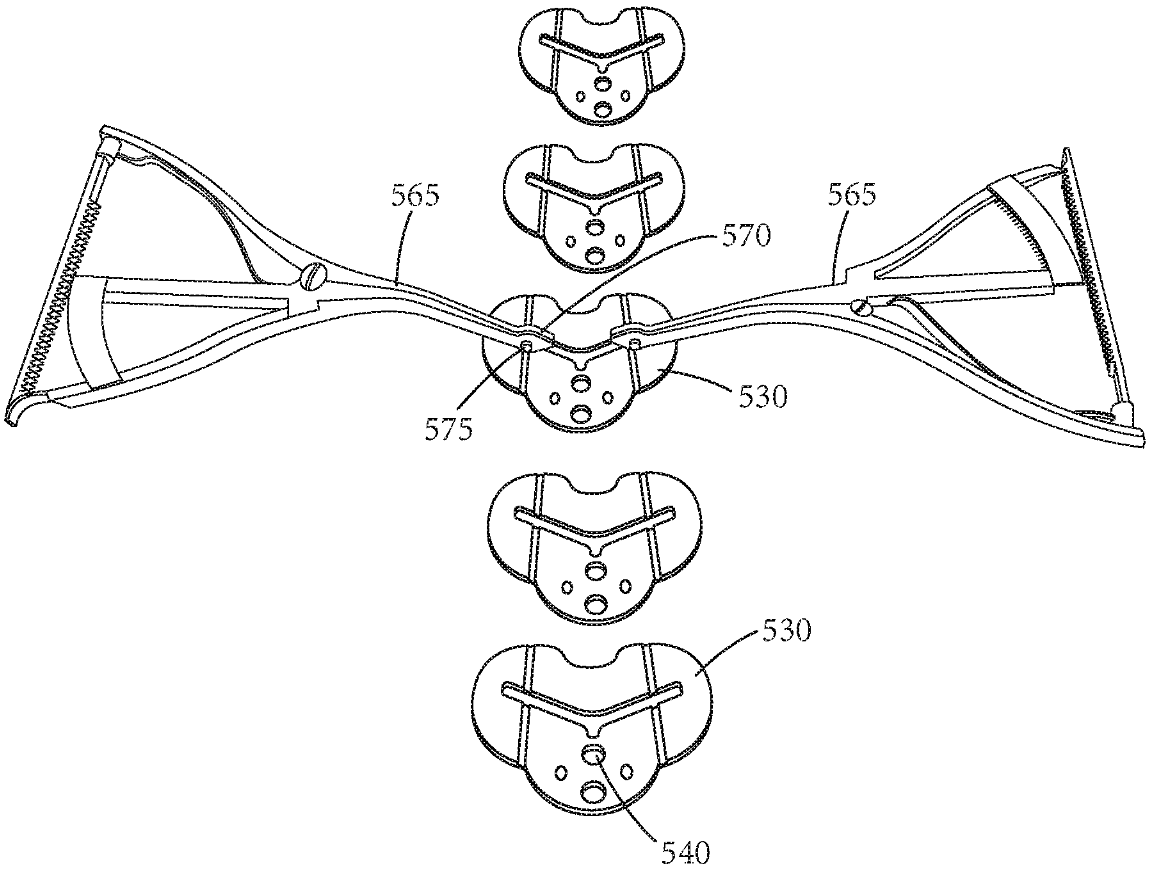
Figure 78:
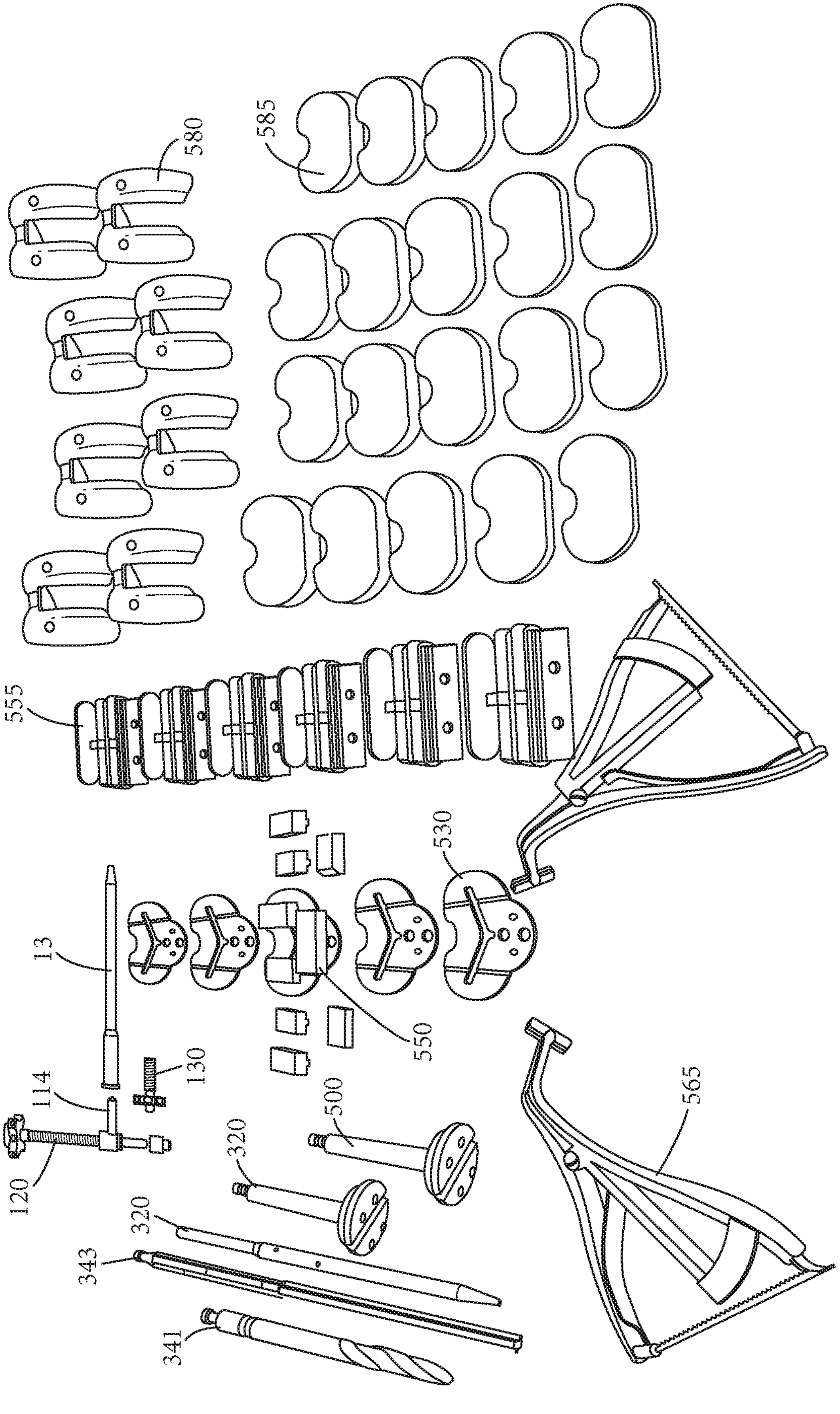
FIG. 78 depicts a representative embodiment of a kit for preparing a knee joint for partial and/or full knee replacement in accordance with some embodiments.
Figure 79:
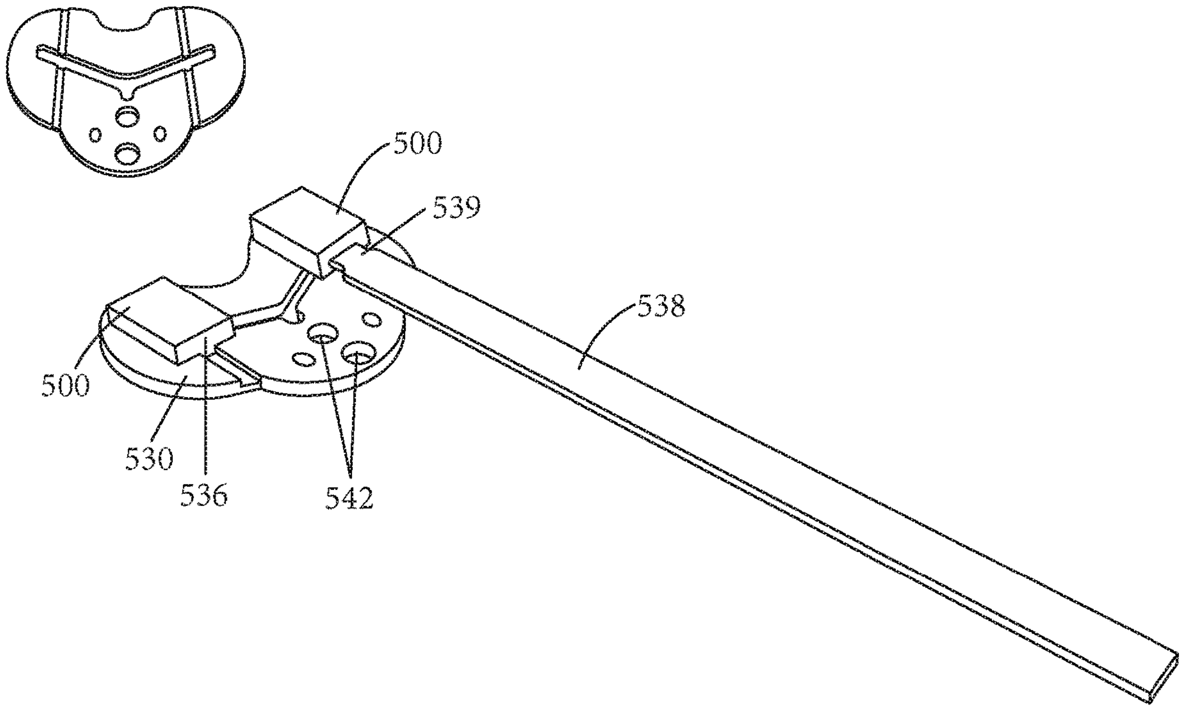
FIG. 79 depicts a view of the tibial baseplate comprising multiple spacers and a handle that is configured to push the spacers into a desired location.

In some other embodiments, one or more retractors (e.g., lamina spreaders, spreaders, reverse pliers, levers, and/or any other suitable device capable spreading the femur 11 and the tibia 12) are used to provide proper tension in the knee joint. By way of non-limiting illustration FIGS. 77A-77D show that in some embodiments one or more modified and/or standard lamina spreaders 565 are used as spacers 500 to provide tension to the knee joint. In such embodiments, the lamina spreaders (and/or other suitable retractors) can have any suitable feature. Indeed, although in some embodiments, the lamina spreaders comprise any suitable conventional or new lamina spreaders, in some other embodiments, the lamina spreaders (or other retractors) are configured to be selectively coupled to and/or decoupled from the baseplate 530.

Where one or more lamina spreaders 565 (and/or other retractors) are configured to be selectively coupled to and decoupled from the baseplate 530 and/or any other suitable component, the spreaders can be coupled to the baseplate (or other component) in any suitable manner, including, without limitation, via one or more: processes that are configured to mate with one or more corresponding recesses in the tibial baseplate (and/or any other suitable component), recesses that are configured to mate with a corresponding process of the baseplate, mechanical engagements, frictional engagements, magnets, rails, grooves, catches, couplers, and/or other suitable mechanisms. By way of non-limiting illustration, FIGS. 77E-77F show some embodiments in which a pad 570 of the lamina spreader 565 comprises one or more processes 575 that are configured to mate with one or more recesses or couplings (e.g., holes 531, grooves 532, tensioner couplings 533, openings 540 (e.g., punch openings and/or otherwise), and/or any other suitable recesses) in the baseplate 530. Accordingly, in some such embodiments, the lamina spreaders (and/or other retractors or spacers 500) can be relatively easy to use and can be retained in place with little to no worry about them slipping out of the knee joint when the knee joint is under tension—both when the knee is in flexion (e.g., as shown in FIGS. 77A and 77C), when the knee is in extension (e.g., as shown in FIGS. 77B and 77D), as well as when the spreaders are used with one or more block-shaped spacers 500 (e.g., reference spacers 550), cutting assemblies 555 (e.g., as shown in FIGS. 77C-77D), and/or any other suitable component.

The described components can be modified in any suitable manner that allows them to function as set forth herein. In one example, one or more of the described components (e.g., the tibial baseplates 530, the tibial tensioning adapters 160, and/or any other suitable component described herein) are configured to serve as a drill bit, keel, and/or punch guide to prepare the tibia for a tibial implant. Indeed, in some embodiments, the tibial baseplate defines one or more openings that are configured to be used to ensure proper drill bit and/or punch placement.

Figure 84A:
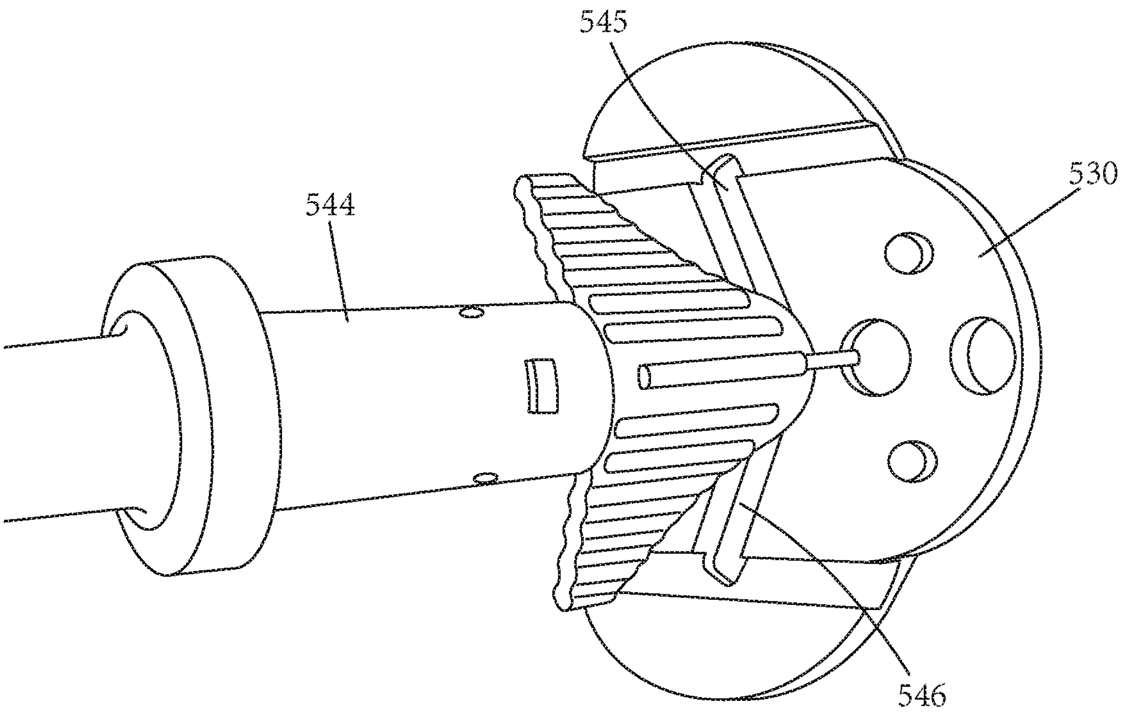
FIGS. 84A-84B depict some embodiments in which the tibial baseplate is configured to guide a punch into a tibia.
Figure 84B:
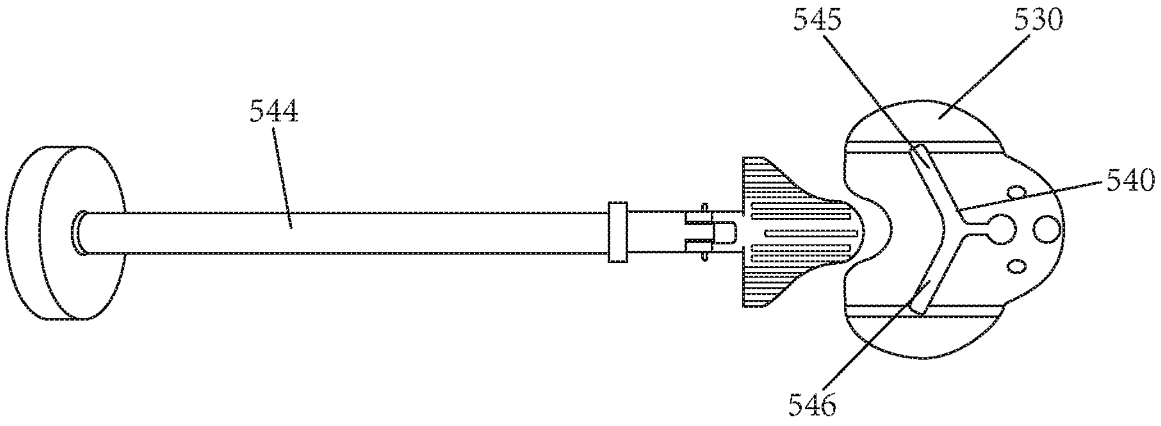

By way of non-limiting illustration, FIGS. 65J, 65W, and 84A-84B show that, in some embodiments, the tibial baseplate 530 optionally defines one or more openings 540 that are configured to guide a punch (e.g., a keel punch 544 and/or any other suitable punch) into the tibia (e.g., to prepare the tibia to receive a stem from a tibial component and/or for any other suitable purpose). In such embodiments, the opening can have any suitable shape (e.g., a chevron shape, a boomerang shape, a circular shape, an elliptical shape, a symmetrical shape, an asymmetrical shape, a polygonal shape, a triangular shape, and/or any other suitable shape). For instance, FIG. 84A shows an embodiment in which the opening 540 comprises a first wing 545 and a second wing 546 that allow the opening 540 to extend over a medial and/or lateral portion of the tibia's proximal end. Additionally, while such an opening 540 can be disposed in any suitable location in the baseplate, FIG. 84B shows that, in some embodiments, the opening is disposed substantially in the middle (i.e., the medial-lateral middle) of the tibial baseplate 530.

Figure 74A:
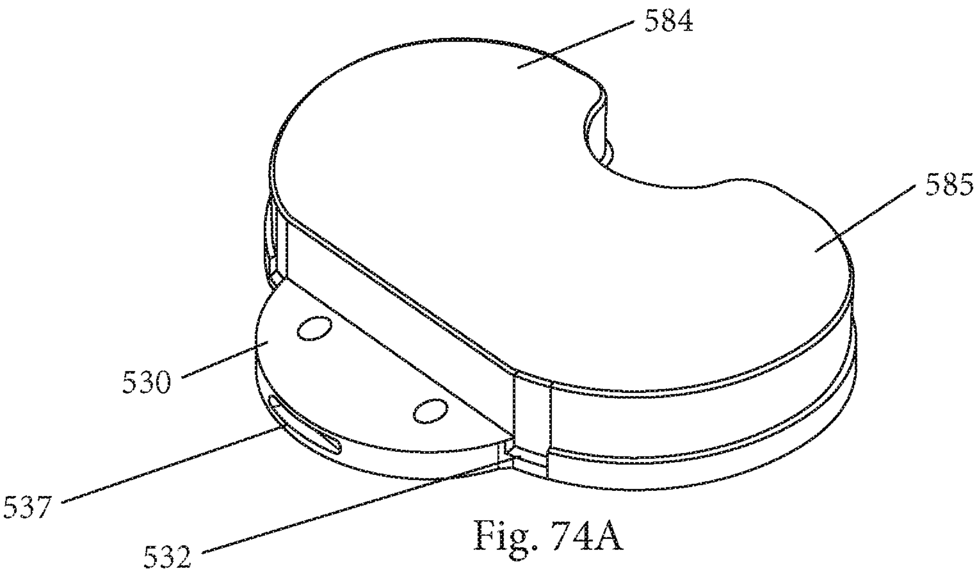
FIG. 74A illustrates a perspective of the tibial baseplate and a trial tibial component in accordance with a representative embodiment.
Figure 74B:
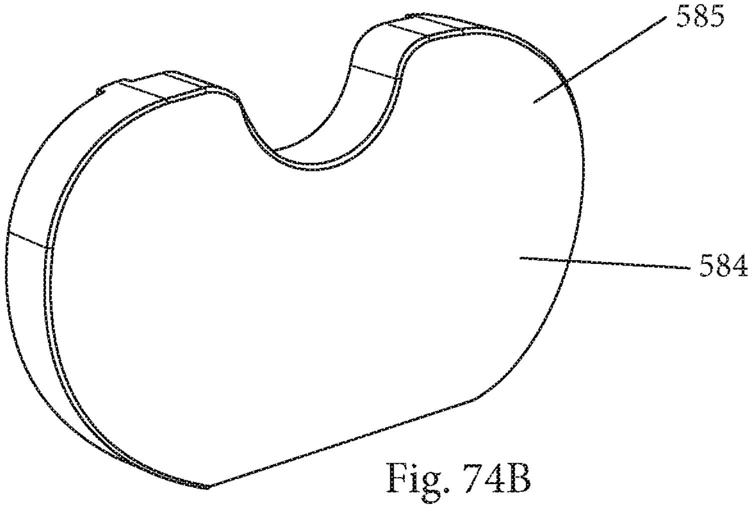
FIGS. 74B-74C and 75A-75C illustrate various views of the trial tibial component in accordance with some embodiments.
Figure 74C:
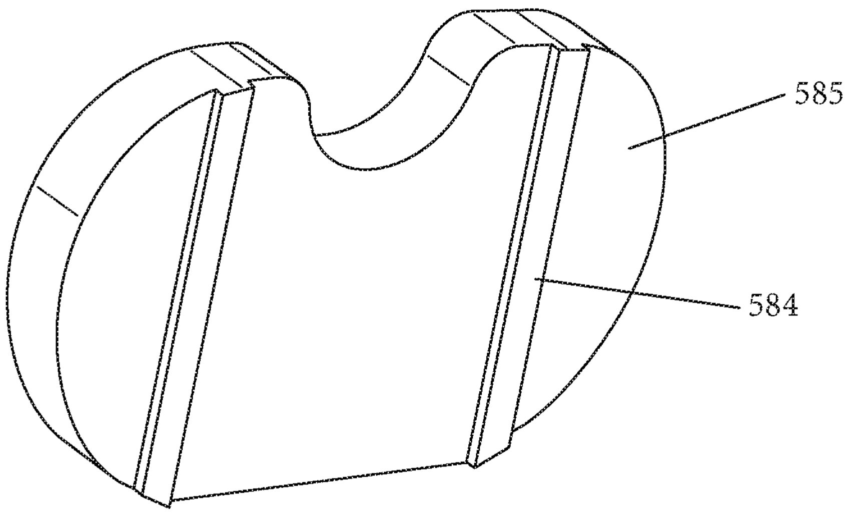
Figure 75A:
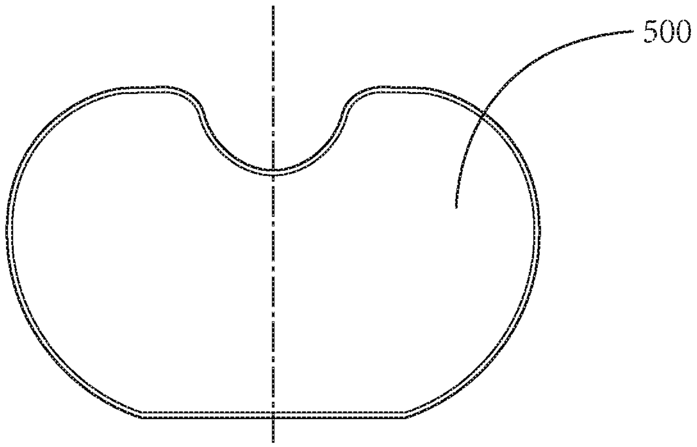
Figure 75B:
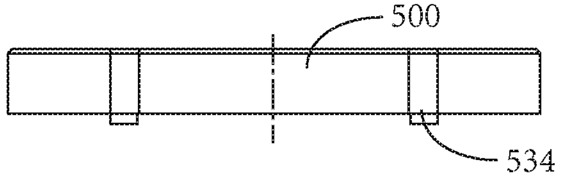
Figure 75C:
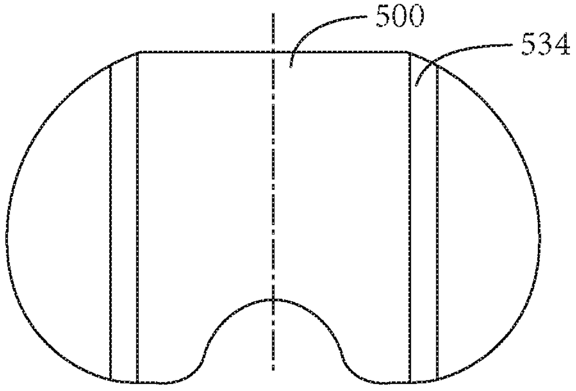
Figure 75D:
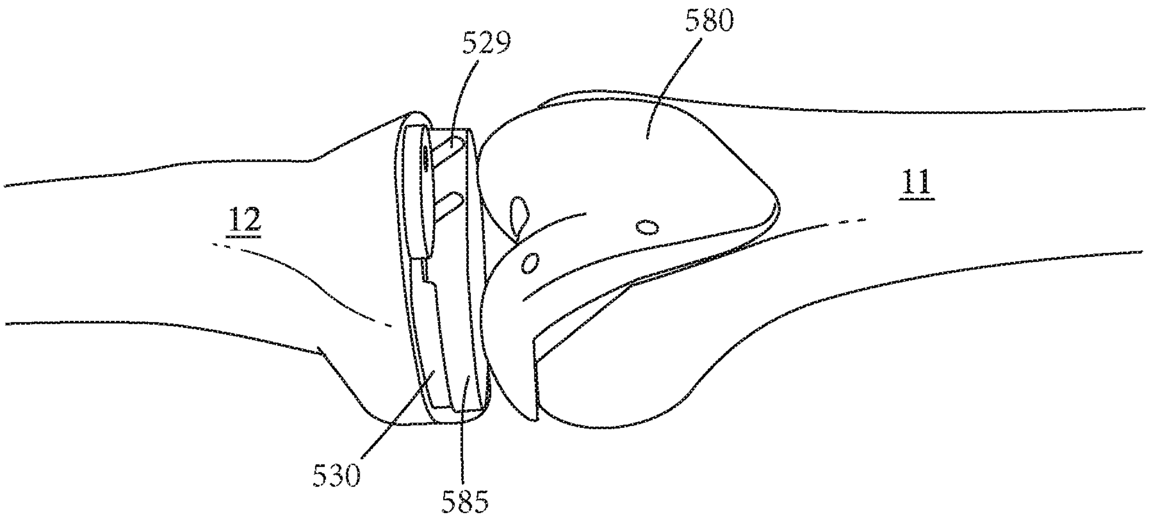
FIG. 75D depicts a perspective view of a knee joint in extension comprising the tibial baseplate and the trial tibial component in accordance with a representative embodiment.
Figure 75E:
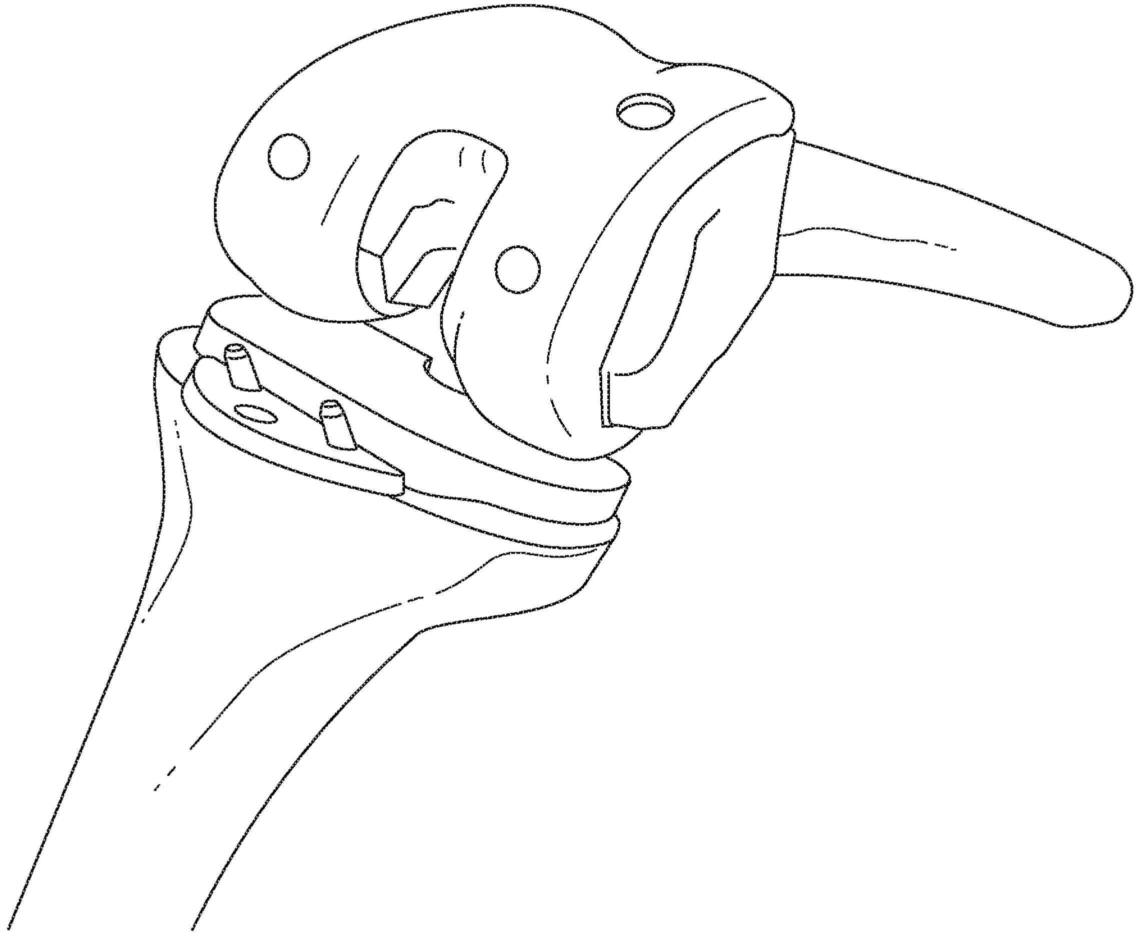
FIG. 75E depicts a perspective view of a knee joint in flexion comprising the tibial baseplate and the trial tibial component in accordance with a representative embodiment.

In another example, some embodiments of the tibial baseplate 530 are configured to receive one or more trial tibial components (complete and/or unilateral components) such that a medical practitioner can determine the proper size of the permanent tibial component and/or permanent femoral component that should be used in the knee. In this regard, the trial tibial components can comprise any suitable feature that allows them to function as described herein. Indeed, in some embodiments, the trial tibial components are configured to be extend over only a medial or a lateral portion of the tibia and to be used in uni-compartmental arthroplasties. In accordance with some other embodiments, however, FIGS. 74A-74C show that the trial tibial components 585 are configured to be used in total knee replacement surgeries. Moreover, while some embodiments of the trial tibial components 585 comprise a proximal surface 584 that is substantially flat (e.g., as shown in FIGS. 74A-74B), in some other embodiments, a lateral and/or medial side of the trial tibial components' proximal surface is recessed so as to cradle the condyles of a femur and/or femoral component.

In some embodiments, the trial tibial component 585 acts a spacer 500. Although some such embodiments have a substantially flat proximal surface 584, in some other embodiments, the proximal surface varies between its medial and lateral sides (e.g., having one side be higher or lower than the other, having one side have a different texture than another, and/or otherwise having one side of the trial tibial component be different than then other side).

Where the tibial baseplate 530 is configured to couple with one or more trial tibial components 585, the trial components can couple with the baseplate in any suitable manner, including, without limitation, via any suitable coupling and/or guide mechanism (e.g., any of the coupling and/or guide mechanisms discussed above with respect to the spacers 500). Indeed, in some embodiments, one or more spacers and trial tibial components are configured to couple to the tibial baseplate via the same couplings (e.g., elongated recesses 532), though at different times (or at the same time, in some other embodiments). By way of illustration, FIGS. 74A and 74C show some embodiments in which the trial tibial component 585 comprises one or more processes 534 that are configured to be received by corresponding recesses 532 in the tibial baseplate 530. Additionally (while not shown), some embodiments of the processes 534 comprise one or more catches 537 (e.g., as described above).

Where the tibial baseplate 530 is used with one or more trial tibial components 585, the trial tibial components can be any suitable thickness or height (e.g., can have any suitable distance between their distal or inferior surface, which is configured to contact the baseplate, and their proximal or superior surface, which is configured to contact one or more condyles of a femur or femoral component). Indeed, in some embodiments, the tibial trial components have a thickness between about 1 mm and about 3 cm (or any subrange thereof). Indeed, in some embodiments, the trial tibial components have a thickness between about 4 mm and about 1.5 cm.

It should be noted that the thickness of the trial tibial components 585 and/or spacers 500 are, in some cases, dependent on a thickness of the tibial baseplate 530. In this regard, the tibial baseplate can have any suitable thickness (e.g., distance between its superior and inferior faces). In some embodiments, the tibial baseplate is between about 1 mm and about 1.5 cm thick (or within subrange thereof). Indeed, in some embodiments, the tibial baseplate is about 6 mm thick±2 mm.

Figure 80:
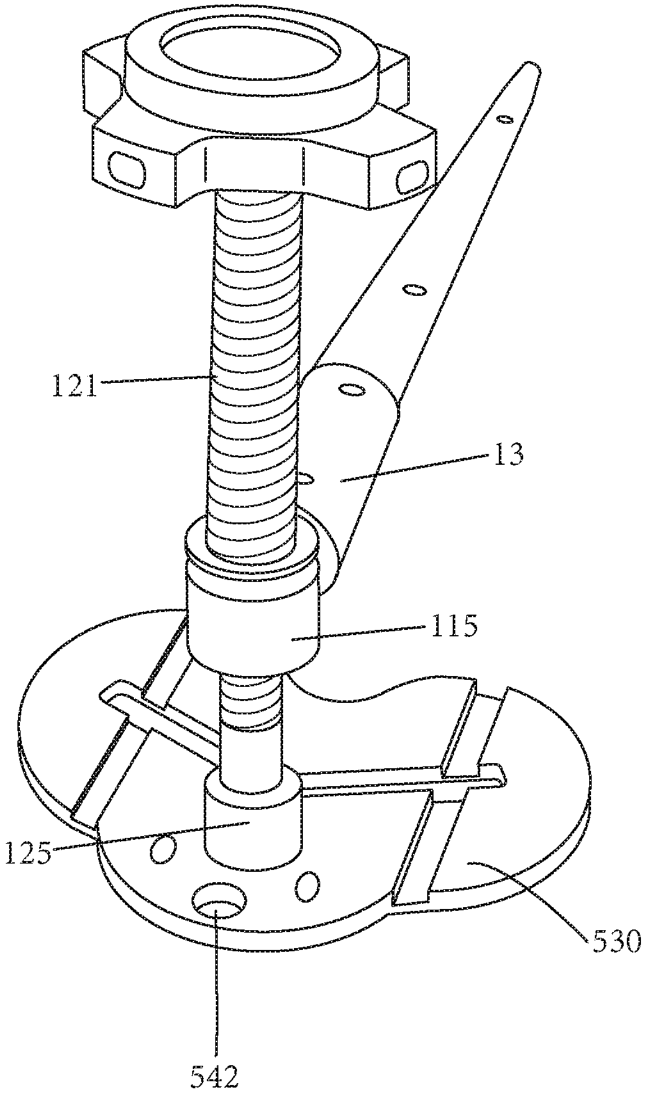
FIGS. 80, 81, 82A-82B depict some embodiments of the described systems used in conjunction with the tibial baseplate.
Figure 81:
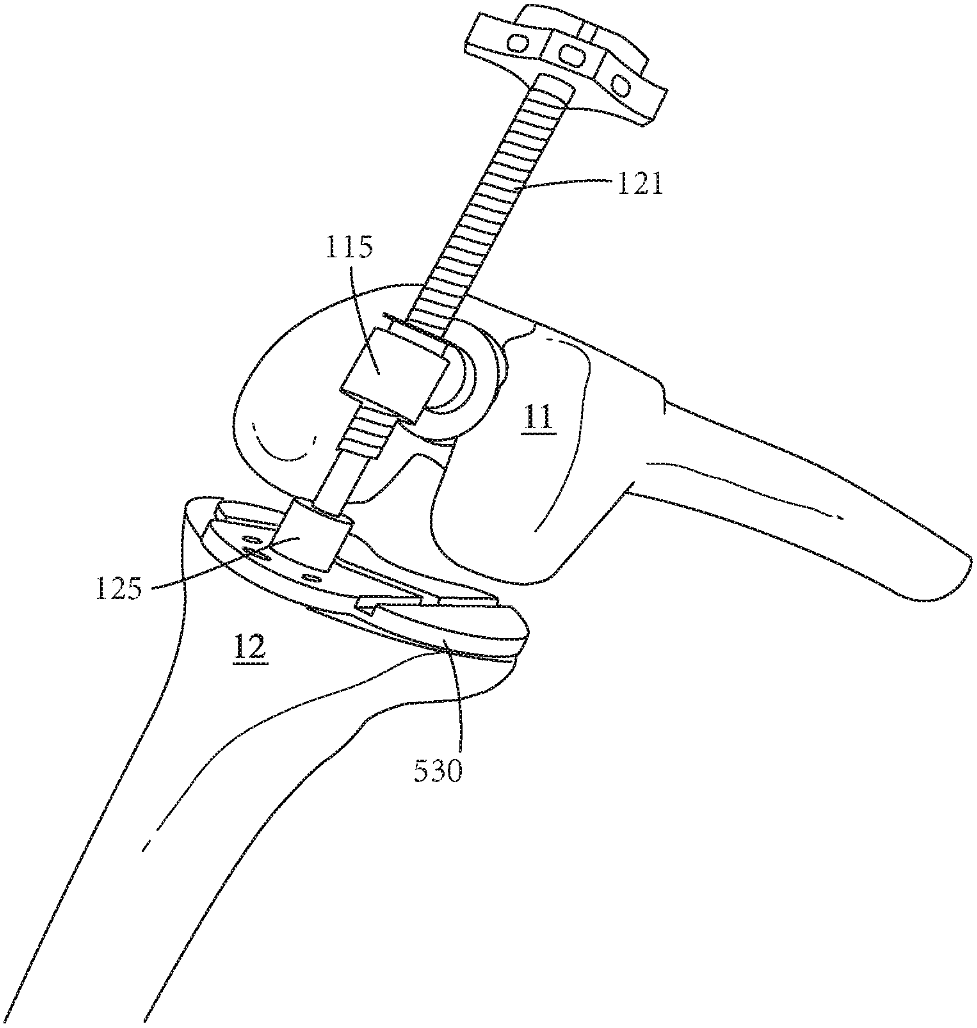
Figure 82A:
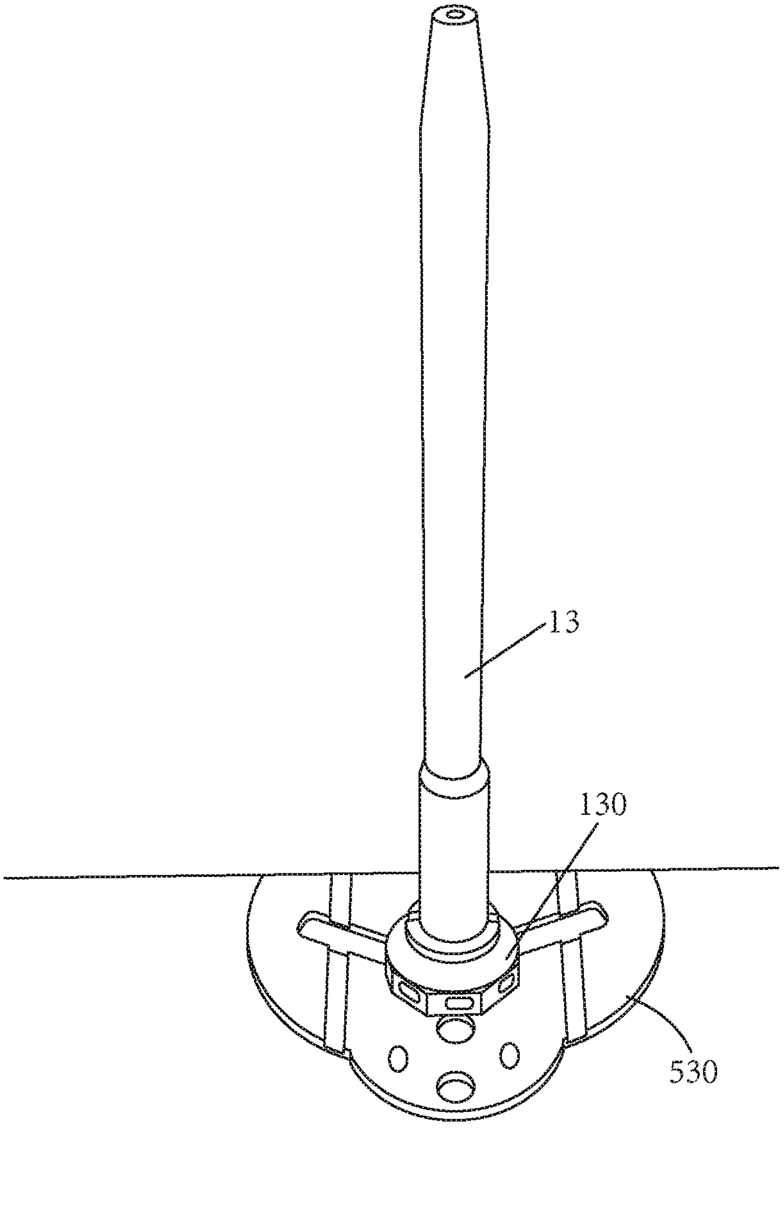
Figure 82B:
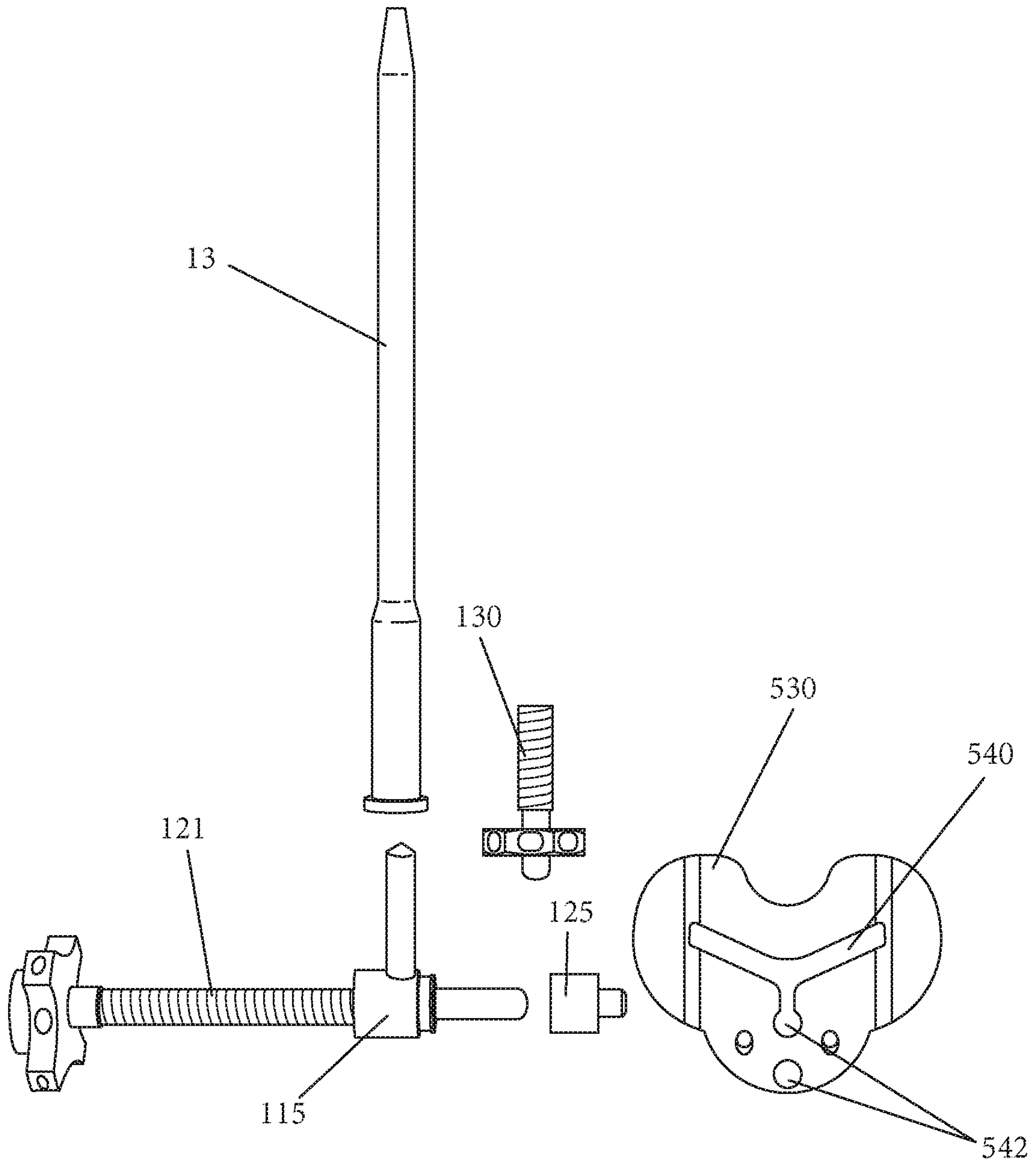
Figure 83:
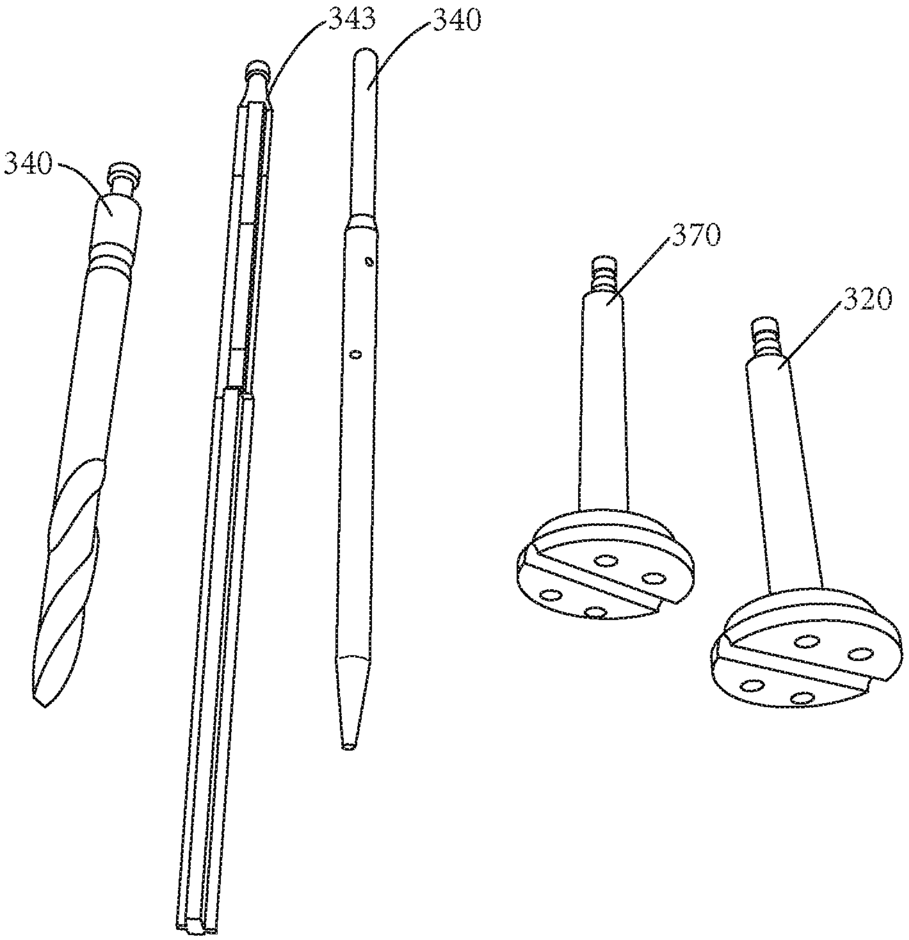
FIG. 83 depict some embodiments of a bone milling kit.

As another example of a suitable modification, in some embodiments, the tibial baseplate 530 is configured to be used with any suitable known or novel tensioner and/or other tensioning assembly that is configured to be actuated (when a knee joint is in flexion and/or extension) to vary a distance between the tibia and femur and/or to allow for changes in varus-valgus angulation between the femur and the tibia when the tensioning assembly is coupled to the tibia (e.g., via the tibial baseplate) and to the femur (e.g., via a femoral component or otherwise). Indeed, in some embodiments, the tibial baseplate is configured to be used with the ratcheting device 142, the extension bolt 96, the flexion bolt 30, the spacers 500, and/or any other suitable component described herein. By way of non-limiting illustration, FIGS. 80-82B show some embodiments in which the tibial baseplate 530 is configured to couple with one or more components of the tensioning assemblies discussed herein (e.g., one or more bushings 125, extension bolts 130, flexion bolts 30, 13 femoral intramedullary rods 13, threaded barrels 115, threaded shafts 121, femoral mounts 15 (e.g., with or without a femoral IM rod), and/or other suitable components).

Where the tibial baseplate 530 is configured to be used with one or more tensioning assemblies, the tensioning assemblies can couple with the tibial baseplate in any suitable manner, including, without limitation, via one or more mechanical engagements, frictional engagements, magnets, catches, recesses, protrusions, detent mechanisms, holes, mating features, and/or any other suitable type of coupling. Indeed, in some embodiments, the tensioning assembly comprises one or more protrusions (e.g., an end of the bushing 125, an end of the extension bolt 130, etc.) that are configured to extend into one or more recesses and/or openings (e.g., opening 540) in the tibial baseplate. By way of illustration, FIGS. 80 and 82B show some embodiments in which the tibial baseplate 530 comprises an opening 540 and one or more other couplings (e.g., tensioner openings 542) that are sized, shaped, and located in specific positions so as to properly function with one or more tensioning assemblies (including, without limitation, any suitable assembly or component described herein).

As another suitable modification, in some embodiments, one or more edges of the tibial baseplate 530 comprise one or more recesses, ridges, protrusions, magnets, hook-and-loop fasteners, couplers, and/or other catches that allow a user to easily grab and lift the baseplate from the tibia (e.g., via a finger, a tool, a magnet, and/or other suitable object). By way of non-limiting illustration, FIG. 74A shows an embodiment in which a recessed catch 537 is disposed at an anterior edge of the tibial baseplate 530.

As still another example of a suitable modification, although some embodiments of the tibial baseplate 530 are configured to substantially cover a resected surface at a proximal end of the tibia (e.g., for full knee replacements), in some other embodiments, the tibial baseplate is configured to extend over a medial portion or a lateral portion of the tibia, so as to be used for uni-compartmental arthroplasties.

In still another example, some embodiments of the tibial baseplate 530 comprise one or more fastener holes (e.g., holes 531) that allow one or more fasteners (e.g., nails, spikes, screws, shafts, pins, etc.) to extend through a proximal and distal side of the baseplate and into the proximal end of the tibia. Additionally, while such holes can extend through the baseplate at any suitable angle (e.g., being perpendicular or at any other angle with respect to the distal surface of the baseplate), in some embodiments, the holes are formed at an angle that guides the fastener in a distal-posterior direction into the tibia (e.g., to allow the fastener to be easily driven in and pulled from the tibia while preventing portions of the knee joint from being undesirably damaged).

In yet another example, while some embodiments of the tibial baseplate 530 and the trial tibial component 585 comprise a rounded notch at their posterior end, in some embodiments, the notch need not be rounded (e.g., the notch is squared, comprises a plurality of angled surfaces, etc.) or need not exist.

In even another example of a suitable modification, in some embodiments (and as mentioned earlier), one or more femoral cutting blocks 572, gap resection blocks 574, saw blade capture blocks 576, alignment rod blocks 578, alignment rods, and/or any other suitable components are configured to couple directly or indirectly to the tibial baseplate 530 (and/or to any other suitable component). In this regard, such components can couple to the tibial baseplate in any suitable manner. For instance, some embodiments of the baseplate comprises one or more grooves, rails, guides, snaps, mechanical engagements, frictional engagements, slides, magnets, clamps, clamping surfaces, clips, sockets, threaded engagements, hook-and-loop fasteners, interlocking components, and/or any other suitable coupling mechanism (collectively and individually, a cutting block guide) that allows one or more of the aforementioned components (directly and/or indirectly) to couple to the baseplate.

By way of non-limiting illustration, FIGS. 65J-65T, 65V, and 65X show some embodiments in which the tibial baseplate 530 comprises a cutting block guide that comprises an elongated slot 581 that is configured to slidingly couple with the femoral cutting block 572, the gap resection block 574, the saw blade capture block 576, the alignment block 578, and/or any other suitable component. In contrast (and not shown), some embodiments of the tibial baseplate comprise one or more raised rails, tabs, processes, projections, couplers, and/or other members that are configured to extend from a superior (or proximal) surface of the tibial baseplate and to couple with the femoral cutting block, the gap resection block, the alignment block, the saw blade capture block, and/or any other suitable component.

Where the tibial baseplate 530 comprises one or more elongated slots 581 that are configured to couple with any of the aforementioned components, the elongated slots can have any suitable characteristic. Indeed, in some embodiment (as shown in FIG. 65V) the elongated slot 581 is configured to extend and/or open from an anterior end portion 583 of the tibial baseplate 530 and extend towards a posterior end portion 586 of the baseplate. Moreover, while the elongated slot can run at any suitable angle (e.g., in an anteroposterior direction, in a medial-lateral direction, at an angle between an anteroposterior direction and a medial-lateral direction, and/or in any other suitable direction, including, without limitation, parallel with and/or at any suitable angle with respect to a longitudinal axis of any elongated grooves 532 or spacer guides), in some embodiments, the elongated slot runs in an anteroposterior direction. Indeed, in some embodiments in which the tibial baseplate optionally comprises on or more elongated grooves, the elongated slot runs substantially parallel with (and in between) such grooves.

Figure 65X:
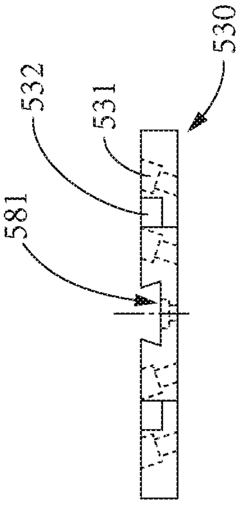

In some embodiments, the elongated slot is not keyed, such that the gap resection block 574, the femoral cutting block 572, the alignment block 578, the saw blade capture block 576, and/or another suitable component can be removed vertically from the elongated slot. In some other embodiments, however, at least a portion of the elongated slot is keyed so as to not allow the gap resection block, femoral cutting block, and/or another component that is coupled to the tibial baseplate via the slot to be vertically removed from a keyed portion of the slot. By way of non-limiting illustration, FIGS. 65Q and 65X show some embodiments in which the elongated slot 581 comprises a dovetailed groove that narrow towards the superior surface of the baseplate 530.

Where the tibial baseplate 530 comprises a cutting block guide (e.g., one or more elongated slots 581) that is configured to slidingly couple with the gap resection block 574, the femoral cutting block 572, and/or any other suitable component, the cutting block guide can have any other suitable characteristic that allows it to function as described herein. Indeed, in some embodiments, the cutting block guide is configured to extend past an anterior end of one or more of the elongated grooves 532. In such embodiments, the anterior end of the cutting block guide (e.g., the elongated slot 581) is configured to extend a distance D of between about 1 mm and about 20 cm (or within any subrange thereof) past an anterior-most end of one or more flanking elongated grooves 532 (e.g., as shown in FIG. 65V). Indeed, in some embodiments, the cutting block guide extends between about 5 mm and about 2.5 cm (e.g., about 1.8 cm±0.5 cm) past an anterior-most end of one or more flanking elongated grooves 532.

In some embodiments, the cutting block guide (e.g., the elongated slot 581) is part of a tongue that extends at an anterior end portion of the tibial baseplate 530. In such embodiments, the tongue and cutting block guide are configured to extend past an anterior-most edge of a resected proximal end of a tibia when the baseplate is properly seated on the tibia. While the tongue and/or cutting block guide can be configured to extend any suitable distance past an anterior-most edge of the resected proximal end of the tibia when the baseplate is properly seated thereon (and/or past the anterior-most end of an elongated groove 532), in some embodiments, the tongue 587 and/or cutting block guide are configured to extend between about 2 mm and about 10 cm (or within any subrange thereof) past the anterior-most end of the resected proximal tibia (and/or the anterior-most end of an elongated groove 532). Indeed, in some embodiments, the tongue and/or cutting block guide are configured to extend between about 5 mm and about 2.5 cm past an anterior-most edge of the resected proximal end of the tibia (and/or the anterior-most end of an elongated groove 532) when the baseplate is properly seated thereon.

In some embodiments, the anterior-most end of the cutting block guide (e.g., the elongated slot 581) is disposed any suitable distance from a posterior-most end of the tibial baseplate 530. Indeed, in some embodiments, the distance D1 (as shown in FIG. 65V) between the anterior-most end of the cutting block guide (e.g., elongated slot 581) and the posterior-most end of the tibial baseplate 530 is between about 4.8 cm and about 12 cm (or within any subrange thereof). Indeed, in some embodiments, D1 is between 5 cm and about 6.5 cm.

In some embodiments, the femoral cutting block 572 is configured to be directly and/or indirectly (e.g., via the gap resection block 574) coupled to the tibial baseplate 530 (e.g., via a dovetailed groove connection and/or in any other suitable manner). In any case, the femoral cutting block can comprise any suitable component that allows it to guide a cutting tool to cut a portion of the femur. For instance, some embodiments of the femoral cutting block define a guide for a posterior femoral cut, a posterior chamfer cut, an anterior chamfer cut, an anterior femoral cut, an anterior rough cut, and/or any other suitable cut. By way of non-limiting illustration, FIGS. 65Q and 65Z-65AC show some embodiments in which the femoral cutting block 572 defines a posterior chamfer cut guide 588, an anterior chamfer cut guide 590, and an anterior femoral cut guide 592.

Although some embodiments of the femoral cutting block 572 define one or more posterior femoral cut guides (e.g., guide that are configured to direct a saw blade and/or any other suitable cutting tool to make a posterior femoral cut), in some other embodiments, the femoral cutting block is configured to couple (e.g., via one or more grooves, slots, rails, couplers, detents, sockets, and/or any other suitable coupling mechanism) to the gap resection block 574, which in turn is configured to couple to the tibial baseplate 530 (e.g., via the elongated slot 581 and/or in any other suitable manner). In some such embodiments (e.g., as shown in FIG. 65Y), a superior portion of the gap resection block 574 and an inferior portion of the femoral cutting block 572 work together to define the posterior cut guide 594.

In this regard, having the femoral cutting block 572 couple to the gap resection block 574 (as opposed to the femoral cutting block coupling directly to the tibial baseplate 530) can provide the tibial baseplate system (or the baseplate with any other component coupled thereto) with one or more features, such as forming the posterior femoral cut guide 594 between the gap resection block and the femoral cutting block. Additionally, in some embodiments, by coupling the femoral cutting block to the gap resection block, a position of the femoral cutting block (and hence its various cutting guides) can be raised and/or lowered with respect to the tibial baseplate by using gap resection blocks of different sizes. In this regard, the gap resection block can have any suitable thickness that causes it to raise or lower the femoral cutting block with respect to the tibial baseplate. Indeed, in some embodiments, the gap resection block is configured to raise the femoral cutting block by between about 1 mm and about 3 cm (or within any subrange thereof) with respect to the tibial baseplate. For instance, some embodiments of the gap resection block are configured to raise the femoral cutting block by between about 6 mm and about 2 cm (e.g., by about 10 mm, 11 mm, 13 mm, 15 mm, 17 mm, etc.). Indeed, in some cases, the described tibial baseplate system comprises a number of gap resection blocks of different sizes, such that a practitioner can pick the gap resection block that is appropriate for a particular knee.

Figure 65Y:
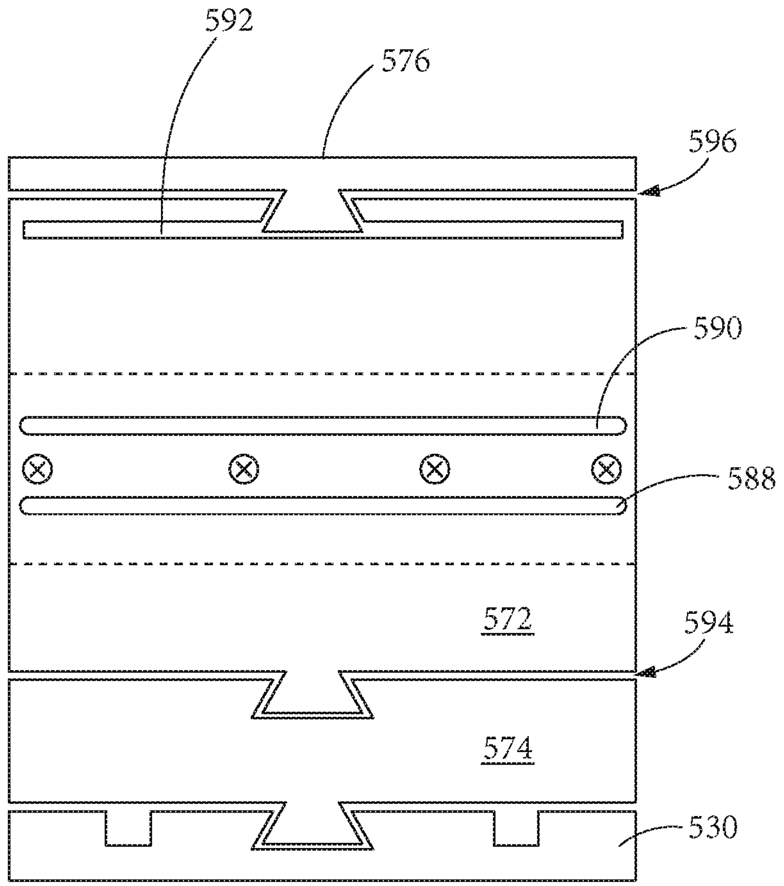
Figure 65A:
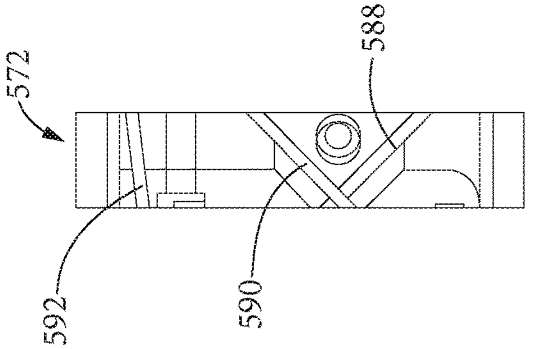
Figure 65Z:
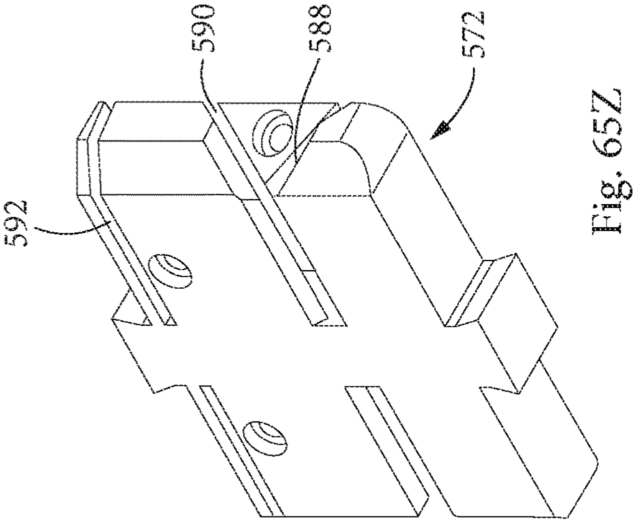
Figure 65A:
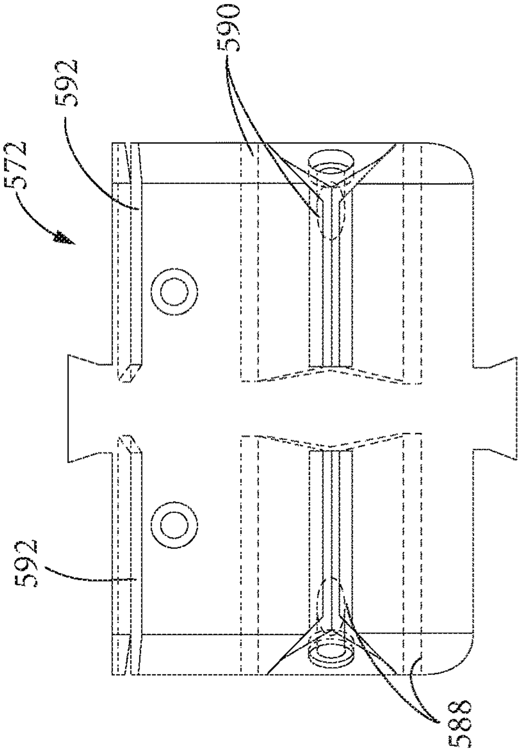
Figure 65A:
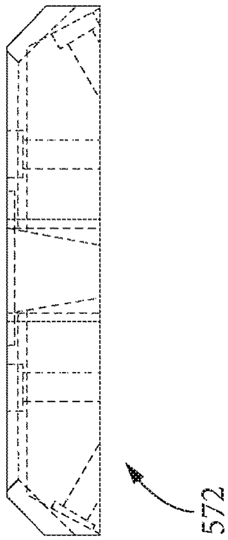
Figure 65A:
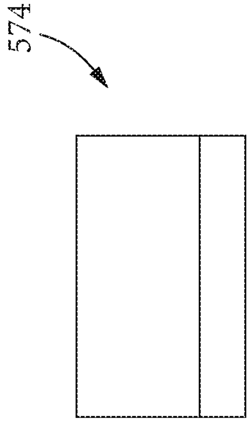
Figure 65A:
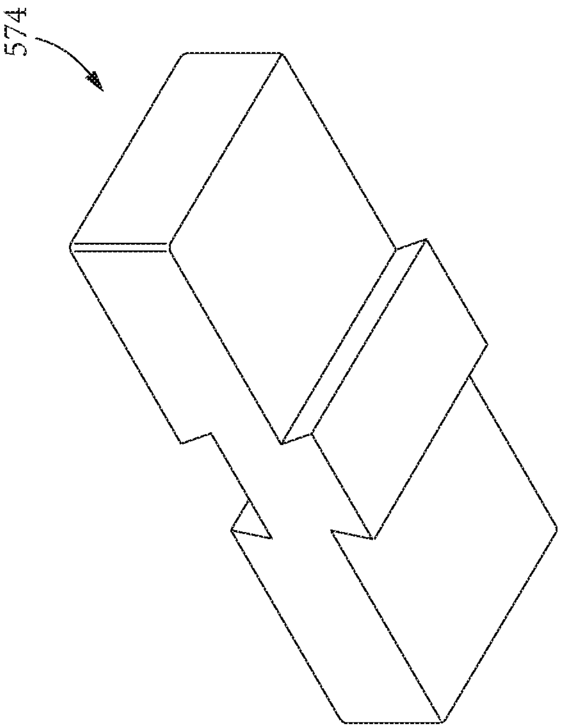
Figure 65A:
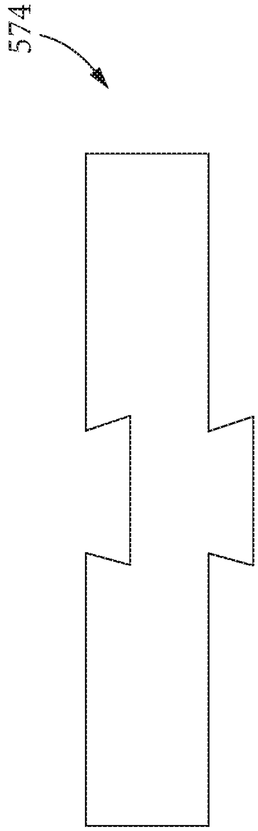
Figure 65A:
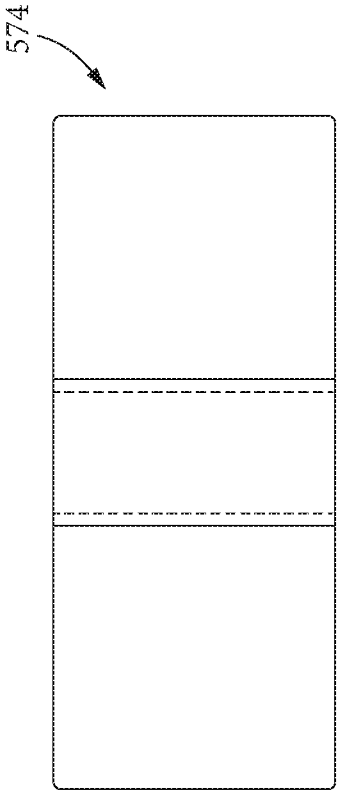
Figure 65A:
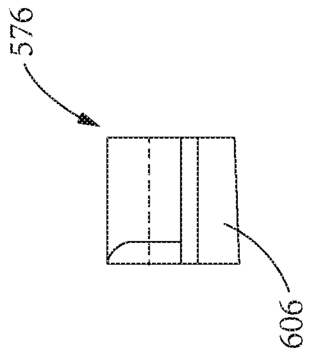
Figure 65A:
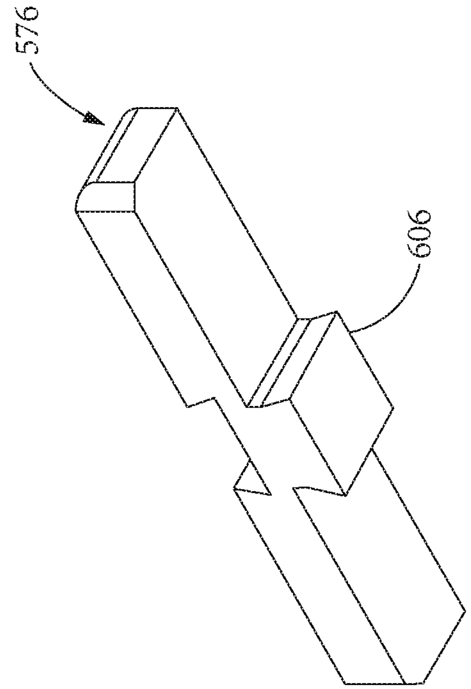
Figure 65A:
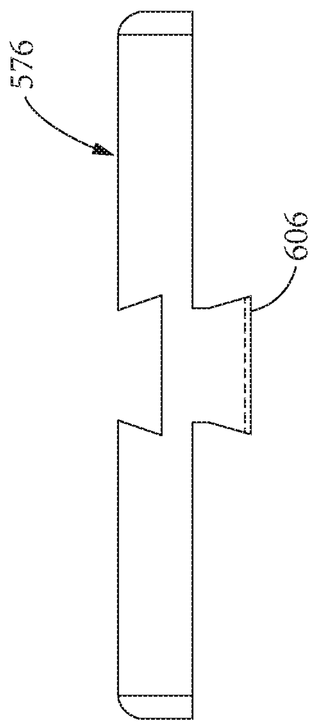
Figure 65A:
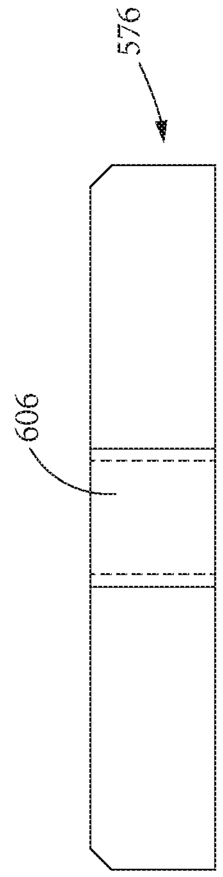
Figure 65A:
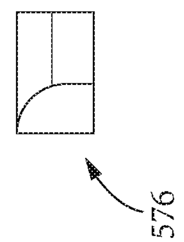
Figure 65A:
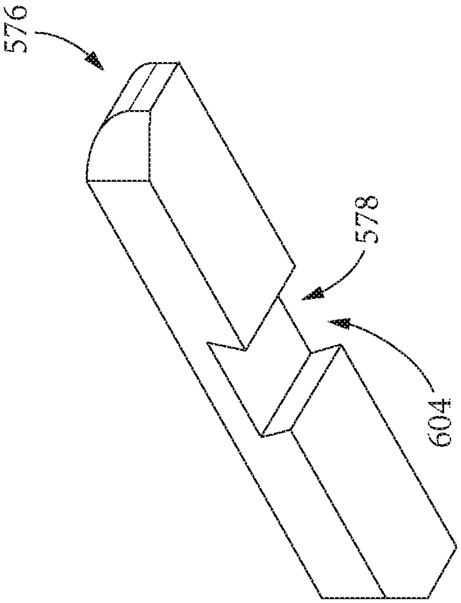
Figure 65A:
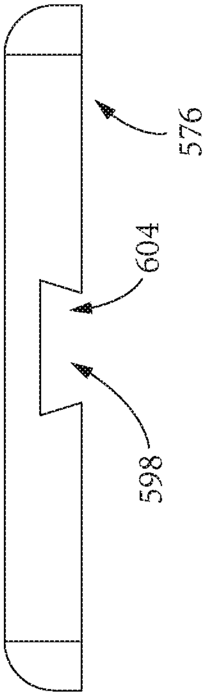
Figure 65A:
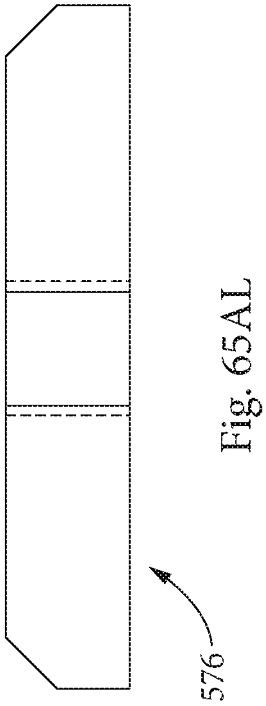
Figure 65A:
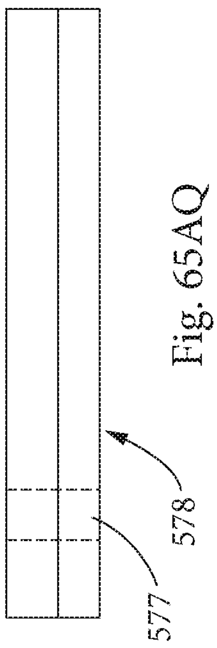
Figure 65A:
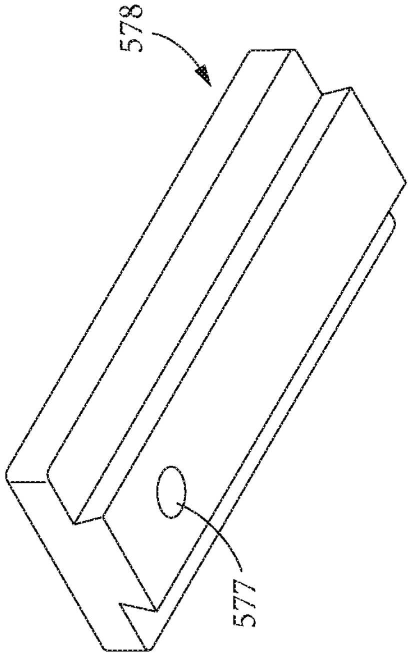
Figure 65A:
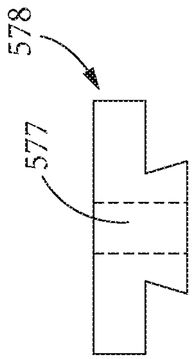
Figure 65A:
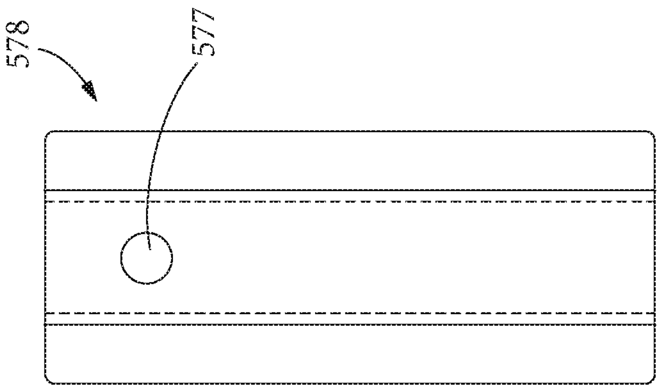
Figure 67A:
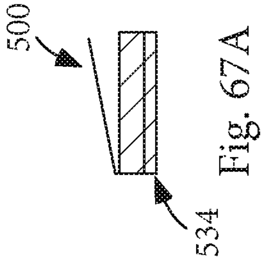
FIGS. 66A-66B, 67A-67C, 68A-68H, 69A-69F, and FIG. 70 illustrate various embodiments of the described systems and methods.
Figure 67B:
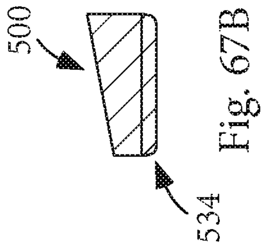
Figure 67C:
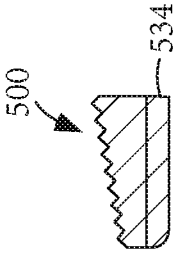
Figure 66B:
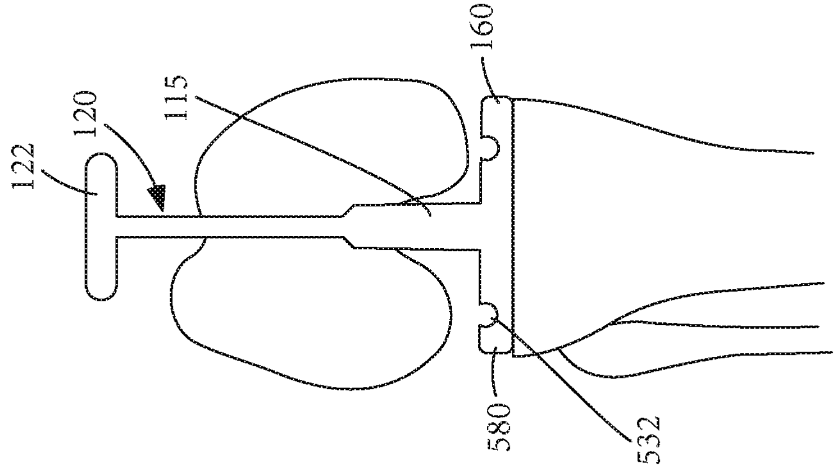
Figure 66A:
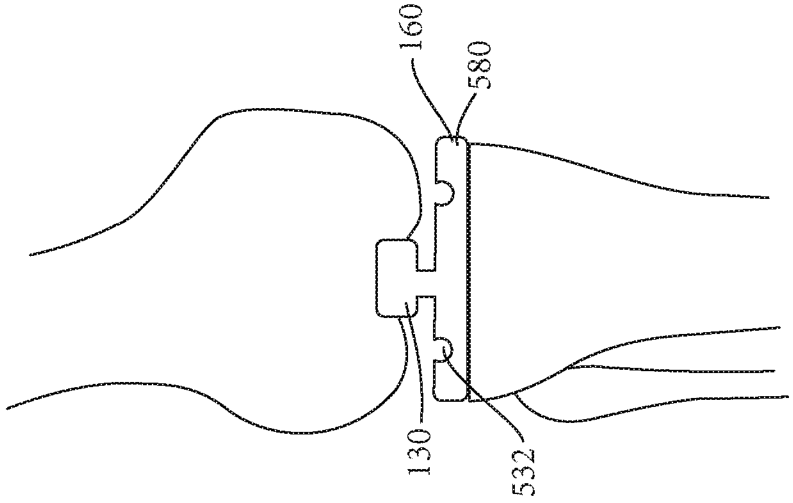
Figures 68A, 68B, 68C, 68D, 68E, 68F, 68G, 68H:
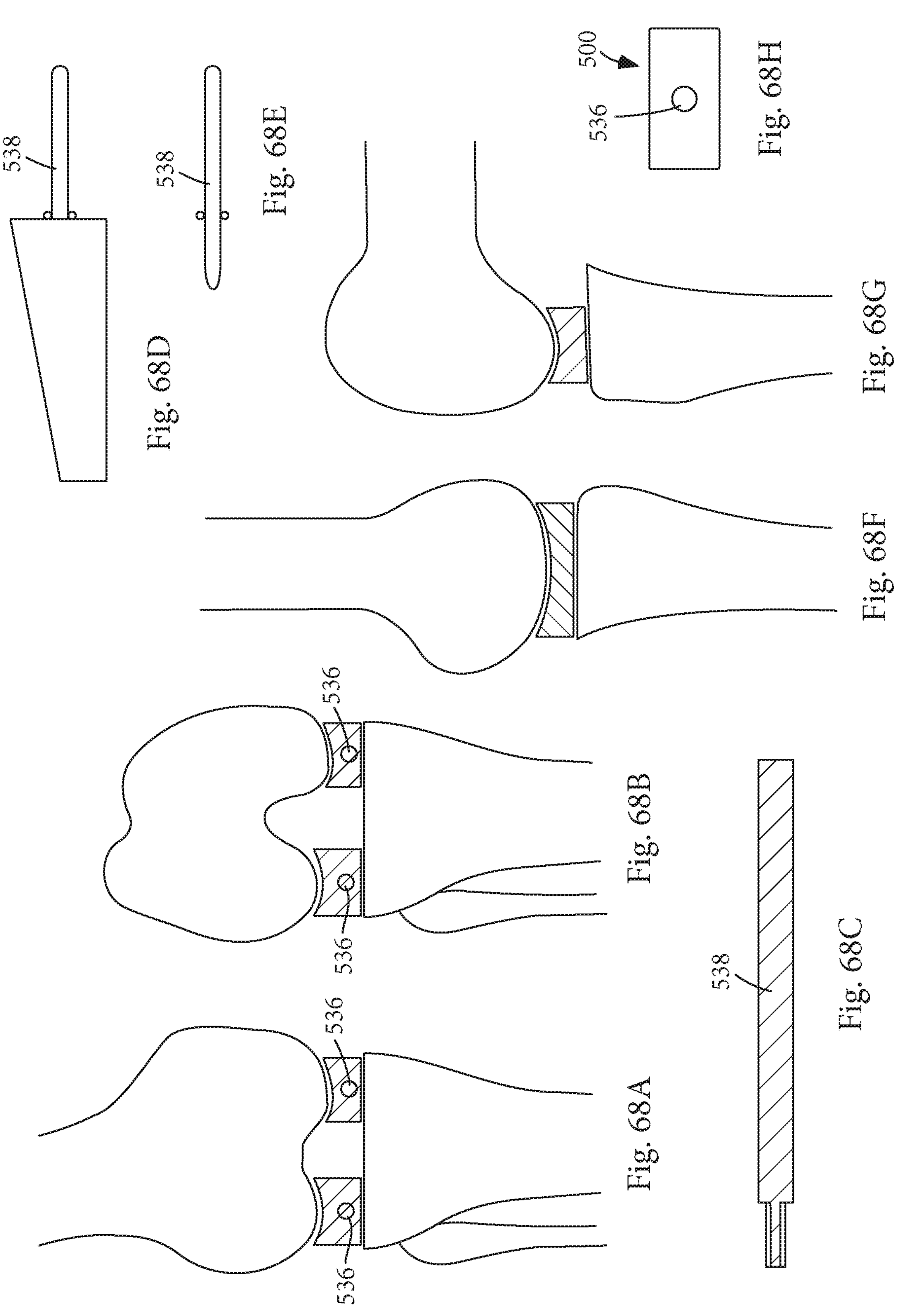
Figure 69A:
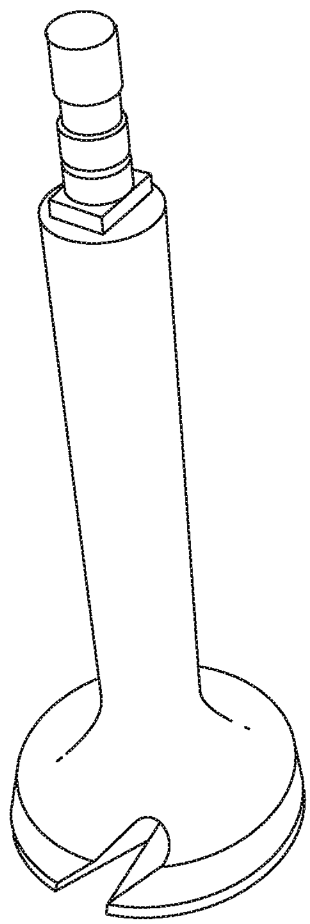
Figure 69B:
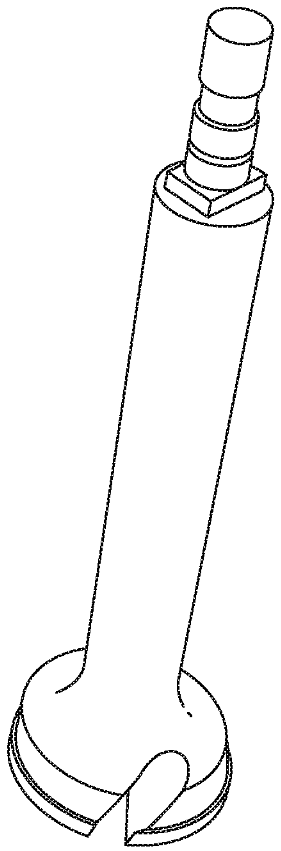
Figure 69C:
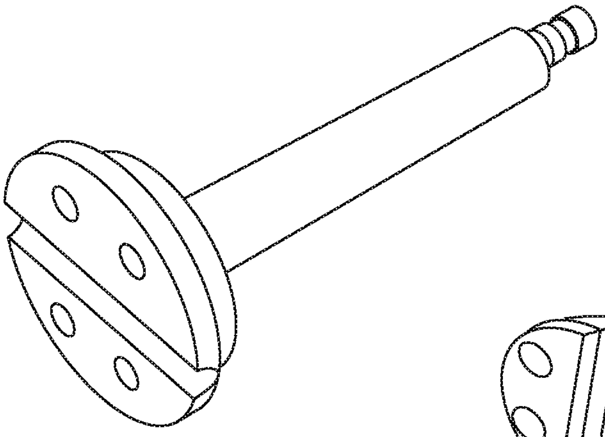
Figure 69D:
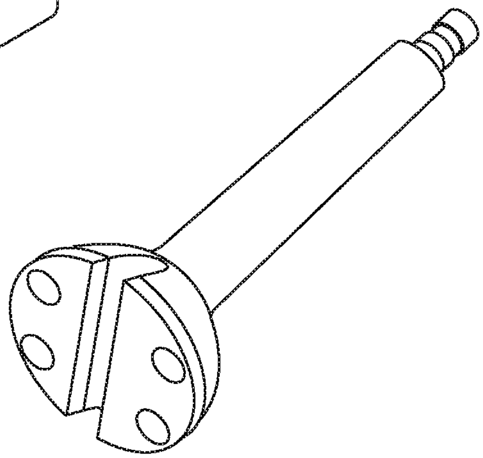
Figure 69E:
Figure 69F:
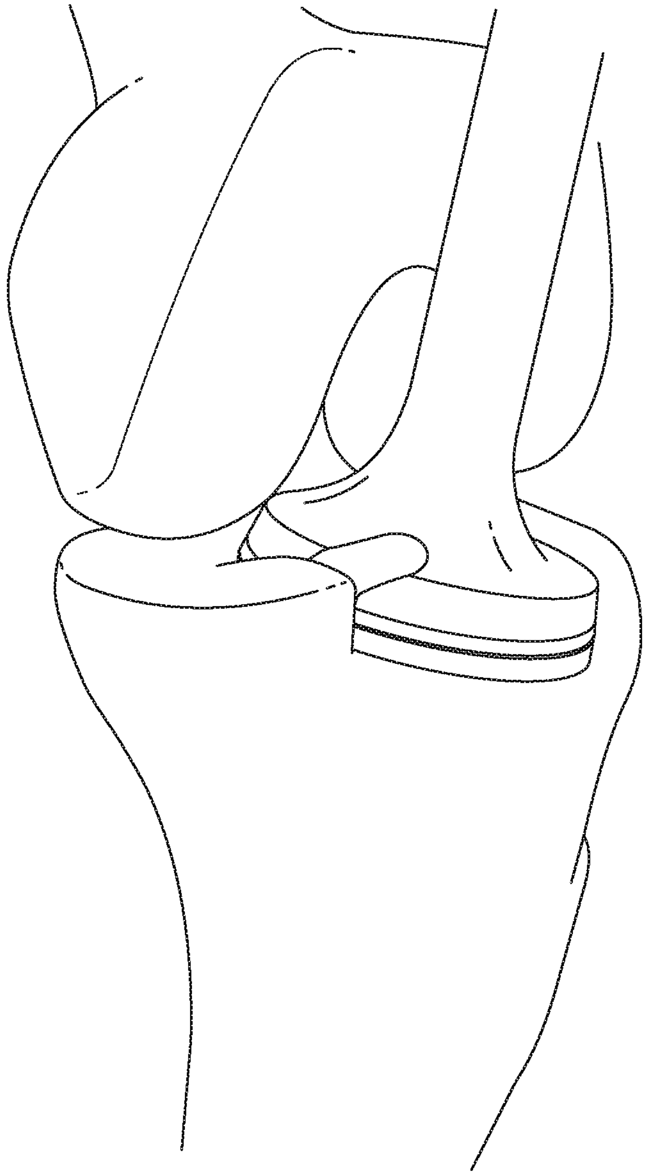
Figure 70:
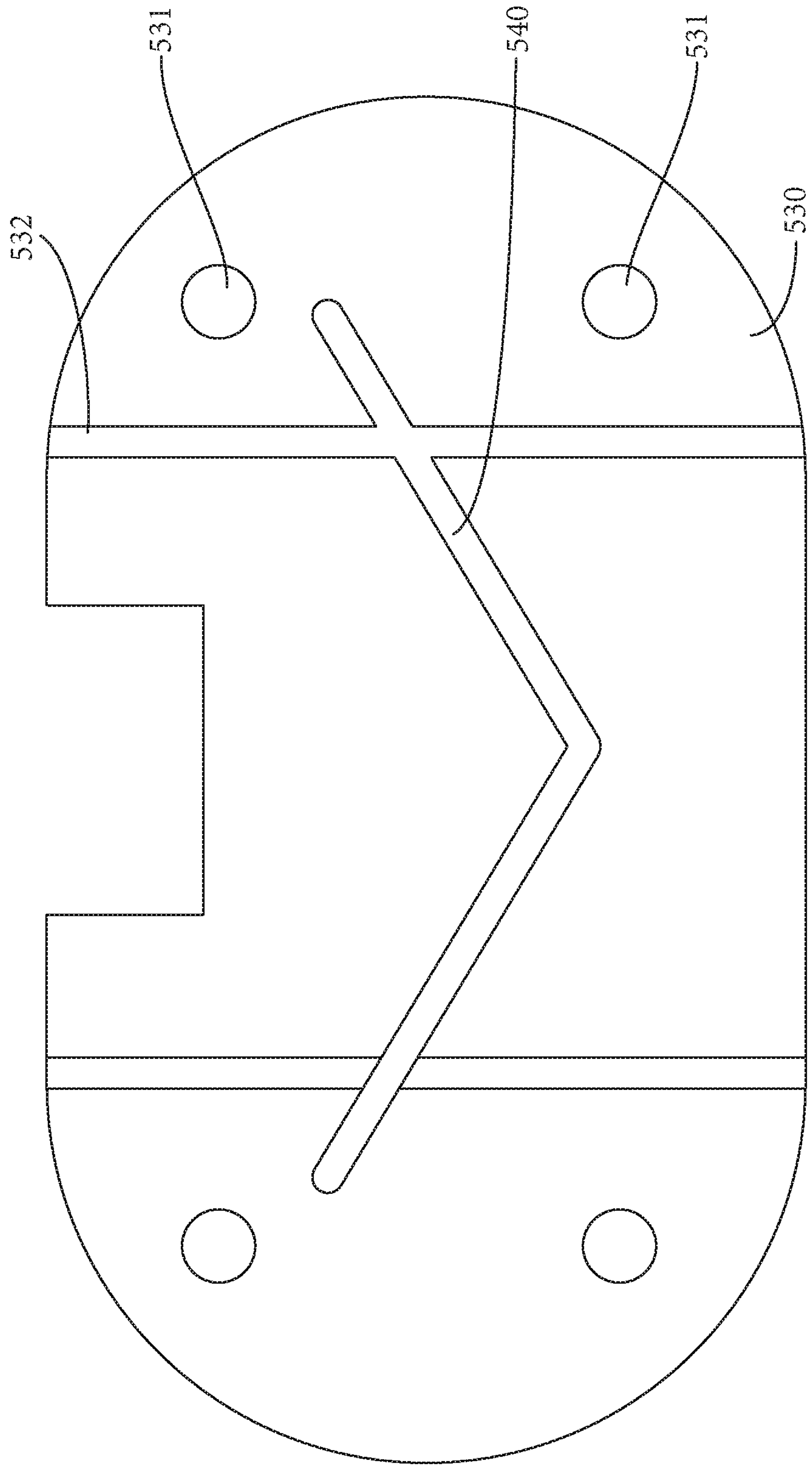
Figure 71A:
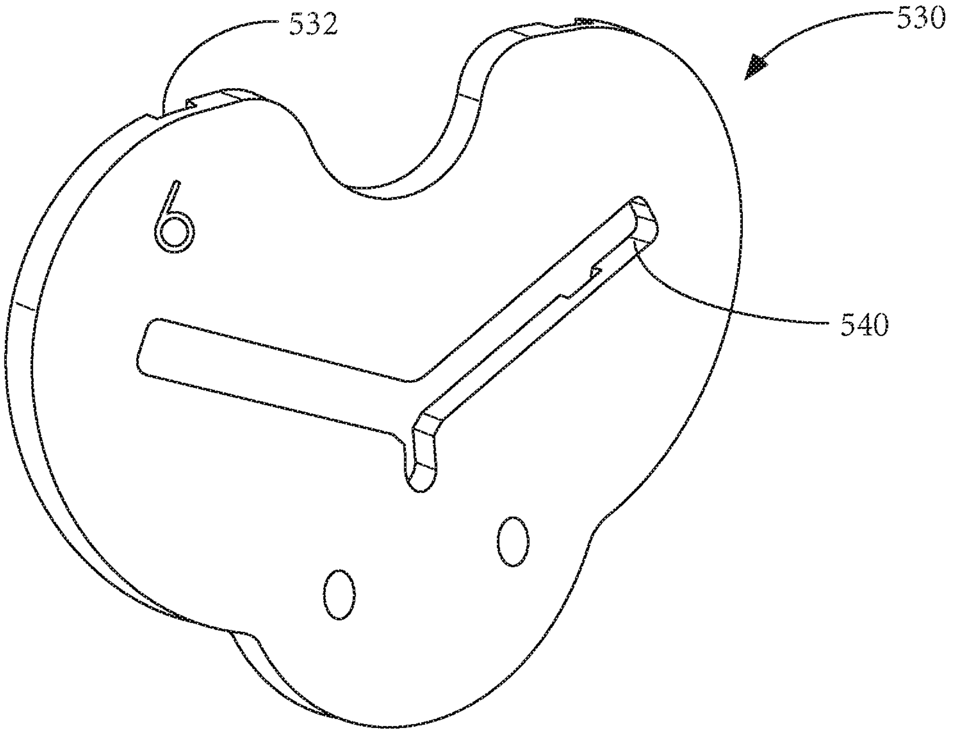
FIGS. 71A-71B, 72A-72B, and 73A-73C illustrate various embodiments of a tibial baseplate.
Figure 71B:
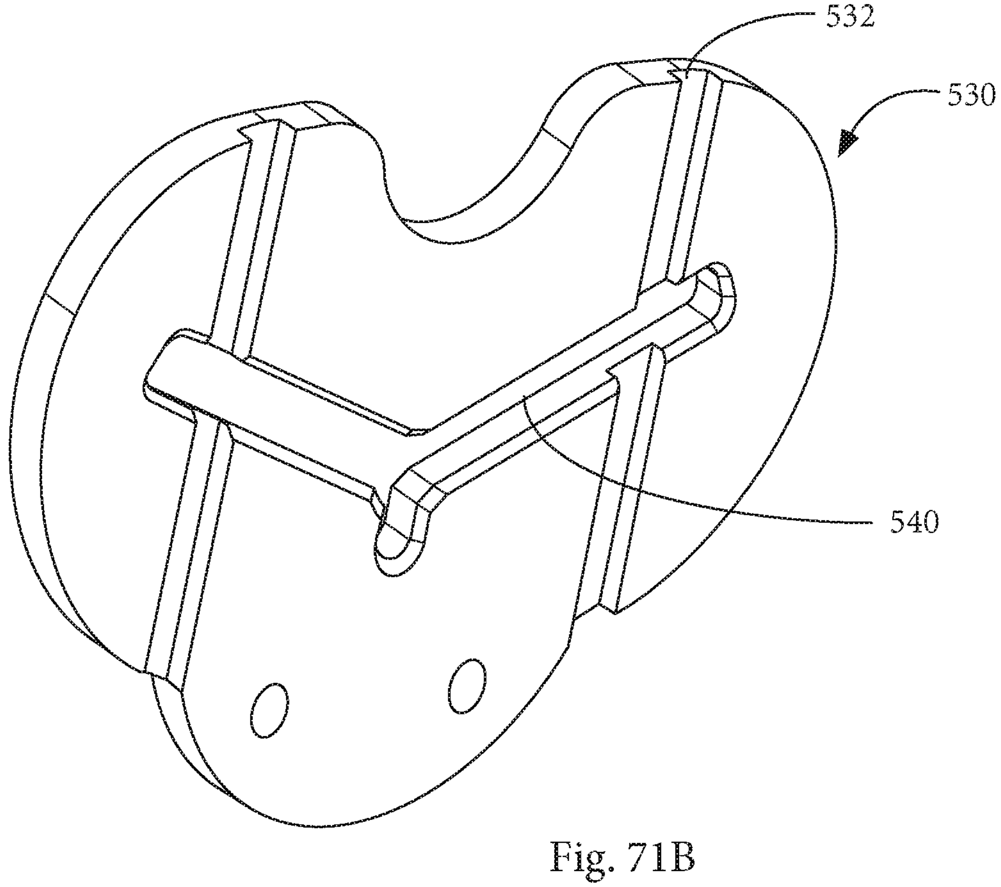
Figure 72B:
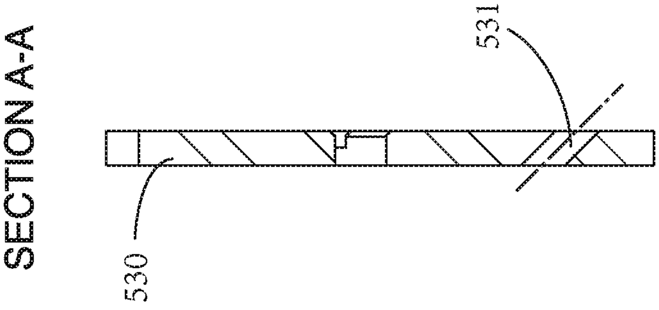
Figure 72A:
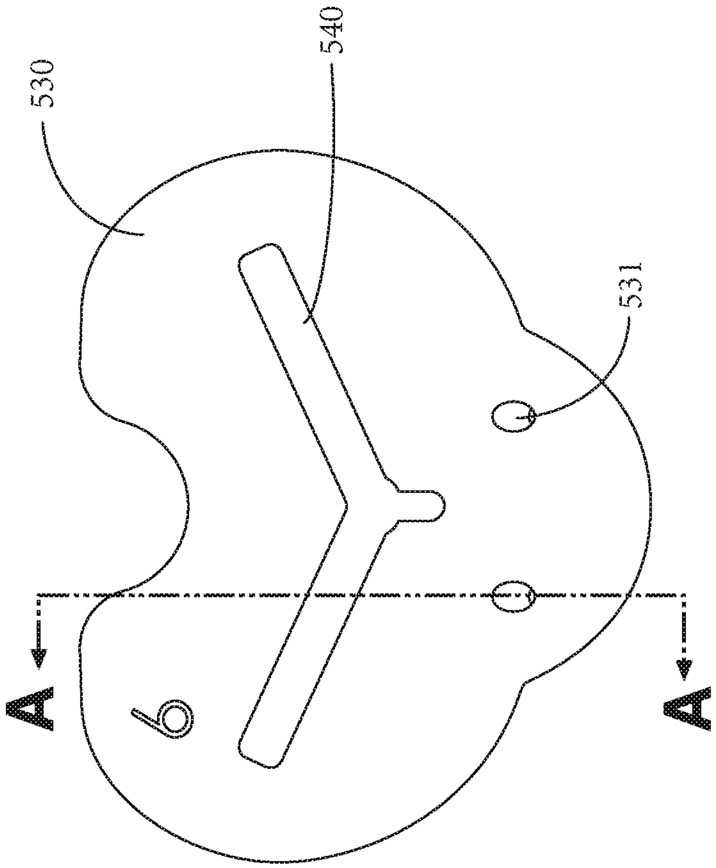

Although (as illustrated in FIG. 65AB) some embodiments of the femoral cutting block 572 define one or more anterior femoral cut guides 592 (e.g., a guide that is configured to direct a saw blade or other suitable cutting tool to make a femoral cut, an anterior rough cut, and/or function as a femoral flexion guide), in some other embodiments, the femoral cutting block is configured to couple (e.g., via one or more grooves, slots, rails, couplers, detents, sockets, and/or any other suitable coupling mechanism) to one or more saw blade capture blocks 576 such that the one or more saw blade capture blocks are disposed at a superior portion of the femoral cutting block (e.g., as shown in FIGS. 65Q and 65Y). In some such embodiments (e.g., as shown in FIGS. 65Q and 65Y), a superior portion of the femoral cutting block 572 and an inferior portion of the saw blade capture block 576 work together to define the anterior rough cut guide 596.

In some embodiments, the saw blade capture block 576 is configured to be placed at the top of one more objects that are coupled to the tibial baseplate 530. By way of non-limiting illustration, FIGS. 65AL-65AO show some embodiments in which the saw blade capture block 576 comprises a single coupler 598 for coupling the saw blade capture block to the superior (or proximal) end of the femoral cutting block 572. In this regard, while FIGS. 65AN-65AO show some embodiments in which the saw blade capture block 576 comprises a single dovetailed or keyed slot 604, in some other embodiments, the saw blade capture block comprises one or more keyed processes 606.

Where the femoral cutting block 572, the gap resection block 574, and/or any other suitable component (either alone or in combination with one or more other components) define one or more cutting guides, the various cutting guides can be any suitable size, including, without limitation, having a height that is between about 0.3 mm and about 3 mm (or within any subrange thereof). Indeed, in some embodiments, one or more of the various cutting guides (e.g., 588, 590, 592, 594, and/or 596) have a height of about 1.25 mm±0.5 mm. Additionally, the cutting guides can have any suitable width, including, without limitation, being between about 5 mm and about 8 cm in width (or within any subrange thereof). Indeed, in some embodiments, one or more of the cutting guides is between about 50 mm and about 65 mm in width.

In some embodiments, the tibial baseplate 530 is configured to couple with one or more alignment blocks 578 (e.g., via the elongated slot 581 and/or through the use of any other suitable coupling mechanism, including, without limitation, any of the couplers described herein with respect to any of the other described systems and components). In this regard, the alignment block can perform any suitable function. For instance, in some embodiments, the alignment block is configured to couple with one or more alignment rods 579 (see e.g., FIG. 65S) that are configured to extend in front of a patient's shin to show if the proximal end of the resectioned tibia has been cut at the proper angle. In this regard, the alignment block can couple with one or more alignment rods in any suitable manner, including, without limitation, through the use of one or more clips, clamps, holes, mechanical engagements, frictional engagements, and/or any other suitable coupling mechanism.

By way of non-limiting illustration, FIGS. 65AP-65AS show some embodiments in which the alignment block 578 defines one or more openings 577 that are configured to receive the alignment rod (not shown in FIGS. 65AP-65AS). While such an opening can have any suitable feature, in some embodiments, the opening is configured to hold the alignment rod such that a longitudinal axis of the alignment rod runs substantially perpendicular (and/or at any other suitable angle) with respect to a width of the alignment rod.

The alignment block 578 can have any other suitable features that allow it to function as intended. For instance, the alignment block can be any suitable length (e.g., being between about 5 mm about 10 cm in length or within any subrange thereof (such as 6 cm±1 cm)) and can be any suitable width (e.g., being between about 5 mm and about 7 cm wide or within any subrange thereof (such as 2.5 cm±1 cm)). Additionally, the alignment block can be any suitable thickness (e.g., between its superior surface and its inferior surface, not including any coupler disposed thereon), including, without limitation, between about 1 mm about 1.5 cm or within any subrange thereof (e.g., about 5 mm±2 mm).

In some embodiments, the couplers that couple the gap resection block 574, the femoral cutting block 572, the saw blade capture block 576, the alignment block 578 and/or any other component to the tibial baseplate 530 and/or to any other component are similarly sized and shaped. Thus, in some embodiments, the positioning and order of the various components are interchangeable and allow the various components to be placed in virtually any location with respect to one or more other components. Indeed, where the femoral cutting block 572, the gap resection block 574, the saw blade capture block 576, and/or the alignment block 577 all comprise similar couplers, each of those components can couple directly to the tibial baseplate (e.g., via the elongated slot 581) and/or to each other. In some other embodiments, however, the various couplers of the various components are sized and shaped so as to allow only specific components to be coupled together. By way of non-limiting example, in some embodiments, the gap resection block, the alignment block, and/or the femoral cutting block are configured to couple directly to the tibial baseplate; the saw blade capture block is configured to couple directly to the femoral cutting block but is not configured to couple directly to the tibial baseplate; and/or the various components can otherwise be configured to only couple together in specific orientations. While this can be useful for a variety of reasons, in some cases, by only allowing one or more of the various components to be coupled in a specific location, some embodiments of the described systems and methods can help to simplify corresponding medical procedures.

The described components can be used in any suitable manner. In this regard, while all of the methods described herein can be reordered, shortened, added to, comprise substitutions, have various portions of the methods be performed simultaneously and/or at different times, and/or otherwise be modified in any suitable manner, in some embodiments, the methods includes resecting a proximal portion of the tibia with one or more conventional and/or novel instruments (e.g., the bone milling device 310 and/or an automated device).

In some embodiments, after the tibia is resected, a baseplate (e.g., tibial baseplate 530, which can be used for tensioning ligaments with a tensioning assembly, balancing the gaps (e.g., with spacers 500), guiding a keel punch 544 or other punch, testing trial tibial components 585, and/or for any other suitable purpose) is placed on the tibia (e.g., is set on the tibia, is attached to the tibia with one or more fasteners 529, or is otherwise placed on the tibia).

In some cases, when the knee is flexed and/or extended, different sized spacers 500 are coupled to the tibial baseplate 530 (e.g., as shown, for flexion, in FIG. 76A) to adjust ligament tension and/or to balance gaps in the knee joint. In some cases, a tensioning assembly (e.g., as described herein) is used (e.g., as a leg holder to hold the knee flexed and as a lift to hold the femur and tibial apart for exposure of the posterior knee) to facilitate medial and/or lateral balancing, and the knee joint is balanced (e.g., via one or more spacers 500 and/or other devices discussed herein).

In some cases, the method continues as one or more reference blocks 550 are placed on the baseplate 500 (e.g., as shown in FIG. 76C). In this regard, any suitable size of reference block can be used (e.g., as discussed above). For instance, if a resection block is chosen that corresponds to a 9 mm, 11 mm, 13 mm, or 16 mm tibial implant, in some embodiments, 8 mm (or any other suitable amount of bone will be resected from the "tight" side of the joint (often the medial side, though it could be taken from the lateral and/or the medial side)).

In some embodiments, the method continues as a cutting assembly 555 is placed on the reference block 550 (e.g., as shown in FIG. 76D). In some such cases, such a cutting assembly can be used to make most, if not all, femoral bone resections. Additionally, in some embodiments, the cutting assembly is selected such that it is configured to guide an anterior femoral resection at a level of an anterior cortex of the femur. In some cases, the cutting assembly is angled to be substantially perpendicular to a flexion angle of the distal femur.

In some instances, once the preliminary anterior femoral resection is made by cutting in line with a top guide of the cutting assembly 555 (e.g., as shown in FIG. 76D), a posterior femoral resection is made (see e.g., FIG. 76E) to set the flexion gap. Alternatively, the posterior femoral resection is made after the distal resection, to set the extension gap.

Figure 76E:
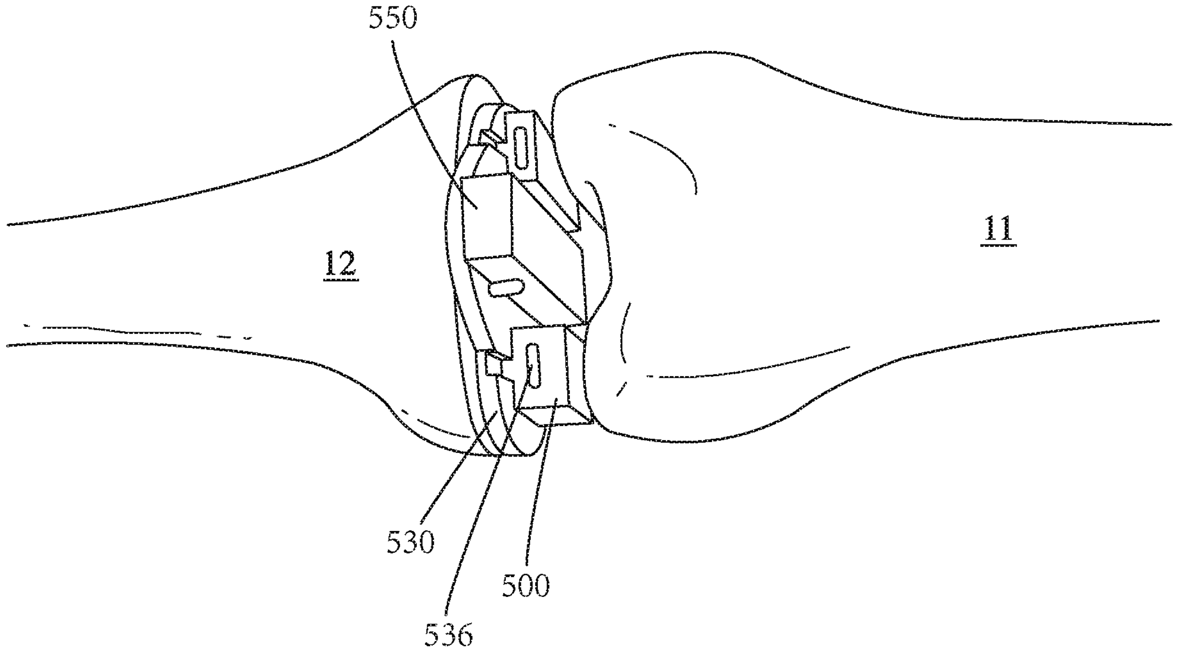
FIG. 76E depicts a perspective view of a knee joint in extension comprising the cutting block reference spacer in accordance with representative embodiment.
Figure 76F:
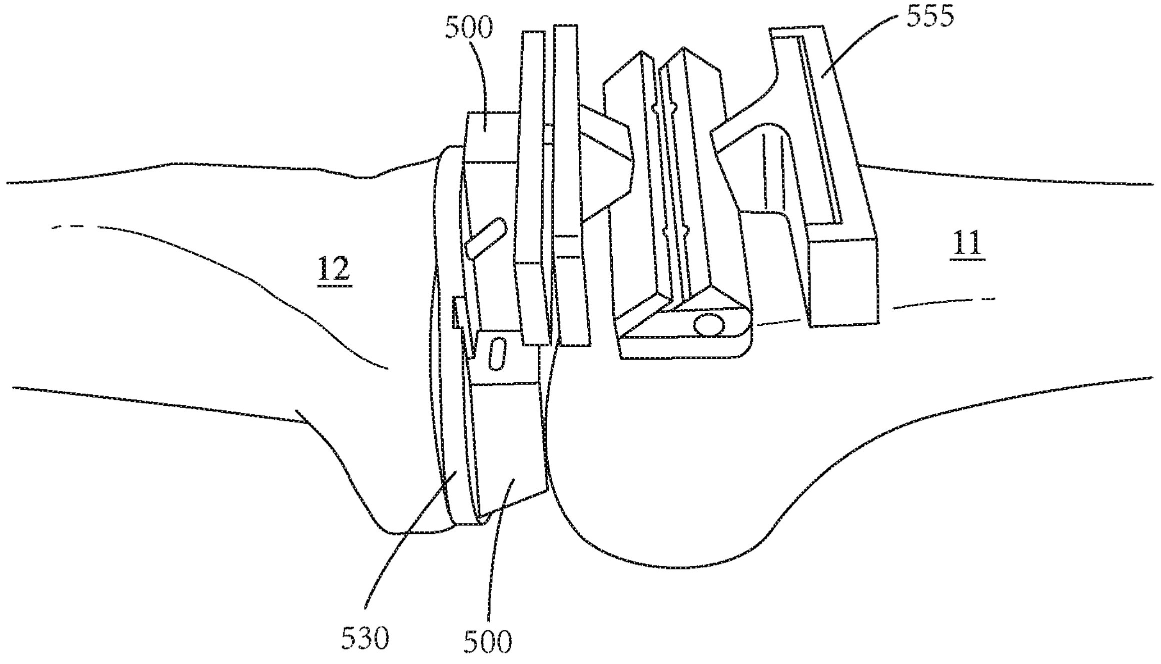
FIG. 76F depicts a perspective view of a knee joint in extension comprising the cutting block reference spacer and the cutting block in accordance with representative embodiment.
Figure 76G:
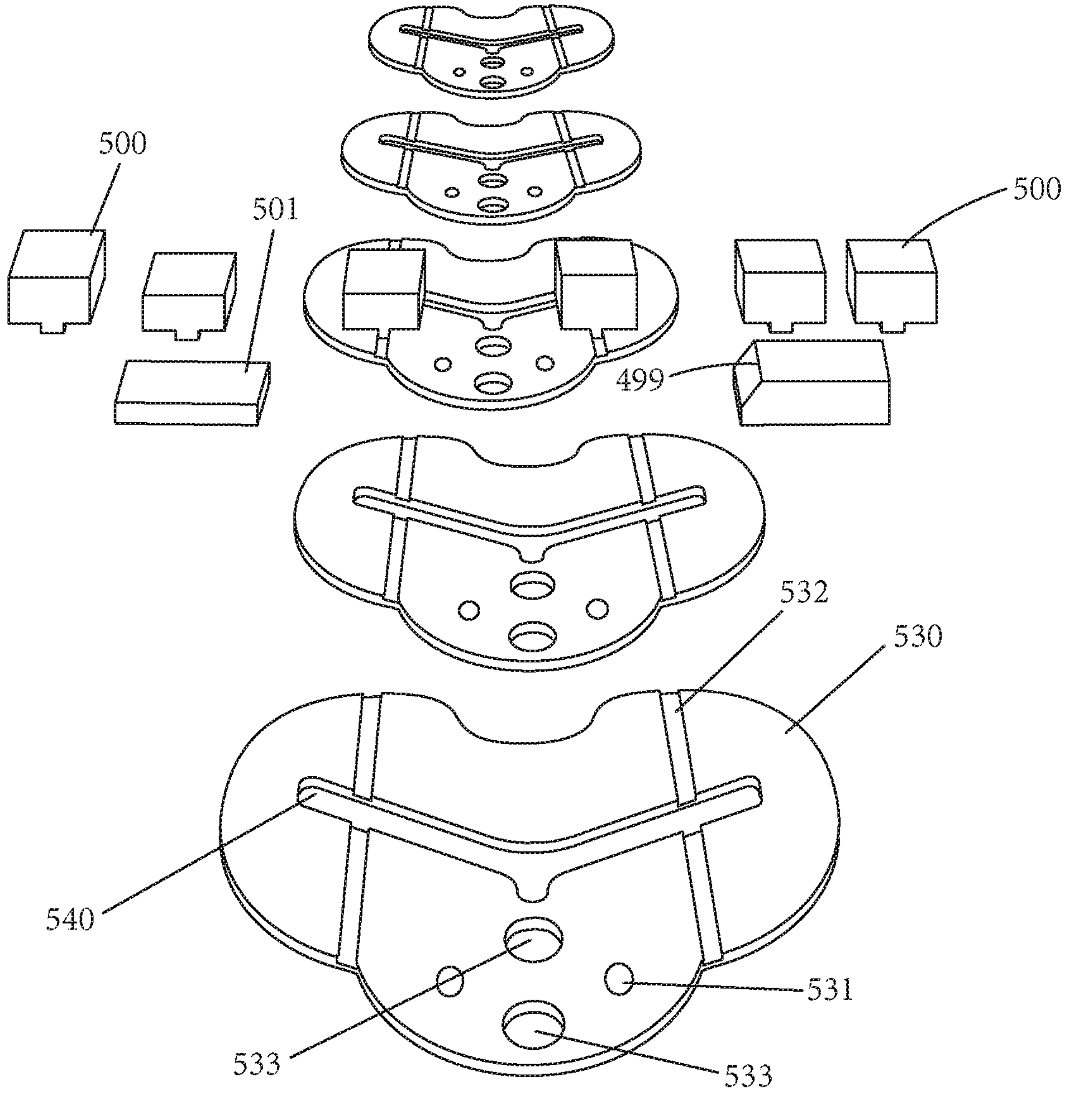
FIGS. 76G-76H illustrate some embodiments of arthroplasty kits.
Figure 76H:
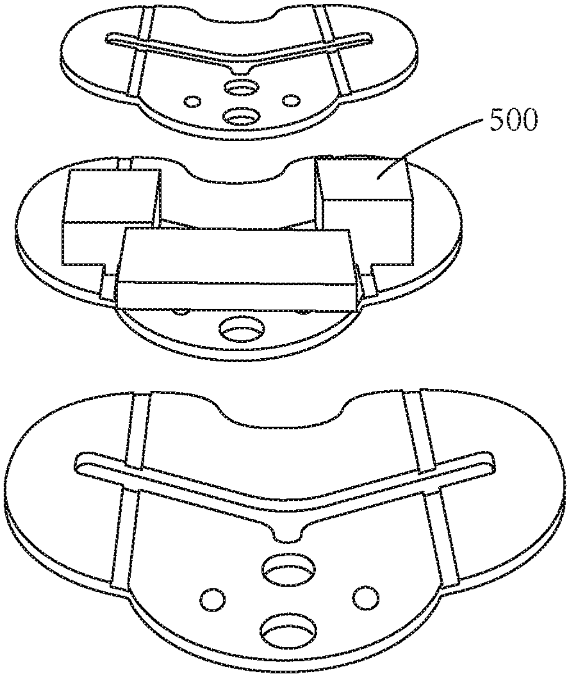

In some cases, as the method continues, the knee joint is placed into extension and spacer 500 blocks are placed in the knee joint on the tibial baseplate 530 (e.g., as shown in FIG. 76E) to adjust ligament tension and/or to balance the knee joint.

In some cases, a femoral resection reference block 550 is again placed onto the baseplate 500 (e.g., as shown in FIG. 76E). In some such cases, the same thickness reference block that was used for cutting the femur (e.g., as discussed above with reference to FIG. 76D) is used again.

In some embodiments, once the cutting assembly 55 is placed on the reference block 550 (also shown as 500 in FIG. 76F), one or more fasteners are driven through the cutting assembly and into the femur to maintain the cutting assembly in the proper location on the resected anterior femur. In instances, the method then continues as the knee is flexed and the distal femoral bone resection is accomplished through a slot in the cutting assembly 555.

In some cases, with the knee flexed, the knee is optionally re-tensioned and/or the flexion gap is balanced (e.g., via shimming with the spacers 500 or otherwise). Additionally, in some cases, one or more fasteners (e.g., pins) are placed in the cutting assembly to attach the guide onto the resected distal femur, with the cutting assembly resting on the reference block 550, and the anterior, posterior, and/or chamber femoral bone resections are made (see e.g., FIG. 76F).

In accordance with some embodiments, instead of completing the process described above with spacers 500 comprising spacer blocks, the method is conducted using one or more retractors 565 and/or lamina spreaders (e.g., as shown in FIGS. 77A-77D).

In some embodiments, once the femoral resections have been made, a trial tibial component 585 is placed on the tibial baseplate 530 and/or a trial femoral component 580 is placed on the femur and the knee joint is evaluated for balance, range of motion, alignment, and/or stability. (See e.g., FIGS. 75D-75E).

In accordance with some embodiments, the method further continues as one or more stem slots are made in the femur and/or tibia. Indeed, in some embodiments, a stem slot is prepared as a punch, drill, and/or other cutting tool forced down through an opening 540 in the top of the baseplate 530 (e.g., an opening having a chevron shaped, a rounded shape, an angled slot, an elliptical opening, a circular opening, a polygonal opening, and/or any other suitably shaped opening) (see e.g., FIG. 84A) and (if screws are to be used) the baseplate serves (in some embodiments) as a template for screw (or other fastener) placement, before the final implants are installed (see e.g., FIG. 70).

As another example of a suitable method, in some embodiments, the proximal end of the tibia is resected (e.g., as described herein) and the tibial baseplate 530 is placed on the resected bone. In some such embodiments, the alignment block 578 is then coupled to the baseplate, and the alignment rod 579 is coupled to the alignment block such that the practitioner can readily determine if the proximal end of the tibia was properly resected.

In some embodiments, the method continues as one or more spacers 500 are coupled to the tibial baseplate 530 so as to balance gaps between the tibia and the femur. In some embodiments, the gap resection block 574, the femoral cutting block 572, and/or the saw blade capture block 576 are then coupled to the tibial baseplate (directly and/or indirectly). Thus, in some embodiments, one or more cuts are made to the distal end of the femur (e.g., when the knee is in flexion and/or extension).

In accordance with some embodiments, once one or more femoral cuts have been made, one or more trial prosthetic components (e.g., the trial tibial component 585 and/or any other trial prosthetic components) can be used to ensure a proper fit of the components and/or movement of the knee. Moreover, in some cases, the knee joint is otherwise prepared for receiving one or more prosthetic components (e.g., by having a keel punch be driven into the tibia). Furthermore, in some cases, the tibial baseplate and/or the other components that couple to the baseplate are removed from the knee, and the final prosthetic components are coupled to the corresponding bones—thus allowing the knee to be closed up and to otherwise heal.

Additionally, while any suitable portion of the methods described above can be performed manually, in some embodiments, similar methods (and/or portions thereof) are performed with the use of one or more robots and/or other automated devices. Indeed, in some such embodiments, the methods include using a robot to make a tibial resection and then placing the tibial baseplate 530 on the resected tibia. In some such cases, when the knee is flexed, spacer blocks 500 (or retractors 565) are placed in the knee joint and the ligament tension is adjusted and the gaps are balanced by shimming the medial and lateral sides independently (see e.g., FIG. 76A). In some such cases, the pose of the knee is then captured (e.g., for use by the robot in making resections).

In some cases, the knee joint is also placed in extension and the ligaments are again placed in proper tension and the gaps are properly balanced (e.g., with spacers 500, reference spacers, retractors, and/or in any other suitable manner). Again, in at least some cases, the pose of the knee is captured.

In some cases, a virtual femoral component is adjusted to balance the gaps in flexion and extension. Moreover, in some cases, the robot is used to make one or more of the femoral resections. Following such resections, a tibial baseplate, a tibial trial component 585, a trial femoral component 580, and/or any other suitable component or components are seated in the knee joint, and the balance, range of motion, alignment, and/or stability of the knee are tested (e.g., with or without aid by computer information gathered by the robot).

In some cases, once the size of the proper tibial and femoral components is determined, a punch 544 can be driven through the tibial baseplate 530 and the permanent femoral and tibial components can be seated in the knee joint.

The various portions of the described apparatuses and systems can be made in any suitable manner. In this regard, some non-limiting examples of methods for making the described apparatuses and systems include boring, machining, etching, cutting, drilling, grinding, shaping, plaining, molding, extruding, sanding, lathing, smoothing, buffing, polishing, casting, bending, tapping, dying, connecting various pieces with one or more adhesives, mechanical fasteners (e.g., nails, clamps, rivets, staples, clips, pegs, crimps, pins, screws, brads, threads, brackets, etc.), welds, and/or by melting pieces together; and/or any other suitable method that allows the described apparatuses and systems to perform their intended functions.

Indeed, in some embodiments, one or more of the described components are formed through a method involving: 3D printing, additive manufacturing, selective laser sintering, direct metal laser sintering, selective laser melting, selective heat sintering, fused deposition molding, stereolithography, laminated object manufacturing, fused filament fabrication, robocasting, electron beam freeform, electron beam melting, digital light processing, computer numerical control milling, computer numerical control electrical discharge machining, vapor deposition, molding, extrusion, sintering, welding, grinding, etching, polishing, drilling, smoothing, coupling with one or more mechanical, chemical, frictional, other suitable fasteners, and/or any other suitable process. Indeed, in some embodiments, one or more of the described components are "printed" via selective laser melting electron-beam freeform fabrication and/or direct metal laser sintering.

The various components of the described apparatuses and systems can comprise any suitable material or materials that allows them to function as intended. Some examples of suitable materials include, but are not limited to, one or more suitable types of: metal (e.g., titanium, titanium alloy, cobalt, cobalt-chromium, cobalt-chromium alloy, tantalum, trabecular metal, zirconium, zirconium alloy, and/or any other biocompatible metal or metals), plastic (e.g., polyethylene, ultra-high cross linked polyethylene, ultra-high molecular weight polyethylene, high density polyethylene, and/or any other biocompatible plastic or plastics), ceramic (e.g., alumina, oxinium oxidized zirconium, zirconia, and/or any other suitable biocompatible ceramic or ceramics), and/or any other biocompatible material or materials. In some non-limiting embodiments, however, the described prosthetic comprises titanium and/or cobalt chromium. In some other embodiments, one or more of the components described herein comprise one or more polymers, plastics, metals, and/or other materials that are relatively inexpensive and/or not harmful to the environment. Thus, in some embodiments, one or more of the described components can be used once and then be discarded and/or recycled.

The various portions of the described apparatuses and systems can comprise any suitable material, including, without limitation, one or more metals, metal alloys, plastics, hard plastics, polymers, synthetic materials, natural materials, ceramics, and/or any other material or materials that are suitable for use in accordance with the described systems and methods.

Additionally, the various components described herein can be used together in any suitable combination, with elements from of the described systems, embodiments, methods, and apparatus being mixed and matched in any suitable manner. By way of non-limiting example, FIGS. 78 and 80-83 illustrate some examples of suitable kits, comprising one or more milling bits 320, guide rods 340, drill bits 341, reamers 343, spacers 500, reference spacers 550, cutting assemblies 555, spreaders 565, trial femoral components 580, trial tibial components 585, tibial baseplates 530, femoral intramedullary rods 13, non-threaded posts 115, flexion bolts 120, and/or extension bolts 130. While some embodiments of such kits have several beneficial features, in some cases, the kits comprise relatively few pieces. As a result, some such kits are relatively lightweight, can fit in a relatively small space (e.g., fewer autoclave trays than other competitive systems (e.g., can fit in a single autoclave tray)), and are relatively inexpensive.

Indeed, the various components, systems, and methods described herein can have several beneficial characteristics. For instance, some embodiments of the described systems and apparatus can be used with manual, power, and/or robotic tools and instrumentation. Additionally, some embodiments of the described systems and apparatus can be used to perform an entirely extramedullary gap balanced total knee arthroplasty and/or uni-compartmental knee arthroplasty.

As yet another example of a beneficial characteristic, one or more components of some embodiments of the described systems and methods are configured to be used with new and/or updated technology. By way of non-limiting example, the described tibial baseplate 50 can be used with a variety of new and conventional spacer 500, retractors (e.g., lamina spreaders 565), tensioning assemblies, trial tibial components 585, punches, fasteners, robotic equipment, and/or any other suitable components. Similarly, the described tensioning assemblies, trial tibial components, punches, fasteners, robotic equipment, and other any other components or apparatus described herein can be used with any new and suitable tibial baseplates and/or other suitable components.

As still another example of a beneficial characteristic, in some embodiments, one or more of the described components comprise one or more disposable materials. Indeed, in some embodiments, the spacers 500, trial tibial components 585, tensioners and/or tensioning assemblies, trial tibial components, trial femoral components, and/or other components or apparatus described herein can be disposable and/or packaged separately (e.g., from different components and/or from similar components of different sizes).

Thus, as discussed herein, the embodiments of the present invention embrace technologies and methods for accurately milling a bone preparatory to an arthroplasty procedure. As will be appreciated by one of skill in the art, the present invention may be embodied in other specific forms without departing from its spirit or essential characteristics. For example, in some embodiments the present invention is modified for use in a uni-compartmental knee arthroplasty procedure. In another embodiment, the present invention is modified for use in a total knee arthroplasty procedure. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A tibial baseplate system, comprising:

a tibial baseplate having a first surface that is configured to be seated on a resected surface at a proximal end of a tibia, a second surface that is substantially opposite to the first surface, an anterior end portion, a posterior end portion, a lateral side portion, and a medial side portion;

a spacer, wherein the tibial baseplate is configured to selectively receive and retain the spacer in a coupling position with relation to the tibial baseplate;

a cutting block guide that runs from the anterior end portion towards the posterior end portion at the second surface of the tibial baseplate;

a gap resection block configured to couple to the tibial baseplate via the cutting block guide;

a femoral cutting block configured to selectively couple to the gap resection block or the tibial baseplate via the cutting block guide, such that the femoral cutting block is configured to slide parallel with the second surface when the femoral cutting block is coupled to the gap resection block or the tibial baseplate via the cutting block guide; and a blade capture block configured to couple to the femoral cutting block, wherein the spacer is configured to prevent at least one of (i) the femoral cutting block, (ii) the gap resection block, (iii) the blade capture block, (iv) an alignment rod block, and (v) a tibial baseplate accessory from being disposed at the posterior end portion of the tibial baseplate when the spacer is coupled to the tibial baseplate.

2. The tibial baseplate system of claim 1, wherein the cutting block guide comprises an elongated groove that is defined in the second surface and that opens from the anterior end portion of the tibial baseplate.

3. The tibial baseplate system of claim 2, wherein the elongated groove comprises a keyed elongated groove that comprises a narrowed opening defined by the second surface that is configured to prevent a coupler of the femoral cutting block from being lifted from a portion of the cutting block guide when the coupler of the femoral cutting block is disposed in the keyed elongated groove.

4. The tibial baseplate system of claim 1, wherein the tibial baseplate further comprises a spacer guide that extends from the anterior end portion of the tibial baseplate toward the posterior end portion, the spacer guide being configured to slidingly couple with a spacer block having a coupler that is configured to slidingly couple with the spacer guide.

5. The tibial baseplate system of claim 4, wherein the spacer guide comprises a first catch that is configured to selectively catch and retain the spacer block at a set position with respect to the tibial baseplate.

6. The tibial baseplate system of claim 4, wherein the anterior end portion of the tibial baseplate comprises an elongated tongue that extends more than 1 cm from an anterior-most end of the spacer guide.

7. The tibial baseplate system of claim 1, further comprising an alignment rod block defining an opening that is configured to receive an alignment rod, wherein the alignment rod block comprises a coupler that is configured to slidingly couple the alignment rod block with the cutting block guide.

8. The tibial baseplate system of claim 1, further comprising a gap resection block that comprises a first coupler that is configured to slidingly couple the gap resection block with the cutting block guide, and wherein the gap resection block further comprises a second coupler that is configured to couple the gap resection block to the femoral cutting block.

9. The tibial baseplate system of claim 1, wherein the anterior end portion of the tibial baseplate is configured to extend anteriorly more than 5 mm past an anterior end of the resected surface at the proximal end of a tibia when the tibial baseplate is seated on and coupled to the resected surface.

10. A tibial baseplate system, comprising:

a tibial baseplate having a first surface that is configured to be seated on a resected surface at a proximal end of a tibia, a second surface that is substantially opposite to the first surface, an anterior end portion, a posterior end portion, a lateral side portion, and a medial side portion;

a spacer, wherein the tibial baseplate is configured to selectively receive and retain the spacer in a coupling position with relation to the tibial baseplate;

a cutting block guide that runs from the anterior end portion towards the posterior end portion at the second surface of the tibial baseplate;

a gap resection block configured to couple to the tibial baseplate via the cutting block guide;

a femoral cutting block configured to selectively couple to the gap resection block or the tibial baseplate via the cutting block guide such that the femoral cutting block is configured to slide parallel with the second surface when the femoral cutting block is coupled to the gap resection block or the tibial baseplate via the cutting block guide;

a blade capture block configured to couple to the femoral cutting block;

a first spacer guide that is disposed at the medial side portion of the tibial baseplate, that extends from the anterior end portion towards the posterior end portion of the tibial baseplate, and that is configured to slidingly couple a first spacer block to the second surface; and a second spacer guide that is disposed at the lateral side portion of the tibial baseplate such that the second spacer guide extends from the anterior end portion towards the posterior end portion of the tibial baseplate, and that is configured to slidingly couple a second spacer block to the second surface, wherein at least one of (i) the first spacer block and (ii) the second spacer block is configured to prevent a tibial baseplate accessory from being disposed at the posterior end portion of the tibial baseplate.

11. The tibial baseplate system of claim 10, further comprising the first spacer block and the second spacer block, wherein the first spacer block is either: (i) shorter or (ii) taller than the second spacer block.

12. The tibial baseplate system of claim 10, wherein the cutting block guide is disposed between, and runs substantially parallel with, the first spacer guide and the second spacer guide.

13. The tibial baseplate system of claim 10, wherein the cutting block guide comprises an elongated groove that is defined in the second surface and that opens from the anterior end portion of the tibial baseplate, and wherein the elongated groove comprises a keyed elongated groove that comprises a narrowed opening defined by the second surface that is configured to prevent a coupler of the femoral cutting block from being lifted from a portion of the cutting block guide when the coupler of the femoral cutting block is disposed in the keyed elongated groove.

14. A tibial baseplate system, comprising:

a tibial baseplate having a first surface that is configured to be seated on a resected surface at a proximal end of a tibia, a second surface that is substantially opposite to the first surface, an anterior end portion, a posterior end portion, a lateral side portion, and a medial side portion;

a spacer, wherein the tibial baseplate is configured to selectively receive and retain the spacer in a coupling position with relation to the tibial baseplate;

a cutting block guide comprising a first elongated groove that runs from the anterior end portion towards the posterior end portion at the second surface of the tibial baseplate;

a gap resection block configured to couple to the tibial baseplate via the cutting block guide;

a femoral cutting block configured to selectively couple to the gap resection block or the tibial baseplate via the cutting block guide such that the femoral cutting block is configured to slide parallel with the second surface when the femoral cutting block is coupled to the gap resection block or the tibial baseplate via the cutting block guide;

a blade capture block configured to couple to the femoral cutting block;

a first spacer guide comprising a second elongated groove that is defined at the medial side portion of the tibial baseplate, that extends from the anterior end portion towards the posterior end portion of the tibial baseplate, and that is configured to slidingly couple a first spacer block to the second surface; and a second spacer guide comprising a third elongated groove that is defined at the lateral side portion of the tibial baseplate, that extends from the anterior end portion towards the posterior end portion of the tibial baseplate, and that is configured to slidingly couple a second spacer block to the second surface, wherein at least one of (i) the first spacer block and (ii) the second spacer block is configured to prevent the femoral cutting block from being disposed at the posterior end portion of the tibial baseplate.

15. The tibial baseplate system of claim 14, wherein a longitudinal axis of the first elongated groove, a longitudinal axis of the second elongated groove, and a longitudinal axis of the third elongated groove each run substantially parallel with each other.

16. The tibial baseplate system of claim 14, wherein the first spacer guide comprises a first catch that is configured to selectively retain the first spacer block in a first position along a length of the first spacer guide.

17. The tibial baseplate system of claim 16, wherein the first catch comprises a recess, wherein an inferior portion of the first spacer block comprises a projection that slidingly mates with the first spacer guide, and wherein the projection comprises a first protrusion that is configured to engage with the first catch to selectively retain the first spacer block in the first position along a length of the first spacer guide.

18. The tibial baseplate system of claim 14, further comprising the first spacer block, wherein an inferior portion of the first spacer block comprises a projection that slidingly mates with the first spacer guide.

19. The tibial baseplate system of claim 14, further comprising the femoral cutting block and the first spacer block, wherein the femoral cutting block is coupled to the cutting block guide, and wherein the first spacer block is coupled to the first spacer guide.

20. The tibial baseplate system of claim 14, wherein the femoral cutting block is coupled to the cutting block guide by being coupled to a gap resection block, which is, in turn, coupled to the cutting block guide.

* * * * *